US012590945B2

(12) United States Patent
Maglia et al.

(10) Patent No.: US 12,590,945 B2
(45) Date of Patent: \*Mar. 31, 2026

(54) NANOPORE-BASED ANALYSIS OF ANALYTES

(71) Applicants:Rijksuniversiteit Groningen, Groningen (NL); Portal Biotech Limited, Guildford (GB)

(72) Inventors: Giovanni Maglia, Glimmen (NL); Shengli Zhang, Shanghai (CN); Andrew Heron, Maidenhead (GB)

(73) Assignees: Rijksuniversiteit Groningen, Groningen (NL); Portal Biotech Limited, Guildford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 19/295,122

(22) Filed: Aug. 8, 2025

(65) Prior Publication Data

US 2025/0369044 A1 Dec. 4, 2025

Related U.S. Application Data

(63) Continuation of application No. 19/020,496, filed on Jan. 14, 2025, which is a continuation of application (Continued)

(30) Foreign Application Priority Data

Oct. 28, 2022 (EP) .................................... 22204590

(51) Int. Cl.
| | |
|---|---|
| *C12Q 1/6869* | (2018.01) |
| *C12Q 1/25* | (2006.01) |
| *C12Q 1/6806* | (2018.01) |

(52) U.S. Cl.
CPC ............. *C12Q 1/6869* (2013.01); *C12Q 1/25* (2013.01); *C12Q 1/6806* (2013.01)

(58) Field of Classification Search
CPC .............................................. G01N 33/48721
(Continued)

(56) References Cited

U.S. PATENT DOCUMENTS

| | | | |
|---|---|---|---|
| 5,795,782 | A | 8/1998 | Church et al. |
| 6,015,714 | A | 1/2000 | Baldarelli et al. |

(Continued)

FOREIGN PATENT DOCUMENTS

| | | |
|---|---|---|
| CN | 104710519 A | 6/2015 |
| CN | 112480204 A | 3/2021 |

(Continued)

OTHER PUBLICATIONS

Afshar Bakshloo, Mazdak, et al., Nanopore-Based Protein Identification. Journal of the American Chemical Society 144(6):2716-2725 (2022).
(Continued)

*Primary Examiner* — Aaron A Priest
(74) *Attorney, Agent, or Firm* — Wilson Sonsini Goodrich & Rosati

(57) ABSTRACT

The present disclosure relates to systems and methods for analysis of proteins, more in particular to nanopore systems, devices and methods for single-molecule protein analysis and sequencing. Provided is a method for translocating a target protein through a nanopore, the nanopore being comprised in a membrane separating a fluidic chamber of a nanopore system into a cis side and a trans side, comprising:

Figure 1:
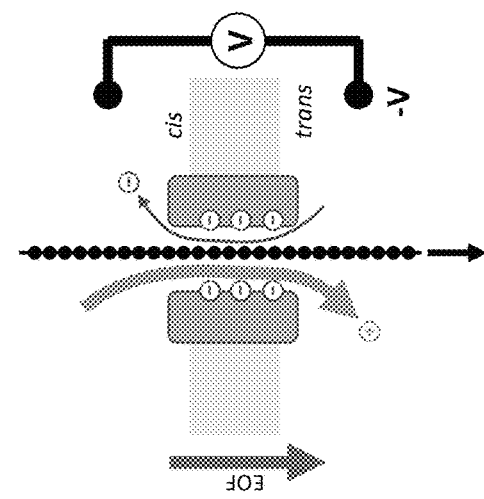
Figure 1:
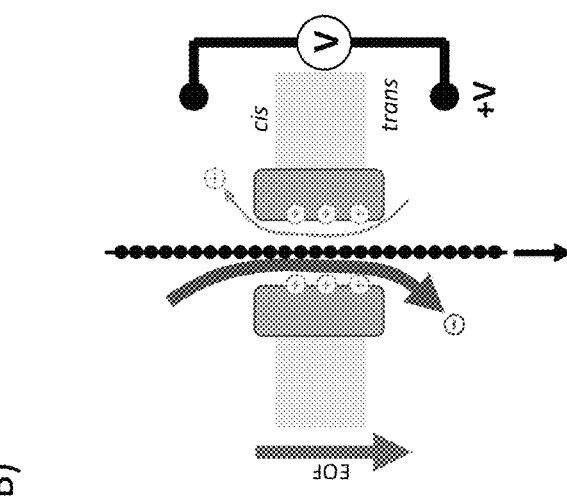
Figure 1:
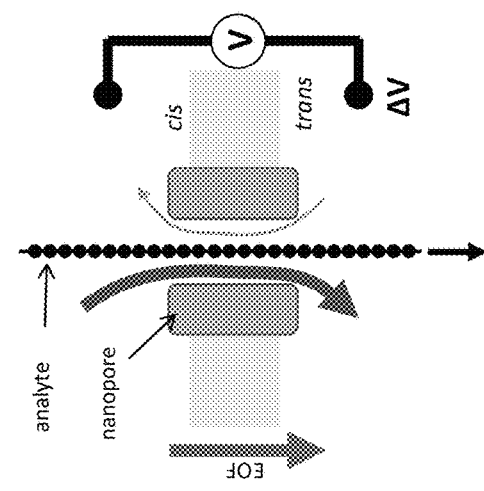

(a) allowing a protein translocase in solution to capture and form a complex with the target protein to be translocated;

(b) contacting the translocase-target protein complex with the cis side of the nanopore and allowing for
(Continued)

translocation of the target protein to the trans side; wherein the nanopore system has a cis to trans electro-osmotic force (EOF) resulting from a large net ionic current flow cis-to-trans relative to the total ionic current flow, so that the target protein is captured in the nanopore with on top of the nanopore the translocase controlling the translocation.

28 Claims, 30 Drawing Sheets

Specification includes a Sequence Listing.

Related U.S. Application Data

No. 18/394,975, filed on Dec. 22, 2023, now Pat. No. 12,235,260, which is a continuation of application No. PCT/NL2023/050570, filed on Oct. 30, 2023.

(58) Field of Classification Search
USPC ............................................................ 435/6
See application file for complete search history.

(56) References Cited

U.S. PATENT DOCUMENTS

| | | | |
|---|---|---|---|
| 6,267,872 B1 | 7/2001 | Akeson et al. |
| 6,362,001 B1 | 3/2002 | Cai et al. |
| 6,362,002 B1 | 3/2002 | Denison et al. |
| 6,428,959 B1 | 8/2002 | Deamer |
| 6,464,842 B1 | 10/2002 | Golovchenko et al. |
| 6,465,946 B1 | 10/2002 | Yoon et al. |
| 6,617,113 B2 | 9/2003 | Deamer |
| 6,627,067 B1 | 9/2003 | Branton et al. |
| 6,673,615 B2 | 1/2004 | Denison et al. |
| 6,746,594 B2 | 6/2004 | Akeson et al. |
| 7,238,485 B2 | 7/2007 | Akeson et al. |
| 7,622,934 B2 | 11/2009 | Hibbs et al. |
| 7,635,572 B2 | 12/2009 | Zhou et al. |
| 7,867,716 B2 | 1/2011 | Kang et al. |
| 7,968,702 B2 | 6/2011 | Wegener et al. |
| 8,324,914 B2 | 12/2012 | Chen et al. |
| 8,377,643 B2 | 2/2013 | Mehra et al. |
| 8,500,982 B2 | 8/2013 | Akeson et al. |
| 8,581,605 B2 | 11/2013 | White et al. |
| 8,673,550 B2 | 3/2014 | Gundlach et al. |
| 8,961,763 B2 | 2/2015 | Dunbar et al. |
| 8,986,928 B2 | 3/2015 | Turner et al. |
| 9,017,937 B1 | 4/2015 | Turner et al. |
| 9,052,275 B2 | 6/2015 | Khattak et al. |
| 9,121,064 B2 | 9/2015 | Turner et al. |
| 9,127,313 B2 | 9/2015 | Brown et al. |
| 9,377,437 B2 | 6/2016 | Chen et al. |
| 9,494,554 B2 | 11/2016 | Davis et al. |
| 9,534,024 B2 | 1/2017 | Gundlach et al. |
| 9,562,874 B2 | 2/2017 | Martin et al. |
| 9,724,691 B2 | 8/2017 | Khattak et al. |
| 9,766,248 B2 | 9/2017 | Lindsay et al. |
| 9,863,912 B2 | 1/2018 | Dunbar et al. |
| 9,868,987 B2 | 1/2018 | Turner |
| 9,903,820 B2 | 2/2018 | Meller et al. |
| 9,983,191 B2 | 5/2018 | Morin |
| 10,036,064 B2 | 7/2018 | Merriman et al. |
| 10,036,739 B2 | 7/2018 | Hovis et al. |
| 10,195,606 B2 | 2/2019 | Khattak et al. |
| 10,209,217 B2 | 2/2019 | Gentalen |
| 10,215,768 B2 | 2/2019 | Sanghera et al. |
| 10,221,450 B2 | 3/2019 | Heron et al. |
| 10,345,240 B2 | 7/2019 | Chan et al. |
| 10,364,462 B2 | 7/2019 | Stava et al. |
| 10,458,978 B2 | 10/2019 | Cary |
| 10,514,380 B2 | 12/2019 | Takulapalli |
| 10,612,083 B2 | 4/2020 | Gundlach et al. |
| 10,656,117 B2 | 5/2020 | Mayer et al. |

| | | | |
|---|---|---|---|
| 10,712,254 B2 | 7/2020 | Bayley et al. |
| 10,787,705 B2 | 9/2020 | Esfandyarpour et al. |
| 10,794,895 B2 | 10/2020 | Xie |
| 10,870,883 B2 | 12/2020 | Gundlach et al. |
| 10,883,140 B2 | 1/2021 | Church et al. |
| 10,900,067 B2 | 1/2021 | Aksimentiev et al. |
| 10,961,576 B2 | 3/2021 | Boyanov et al. |
| 10,976,311 B2 | 4/2021 | Maglia et al. |
| 10,996,219 B2 | 5/2021 | Chee |
| 11,002,657 B2 | 5/2021 | Pelta et al. |
| 11,034,734 B2 | 6/2021 | Howorka et al. |
| 11,061,013 B2 | 7/2021 | Mir |
| 11,150,216 B2 | 10/2021 | Chen et al. |
| 11,162,935 B2 | 11/2021 | Wang et al. |
| 11,261,488 B2 | 3/2022 | Craig et al. |
| 11,282,585 B2 | 3/2022 | Patel et al. |
| 11,312,755 B2 | 4/2022 | Maglia et al. |
| 11,313,857 B2 | 4/2022 | Wanunu et al. |
| 11,339,365 B2 | 5/2022 | Nivala et al. |
| 11,391,693 B2 | 7/2022 | Boyanov et al. |
| 11,618,897 B2 | 4/2023 | Kim et al. |
| 11,644,437 B2 | 5/2023 | Xie et al. |
| 11,703,476 B2 | 7/2023 | Wanunu et al. |
| 11,821,903 B2 | 11/2023 | Woolfson et al. |
| 11,840,556 B2 | 12/2023 | Jayasinghe et al. |
| 11,845,779 B2 | 12/2023 | Dal Peraro et al. |
| 12,105,079 B2 | 10/2024 | Huang et al. |
| 12,235,260 B2 | 2/2025 | Maglia et al. |
| 2003/0104428 A1 | 6/2003 | Branton et al. |
| 2004/0121525 A1 | 6/2004 | Chopra et al. |
| 2008/0287656 A1 | 11/2008 | Peters et al. |
| 2010/0297638 A1 | 11/2010 | Bayley et al. |
| 2011/0174625 A1 | 7/2011 | Akeson et al. |
| 2011/0193249 A1 | 8/2011 | Chen et al. |
| 2011/0249259 A1 | 10/2011 | Van Dorpe et al. |
| 2011/0311965 A1 | 12/2011 | Maglia et al. |
| 2012/0055792 A1 | 3/2012 | Gundlach et al. |
| 2012/0107802 A1 | 5/2012 | Stoddart et al. |
| 2013/0017538 A1 | 1/2013 | Ionescu-Zanetti et al. |
| 2013/0161194 A1 | 6/2013 | Jeon et al. |
| 2014/0106472 A1 | 4/2014 | Ervin et al. |
| 2014/0255921 A1 | 9/2014 | Moysey et al. |
| 2014/0335527 A1 | 11/2014 | Goel |
| 2015/0031020 A1 | 1/2015 | Jayasinghe et al. |
| 2015/0191709 A1* | 7/2015 | Heron ........... C12Y 599/01003 435/375 |
| 2016/0018384 A1 | 1/2016 | Lindsay et al. |
| 2016/0032235 A1 | 2/2016 | Segard |
| 2016/0032236 A1 | 2/2016 | Nivala et al. |
| 2016/0169864 A1 | 6/2016 | Grinstaff et al. |
| 2016/0273032 A1 | 9/2016 | Esfandyarpour et al. |
| 2017/0315109 A1 | 11/2017 | Alden et al. |
| 2018/0364214 A1 | 12/2018 | Maglia et al. |
| 2019/0071721 A1 | 3/2019 | Jayasinghe et al. |
| 2019/0128867 A1 | 5/2019 | Movileanu et al. |
| 2019/0227028 A1 | 7/2019 | Patolsky et al. |
| 2020/0123594 A1 | 4/2020 | Rothberg et al. |
| 2020/0348307 A1 | 11/2020 | Beierle et al. |
| 2021/0033591 A1 | 2/2021 | Ambroso et al. |
| 2021/0088511 A1 | 3/2021 | Crisalli et al. |
| 2021/0189482 A1 | 6/2021 | Akeson et al. |
| 2021/0255075 A1 | 8/2021 | Ren et al. |
| 2021/0308677 A1 | 10/2021 | Goel |
| 2021/0325365 A1 | 10/2021 | Huang et al. |
| 2021/0340192 A1 | 11/2021 | Nivala |
| 2021/0363577 A1 | 11/2021 | Clarke et al. |
| 2021/0372959 A1 | 12/2021 | Liu et al. |
| 2022/0091093 A1 | 3/2022 | Wanunu et al. |
| 2022/0162568 A1 | 5/2022 | Haque et al. |
| 2022/0226820 A1 | 7/2022 | Khurana et al. |
| 2022/0242922 A1 | 8/2022 | Maglia et al. |
| 2022/0277814 A1 | 9/2022 | Nivala |
| 2022/0283140 A1* | 9/2022 | Wanunu ........... G01N 33/48721 |
| 2022/0299469 A1 | 9/2022 | Boyanov et al. |
| 2022/0396758 A1* | 12/2022 | Nivala ............. G01N 33/54366 |
| 2022/0412948 A1 | 12/2022 | Maglia et al. |
| 2023/0024319 A1* | 1/2023 | Heron .................... C12N 15/11 |
| 2023/0048421 A1 | 2/2023 | Zhang et al. |
| 2023/0090454 A1 | 3/2023 | Kapp et al. |

(56) References Cited

U.S. PATENT DOCUMENTS

| | | |
|---|---|---|
| 2023/0194499 A1 | 6/2023 | Zou et al. |
| 2023/0220002 A1 | 7/2023 | Long et al. |
| 2023/0221296 A1 | 7/2023 | Long et al. |
| 2024/0002925 A1 | 1/2024 | Anslyn et al. |
| 2024/0003909 A1 | 1/2024 | Li |
| 2024/0159768 A1 | 5/2024 | Lucas et al. |
| 2024/0201165 A1 | 6/2024 | Maglia et al. |
| 2024/0288416 A1 | 8/2024 | Maglia et al. |

FOREIGN PATENT DOCUMENTS

| | | |
|---|---|---|
| CN | 112500459 A | 3/2021 |
| EP | 1956367 A1 | 8/2008 |
| EP | 2350122 A1 | 8/2011 |
| EP | 2814939 A2 | 12/2014 |
| EP | 2978773 A1 | 2/2016 |
| EP | 2814939 B1 | 4/2018 |
| EP | 3485029 A1 | 5/2019 |
| EP | 3598133 A1 | 1/2020 |
| EP | 3955002 A1 | 2/2022 |
| EP | 4070092 A1 | 10/2022 |
| EP | 4070092 B1 | 8/2023 |
| EP | 4392437 A1 | 7/2024 |
| GB | 2431013 B | 5/2008 |
| JP | 2013540423 A | 11/2013 |
| NL | 2023062 B1 | 11/2020 |
| WO | WO-0079257 A1 | 12/2000 |
| WO | WO-0116328 A2 | 3/2001 |
| WO | WO-2005124888 A1 | 12/2005 |
| WO | WO-2006028508 A2 | 3/2006 |
| WO | WO-2009020682 A2 | 2/2009 |
| WO | WO-2009044170 A1 | 4/2009 |
| WO | WO-2010004265 A1 | 1/2010 |
| WO | WO-2010034018 A2 | 3/2010 |
| WO | WO-2010055307 A1 | 5/2010 |
| WO | WO-2010082860 A1 | 7/2010 |
| WO | WO-2010117470 A2 | 10/2010 |
| WO | WO-2013014451 A1 | 1/2013 |
| WO | WO-2013123379 A2 | 8/2013 |
| WO | WO-2014153625 A1 | 10/2014 |
| WO | WO-2014190299 A2 | 11/2014 |
| WO | WO-2015040423 A1 | 3/2015 |
| WO | WO-2015081178 A1 | 6/2015 |
| WO | WO-2016166232 A1 | 10/2016 |
| WO | WO-2018012963 A1 | 1/2018 |
| WO | WO-2020055246 A1 | 3/2020 |
| WO | WO-2020152563 A1 | 7/2020 |
| WO | WO-2020160559 A1 | 8/2020 |
| WO | WO-2021021592 A1 | 2/2021 |
| WO | WO-2021101378 A1 | 5/2021 |
| WO | WO-2021111125 A1 | 6/2021 |
| WO | WO-2022020461 A1 | 1/2022 |
| WO | WO-2022150659 A1 | 7/2022 |
| WO | WO-2023055246 A1 | 4/2023 |
| WO | WO-2023102502 A2 | 6/2023 |
| WO | WO-2023240337 A1 | 12/2023 |

OTHER PUBLICATIONS

Akeson, M, et al., Microsecond time-scale discrimination among polycytidylic acid, polyadenylic acid, and polyuridylic acid as homopolymers or as segments within single RNA molecules. Biophysical Journal 77(6):3227-3233 (1999).

Akopian, Tatos, et al., Processive Degradation of Proteins and Other Catalytic Properties of the Proteasome From Thermoplasma Acidophilum. The Journal of biological chemistry 272(3):1791-1798 (1997).

Aksoyoglu, Alphan, et al., Size-dependent forced PEG partitioning into channels: VDAC, OmpC, and α-hemolysin. PNAS USA 113(32):9003-9008 (2016).

Alfaro, Javier Antonio et al., The Emerging Landscape of Single-molecule Protein Sequencing Technologies. Nature Methods 18:604-617 (2021).

An, Na, et al., Single-molecule investigation of G-quadruplex folds of the human telomere sequence in a protein nanocavity. PNAS USA 111(40):14325-14331 (2014).

Anderluh, Gregor et al.: Cytolytic peptide and protein toxins from sea anemones (Anthozoa: actiniaria). Toxicon 40(2):111-124 (2002).

André, Ingemar., et al., Prediction of the structure of symmetrical protein assemblies. PNAS USA 104(45):17656-17661 (2007).

Aqvist, et al., Dipoles localized at helix termini of proteins stabilize charges. PNAS USA 88(5):2026-2030 (1991).

Asandei, Alina, et al., Electroosmotic Trap Against the Electrophoretic Force Near a Protein Nanopore Reveals Peptide Dynamics During Capture and Translocation. ACS Applied Materials & Interfaces 8(20):13166-13179 (2016).

Baaken, Gerhard, et al., High-resolution size-discrimination of single nonionic synthetic polymers with a highly charged biological nanopore. ACS Nano 9(6):6443-6449 (2015).

Bacri, Laurent, et al., Discrimination of neutral oligosaccharides through a nanopore. Biochem Biophys Res Commun 412(4):561-564 (2011).

Bakrac, Biserka, et al., Molecular determinants of sphingomyelin specificity of a eukaryotic pore-forming toxin. Journal of Biological Chemistry 283(27):18665-18677 (2008).

Balakrishna, B.H. et al. Binding of a pleurotolysin ortholog from Pleurotus eryngii to sphingomyelin and cholesterol-rich membrane domains. Journal of Lipid Research 54(10):2933-43 (2013).

Balijepalli, Arvind, et al., Theory of Polymer-nanopore Interactions Refined Using Molecular Dynamics Simulations. Journal of the American Chemical Society 135(18):7064-7072 (2013).

Baniandres; Pablo Martin et al.: Enzyme-less Nanopore Detection of Post-translational Modifications Within Long Polypeptides. Nature Nanotechnology 18:1335-1340 (2023).

Barkow, Sarah R, et al., Polypeptide translocation by the AAA+ ClpXP protease machine. Chemical Biology 16(6):605-612 (2009).

Barlic, Ariana, et al., Lipid Phase Coexistence Favors Membrane Insertion of Equinatoxin-II, a Pore-forming Toxin from Actinia equina. Journal of Biological Chemistry 279(33):34209-34216 (2004).

Bayat, Parisa et al., Comprehensive Structural Assignment of Glycosaminoglycan Oligo and Polysaccharides by Protein Nanopore. Nature Communications. 13(1):5113 (2022).

Baytshtok, Vladimir, et al., A Structurally Dynamic Region of the HsLU Intermediate Domain Controls Protein Degradation and ATP Hydrolysis. Structure 24(10):1766-1777 (2016).

Becker, Samuel H, et al., Bacterial Proteasomes: Mechanistic and Functional Insights. Microbiology and Molecular Biology Reviews :MMBR 81(1):1-20 (2016).

Bell, Nicholas, Nanopores Formed by DNA Origami: A Review. FEBS letters 588(19):3564-3570 (2014).

Bellomio, Augusto, et al., Purification, Cloning and Characterization of Fragaceatoxin C, A Novel Actinoporin From the Sea Anemone Actinia Fragacea. Toxicon 54(6):869-880 (2009).

Benaroudj, Nadia, et al., ATP hydrolysis by the proteasome regulatory complex PAN serves multiple functions in protein degradation. Molecular cell 1:69-78 (2003).

Beta-channel forming cytolysin—Bacillus cytotoxicus | UniProtKB | UniProt. Accession No. A0A2S1A9G3_9BACI in UniProt 2002-2024.

Bezrukov, S., et al., Dynamics and free energy of polymers partitioning into a nanoscale pore. Macromolecules 29, 8517-8522 (1996).

Biesemans, Annemie., et al., A Protein Rotaxane Controls the Translocation of Proteins Across a ClyA Nanopore. Nano Lett 15(9):6076-6081 (2015).

Boersma, Arnold J, et al., Continuous stochastic detection of amino acid enantiomers with a protein nanopore. Angewandte Chemie International Edition English 51(38):9606-9609 (2012).

Booner, Oscar, et al., Osmotic and Activity Coefficients of Sodium and Potassium Glutamate at 298.15 K. Journal of Chemical & Engineering Data 26:147-148 (1981).

Bouchnak, Imen, et al., Structure, function, and substrates of Clp AAA+ protease systems in cyanobacteria, plastids, and apicoplasts: A comparative analysis. Journal of Biological Chemistry 296:1-16 (2021).

(56)　　　　　References Cited

OTHER PUBLICATIONS

Brauning, Bastian et al. Structure and mechanism of the two-component α-helical pore-forming toxin YaxAB. Nature communications 9(1):1806, 1-14 (2018).

Brinkerhoff, Henry, et al., Multiple Rereads of Single Proteins at Single-amino Acid Resolution Using Nanopores. Science 374(6574):1509-1513 (2021).

Buchberger, Alexander, et al., Roles of Cdc48 in Regulated Protein Degradation in Yeast. Sub-cellular Biochemistry 66:195-222 (2013).

Burns, Jonathan, et al., Lipid-bilayer-spanning DNA nanopores with a bifunctional porphyrin anchor. Angewandte Chemie 52(46):12069-12072 (2013).

Butler, Tom Z. et al., Single-molecule DNA Detection With an Engineered MspA Protein Nanopore. PNAS USA 105(52):20647-20652 (2008).

Cajado-Carvalho, Daniela et al. Insights into the Hypertensive Effects of Tityus serrulatus Scorpion Venom: Purification of an Angiotensin-Converting Enzyme-Like Peptidase. Toxins 8(12)348:1-16 (2016).

Cao, Chan, et al., Discrimination of oligonucleotides of different lengths with a wild-type aerolysin nanopore. Nature Nanotechnology 11(8):713-718 (2016).

Cao; Chan et al.: Single-molecule sensing of peptides and nucleic acids by engineered aerolysin nanopores. Nature Communications 10: 4918 (2019).

Castanzo, Dominic, et al., The AAA+ ATPase Msp1 is a Processive Protein Translocase with Robust Unfoldase Activity. PNAS USA 117(26):14970-14977 (2020).

Chavis, Amy E, et al., Single Molecule Nanopore Spectrometry for Peptide Detection. ACS Sensors 2(9):1319-1328 (2017).

Chen, Baoyu, et al., Engagement of arginine finger to ATP triggers large conformational changes in NtrC1 AAA+ ATPase for remodeling bacterial RNA polymerase. Structure 18(11):1420-1430 (2010).

Chinappi, Mauro, and Fabio Cecconi. Protein sequencing via nanopore based devices: a nanofluidics perspective. Journal of Physics: Condensed Matter 30(20):204002, 1-14 (2018).

Chinappi, Mauro, et al., Analytical Model for Particle Capture in Nanopores Elucidates Competition Among Electrophoresis, Electroosmosis, and Dielectrophoresis. ACS Nano 14(11):15816-15828 (2020).

Clarke, James et al. Continuous base identification for single-molecule nanopore DNA sequencing. Nature Nanotechnology 4(4):265-270 (2009).

Cressiot, Benjamin, et al., Dynamics and Energy Contributions for Transport of Unfolded Pertactin Through a Protein Nanopore. ACS Nano 9(9):9050-61 (2015).

Cressiot, Benjamin, et al., Protein Transport Through a Narrow Solid-state Nanopore at High Voltage: Experiments and Theory. American Chemical Society nano 6(7):6236-6243 (2012).

Crnković, Ana, et al., Biological Nanopores: Engineering on Demand. Life (Basel) 11(1):27 (2021).

Dal-Peraro, Matteo, et al., Pore-forming toxins: ancient, but never really out of fashion. Nature reviews. Microbiology 14(2):77-92 (2016).

Database UniProt B9W5G6 XP002796191 (Sep. 1, 2009 v2).

Delta-Actitoxin-Aeq1b-like [Orbicella faveolata]. BioProject PRJNA381078, XP-020600665.1. (2017) https://www.ncbi.nlm.nih.gov/protein/1176123762?sat=4&satkey=191642050.

Derrington, Ian M, et al., Nanopore DNA sequencing with MspA. PNAS USA 107(37):16060-16065 (2010).

Derrington, Ian M. et al.: Subangstrom single-molecule measurements of motor proteins using a nanopore. Nature Biotechnology Sep. 28, 2015.

Dong, Changjiang et al.: The structure of Wza, the translocon for group 1 capsular polysaccharides in Escherichia coli, identifies a new class of outer membrane protein. Nature 444(7116):226-229 (2006). doi: 10.1038/nature05267.

Dong, Changjiang, et al., Wza the Translocon for E. coli Capsular Polysaccharides Defines a New Class of Membrane Protein. Nature 444:226-229 (2006).

Dougana, David, et al., AAA+ proteins and substrate recognition, it all depends on their partner in crime. FEBS Letters 529:6-10 (2002).

Effantin, Gregory, et al., Binding of the ClpA Unfoldase Opens the Axial Gate of ClpP Peptidase. The Journal of Biological Chemistry 285(19):14834-14840 (2010).

Erlandson, Karl et al., A Role for the Two-helix Finger of the Seca ATpase in Protein Translocation. Nature 455:7215:984-987 (2008).

Faller, Michael, et al., The structure of a mycobacterial outer-membrane channel. Science 303(5661):1189-1192 (2004).

Flynn, Julia, et al., Overlapping Recognition Determinants Within the ssrA Degradation Tag Allow Modulation of Proteolysis. PNAS USA 98(19):10584-10589 (2001).

Forouzan, Dara, et al., The Archaeal Proteasome is Regulated by a Network of AAA ATPases. The Journal of Biological Chemistry 287(46):39254-62 (2012).

Forster, Andreas et al.: The 1.9 Å structure of a proteasome-11S activator complex and implications for proteasome-PAN/PA700 interactions. Molecular Cell 18:589-599 (2005).

Franceschini, Lorenzo, et al., A nanopore machine promotes the vectorial transport of DNA across membranes. Nature Communications 4(2415): 8 Pages (2013).

Frees, Dorte, et al., Clp ATPases Are Required for Stress Tolerance, Intracellular Replication and Biofilm Formation in Staphylococcus aureus. Molecular Microbiology 54(5):1445-62 (2004).

Furini, Simone, et al., Model-based Prediction of the Alpha-hemolysin Structure in the Hexameric State. Biophysical journal 95 (5): 2265-2274 (2008).

García-Ortega, Lucia et al. The Behavior of Sea Anemone Actinoporins at the Water-membrane Interface. Biochimica Et Biophysica Acta 1808(9):2275-2288 (2011).

Gerega, Alexandra, et al., VAT, the Thermoplasma Homolog of Mammalian p97/VCP, Is an N Domain-regulated Protein Unfoldase. The Journal of Biological Chemistry 280(52):42856-42862 (2020).

Gimenez-Andres, Manuel, et al., The Many Faces of Amphipathic Helices. Biomolecules 8(45):1-14 (2018).

Glynn, Steven E, et al., Dynamic and Static Components Power Unfolding in Topologically Closed Rings of a AAA+ Proteolytic Machine. Nature Structural & Molecular Biology 19(6):616-622 (2012).

Gonzalez-Perez, Alfredo, et al., Biomimetic Triblock Copolymer Membrane Arrays: A Stable Template for Functional Membrane Proteins. Langmuir 25(18):10447-10450 (2009).

Gouaux, J,E, et al., Subunit stoichiometry of staphylococcal alpha-hemolysin in crystals and on membranes: a heptameric transmembrane pore. PNAS USA 91(26):12828-31 (1994).

Gu, Li-qun et al. Electroosmotic Enhancement of the Binding of a Neutral Molecule to a Transmembrane Pore. PNAS USA 100(26):15498-15503 (2003).

Gu, Li-qun, et al., Interaction of the Noncovalent Molecular Adapter, Beta-cyclodextrin, With the Staphylococcal Alpha-hemolysin Pore. Biophysical journal 79(4):1967-75 (2000).

Gu, Li-qun, et al., Stochastic Sensing of Organic Analytes by a Pore-forming Protein Containing a Molecular Adapter. Nature 398:686-690(1999).

Guimaraes, Carla P, et al., Site-specific C-terminal and internal loop labeling of proteins using sortase-mediated reactions. Nature Protocols 8(9):1787-1799 (2013).

Hammerstein, Anne, et al., Subunit Dimers of Alpha-hemolysin Expand the Engineering Toolbox for Protein Nanopores. The Journal of Biological Chemistry 286(16):14324-34 (2011).

Hardy, Simon.P, et al., CytK Toxin of Bacillus Cereus Forms Pores in Planar Lipid Bilayers and is Cytotoxic to Intestinal Epithelia. FEMS Microbiology Letters 197:47-51 (2001).

Henning-Knechtel; Anja et al.: DNA-assisted oligomerization of pore-forming toxin monomers into precisely-controlled protein channels. Nucleic Acids Research 45(21):12057-12068 (2017).

Heron, Andrew, et al., Simultaneous Measurement of Ionic Current and Fluorescence from Single Protein Pores. Journal of the American Chemical Society 131(5):1652-1653 (2009).

Hille, Bertil, Ion Channels of Excitable Membranes, Third edition. Sinauer Associates Inc 37 Pages (2001).

Ho, Ching-Wen., et al., Engineering a nanopore with co-chaperonin function. Sci Adv 1(11):1-9 (2015).

(56) References Cited

OTHER PUBLICATIONS

Horton, Robert, et al. Engineering hybrid genes without the use of restriction enzymes: gene splicing by overlap extension. Gene 77(1):61-68 (1989).

Huang, Gang, et al., Detection of Single Amino Acid Differences in Haemoglobin From Blood Samples Using a Nanopore. ChemRxiv: 24 Pages (2021).

Huang, Gang, et al., Electro-Osmotic Capture and Ionic Discrimination of Peptide and Protein Biomarkers With Frac Nanopores. Nature Communications 8:935, 1-11 (2017).

Huang, Gang, et al., Electro-Osmotic Vortices Promote the Capture of Folded Proteins by PlyAB Nanopores. Nano Letters 20(5):3819-3827 (2020).

Huang, Gang et al., FraC nanopores with adjustable diameter identify the mass of opposite-charge peptides with 44 dalton resolution. Nature Communications 10:1-10 (2019).

Huang, Gang, et al., PlyAB Nanopores Detect Single Amino Acid Differences In Folded Haemoglobin From Blood. Angewandte Chemie International Edition 61(34): 8 Pages (2022).

Huang, Kevin: Engineering biological nanopores for proteomics study. Thesis University of Groningen (pp. 1-201) (2019).

Huang, Rui, et al., Unfolding the mechanism of the AAA+ unfoldase VAT by a combined cryo-EM, solution NMR study. PNAS USA 113(20):E4190-9, 1-10 (2016).

Huang, Shuo et al. High-throughput optical sensing of nucleic acids in a nanopore array. Nature Nanotechnology 10(11):986-991 (2015).

Huber, Eva, et al., A Unified Mechanism for Proteolysis and Autocatalytic Activation in the 20s Proteasome. Nature communications 7:1-10 (2016).

Huber, Eva, et al., The mammalian proteasome activator PA28 forms an asymmetric α4β3 complex. Structure 25(10):1473-1480 (2017).

Humbard, Matthew A, et al., Ubiquitin-like Small Archaeal Modifier Proteins (SAMPs) in Haloferax Volcanii. Nature 463:54-60 (2010).

Ivanov, Aleksandar P, et al., DNA tunneling detector embedded in a nanopore. Nano Letters 11(1):279-285 (2011).

Jiang, Jiansen, et al., Atomic structure of anthrax protective antigen pore elucidates toxin translocation. Nature 521(7553):545-549 (2015).

Kasianowicz, John J. et al. Characterization of Individual Polynucleotide Molecules Using a Membrane Channel. PNAS USA 93(24):13770-13773 (1996).

Kavalchuk, Mikhail, et al., Structural Basis of Prokaryotic Ubiquitin-like Protein Engagement and Translocation by the Mycobacterial Mpa-proteasome Complex. Nature Communications 13(1):276 (2022).

Kennedy, Eamonn et al. Reading the primary structure of a protein with 0.07 nm3 resolution using a subnanometre-diameter pore. Nature nanotechnology 11(11):968-976 (2016).

Kim, Yong-In, et al., Dynamics of Substrate Denaturation and Translocation by the Clpxp Degradation Machine. Molecular cell 5(4):639-648 (2000).

Kisselev, Alexei, et al., Why Does Threonine, and Not Serine, Function as the Active Site Nucleophile in Proteasomes?. The Journal of Biological Chemistry 275(20):14831-14837 (2000).

Klavius, G. M. et al., Low temperature incommensurately modulated and noncollinear spin structure in FeCr2S4. Journal of Physics: Condensed Matter 22(5):1-21 (2010).

Kowalczyk, Stefan W, et al., Detection of Local Protein Structures Along DNA Using Solid-state Nanopores. Nano Letters 10(1):324-328 (2010).

Krasilnikov, Oleg V, et al., Single Polymer Molecules in a Protein Nanopore in the Limit of a Strong Polymer-Pore Attraction. Physical Review Letters 97(1):018301, 1-4 (2006).

Kravats, Andrea, et al., Unfolding and translocation pathway of substrate protein controlled by structure in repetitive allosteric cycles of the ClpY ATPase. PNAS USA 108(6):2234-2239 (2011).

Krishnan R, Smrithi, et al., Autonomously Assembled Synthetic Transmembrane Peptide Pore. Journal of the American Chemical Society 141(7):2949-2959 (2019).

Krishnan Smrithi et al., Designed Alpha-helical Barrels for Charge-selective Peptide Translocation. Chemical Science 12(2):639-649 (2021).

Kristan, Katarina Crnigoj, et al., Molecular Mechanism of Pore Formation by Actinoporins. Toxicon 54(8):1125-34 (2009).

Kuehn et al., Proteasome activator PA28 and its interaction with 20 S proteasomes. Archives of biochemistry and biophysics 329(1):87-96 (1996).

Lamichhane, Usha, et al., Peptide translocation through the mesoscopic channel: binding kinetics at the single molecule level. Eur Biophys J 42(5):363-369 (2013).

Langklotz, Sina, et al., Structure and Function of the Bacterial AAA Protease FtsH. Biochim Biophys Acta 1823(1):40-48 (2012).

Laszlo, Andrew H. et al. Decoding long nanopore sequencing reads of natural DNA. Nature Biotechnology 32(8):829-834 (2014).

Lee, Irene et al., Functional Mechanics of the ATP-dependent Lon Protease—Lessons From Endogenous Protein and Synthetic Peptide Substrates. Biochimica Et Biophysica Acta 1784(5):727-35 (2008).

Li, Bisheng, et al., Black Phosphorus, a Rising Star 2D Nanomaterial in the Post-Graphene Era: Synthesis, Properties, Modifications, and Photocatalysis Applications. Small 15:1-30 (2019).

Li, et al., Detection of Peptides with Different Charges and Lengths by Using the Aerolysin Nanopore.4:1-5 (2018).

Li, Jianfeng, et al., A comparative study of point-to-point algorithms for matching spectra. Chemometrics and Intelligent Laboratory Systems 82(1-2): 50-58 (2006).

Li, Shuang et al. Detection of peptides with different charge and length by aerolysin nanopore. ChemElectroChem 6(1):126-129 (2018).

Lide, David R, et al., CRC Handbook of Chemistry and Physics, 84th edition. Journal of the American Chemical Society 126(5):1585-1588 (2003).

Liu, Huanting, et al., An Efficient One-step Site-directed Deletion, Insertion, Single and Multiple-site Plasmid Mutagenesis Protocol. BMC biotechnology 8:91 (2008).

Liu, Wenxing et al., Probing Protein Nanopores With Poly EthyleneGlycols. Proteomics. vol. 22, No. 5-6 (2022): 16 pages.

Liu, Xi, et al., High Expression of Nfat2 Contributes to Carboplatin Resistance in Lung Cancer. Experimental and Molecular Pathology 110:104290 (2019).

Lowe, Jan, et al., Crystal structure of the 20S Proteasome From the archaeon T. acidophilum at 3.4 A resolution. Science 268(5210):533-539 (1995).

Lucas, Florian Leonardus Rudolfus, et al., Protein identification by nanopore peptide profiling. Nature Communications 12(1):5795 (2021).

Lucas, Florian Leonardus Rudolfus, et al., The Manipulation of the Internal Hydrophobicity of FraC Nanopores Augments Peptide Capture and Recognition. ACS Nano 15(6):9600-9613 (2021).

Ma, Wenzhe, et al., Specificity of Trypsin and Chymotrypsin: Loop-motion-controlled Dynamic Correlation as a Determinantma. Biophysical journal 89 (2):1183-1193 (2005).

Macrander, Jason, et al., Evolution of the Cytolytic Pore-Forming Proteins (Actinoporins) in Sea Anemones. Toxins 8(12):1-16 (2016).

Maglia, Giovanni, et al., Analysis of Single Nucleic Acid Molecules With Protein Nanopores. Methods in Enzymology 475:591-623 (2010).

Maglia, Giovanni, et al., Enhanced translocation of single DNA molecules through alpha-hemolysin nanopores by manipulation of internal charge. PNAS USA 105(50):19720-19725 (2008).

Maillard, Rodrigo A, et al., ClpX(P) Generates Mechanical Force to Unfold and Translocate Its Protein Substrates. Cell 145(3):459-469 (2011).

Manning, Gerald S, The Persistence Length of DNA is Reached From the Persistence Length of Its Null Isomer Through an Internal Electrostatic Stretching Force. Biophysical Journal 91(10):3607-3616 (2006).

Manrao, Elizabeth A, et al., Nucleotide discrimination with DNA immobilized in the MspA nanopore. PLOS One 6(10):e25723 (pp. 1-7) (2011).

Manrao, Elizabeth, et al., Reading DNA at Single-nucleotide Resolution With a Mutant MspA Nanopore and phi29 DNA Polymerase. Nature Biotechnology 30(4):349-353 (2012).

(56)  References Cited

OTHER PUBLICATIONS

Martin, Andreas, et al., Pore Loops of the AAA+ ClpX Machine Grip Substrates to Drive Translocation and Unfolding. Nature Structural & Molecular Biology 15(11):1147-1151 (2008).

Martin, Andreas, et al., Rebuilt AAA + Motors Reveal Operating Principles for ATP-Fuelled Machines. Nature 437:1115-1120 (2005).

Martin, et al. Protein unfolding by a AAA+ protease is dependent on ATP-hydrolysis rates and substrate energy landscapes. Nature Structural & Molecular Biology. 15(2):139-145 (2008).

Mathe, Jerome et al. Nanopore unzipping of individual DNA hairpin molecules. Biophysical Journal 87(5):3205-3212 (2004).

Mechaly, Ariel E. et al., Structural Insights Into the Oligomerization and Architecture of Eukaryotic Membrane Pore-forming Toxins. Structure 19 (2):181-91 (2011).

Mesa-Galloso, Haydee et al.: Disrupting a key hydrophobic pair in the oligomerization interface of the actinoporins impairs their pore-forming activity. Protein Science 26:550-565 (2017). https://onlinelibrary.wiley.com/doi/full/10.1002/pro.3104.

Miethke, Marcus, et al., Involvement of Bacillus Subtilis ClpE in CtsR Degradation and Protein Quality Control. Journal of Bacteriology 188(13):4610-4619 (2006).

Miles, George, et al., Assembly of the Bi-component Leukocidin Pore Examined by Truncation Mutagenesis. The Journal of Biological Chemistry 281(4):2205-14 (2006).

Miles, George, et al., The Staphylococcal Leukocidin Bicomponent Toxin Forms Large Ionic Channels. Biochemistry 40(29):8514-8522 (2001).

Mishra, Ribhav, et al., Proteasome-mediated Proteostasis: Novel Medicinal and Pharmacological Strategies for Diseases. Medicinal Research Reviews 38(6):1916-1973 (2018).

Mitchell, Jonathan, et al., Sequence-Dependent Persistence Lengths of DNA. Journal of Chemical Theory and Computation 13(4):1539-1555 (2017).

Mohammad, Mohammad, et al., Controlling a single protein in a nanopore through electrostatic traps. 130(12):4081-4088 (2008).

Morante, Koldo, et al., A Pore-Forming Toxin Requires a Specific Residue for Its Activity in Membranes with Particular Physicochemical Properties. Journal of Biological Chemistry 290(17):10850-10861 (2015).

Morante, Koldo et al.: Functional characterization of Val60, a key residue involved in the membrane-oligomerization of fragaceatoxin C, an actinoporin from Actinia fragacea. FEBS Letters 589(15):1840-1846 (2015).

Motone, Keisuke et. al., Multi-pass, Single-molecule Nanopore Reading of Long Protein Strands With Single-amino Acid Sensitivity. bioRxiv : The Preprint Server for Biology (2023): 47 pages.

Motone; Keisuke et al.: Not if but when nanopore protein sequencing meets single-cell proteomics. Nature Methods 20:336-338 (2023).

Movileanu, Liviu, et al., Interactions of peptides with a protein pore. Biophysical Journal 89(2):1030-1045 (2005).

Movileanu, Liviu, et al., Interrogating single proteins through nanopores: challenges and opportunities. Trends in Biotechnology 27(6):333-341 (2009).

Muccio, Giovanni Di, et al., Geometrically Induced Selectivity and Unidirectional Electroosmosis in Uncharged Nanopores. ACS Nano 16(6):8716-8728 (2022).

Mullner, Daniel, et al., fastcluster: Fast Hierarchical, Agglomerative Clustering Routines for R and Python. Journal of Statistical Software 53(9): 1-18 (2013).

Niitsu: AI et al.: Membrane-spanning a-helical barrels as tractable protein-design targets. Phil. Trans. R. Soc. B 372:20160213 (2016).

Nivala, Jeff, et al., Discrimination Among Protein Variants Using an Unfoldase-coupled Nanopore. ACS Nano 8(12):12365-12375 (2014).

Nivala, Jeff, et al., Unfoldase-mediated Protein Translocation Through an α-hemolysin Nanopore. Nature Biotechnology 31(3):247-250 (2013).

Noakes, Matthew, et al., Increasing the Accuracy of Nanopore DNA Sequencing Using a Time-varying Cross Membrane Voltage. Nature Biotechnology 37(6):651-656 (2019).

Nouwen, Nico, et al., Charged Amino Acids in a Preprotein Inhibit SecA-dependent Protein Translocation. Journal of Molecular Biology 386(4):1000-1010 (2009).

Nuijens, Timo, et al., Engineering a Diverse Ligase Toolbox for Peptide Segment Condensation. Advanced Synthesis and catalysis 358(24):4041-4048 (2016).

Olivare, Adrian, et al., SMechanistic insights into bacterial AAA+ proteases and protein-remodelling machines. Nature reviews. Microbiology 14(1):33-44(2016).

Ortega, Joaquin, et al., Visualization of Substrate Binding and Translocation by the Atp-dependent Protease, ClpXp, Molecular cell 6(6):1515-1521 (2000).

Oukhaled, Abdel., et al., Transport of long neutral polymers in the semidilute regime through a protein nanopore. Phys Rev Lett 108(8):1-4 (2012).

Oukhaled, G, et al., Unfolding of Proteins and Long Transient Conformations Detected by Single Nanopore Recording. Physical review letters 98(15):158101 (2007).

Pastoriza-Gallego, Manuela, et al., Evidence of Unfolded Protein Translocation through a Protein Nanopore. ACS Nano 8(11):11350-11360 (2014).

Pavlenok, Mikhail, et al., Control of Subunit Stoichiometry in Single-chain MspA Nanopores. Biophysical Journal 121(5):742-754 (2022).

PCT/GB2024/052258 International Search Report and Written Opinion dated Jan. 23, 2025.

PCT/GB2024/052258 Invitation to Pay Additional Fees dated Nov. 27, 2024.

PCT/NL2017/050331 International Search Report and Written Opinion dated Sep. 5, 2017.

PCT/NL2019/050588 International Search Report and Written Opinion dated Dec. 17, 2019.

PCT/NL2019/050588 International Search Report dated Dec. 17, 2019.

PCT/NL2020/050726 International Search Report and Written Opinion dated Feb. 19. 2021.

PCT/NL2022/050266 International Search Report dated Nov. 28, 2022.

PCT/NL2023/050568 International Search Report dated Jan. 24, 2024.

PCT/NL2023/050570 International Search Report and Written Opinion dated Apr. 5, 2024.

Piguet, Fabien, et al., Identification of single amino acid differences in uniformly charged homopolymeric peptides with aerolysin nanopore. Nature communications 9(966):1-13 (2018).

Purnell, Robert F, et al., Discrimination of single base substitutions in a DNA strand immobilized in a biological nanopore. ACS Nano 3(9):2533-2538 (2009).

QIAO Dan et al., Synthetic Macrocycle Nanopore for Potassium-Selective Transmembrane Transport. Journal of the American Chemical Society 143(39):15975-15983 (2021).

Rincon-Restrepo, Marcela., et al., Controlled translocation of individual DNA molecules through protein nanopores with engineered molecular brakes. 11(2):746-750 (2011).

Ripstein, Zev, et al., Structure of a AAA+ unfoldase in the process of unfolding substrate. eLife 6:e25754 (2017).

Robertson, Joseph W F, et al., Nanopore Sensing: a Physical-chemical Approach. Biochimica Et Biophysica Acta. Biomembranes 1863(9):1-15 ( 2021).

Robertson, Joseph W F, et al., Single-molecule mass spectrometry in solution using a solitary nanopore. Proceedings of the National Academy of Sciences of the United States of America 104(20):8207-8211 (2007).

Robertson, Joseph W.F. et al. Nanopore sensing: A physical-chemical approach. Biochimica et Biophysica Acta (BBA)—Biomembranes 1863(9):183644 (2021).

Rodriguez-Vazquez, Nuria, et al., Membrane-targeted Self-assembling Cyclic Peptide Nanotubes. Current Topics in Medicinal Chemistry 14(23):2647-61 (2014).

Rojko, Nejc et al.: Pore Formation by Actinoporins, Cytolysins From Sea Anemones. Biochimica et Biophysica Acta 1858(3):446-456 (2016).

(56) References Cited

OTHER PUBLICATIONS

Rosen, Christian B., and Matthew B. Francis. Targeting the N terminus for site-selective protein modification. Nature chemical biology 13(7):697-705 (2017).

Rosen, Christian B, et al., Single-molecule Site-specific Detection of Protein Phosphorylation With a Nanopore. Nature Biotechnology 32(2):179-181 (2014).

Sauciuc Adina et al., An Engineered Electroosmotic Flow Transports Unravelled Proteins Across Nanopores. bioRxiv (2023).

Sauciuc, Adina et al., Translocation of Linearized Full-length Proteins Through an Engineered Nanopore Under Opposing Electrophoretic Force. Nature Biotechnology (2023): 63 pages.

Sauer, Rolf, et al., Preoperative Versus Postoperative Chemoradiotherapy for Rectal Cancer. The New England Journal of Medicine. 351(17):1731-1740 (2004).

Schmidt, Bernhard, Hydrophilic Polymers. Polymers (Basel) 11(4): 693 (2019).

Schon, Peter, et al., Equinatoxin II Permeabilizing Activity Depends on the Presence of Sphingomyelin and Lipid Phase Coexistence. Biophysical Journal 95(2):691-698 (2008).

Scott, Alistair, et al., Constructing Ion Channels From Water-soluble A-helical Barrels. Nature chemistry 13(7):643-650 (2021).

Seemüller, Erika, et al., Proteasome From Thermoplasma Acidophilum: A Threonine Protease. Science 268(5210):579-82 (1995).

Serek-Heuberger, Justyna, et al., Two Unique Membrane-bound Aaa Proteins From Sulfolobus Solfataricus. Biochemical Society Transactions 37(1):118-122 (2009).

Shimizu, Keisuke, et al., De Novo Design of a Nanopore for Single-molecule Detection That Incorporates a β-hairpin Peptide. Nature Nanotechnology 17(1):67-75 (2022).

Singh, Satyendra, et al., Functional Domains of the ClpA and ClpX Molecular Chaperones Identified by Limited Proteolysis and Deletion Analysis. The Journal of Biological Chemistry 276(31):29420-29429 (2001).

Soskine, Misha, et al., Single-molecule Analyte Recognition With Clya Nanopores Equipped With Internal Protein Adaptors. Journal of the American Chemical Society 137(17):5793-5797 (2015).

Soskine, Misha, et al., Tuning the size and properties of ClyA nanopores assisted by directed evolution. Journal of the American Chemical Society 135(36):13456-13463 (2013).

Spaan, Andras, et al., Leukocidins: staphylococcal bi-component pore-forming toxins find their receptors. Nature reviews. Microbiology 15(7):435-447 (2019).

Spruijt, Evan, et al., DNA scaffolds support stable and uniform peptide nanopores. Nature Nanotechnology 13:739-745 (2018).

Stadtmueller, Beth M et al.: Proteasome Activators. Molecular Cell 41:8-19 (2011).

Stefureac, Radu, et al., Nanopore Analysis of a Small 86-residue Protein. Small 4(1):59-63 (2008).

Stefureac, Radu, et al., Transport of Alpha-helical Peptides Through Alpha-hemolysin and Aerolysin Pores. Biochemistry 45(30):9172-9 (2006).

Stoddart, David., et al., DNA stretching and optimization of nucleobase recognition in enzymatic nanopore sequencing Nanotechnology 26(8):10-16 (2015).

Stoddart, David, et al., Functional Truncated Membrane Pores. Proceedings of the National Academy of Sciences of the United States of America 111(7):2425-2430 (2014).

Stoddart, David, et al., Multiple base-recognition sites in a biological nanopore: two heads are better than one. Angewandte Chemie International Edition English 49(3):556-559 (2010).

Stoddart, David, et al., Nucleobase recognition in ssDNA at the central constriction of the alpha-hemolysin pore. Nano Letters 10(9):3633-3637 (2010).

Stoddart, David, et al., Single-nucleotide discrimination in immobilized DNA oligonucleotides with a biological nanopore. Proceedings of the National Academy of Sciences of the United States of America 106(19):7702-7707 (2009).

Stranges, Benjamin, et al., Design and Characterization of a Nanopore-coupled Polymerase for Single-molecule Dna Sequencing by Synthesis on an Electrode Array. PNAS USA 113(44):E6749-E6756 (2016).

Stryer: Biochemistry 4th Ed. WH Freeman, New York. p. 18-23 (1995).

Sugiyama, Masaaki, et al., Spatial Arrangement and Functional Role of a Subunits of Proteasome Activator Pa28 in Hetero-oligomeric Form. Biochemical and biophysical research communications 432:141-145 (2013).

Talaga, David S, et al., Single-molecule Protein Unfolding in Solid State Nanopores. Journal of the American Chemical Society 131(26):9287-9297 (2009).

Tanaka, Koji, et al., Bidirectional Transformation of a Metamorphic Protein between the Water-Soluble and Transmembrane Native States. Biochemistry 54(46):6863-6866 (2015).

Tanaka, Koji et al.: Structural Basis for Self-assembly of a Cytolytic Pore Lined by Protein and Lipid. Nature Communications 6: 6337 (2015).

Thapa, Parashar, et al., Native chemical ligation: a boon to peptide chemistry. Molecules 19(9):14461-83 (2014).

Too, Priscilla Hiu-mei, et al., Slippery Substrates Impair Function of a Bacterial Protease ATPase by Unbalancing Translocation Versus Exit. The Journal of Biological Chemistry 288(19):13243-57 (2013).

Toplak, Ana, et al., Peptiligase an Enzyme for efficient Chemoenzymatic peptide Synthesis and Cyclization in Water. Advanced Synthesis and catalysis 358:2140-2147 (2016).

Tsutsui, Makusu, et al., Sparse Multi-nanopore Osmotic Power Generators. Cell Press Physical Science 3:1-12 (2022).

UniProt XP 002796191, Review, 2009.

U.S. Appl. No. 16/317,119 Office Action dated Apr. 28, 2021.

U.S. Appl. No. 17/269,771 Office Action dated Feb. 9, 2024.

U.S. Appl. No. 17/777,757 Office Action dated Jul. 16, 2025.

U.S. Appl. No. 18/394,833 Office Action dated Dec. 13, 2024.

U.S. Appl. No. 18/394,833 Office Action dated Jul. 16, 2025.

U.S. Appl. No. 18/394,833 Office Action dated Sep. 17, 2024.

U.S. Appl. No. 18/394,975 Office Action dated Apr. 18, 2024.

U.S. Appl. No. 18/394,975 Office Action dated Jul. 16, 2024.

Van Der Verren, Sander E, et al., A Dual-constriction Biological Nanopore Resolves Homonucleotide Sequences With High Fidelity. Nature biotechnology 38:1415-1420 (2020).

Vernier, et al. Solubilization and characterization of the anthrax toxin pore in detergent micelles. Protein Science 18:1882-1895 (2009).

Versloot, Roderick Corstiaan Abraham, et al., β-Barrel Nanopores with an Acidic-Aromatic Sensing Region Identify Proteinogenic Peptides at Low pH. ACS Nano 16(5):7258-7268 (2022).

Wallace et al.: Identification of epigenetic DNA modifications with a protein nanopore. Chemical Communications 46:8195-8197 (2010).

Wang, Jimin, et al., The structure of ClpP at 2.3 A resolution suggests a model for ATP-dependent proteolysis. Cell 91(4):447-456 (1997).

Wanunu, Meni, et al., DNA translocation governed by interactions with solid-state nanopores. Biophys J 95(10):4716-4725 (2008).

Wanunu, Meni., et al., Electrostatic focusing of unlabelled DNA into nanoscale pores using a salt gradient. Nat Nanotechnol 5(2):160-165 (2010).

Watanabe, Hirokazu, et al., Analysis of Pore Formation and Protein Translocation Using Large Biological Nanopores. Analytical Chemistry 89(21):11269-11277 (2017).

Weber, Daniel K. et al. Characterization of the Lipid-Binding Site of Equinatoxin II by NMR and Molecular Dynamics Simulation. Biophysical Journal 108(8):1987-1996 (2015).

Wei, Bryan, et al. Complex Shapes Self-assembled From Single-stranded DNA tiles. Nature vol. 485,7400: pp. 623-626 (2012).

Wendell, David, et al., Translocation of double-stranded DNA through membrane-adapted phi29 motor protein nanopores. Nature Nanotechnology 4(11):765-72 (2009).

Wilson, Jason S. et al.: Identification and structural analysis of the tripartite a-pore forming toxin of Aeromonas hydrophila. Nature Communications 10:2900 (2019).

(56) References Cited

OTHER PUBLICATIONS

Wloka , Carsten, et al., Alpha-Helical Fragaceatoxin C Nanopore Engineered for Double-Stranded and Single-Stranded Nucleic Acid Analysis. Angewandte Chemie 55(40):12494-12498 (2016).

Wong, C Ta, et al., Polymer Capture by Electro-osmotic Flow of Oppositely Charged Nanopores. The Journal of chemical physics 126(16):164903 (2007).

Xue, Liang, et al., Solid-state Nanopore Sensors. Nature Reviews Materials 21 Pages (2020).

Ye, Cheng, et al., Pandemic-scale Phylogenetics. bioRxiv : the preprint server for biology 1-16 (2021).

Ying, Yi-Lun, et al., Handling A Protein With a Nanopore Machine. Nature Chemistry 13:1160-1162 (2021).

Yu, Luning et al.: Unidirectional Single-File Transport of Full-Length Proteins Through a Nanopore. Nature Biotechnology 41:1130-1139 (2023).

Yusupov, Marat, et al., Crystal Structure of the Ribosome at 5.5 a Resolution. Science 292(5518):883-896 (2001).

Zhang, Shengli, et al., Bottom-up Fabrication of a Proteasome-nanopore That Unravels and Processes Single Proteins. Nature Chemistry 13(12):1192-1199 (2021).

Zhao, Qitao et al. Study of Peptide Transport through Engineered Protein Channels. J. Phys. Chem. Bio. 113(11):3572-3578 (2009).

Zhao, Yanan, et al., Single Molecule Spectroscopy of Amino Acids and Peptides by Recognition Tunneling. Nature Nanotechnology 9(6):466-473 (2014).

Zhao, Yingqi, et al., Label-Free Optical Analysis of Biomolecules in Solid-StateNanopores: Toward Single-Molecule Protein Sequencing. ACS Photonics 9:730-742 (2022).

Ziemski, Michal, et al., Cdc48-Like Protein of Actinobacteria (Cpa) is a Novel Proteasome Interactor in Mycobacteria and Related Organisms. Elife 29(7):e34055 (2018).

\* cited by examiner

C)

B)

A)

Replacement Sheet

27/30

SEQUENCE LISTING

Sequence total quantity: 58
SEQ ID NO: 1          moltype = AA  length = 15
FEATURE               Location/Qualifiers
source                1..15
                      mol_type = protein
                      organism = synthetic construct
SEQUENCE: 1
GGGGSGGGGS GGGGS                                          15

SEQ ID NO: 2          moltype = AA  length = 5

-continued

```
FEATURE               Location/Qualifiers
source                1..5
                      mol_type = protein
                      organism = synthetic construct
SEQUENCE: 2
GGGGS                                                                  5

SEQ ID NO: 3          moltype = AA   length = 8
FEATURE               Location/Qualifiers
source                1..8
                      mol_type = protein
                      organism = synthetic construct
SEQUENCE: 3
GGGGGGGG                                                               8

SEQ ID NO: 4          moltype = AA   length = 6
FEATURE               Location/Qualifiers
source                1..6
                      mol_type = protein
                      organism = synthetic construct
SEQUENCE: 4
GGGGGG                                                                 6

SEQ ID NO: 5          moltype = AA   length = 15
FEATURE               Location/Qualifiers
source                1..15
                      mol_type = protein
                      organism = synthetic construct
SEQUENCE: 5
EAAAKEAAAK EAAAK                                                       15

SEQ ID NO: 6          moltype = AA   length = 5
FEATURE               Location/Qualifiers
source                1..5
                      mol_type = protein
                      organism = synthetic construct
SEQUENCE: 6
EAAAK                                                                  5

SEQ ID NO: 7          moltype = AA   length = 17
FEATURE               Location/Qualifiers
source                1..17
                      mol_type = protein
                      organism = synthetic construct
SEQUENCE: 7
VSQTSKLTRA ETVFPDV                                                    17

SEQ ID NO: 8          moltype = AA   length = 6
FEATURE               Location/Qualifiers
source                1..6
                      mol_type = protein
                      organism = synthetic construct
SEQUENCE: 8
PLGLWA                                                                 6

SEQ ID NO: 9          moltype = AA   length = 6
FEATURE               Location/Qualifiers
source                1..6
                      mol_type = protein
                      organism = synthetic construct
SEQUENCE: 9
RVLAEA                                                                 6

SEQ ID NO: 10         moltype = AA   length = 10
FEATURE               Location/Qualifiers
source                1..10
                      mol_type = protein
                      organism = synthetic construct
SEQUENCE: 10
EDVVCCSNSY                                                            10

SEQ ID NO: 11         moltype = AA   length = 8
FEATURE               Location/Qualifiers
source                1..8
                      mol_type = protein
                      organism = synthetic construct
SEQUENCE: 11
GGIEGRGS                                                               8
```

-continued

```
SEQ ID NO: 12              moltype = AA   length = 10
FEATURE                    Location/Qualifiers
source                     1..10
                           mol_type = protein
                           organism = synthetic construct
SEQUENCE: 12
TRHRQPRGWE                                                        10

SEQ ID NO: 13              moltype = AA   length = 10
FEATURE                    Location/Qualifiers
source                     1..10
                           mol_type = protein
                           organism = synthetic construct
SEQUENCE: 13
AGNRVRRSVG                                                        10

SEQ ID NO: 14              moltype = AA   length = 9
FEATURE                    Location/Qualifiers
source                     1..9
                           mol_type = protein
                           organism = synthetic construct
SEQUENCE: 14
RRRRRRRRR                                                        9

SEQ ID NO: 15              moltype = AA   length = 4
FEATURE                    Location/Qualifiers
source                     1..4
                           mol_type = protein
                           organism = synthetic construct
SEQUENCE: 15
GFLG                                                             4

SEQ ID NO: 16              moltype = AA   length = 46
FEATURE                    Location/Qualifiers
source                     1..46
                           mol_type = protein
                           organism = synthetic construct
SEQUENCE: 16
AEAAAKEAAA KEAAAKEAAA KALEAEAAAK EAAAKEAAAK EAAAKA             46

SEQ ID NO: 17              moltype = AA   length = 5
FEATURE                    Location/Qualifiers
source                     1..5
                           mol_type = protein
                           organism = synthetic construct
SEQUENCE: 17
PAPAP                                                            5

SEQ ID NO: 18              moltype = AA   length = 12
FEATURE                    Location/Qualifiers
source                     1..12
                           mol_type = protein
                           organism = synthetic construct
SEQUENCE: 18
AEAAAKEAAA KA                                                    12

SEQ ID NO: 19              moltype = AA   length = 11
FEATURE                    Location/Qualifiers
source                     1..11
                           mol_type = protein
                           organism = synthetic construct
SEQUENCE: 19
AANDENYALA A                                                    11

SEQ ID NO: 20              moltype = AA   length = 64
FEATURE                    Location/Qualifiers
source                     1..64
                           mol_type = protein
                           organism = synthetic construct
SEQUENCE: 20
MAQEQTKRGG GGGDDDDIAG STAAGQERRE KLTEETDDLL DEIDDVLEEN AEDFVRAYVQ 60
KGGQ                                                             64

SEQ ID NO: 21              moltype = AA   length = 21
FEATURE                    Location/Qualifiers
source                     1..21
                           mol_type = protein
                           organism = synthetic construct
SEQUENCE: 21
```

```
SASSHATRQL SGLKIHSNLY H                                                   21

SEQ ID NO: 22              moltype = AA  length = 56
FEATURE                    Location/Qualifiers
source                     1..56
                           mol_type = protein
                           organism = synthetic construct
SEQUENCE: 22
AKSKGKQRGV KQKIHHFHEP MLHNSSEEQV KVEDAFNQRT STDSRLQSTG TAPRKK           56

SEQ ID NO: 23              moltype = AA  length = 267
FEATURE                    Location/Qualifiers
source                     1..267
                           mol_type = protein
                           organism = synthetic construct
SEQUENCE: 23
SEVFQECVNL FIKRDIKDCL EKMSEVGFID ITVFKSNPMI LDLFVSACDI MPSFTKLGLT        60
LQSEILNIFT LDTPQCIETR KIILGDLSKL LVINKFFRCC IKVIQFNLTD HTEQEEKTLE       120
LESIMSDFIF VYITKMRTTI DVVGLQELIE IFIFQVKVKL HHKKPSPNMY WALCKTLPKL       180
SPTLKGLYLS KDVSIEDAIL NSIDNKIQKD KAKSKGKQRG VKQKIHHFHE PMLHNSSEEQ       240
VKVEDAFNQR TSTDSRLQST GTAPRKK                                           267

SEQ ID NO: 24              moltype = AA  length = 309
FEATURE                    Location/Qualifiers
source                     1..309
                           mol_type = protein
                           organism = synthetic construct
SEQUENCE: 24
MAASEIMNNL PMHSLDSSLR DLLNDDLFIE SDESTKSVND QRSEVFQECV NLFIKRDIKD        60
CLEKMSEVGF IDITVFKSNP MILDLFVSAC DIMPSFTKLG LTLQSEILNI FTLDTPQCIE       120
TRKIILGDLS KLLVINKFFR CCIKVIQFNL TDHTEQEEKT LELESIMSDF IFVYITKMRT       180
TIDVVGLQEL IEIFIFQVKV KLHHKKPSPN MYWALCKTLP KLSPTLKGLY LSKDVSIEDA       240
ILNSIDNKIQ KDKAKSKGKQ RGVKQKIHHF HEPMLHNSSE EQVKVEDAFN QRTSTDSRLQ       300
STGTAPRKK                                                               309

SEQ ID NO: 25              moltype = AA  length = 250
FEATURE                    Location/Qualifiers
source                     1..250
                           mol_type = protein
                           organism = synthetic construct
SEQUENCE: 25
MGHHHHHHSS ASKGEELFTG VVPILVELDG DVNGHKFSVS GEGEGDATYG KLTLKFICTT        60
GKLPVPWPTL VTTFSYGVQC FSRYPDHMKR HDFFKSAMPE GYVQERTIFF KDDGNYKTRA       120
EVKFEGDTLV NRIELKGIDF KEDGNILGHK LEYNYNSHNV YIMADKQKNG IKVNFKIRHN       180
IEDGSVQLAD HYQQNTPIGD GPVLLPDNHY LSTQSALSKD PNEKRDHMVL LEFVTAAGIA       240
ANDENYALAA                                                             250

SEQ ID NO: 26              moltype = AA  length = 278
FEATURE                    Location/Qualifiers
source                     1..278
                           mol_type = protein
                           organism = synthetic construct
SEQUENCE: 26
MGHHHHHHSS ASKGEELFTG VVPILVELDG DVNGHKFSVS GEGEGDATYG KLTLKFICTT        60
GKLPVPWPTL VTTFSYGVQC FSRYPDHMKR HDFFKSAMPE GYVQERTIFF KDDGNYKTRA       120
EVKFEGDTLV NRIELKGIDF KEDGNILGHK LEYNYNSHNV YIMADKQKNG IKVNFKIRHN       180
IEDGSVQLAD HYQQNTPIGD GPVLLPDNHY LSTQSALSKD PNEKRDHMVL LEFVTAAGIG       240
GGGGGGGGGG GSRRRRRRRR RRRRRRRAAN DENYALAA                               278

SEQ ID NO: 27              moltype = AA  length = 255
FEATURE                    Location/Qualifiers
source                     1..255
                           mol_type = protein
                           organism = synthetic construct
SEQUENCE: 27
MGHHHHHHSS ASKGEELFTG VVPILVELDG DVNGHKFSVS GEGEGDATYG KLTLKFICTT        60
GKLPVPWPTL VTTFSYGVQC FSRYPDHMKR HDFFKSAMPE GYVQERTIFF KDDGNYKTRA       120
EVKFEGDTLV NRIELKGIDF KEDGNILGHK LEYNYNSHNV YIMADKQKNG IKVNFKIRHN       180
IEDGSVQLAD HYQQNTPIGD GPVLLPDNHY LSTQSALSKD PNEKRDHMVL LEFVTAAGIR       240
RRRRAANDEN YALAA                                                        255

SEQ ID NO: 28              moltype = AA  length = 262
FEATURE                    Location/Qualifiers
source                     1..262
                           mol_type = protein
                           organism = synthetic construct
SEQUENCE: 28
MGHHHHHHSS ASKGEELFTG VVPILVELDG DVNGHKFSVS GEGEGDATYG KLTLKFICTT        60
GKLPVPWPTL VTTFSYGVQC FSRYPDHMKR HDFFKSAMPE GYVQERTIFF KDDGNYKTRA       120
```

-continued

```
EVKFEGDTLV NRIELKGIDF KEDGNILGHK LEYNYNSHNV YIMADKQKNG IKVNFKIRHN    180
IEDGSVQLAD HYQQNTPIGD GPVLLPDNHY LSTQSALSKD PNEKRDHMVL LEFVTAAGIG    240
EGDGEGDGEG DAANDENYAL AA                                            262

SEQ ID NO: 29              moltype = AA   length = 422
FEATURE                    Location/Qualifiers
source                     1..422
                           mol_type = protein
                           organism = synthetic construct
SEQUENCE: 29
MHHHHHHSSP WKIEEGKLVI WINGDKGYNG LAEVGKKFEK DTGIKVTVEH PDKLEEKFPQ    60
VAATGDGPDI IFWAHDRFGG YAQSGLLAEI TPDKAFQDKL YPFTWDAVRY NGKLIAYPIA    120
VEALSLIYNK DLLPNPPKTW EEIPALDKEL KAKGKSALMF NLQEPYFTWP LIAADGGYAF    180
KYENGKYDIK DVGVDNAGAK AGLTFLVDLI KNKHMNADTD YSIAEAAFNK GETAMTINGP    240
WAWSNIDTSK VNYGVTVLPT FKGQPSKPFV GVLSAGINAA SPNKELAKEF LENYLLTDEG    300
LEAVNKDKPL GAVALKSYEE ELAKDPRIAA TMENAQKGEI MPNIPQMSAF WYAVRTAVIN    360
AASGRQTVDE ALKDAQTRIT KHMGGGGGGG GGGGGSRRRR RRRRRRRRRR RAANDENYAL    420
AA                                                                  422

SEQ ID NO: 30              moltype = AA   length = 419
FEATURE                    Location/Qualifiers
source                     1..419
                           mol_type = protein
                           organism = synthetic construct
SEQUENCE: 30
MHHHHHHSSP WGAPKIEEGK LVIWINGDKG YNGLAEVGKK FEKDTGIKVT VEHPDKLEEK    60
FPQVAATGDG PDIIFWAHDR FGGYAQSGLL AEITPDKAFQ DKLYPFTWDA VRYNGKLIAY    120
PIAVEALSLI YNKDLLPNPP KTWEEIPALD KELKAKGKSA LMFNLQEPYF TWPLIAADGG    180
YAFKYENGKY DIKDVGVDNA GAKAGLTFLV DLIKNKHMNA DTDYSIAEAA FNKGETAMTI    240
NGPWAWSNID TSKVNYGVTV LPTFKGQPSK PFVGVLSAGI NAASPNKELA KEFLENYLLT    300
DEGLEAVNKD KPLGAVALKS YEEELAKDPR IAATMENAQK GEIMPNIPQM SAFWYAVRTA    360
VINAASGRQT VDEALKDAQT RITKHMGGGG GGSRRRRRRR RRRRRRRRAA NDENYALAA     419

SEQ ID NO: 31              moltype = AA   length = 420
FEATURE                    Location/Qualifiers
source                     1..420
                           mol_type = protein
                           organism = synthetic construct
SEQUENCE: 31
MHHHHHHSSP WGAPKIEEGK LVIWINGDKG YNGLAEVGKK FEKDTGIKVT VEHPDKLEEK    60
FPQVAATGDG PDIIFWAHDR FGGYAQSGLL AEITPDKAFQ DKLYPFTWDA VRYNGKLIAY    120
PIAVEALSLI YNKDLLPNPP KTWEEIPALD KELKAKGKSA LMFNLQEPYF TWPLIAADGG    180
YAFKYENGKY DIKDVGVDNA GAKAGLTFLV DLIKNKHMNA DTDYSIAEAA FNKGETAMTI    240
NGPWAWSNID TSKVNYGVTV LPTFKGQPSK PFVGVLSAGI NAASPNKELA KEFLENYLLT    300
DEGLEAVNKD KPLGAVALKS YEEELAKDPR IAATMENAQK GEIMPNIPQM SAFWYAVRTA    360
VINAASGRQT VDEALKDAQT RITKHMGGGG GGGGGGGGGS DDDDDDDDDD AANDENYALA    420

SEQ ID NO: 32              moltype = AA   length = 6
FEATURE                    Location/Qualifiers
source                     1..6
                           mol_type = protein
                           organism = synthetic construct
SEQUENCE: 32
HHHHHH                                                              6

SEQ ID NO: 33              moltype = AA   length = 310
FEATURE                    Location/Qualifiers
source                     1..310
                           mol_type = protein
                           organism = synthetic construct
SEQUENCE: 33
MADSDINIKT GTTDIGSNTT VKTGDLVTYD KENGMHKKVF YSFIDDKNHN KKLLVIRTKG    60
TIAGQYRVYS EEGANKSGLA WPSAFKVQLQ LPDNEVAQIS DYYPRNSIDT KEYMSTLTYG    120
FNGNVTGDDT GKIGGLIGAN VSIGHTLKYV QPDFKTILES PTDKKVGWKV IFNNMVNQNW    180
GPYDRDSWNP VYGNQLFMKT RNGSMKAADN FLDPNKASSL LSSGFSPDFA TVITMDRKAS    240
KQQTNIDVIY ERVRDDYQLH WTSTNWKGTN TKDKWTDRSS ERYKIDWEKE EMTNRGSGSS    300
GGSSHHHHHH                                                          310

SEQ ID NO: 34              moltype = AA   length = 316
FEATURE                    Location/Qualifiers
source                     1..316
                           mol_type = protein
                           organism = synthetic construct
SEQUENCE: 34
MAQTTSQVVT DIGQNAKTHT SYNTFNNEQA DNMTMSLKVT FIDDPSADKQ IAVINTTGSF    60
MKANPTLSDA PVDGYPIPGA SVTLRYPSQY DIAMNLQDNT SRFFHVAPTN AVEETTVTSS    120
VSYQLGGSIK ASVTPSGPSG ESGATGQVTW SDSVSYKQTS YKTNLIDQTN KHVKWNVFFN    180
GYNNQNWGIY TRDSYHALYG NQLFMYSRTY PHETDARGNL VPMNDLPTLT NSGFSPGMIA    240
VVISEKDTEQ SSIQVAYTKH ADDYTLRPGF TFGTGNWVGN NIKDVDQKTF NKSFVLDWKN    300
```

-continued

```
KKLVEKKGSA HHHHHH                                                          316

SEQ ID NO: 35            moltype = AA   length = 316
FEATURE                  Location/Qualifiers
source                   1..316
                         mol_type = protein
                         organism = synthetic construct
SEQUENCE: 35
MAQTTSQVVT DIGQNAKTHT SYNTFNNEQA DNMTMSLKVT FIDDPSADKQ IAVINTTGSF          60
MKANPTLSDA PVDGYPIPGA SVTLRYPSQY DIAMNLQDNT SRFFHVAPTN AVEETTVTSS          120
VDYDLGGSID ASVTPSGPSG ESGATGQVTW SDSVSYDQTS YKTNLIDQTN KHVKWNVFFN          180
GYNNQNWGIY TRDSYHALYG NQLFMYSRTY PHETDARGNL VPMNDLPTLT NSGFSPGMIA          240
VVISEKDTEQ SSIQVAYTKH ADDYTLRPGF TFGTGNWVGN NIKDVDQKTF NKSFVLDWKN          300
KKLVEKKGSA HHHHHH                                                          316

SEQ ID NO: 36            moltype = AA   length = 316
FEATURE                  Location/Qualifiers
source                   1..316
                         mol_type = protein
                         organism = synthetic construct
SEQUENCE: 36
MAQTTSQVVT DIGQNAKTHT SYNTFNNEQA DNMTMSLKVT FIDDPSADKQ IAVINTTGSF          60
MKANPTLSDA PVDGYPIPGA SVTLRYPSQY DIAMNLQDNT SRFFHVAPTN AVEETTVTSS          120
VDYQLGGSID ASVTPSGPSG ESGATGQVDW SDSVSYDQTS YKTNLIDQTN KHVKWNVFFN          180
GYNNQNWGIY TRDSYHALYG NQLFMYSRTY PHETDARGNL VPMNDLPTLT NSGFSPGMIA          240
VVISEKDTEQ SSIQVAYTKH ADDYTLRPGF TFGTGNWVGN NIKDVDQKTF NKSFVLDWKN          300
KKLVEKKGSA HHHHHH                                                          316

SEQ ID NO: 37            moltype = AA   length = 316
FEATURE                  Location/Qualifiers
source                   1..316
                         mol_type = protein
                         organism = synthetic construct
SEQUENCE: 37
MAQTTSQVVT DIGQNAKTHT SYNTFNNEQA DNMTMSLKVT FIDDPSADKQ IAVINTTGSF          60
MKANPTLSDA PVDGYPIPGA SVTLRYPSQY DIAMNLQDNT SRFFHVAPTN AVEETTVTSS          120
VDYQLGGSID ASVTPSGPSG ESGATGQVTW SDDVSYDQTS YKTNLIDQTN KHVKWNVFFN          180
GYNNQNWGIY TRDSYHALYG NQLFMYSRTY PHETDARGNL VPMNDLPTLT NSGFSPGMIA          240
VVISEKDTEQ SSIQVAYTKH ADDYTLRPGF TFGTGNWVGN NIKDVDQKTF NKSFVLDWKN          300
KKLVEKKGSA HHHHHH                                                          316

SEQ ID NO: 38            moltype = AA   length = 316
FEATURE                  Location/Qualifiers
source                   1..316
                         mol_type = protein
                         organism = synthetic construct
SEQUENCE: 38
MAQTTSQVVT DIGQNAKTHT SYNTFNNEQA DNMTMSLKVT FIDDPSADKQ IAVINTTGSF          60
MKANPTLSDA PVDGYPIPGA SVTLRYPSQY DIAMNLQDNT SRFFHVAPTN AVEETTVTSS          120
VDYDLGGSIF ASVTPSGPSG ESGATGQVTW SDSVSYKQTS YKTNLIDQTN KHVKWNVFFN          180
GYNNQNWGIY TRDSYHALYG NQLFMYSRTY PHETDARGNL VPMNDLPTLT NSGFSPGMIA          240
VVISEKDTEQ SSIQVAYTKH ADDYTLRPGF TFGTGNWVGN NIKDVDQKTF NKSFVLDWKN          300
KKLVEKKGSA HHHHHH                                                          316

SEQ ID NO: 39            moltype = AA   length = 316
FEATURE                  Location/Qualifiers
source                   1..316
                         mol_type = protein
                         organism = synthetic construct
SEQUENCE: 39
MAQTTSQVVT DIGQNAKTHT SYNTFNNEQA DNMTMSLKVT FIDDPSADKQ IAVINTTGSF          60
MKANPTLSDA PVDGYPIPGA SVTLRYPSQY DIAMNLQDNT SRFFHVAPTN AVEETTVTSS          120
VDYDLGGSIF ASVTPSGPSG ESGATGQVTW SDSVSYDQTS YKTNLIDQTN KHVKWNVFFN          180
GYNNQNWGIY TRDSYHALYG NQLFMYSRTY PHETDARGNL VPMNDLPTLT NSGFSPGMIA          240
VVISEKDTEQ SSIQVAYTKH ADDYTLRPGF TFGTGNWVGN NIKDVDQKTF NKSFVLDWKN          300
KKLVEKKGSA HHHHHH                                                          316

SEQ ID NO: 40            moltype = AA   length = 15
FEATURE                  Location/Qualifiers
source                   1..15
                         mol_type = protein
                         organism = synthetic construct
SEQUENCE: 40
RRRRRRRRRR RRRRR                                                           15

SEQ ID NO: 41            moltype = AA   length = 12
FEATURE                  Location/Qualifiers
source                   1..12
                         mol_type = protein
```

-continued

```
                        organism = synthetic construct
SEQUENCE: 41
GGGGGGGGGG GG                                                                    12

SEQ ID NO: 42            moltype = AA   length = 425
FEATURE                  Location/Qualifiers
source                   1..425
                         mol_type = protein
                         organism = synthetic construct
SEQUENCE: 42
MHHHHHHSSP WGAPKIEEGK LVIWINGDKG YNGLAEVGKK FEKDTGIKVT VEHPDKLEEK   60
FPQVAATGDG PDIIFWAHDR FGGYAQSGLL AEITPDKAFQ DKLYPFTWDA VRYNGKLIAY   120
PIAVEALSLI YNKDLLPNPP KTWEEIPALD KELKAKGKSA LMFNLQEPYF TWPLIAADGG   180
YAFKYENGKY DIKDVGVDNA GAKAGLTFLV DLIKNKHMNA DTDYSIAEAA FNKGETAMTI   240
NGPWAWSNID TSKVNYGVTV LPTFKGQPSK PFVGVLSAGI NAASPNKELA KEFLENYLLT   300
DEGLEAVNKD KPLGAVALKS YEEELAKDPR IAATMENAQK GEIMPNIPQM SAFWYAVRTA   360
VINAASGRQT VDEALKDAQT RITKHMGGGG GGGGGGGGSR RRRRRRRRRR RRRRAANDEN   420
YALAA                                                             425

SEQ ID NO: 43            moltype = AA   length = 766
FEATURE                  Location/Qualifiers
source                   1..766
                         mol_type = protein
                         organism = synthetic construct
SEQUENCE: 43
MHHHHHHSSG EDIKVAVVGA MSGPVAQYGD QEFTGAEQAV ADINAKGGIK GNKLQIVKYD   60
DACDPKQAVA VANKVVNDGI KYVIGHLCSS STQPASDIYE DEGILMITPA ATAPELTARG   120
YQLILRTTGL DSDQGPTAAK YILEKVKPQR IAIVHDKQQY GEGLARAVQD GLKKGNANVV   180
FFDGITAGEK DFSTLVARLK KENIDFVYYG GYHPEMGQIL RQARAAGLKT QFMGPEGVAN   240
VSLSNIAGES AEGLLVTKPK NYDQVPANKP IVDAIKAKKQ DPSGAFVWTT YAALQSLQAG   300
LNQSDDPAEI AKYLKANSVD TVMGPLTWDE KGDLKGFEFG VFDWHANGTA TDAKVKIEEG   360
KLVIWINGDK GYNGLAEVGK KFEKDTGIKV TVEHPDKLEE KFPQVAATGD GPDIIFWAHD   420
RFGGYAQSGL LAEITPDKAF QDKLYPFTWD AVRYNGKLIA YPIAVEALSL IYNKDLLPNP   480
PKTWEEIPAL DKELKAKGKS ALMFNLQEPY FTWPLIAADG GYAFKYENGK YDIKDVGVDN   540
AGAKAGLTFL VDLIKNKHMN ADTDYSIAEA AFNKGETAMT INGPWAWSNI DTSKVNYGVT   600
VLPTFKGQPS KPFVGVLSAG INAASPNKEL AKEFLENYLL TDEGLEAVNK DKPLGAVALK   660
SYEEELAKDP RIAATMENAQ KGEIMPNIPQ MSAFWYAVRT AVINAASGRQ TVDEALKDAQ   720
TRITKHMGGG GGGGGGGGGS RRRRRRRRRR RRRRAANDE NYALAA                   766

SEQ ID NO: 44            moltype = AA   length = 764
FEATURE                  Location/Qualifiers
source                   1..764
                         mol_type = protein
                         organism = synthetic construct
SEQUENCE: 44
MHHHHHHSSG EKKSLHIYNW TDYIAPTTLK DFTKESGIDV SYDVFDSNET LEGKLVSGHS   60
GYDIVVPSNN FLGKQIQAGA FQKLDKSKLP NWKNLDPALL KQLEVSDPGN QYAVPYLWGT   120
NGIGYNVAKV KEVLGDQPID SWAILFEPEN MKKLAKCGVA FMDSGDEMLP AALNYLGLDP   180
NTHDPKDYKK AEEVLTKVRP YVSYFHSSKY ISDLANGNIC VAFGYSGDVF QAAARAEEAG   240
KGIDIQYVIP KEGANLWFDL MAIPADAKAA DNAYAFIDYL LRPEVIAKVS DYVGYANAIP   300
GARPLMDKSV SDSEEVYPPQ AVLDKLYVSA VLPAKVLRLQ TRTWTRIKTG KLEKIEEGKL   360
VIWINGDKGY NGLAEVGKKF EKDTGIKVTV EHPDKLEEKF PQVAATGDGP DIIFWAHDRF   420
GGYAQSGLLA EITPDKAFQD KLYPFTWDAV RYNGKLIAYP IAVEALSLIY NKDLLPNPPK   480
TWEEIPALDK ELKAKGKSAL MFNLQEPYFT WPLIAADGGY AFKYENGKYD IKDVGVDNAG   540
AKAGLTFLVD LIKNKHMNAD TDYSIAEAAF NKGETAMTIN GPWAWSNIDT SKVNYGVTVL   600
PTFKGQPSKP FVGVLSAGIN AASPNKELAK EFLENYLLTD EGLEAVNKDK PLGAVALKSY   660
EEELAKDPRI AATMENAQKG EIMPNIPQMS AFWYAVRTAV INAASGRQTV DEALKDAQTR   720
ITKHMGGGGG GGGGGGSRR RRRRRRRRR RRRAANDENY ALAA                     764

SEQ ID NO: 45            moltype = AA   length = 731
FEATURE                  Location/Qualifiers
source                   1..731
                         mol_type = protein
                         organism = synthetic construct
SEQUENCE: 45
MHHHHHHSSG ADTRIGVTIY KYDDNFMSVV RKAIEQDAKA APDVQLLMND SQNDQSKQND   60
QIDVLLAKGV KALAINLVDP AAAGTVIEKA RGQNVPVVFF NKEPSRKALD SYDKAYYVGT   120
DSKESGIIQG DLIAKHWAAN QGWDLNKDGQ IQFVLLKGEP GHPDAEARTT YVIKELNDKG   180
IKTEQLQLDT AMWDTAQAKD KMDAWLSGPN ANKIEVVIAN NDAMAMGAVE ALKAHNKSSI   240
PVFGVDALPE ALALVKSGAL AGTVLNDANN QAKATFDLAK NLADGKGAAD GTNWKIDNKV   300
VRVPYVGVDK DNLAEFSKKG KIEEGKLVIW INGDKGYNGL AEVGKKFEKD TGIKVTVEHP   360
DKLEEKFPQV AATGDGPDII FWAHDRFGGY AQSGLLAEIT PDKAFQDKLY PFTWDAVRYN   420
GKLIAYPIAV EALSLIYNKD LLPNPPKTWE EIPALDKELK AKGKSALMFN LQEPYFTWPL   480
IAADGGYAFK YENGKYDIKD VGVDNAGAKA GLTFLVDLIK NKHMNADTDY SIAEAAFNKG   540
ETAMTINGPW AWSNIDTSKV NYGVTVLPTF KGQPSKPFVG VLSAGINAAS PNKELAKEFL   600
ENYLLTDEGL EAVNKDKPLG AVALKSYEEE LAKDPRIAAT MENAQKGEIM PNIPQMSAFW   660
YAVRTAVINA ASGRQTVDEA LKDAQTRITK HMGGGGGGGG GGGSRRRRRR RRRRRRRRRR   720
AANDENYALA A                                                      731
```

```
SEQ ID NO: 46            moltype = AA   length = 804
FEATURE                  Location/Qualifiers
source                   1..804
                         mol_type = protein
                         organism = synthetic construct
SEQUENCE: 46
MGSSHHHHHH SSGLVPRGSH NKIEEGKLVI WINGDKGYNG LAEVGKKFEE DTGIKVTVEH   60
PDKLEEKFPQ VAATGDGPDI IFWAHDRFGG YAQSGLLAEI TPDKAFQDKL YPFTWDAVRY  120
NGKLIAYPIA VEALSLIYNK DLLPNPPKTW EEIPALDKEL KAKGKSALMF NLQEPYFTWP  180
LIAADGGYAF KYENGKYDIK DVGVDNAGAK AGLTFLVDLI KNKHMNADTD YSIAEAAFNK  240
GETAMTINGP WAWSNIDTSK VNYGVTVLPT FKGQPSKPFV GVLSAGINAA SPNKELAKEF  300
LENYLLTDEG LEAVNKDKPL GAVALKSYEE ELAKDPRIAA TMENAQKGEI MPNIPQMSAF  360
WYAVRTAVIN AASGRQTVDE ALKDAQTRIT KGAPKIEEGK LVIWINGDKG YNGLAEVGKK  420
FEKDTGIKVT VEHPDKLEEK FPQVAATGDG PDIIFWAHDR FGGYAQSGLL AEITPDKAFQ  480
DKLYPFTWDA VRYNGKLIAY PIAVEALSLI YNKDLLPNPP KTWEEIPALD KELKAKGKSA  540
LMFNLQEPYF TWPLIAADGG YAFKYENGKY DIKDVGVDNA GAKAGLTFLV DLIKNKHMNA  600
DTDYSIAEAA FNKGETAMTI NGPWAWSNID TSKVNYGVTV LPTFKGQPSK PFVGVLSAGI  660
NAASPNKELA KEFLENYLLT DEGLEAVNKD KPLGAVALKS YEEELAKDPR IAATMENAQK  720
GEIMPNIPQM SAFWYAVRTA VINAASGRQT VDEALKDAQT RITKHMGGGG GGGGGGGGSR  780
RRRRRRRRRR RRRRAANDEN YALA                                        804

SEQ ID NO: 47            moltype = AA   length = 273
FEATURE                  Location/Qualifiers
source                   1..273
                         mol_type = protein
                         organism = synthetic construct
SEQUENCE: 47
MGHHHHHHSS ASKGEELFTG VVPILVELDG DVNGHKFSVS GEGEGDATYG KLTLKFICTT   60
GKLPVPWPTL VTTFSYGVQC FSRYPDHMKR HDFFKSAMPE GYVQERTIFF KDDGNYKTRA  120
EVKFEGDTLV NRIELKGIDF KEDGNILGHK LEYNYNSHNV YIMADKQKNG IKVNFKIRHN  180
IEDGSVQLAD HYQQNTPIGD GPVLLPDNHY LSTQSALSKD PNEKRDHMVL LEFVTAAGIG  240
GGGGGGGGGG GSRRRRRRRR RRAANDENYA LAA                              273

SEQ ID NO: 48            moltype = AA   length = 278
FEATURE                  Location/Qualifiers
source                   1..278
                         mol_type = protein
                         organism = synthetic construct
SEQUENCE: 48
MKHHHHHHGV SKGEEDNMAS LPATHELHIF GSINGVDFDM VGQGTGNPND GYEELNLKST   60
KGDLQFSPWI LVPHIGYGFH QYLPYPDGMS PFQAAMVDGS GYQVHRTMQF EDGASLTVNY  120
RYTYEGSHIK GEAQVKGTGF PADGPVMTNS LTAADWCRSK KTYPNDKTII STFKWSYTTG  180
NGKRYRSTAR TTYTFAKPMA ANYLKNQPMY VFRKTELKHS KTELNFKEWQ KAFTDVMGMD  240
ELYKGGSGSG DYMERWYRYY NEFSGGVAAN DENYALAA                         278

SEQ ID NO: 49            moltype = AA   length = 300
FEATURE                  Location/Qualifiers
source                   1..300
                         mol_type = protein
                         organism = synthetic construct
SEQUENCE: 49
MKHHHHHHGV SKGEEDNMAS LPATHELHIF GSINGVDFDM VGQGTGNPND GYEELNLKST   60
KGDLQFSPWI LVPHIGYGFH QYLPYPDGMS PFQAAMVDGS GYQVHRTMQF EDGASLTVNY  120
RYTYEGSHIK GEAQVKGTGF PADGPVMTNS LTAADWCRSK KTYPNDKTII STFKWSYTTG  180
NGKRYRSTAR TTYTFAKPMA ANYLKNQPMY VFRKTELKHS KTELNFKEWQ KAFTDVMGMD  240
ELYKGGSGSG DELAQLEREL MKLKAQGVDS DELEALARKL AMLARSGGVA ANDENYALAA  300

SEQ ID NO: 50            moltype = AA   length = 279
FEATURE                  Location/Qualifiers
source                   1..279
                         mol_type = protein
                         organism = synthetic construct
SEQUENCE: 50
MKHHHHHHGV SKGEEDNMAS LPATHELHIF GSINGVDFDM VGQGTGNPND GYEELNLKST   60
KGDLQFSPWI LVPHIGYGFH QYLPYPDGMS PFQAAMVDGS GYQVHRTMQF EDGASLTVNY  120
RYTYEGSHIK GEAQVKGTGF PADGPVMTNS LTAADWCRSK KTYPNDKTII STFKWSYTTG  180
NGKRYRSTAR TTYTFAKPMA ANYLKNQPMY VFRKTELKHS KTELNFKEWQ KAFTDVMGMD  240
ELYKGGSGSG RGKITVNGKT YEGRSGGVAA NDENYALAA                        279

SEQ ID NO: 51            moltype = AA   length = 584
FEATURE                  Location/Qualifiers
source                   1..584
                         mol_type = protein
                         organism = synthetic construct
SEQUENCE: 51
MGSSHHHHHH GSGLVPRGSA GEVSRISYED IGGLSEQLGK IREMIELPLK HPELFERLGI   60
TPPKGVILYG PPGTGKTLIA RAVANESGAN FLSINGPEIM SKYYGQSEQK LREIFSKAEE  120
TAPSIIFIDE IDSIAPKREE VQGEVERRVV AQLLTLMDGM KERGHVIVIG ATNRIDAIDP  180
ALRRPGRFDR EIEIGVPDRN GRKEILMIHT RNMPLGMSEE EKNKFLEEMA DYTYGFVGAD  240
```

-continued

```
LAALVRESAM NALRRYLPEI DLDKPIPTEI LEKMVVTEDD FKNALKSIEP SSLREVMVEV  300
PNVHWDDIGG LEDVKREIKE TVELPLLKPD VFKRLGIRPS KGFLLYGPPG VGKTLLAKAV  360
ATESNANFIS IKGPEVLSKW VGESEKAIRE IFKKAKQVAP AIVFLDEIDS IAPRRGTTSD  420
SGVTERIVNQ LLTSLDGIEV MNGVVVIGAT NRPDIMDPAL LRAGRFDKLI YIPPPDKEAR  480
LSILKVHTKN MPLAPDVDLN DIAQRTEGYV GADLENLCRE AGMNAYRENP DATSVSQKNF  540
LDALKTIRPS VDEEVIKFYR TLSETMSKSV SERRKQLQDQ GLYL                   584
```

SEQ ID NO: 52                 moltype = AA  length = 392
FEATURE                       Location/Qualifiers
source                        1..392
                              mol_type = protein
                              organism = synthetic construct
SEQUENCE: 52

```
MGCHHHHHHS SGLVPRGSHN KIEEGKLVIW INGDKGYNGL AEVGKKFEED TGIKVTVEHP  60
DKLEEKFPQV AATGDGPDII FWAHDRFGGY AQSGLLAEIT PDKAFQDKLY PFTWDAVRYN  120
GKLIAYPIAV EALSLIYNKD LLPNPPKTWE EIPALDKELK AKGKSALMFN LQEPYFTWPL  180
IAADGGYAFK YENGKYDIKD VGVDNAGAKA GLTFLVDLIK NKHMNADTDY SIAEAAFNKG  240
ETAMTINGPW AWSNIDTSKV NYGVTVLPTF KGQPSKPFVG VLSAGINAAS PNKELAKEFL  300
ENYLLTDEGL EAVNKDKPLG AVALKSYEEE LAKDPRIAAT MENAQKGEIM PNIPQMSAFW  360
YAVRTAVINA ASGRQTVDEA LKDAQTRITK SS                                392
```

SEQ ID NO: 53                 moltype = AA  length = 394
FEATURE                       Location/Qualifiers
source                        1..394
                              mol_type = protein
                              organism = synthetic construct
SEQUENCE: 53

```
MGSSHHHHHH SSGLVPRGSH NKIEEGKLVI WINGDKGYNG LAEVGKKFEE DTGIKVTVEH  60
PDKLEEKFPQ VAATGDGPDI IFWAHDRFGG YAQSGLLAEI TPDKAFQDKL YPFTWDAVRY  120
NGKLIAYPIA VEALSLIYNK DLLPNPPKTW EEIPALDKEL KAKGKSALMF NLQEPYFTWP  180
LIAADGGYAF KYENGKYDIK DVGVDNAGAK AGLTFLVDLI KNKHMNADTD YSIAEAAFNK  240
GETAMTINGP WAWSNIDTSK VNYGVTVLPT FKGQPSKPFV GVLSAGINAA SPNKELAKEF  300
LENYLLTDEG LEAVNKDKPL GAVALKSYEE ELAKDPRIAA TMENAQKGEI MPNIPQMSAF  360
WYAVRTAVIN AASGRQTVDE ALKDAQTRIT KSSC                              394
```

SEQ ID NO: 54                 moltype = AA  length = 42
FEATURE                       Location/Qualifiers
source                        1..42
                              mol_type = protein
                              organism = synthetic construct
SEQUENCE: 54

```
GGGGGGGGGG GGRRRRRRRR RRRRRRRSGG VAANDENYAL AA                      42
```

SEQ ID NO: 55                 moltype = AA  length = 293
FEATURE                       Location/Qualifiers
source                        1..293
                              mol_type = protein
                              organism = synthetic construct
SEQUENCE: 55

```
ADSDINIKTG TTDIGSNTTV KTGDLVTYDK ENGMHKKVFY SFIDDKNHNK KLLVIRTKGT  60
IAGQYRVYSE EGANKSGLAW PSAFKVQLQL PDNEVAQISD YYPRNSIDTK EYMSTLTYDF  120
DGDVDGDDTG KIGGCIGANV SIGHTLKYVQ PDFKTILESP TDKKVGWKVI FNNMVNQNWG  180
PYDRDSWNPV YGNQLFMKTR NGSMKAADNF LDPNKASSLL SSGFSPDFAT VITMDRKASK  240
QQTNIDVIYE RVRDDYQLHW TSTNWKGTNT KDKWTDRSSE RYKIDWEKEE MTN          293
```

SEQ ID NO: 56                 moltype = AA  length = 262
FEATURE                       Location/Qualifiers
source                        1..262
                              mol_type = protein
                              organism = synthetic construct
SEQUENCE: 56

```
CLTAPPKEAA RPTLMPRAQS YKDLTHLPAP TGKIFVSVYN IQDETGQFKP YPASNDSTAV  60
PQSATAMLVT ALKDSRWFIP LERQGLQNLL NERKIIRAAQ ENGTVAINNR IPLQSLTAAN  120
IMVEGSIIGY ESNVKSGGVG ARYFGIGADT QYQLDQIAVN LRVVNVSTGE ILSSVNTSKT  180
ILSYEVQAGV FRFIDYQRLL EGEVGYTSNE PVMLCLMSAI ETGVIFLIND GIDRGLWDLQ  240
NKAERQNDIL VKYRHMSVPP ES                                           262
```

SEQ ID NO: 57                 moltype = AA  length = 119
FEATURE                       Location/Qualifiers
source                        1..119
                              mol_type = protein
                              organism = synthetic construct -continued

```
SEQUENCE: 57
GTMTFQFRNP NFGGNPNNGA FLLNSAQAQN SYKDPSYNDD FGIETPSALD NFTQAIQSQI  60
LGGLLSNINT GKPGRMVTND YIVDIANRDG QLQLNVTDRK TGQTSTIQVS GLQNNSTDF   119

SEQ ID NO: 58              moltype = AA  length = 9
FEATURE                    Location/Qualifiers
source                     1..9
                           mol_type = protein
                           organism = synthetic construct
SEQUENCE: 58
GGGGGGGGG                                                          9
```

NANOPORE-BASED ANALYSIS OF ANALYTES

CROSS-REFERENCE TO RELATED APPLICATIONS

This application is a continuation of U.S. patent application Ser. No. 19/020,496, filed Jan. 14, 2025 which is a continuation of U.S. patent application Ser. No. 18/394,975, filed Dec. 22, 2023, now U.S. Pat. No. 12,235,260, which is a continuation of International Application No. PCT/NL2023/050570, filed Oct. 30, 2023, which claims the benefit of European Patent Application No. 22204590.8, filed Oct. 28, 2022, each of which is entirely incorporated herein by reference.

SEQUENCE LISTING

The instant application contains a Sequence Listing which has been submitted electronically in XML file format and is hereby incorporated by reference in its entirety. Said XML copy, created on Aug. 12, 2025, is named 64828-707_303_SL.xml and is 62,899 bytes in size.

BACKGROUND

Determining characteristics of analytes is an important aspect of scientific studies. The characteristics of the analytes can be important for further scientific studies or clinical aspects.

SUMMARY

In an aspect, the present disclosure provides a method comprising: (a) providing: a nanopore system, wherein the nanopore system comprises a fluidic chamber and a membrane comprising a nanopore, wherein the membrane separates the fluidic chamber into a cis side and a trans side; (b) contacting a complex comprising a non-nucleic acid based polymer analyte and a translocase with the cis side of the nanopore; and (c) translocating the non-nucleic acid based polymer analyte to the trans side of the fluidic channel using a cis side to trans side electro-osmotic force, wherein the cis side to trans side electro-osmotic force maintains the translocase of the complex at a cis side entrance of a channel of the nanopore.

In some embodiments, prior to (c), the method further comprises contacting the non-nucleic acid based polymer analyte with the translocase to generate the complex. In some embodiments, the complex is generated in the cis side of the fluidic chamber. In some embodiments, the cis side to trans side electro-osmotic force comprises a net cis side to trans side ionic current flow. In some embodiments, the cis side to trans side electro-osmotic force is modulated by a pH, a type of a salt, a concentration of a salt, an osmotic pressure across the membrane, a modification of the nanopore, or any combination thereof. In some embodiments, the modification of the nanopore comprises a modification of a charge of the nanopore. In some embodiments, the cis side to trans side electro-osmotic force is modulated by an asymmetric salt distribution between the cis side and the trans side of the fluidic chamber. In some embodiments, the complex is formed in a solution on the cis side of the fluidic chamber. In some embodiments, the complex is formed prior to the contacting the complex to the cis side of the nanopore. In some embodiments, the translocase comprises an Adenosine triphosphate (ATP)-driven unfoldase. In some embodiments, the translocase comprises a Nucleotide tri-phosphate (NTP)-driven unfoldase. In some embodiments, the translocase comprises an ATPases associated with various cellular activities (AAA+) enzyme. In some embodiments, the AAA+ enzyme is selected from the group consisting of ATP-dependent Clp protease ATP-binding subunit ClpX (ClpX) and ClpX-like proteases, ATP-dependent Clp protease ATP-binding subunit ClpA (ClpA), proteasome-activating nucleotidase (PAN), LON protease, VCP-like ATPase (VAT), AMA, 854, membrane-bound AAA (MBA), small archaeal ubiquitin-like modifier protein (SAMP), ATP-dependent Clp protease ATP-binding subunit ClpC (ClpC), ATP-dependent Clp protease ATP-binding subunit ClpE (ClpE), ATP-dependent protease ATPase subunit HslU (HslU), Caseinolytic mitochondrial matrix peptidase chaperone subunit Y (ClpY), LonA, LonB, ATP-dependent zinc metalloprotease FtsH (FtsH), Proteasome-associated ATPase (Mpa), Cell division cycle protein 48 (Cdc48, also called p97 and VCP) and Cdc48-like protein of actinobacteria (Cpa), Outer mitochondrial transmembrane helix translocase (Msp1), Protein translocase subunit SecA (SecA), and functional homologs, orthologs, or paralogs thereof.

In some embodiments, the system further comprises a pair of electrodes. In some embodiments, the pair of electrodes are configured to provide an applied voltage to generate an electrophoretic force. In some embodiments, the applied voltage is a negative voltage on the trans side. In some embodiments, the applied voltage is a positive voltage on the trans side.

In some embodiments, a magnitude of the applied voltage is less than 300 millivolts (mVs). In some embodiments, a magnitude of the applied voltage is greater than 20 m Vs. In some embodiments, an absolute relative net electro-osmotic current over the applied voltage is greater than about 0.10 picoampere/millivolt (pA/mV).

In some embodiments, the non-nucleic acid based polymer analyte comprises a leader construct at a N-terminus or a C-terminus. In some embodiments, the leader construct is configured to couple one or more translocases to the non-nucleic acid based polymer analyte. In some embodiments, the leader construct is configured to stall one or more translocases. In some embodiments, the leader construct comprises a recognition motif. In some embodiments, the leader construct further comprises a capture motif, a stall motif, a block motif, or a combination thereof.

In another aspect, the present disclosure provides a system comprising: a fluidic chamber; and a membrane comprising a nanopore that separates the fluidic chamber into a cis side comprising a first solution and a trans side comprising a second solution, wherein the first solution and the second solution are configured to generate an electro-osmotic force, wherein the electro-osmotic force is configured to couple a translocase of a complex at a cis side entrance of a channel of the nanopore, wherein the complex comprises a non-nucleic acid based polymer analyte and the translocase.

In some embodiments, the system further comprises a translocase. In some embodiments, the translocase comprises an ATP-driven unfoldase. In some embodiments, the translocase comprises an NTP-driven unfoldase. In some embodiments, the translocase comprises an AAA+ enzyme. In some embodiments, the AAA+ enzyme is selected from the group consisting of ClpX, ClpA, Pan, LON, VAT, AMA, 854, MBA, SAMP, ClpC, ClpE, HslU, ClpY, LonA, LonB, FtsH, Mpa, Cpa, Msp1, SecA, and functional homologs, orthologs, paralogs thereof.

In some embodiments, the translocase is configured to translocate the non-nucleic acid based polymer analyte through the nanopore in a sequential order. In some embodiments, the first solution comprises a first concentration of a solute and the second solution comprises a second concentration of a solute. In some embodiments, the solute comprises an ion or an osmolyte. In some embodiments, a difference between the first concentration of the solute and the second concentration of the solute is configured to generate the electro-osmotic force. In some embodiments, the electro-osmotic force comprises a net ionic current flow from the cis side to the trans side. In some embodiments, the electro-osmotic force is modulated by a pH, a type of a salt, a concentration of a salt, an osmotic pressure across the membrane of the system, a modification of the nanopore, or any combinations thereof. In some embodiments, the electro-osmotic force is modulated by a modification of a charge of the nanopore. In some embodiments, the electro-osmotic force is modulated by an asymmetric salt distribution between the cis side and trans side of the membrane.

In some embodiments, the system further comprises a pair of electrodes. In some embodiments, a first electrode of the pair of electrodes is disposed on the cis side and a second electrode of the pair of electrodes is disposed on the trans side of the membrane. In some embodiments, the pair of electrodes is configured to detect a signal during a translocation of a non-nucleic acid based polymer analyte. In some embodiments, the signal is associated with a characteristic of the non-nucleic acid based polymer analyte. In some embodiments, the pair of electrodes is configured to provide an applied voltage to generate an electrophoretic force. In some embodiments, the applied voltage is a negative voltage on the trans side. In some embodiments, the applied voltage is a positive voltage on the trans side. In some embodiments, a magnitude of the applied voltage is less than 300 mV. In some embodiments, a magnitude of the applied voltage is greater than 20 mV. In some embodiments, an absolute relative net electro-osmotic current over the applied voltage is greater than about 0.10 pA/mV. In some embodiments, the signal comprises an ionic current or a change thereof.

In another aspect, the present disclosure provides a method comprising: providing: a nanopore system, wherein the nanopore system comprises a fluidic chamber and a membrane comprising a nanopore, wherein the membrane separates the fluidic chamber into a cis side and a trans side; a non-nucleic acid based polymer analyte, wherein the non-nucleic acid based polymer analyte is coupled to a leader construct comprising a stall motif, a block motif, a coupling motif, or a combination thereof; and a translocase; and translocating the non-nucleic acid based polymer analyte from the cis side to the trans side of the fluidic chamber.

In some embodiments, the leader construct comprises nucleic acid. In some embodiments, the leader construct comprises peptides. In some embodiments, the leader construct comprises nucleic acid and peptides. In some embodiments, the stall motif is configured to disrupt interaction of a translocase with the non-nucleic acid based polymer analyte. In some embodiments, the stall motif comprises a sequence of amino acids. In some embodiments, the sequence of amino acids comprises n repeats of (Glycine)n, (Serine-Glycine)n, (Glycine-Serine)n, (Alanine)n, (Valine) n, (Alanine-Serine)n, (Serine-Alanine)n, (Valine-Serine)n, or (Serine-Valine)n. In some embodiments, n is greater than about 2, 3, 6, 9, 12, 15, 18, or 21. In some embodiments, the stall motif comprises a region of non-amino acid chemistry. In some embodiments, the region of non-amino acid chemistry comprises polyethylene glycol.

In some embodiments, the block motif is configured to prevent a translocase from translocating the non-nucleic acid based polymer analyte past the block motif. In some embodiments, the block motif is configured to prevent a translocase from translocating the non-nucleic acid based polymer analyte past the leader construct. In some embodiments, the block motif is configured to prevent a translocase from translocating the non-nucleic acid based polymer analyte through the nanopore. In some embodiments, the block motif comprises a steric obstruction. In some embodiments, the steric obstruction comprises one or more bulky amino acids. In some embodiments, the one or more bulky amino acids comprise histidine, phenylalanine, tyrosine, or tryptophan. In some embodiments, the steric obstruction comprises at least one bulky amino acid. In some embodiments, the steric obstruction comprises at least five bulky amino acids. In some embodiments, the steric obstruction comprises at least a portion of an unfolding-resistant protein. In some embodiments, the unfolding-resistant protein comprises Maltose Binding Protein, Titin, dihydrofolate reductase, barnase, or combinations thereof. In some embodiments, the unfolding-resistant protein comprises disulfide bonds. In some embodiments, the steric obstruction comprises a large bound molecule. In some embodiments, the large bound molecule comprises a carbohydrate, a multi-ring molecule, a branched dextran, biotin, streptavidin, a nanobody, an antibody, or a small antigen element.

In some embodiments, the coupling motif is configured to couple the leader construct to the non-nucleic acid based polymer analyte. In some embodiments, the non-nucleic acid based polymer analyte comprises a peptide. In some embodiments, the coupling motif attaches to a C-terminal of the peptide. In some embodiments, the coupling motif attaches to a N-terminal of the peptide. In some embodiments, the coupling motif comprises a recognition sequence that an enzyme with peptide ligase activity can recognize. In some cases, the enzyme can interact with the recognition sequence in the coupling motif. In some embodiments, the coupling motif comprises a chemical group. In some embodiments, the chemical group comprises maleimide, iodoacetamide, 2-thiopyridine, 3-arylpropiolonitrile, NHS-ester, isocyanate, isothiocyanate, benzoyl fluoride, diazonium salt, or PTAD. In some embodiments, the coupling motif comprises an enzyme coupling region. In some embodiments, the enzyme coupling region attaches the coupling motif to an enzyme. In some cases, the enzyme can interact with the coupling motif.

In some embodiments, the enzyme comprises peptiligase, omniligase, or sortase. In some embodiments, the coupling motif of the leader construct is coupled to the non-nucleic acid based polymer analyte via a covalent bond. In some embodiments, the coupling motif of the leader construct is coupled to the non-nucleic acid based polymer analyte via a linker.

In some embodiments, the leader construct further comprises at least one of: a recognition motif; or a capture motif.

In some embodiments, the capture motif comprises a polycation tag. In some embodiments, the polycation tag comprises n repeats of (Serine-Glycine-Arginine)n, (Serine-Arginine)n, (Lysine)n, or (Arginine)n. In some cases, the polycation tag can comprise serine, glycine, arginine, lysine, or any combination thereof. In some embodiments, the capture motif comprises a polyanion tag. In some embodiments, the polyanion tag comprises n repeats of (Serine-Glycine-Aspartic Acid)n, (Serine-Aspartic Acid)n, (Aspartic Acid)n, (Serine-Glycine-Glutamic Acid)n, (Serine-Glutamic Acid)n, or (Glutamic Acid)n. In some cases, the polyanion tag can comprise serine, glycine, aspartic acid, glutamic acid, or any combination thereof. In some embodiments, the recognition motif comprises a portion of ssrA, a Prokaryotic Ubiquitin-like Protein, SulA, peroxisomal membrane protein (Pex15), or combinations thereof. In some embodiments, a sequence of the recognition motif comprises one or more of SEQ ID NOs: 201-206.

In some embodiments, the leader construct is attached to a C-terminal or a N-terminal of the non-nucleic acid based polymer analyte. In some embodiments, the non-nucleic acid based polymer analyte comprises a polypeptide. In some embodiments, the leader construct is coupled to a N terminus of the polypeptide. In some embodiments, the leader construct is coupled to a C terminus of the polypeptide. In some embodiments, the non-nucleic acid based polymer analyte comprises another leader construct. In some embodiments, the leader construct and the another leader construct are configured to translocate the non-nucleic acid based polymer analyte through the nanopore in a C-terminal to N-terminal direction, a N-terminal to C-terminal direction, or a C-terminal to N-terminal direction and a N-terminal direction to C-terminal direction. In some embodiments, the non-nucleic acid based polymer analyte is translocated using an electro-osmotic force.

In some embodiments, the method further comprises: providing an electrophoretic force acting in an opposite direction to the electro-osmotic force. In some embodiments, the electro-osmotic force pushes the non-nucleic acid based polymer analyte through the nanopore against the electrophoretic force. In some embodiments, the electro-osmotic force comprises a net ionic current flow cis side-to-trans side. In some embodiments, the electro-osmotic force is modulated by a pH, a type of a salt, a concentration of a salt, an osmotic pressure across the membrane of the nanopore system, a modification of the nanopore, or any combinations thereof. In some embodiments, the electro-osmotic force is modulated by a modification of a charge of the nanopore. In some cases, the charge of the nanopore can be modified at the cis entrance of the channel. In some cases, the charge of the nanopore can be modified at the trans entrance of the channel. In some cases, the charge of the nanopore can be modified in a central channel of the nanopore. In some embodiments, the electro-osmotic force is modulated by an asymmetric salt distribution between the cis side and trans side of the membrane.

In some embodiments, the nanopore system further comprises a pair of electrodes. In some embodiments, the pair of electrodes are configured to provide an applied voltage to generate an electrophoretic force. In some embodiments, the applied voltage is a negative voltage on the trans side. In some embodiments, the applied voltage is a positive voltage on the trans side. In some embodiments, a magnitude of the applied voltage is less than 300 mV. In some embodiments, a magnitude of the applied voltage is greater than 20 mV. In some embodiments, an absolute relative net electro-osmotic current over the applied voltage is greater than about 0.10 pA/mV.

In some embodiments, the non-nucleic acid based polymer analyte is translocated using an translocase. In some embodiments, the translocase comprises an ATP-driven unfoldase. In some embodiments, the translocase comprises an NTP-driven unfoldase. In some embodiments, the translocase comprises an AAA+ enzyme. In some embodiments, the AAA+ enzyme is selected from the group consisting of ClpX, ClpA, Pan, LON, VAT, AMA, 854, MBA, SAMP, ClpC, ClpE, HsIU, ClpY, LonA, LonB, FtsH, Mpa, Cpa, Msp1, SecA, and functional homologs, orthologs, paralogs thereof.

In another aspect, the present disclosure provides a system comprising: a fluidic chamber; a membrane comprising a nanopore, wherein the membrane separates the fluidic chamber into a cis side comprising a first solution and a trans side comprising a second solution, wherein the first solution and the second solution are configured to translocate a non-nucleic acid based polymer analyte; a translocase; and a leader construct comprising at least one of a stall motif, a block motif, or a coupling motif, or a combination thereof, wherein the leader construct is configured to couple to the non-nucleic acid based polymer analyte.

In another aspect, the present disclosure provides a system comprising: a fluidic chamber; a membrane comprising a nanopore, wherein the membrane separates the fluidic chamber into a cis side comprising a first solution and a trans side comprising a second solution, wherein the first solution and the second solution are configured to translocate a non-nucleic acid based polymer analyte; and a controller operatively coupled to the fluidic chamber and the nanopore, wherein the controller is configured to detect one or more signals associated with at least one characteristic of a leader construct and one or more signals associated with at least one characteristic of the non-nucleic acid based polymer analyte during or subsequent to translocation of the non-nucleic acid based polymer analyte coupled to the leader construct through the nanopore using a translocase, wherein the leader construct comprises at least one of a stall motif, a block motif, or a coupling motif, or a combination thereof.

In some embodiments, the controller is further configured to use a pair of electrodes to detect the one or more signals associated with the at least one characteristic of the leader construct and the one or more signals associated with the at least one characteristic of the non-nucleic acid based polymer analyte. In some embodiments, the controller is further configured to separate the one or more signals associated with the at least one characteristic of the leader construct from the one or more signals associated with the at least one characteristic of the non-nucleic acid based polymer analyte.

In some embodiments, the leader construct comprises one or more nucleic acid molecules. In some embodiments, the leader construct comprises one or more peptides. In some embodiments, the leader construct comprises one or more nucleic acid molecules and one or more peptides. In some embodiments, the stall motif is configured to disrupt interaction of a translocase with the non-nucleic acid based polymer analyte. In some embodiments, the stall motif comprises a sequence of amino acids. In some embodiments, the sequence of amino acids comprises n repeats of (Glycine)n, (Serine-Glycine)n, (Glycine-Serine)n, (Alanine)n, (Valine)n, (Alanine-Serine)n, (Serine-Alanine)n, (Valine-Serine)n, or (Serine-Valine)n. In some embodiments, n can be from about 1 to about 50. In some embodiments, n can be from about 1 to about 2, about 1 to about 3, about 1 to about 4, about 1 to about 5, about 1 to about 10, about 1 to about 15, about 1 to about 20, about 1 to about 25, about 1 to about 30, about 1 to about 40, about 1 to about 50, about 2 to about 3, about 2 to about 4, about 2 to about 5, about 2 to about 10, about 2 to about 15, about 2 to about 20, about 2 to about 25, about 2 to about 30, about 2 to about 40, about 2 to about 50, about 3 to about 4, about 3 to about 5, about 3 to about 10, about 3 to about 15, about 3 to about 20, about 3 to about 25, about 3 to about 30, about 3 to about 40, about 3 to about 50, about 4 to about 5, about 4 to about 10, about 4 to about 15, about 4 to about 20, about 4 to about 25, about 4 to about 30, about 4 to about 40, about 4 to about 50, about 5 to about 10, about 5 to about 15, about 5 to about 20, about 5 to about 25, about 5 to about 30, about 5 to about 40, about 5 to about 50, about 10 to about 15, about 10 to about 20, about 10 to about 25, about 10 to about 30, about 10 to about 40, about 10 to about 50, about 15 to about 20, about 15 to about 25, about 15 to about 30, about 15 to about 40, about 15 to about 50, about 20 to about 25, about 20 to about 30, about 20 to about 40, about 20 to about 50, about 25 to about 30, about 25 to about 40, about 25 to about 50, about 30 to about 40, about 30 to about 50, or about 40 to about 50.

In some embodiments, n can be about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 40, about 45, or about 50. In some embodiments, the stall motif comprises a region of non-amino acid chemistry. In some embodiments, the region of non-amino acid chemistry comprises polyethylene glycol.

In some embodiments, the block motif is configured to prevent a translocase from translocating the non-nucleic acid based polymer analyte past the block motif. In some embodiments, the block motif is configured to prevent the translocase from translocating the non-nucleic acid based polymer analyte past the leader construct. In some embodiments, the block motif is configured to prevent the translocase from translocating the non-nucleic acid based polymer analyte through the nanopore. In some embodiments, the block motif comprises a steric obstruction. In some embodiments, the steric obstruction comprises one or more bulky amino acids. In some embodiments, the one or more bulky amino acids comprise histidine, phenylalanine, tyrosine, or tryptophan. In some embodiments, the steric obstruction comprises at least one bulky amino acids. In some embodiments, the steric obstruction comprises at least five bulky amino acids. In some embodiments, the steric obstruction comprises at least a portion of an unfolding-resistant protein. In some cases, the unfolding-resistant protein can comprise any folded protein. In some cases, the unfolding-resistant protein can comprise alpha-helices, beta-strands, beta-turns, helix-hairpin-helix motifs, or any combination thereof. In some cases, the unfolding-resistant protein can comprise one or more unfolding-resistant domains. In some cases, the one or more unfolding-resistant domains can comprise alpha-helices, beta-strands, beta-turns, helix-hairpin-helix motifs, or any combination thereof. In some cases, the unfolding resistant protein can have from about one to about 10 unfolding-resistant domains. In some cases, the unfolding resistant protein can have at least about one unfolding-resistant domain, at least about two unfolding-resistant domains, at least about three unfolding-resistant domains, at least about four unfolding-resistant domains, at least about five unfolding-resistant domains, at least about six unfolding-resistant domains, at least about seven unfolding-resistant domains, at least about eight unfolding-resistant domains, at least about nine unfolding-resistant domains, at least about ten unfolding-resistant domains, or more than ten unfolding-resistant domains. In some cases, the unfolding resistant protein can have at most about ten unfolding-resistant domains, at most about nine unfolding-resistant domains, at most about eight unfolding-resistant domains, at most about seven unfolding-resistant domains, at most about six unfolding-resistant domains, at most about five unfolding-resistant domains, at most about four unfolding-resistant domains, at most about three unfolding-resistant domains, at most about two unfolding-resistant domains, at most about one unfolding-resistant domain, or less than one unfolding-resistant domain. In some cases, the unfolding resistant protein can have about one unfolding-resistant domain, about two unfolding-resistant domains, about three unfolding-resistant domains, about four unfolding-resistant domains, about five unfolding-resistant domains, about six unfolding-resistant domains, about seven unfolding-resistant domains, about eight unfolding-resistant domains, about nine unfolding-resistant domains, or about ten unfolding-resistant domains. In some embodiments, the unfolding-resistant protein comprises Maltose Binding Protein, Titin, dihydrofolate reductase, barnase, or combinations thereof. In some embodiments, the unfolding-resistant protein comprises disulfide bonds. In some embodiments, the steric obstruction comprises a large bound molecule. In some embodiments, the large bound molecule comprises a carbohydrate, a multi-ring molecule, a branched dextran, biotin, streptavidin, a nanobody, an antibody, or a small antigen element.

In some embodiments, the coupling motif is configured to couple the leader construct to the non-nucleic acid based polymer analyte. In some embodiments, the non-nucleic acid based polymer analyte comprises a peptide. In some embodiments, the coupling motif attaches to a C-terminal of the peptide. In some embodiments, the coupling motif attaches to a N-terminal of the peptide. In some embodiments, the coupling motif comprise an enzyme with peptide ligase activity. In some embodiments, the coupling motif comprises a recognition sequence that an enzyme with peptide ligase activity can recognize. In some cases, an enzyme can interact with the coupling motif. In some embodiments, the coupling motif comprises a chemical group. In some embodiments, the chemical group comprises maleimide, iodoacetamide, 2-thiopyridine, 3-arylpropiolonitrile, NHS-ester, isocyanate, isothiocyanate, benzoyl fluoride, diazonium salt, or PTAD. In some embodiments, the coupling motif comprises an enzyme coupling region. In some embodiments, the enzyme coupling region attaches the coupling motif to an enzyme. In some embodiments, the enzyme comprises peptiligase, omniligase, butelase, trypsiligase, peptide amidase, asparaginyl endopeptidase, or sortase. In some embodiments, the coupling motif of the leader construct is coupled to the non-nucleic acid based polymer analyte via a bond. In some embodiments, the coupling motif of the leader construct is coupled to the non-nucleic acid based polymer analyte via a linker.

In some embodiments, the leader construct further comprises at least one of: a recognition motif; or a capture motif. In some embodiments, the capture motif comprises a polycation tag. In some embodiments, the polycation tag comprises n repeats of (Serine-Glycine-Arginine)n, (Serine-Arginine)n, (Arginine)n wherein the capture motif comprises a polyanion tag. In some embodiments, the capture motif comprises a polyanion tag. In some embodiments, the polyanion tag comprises n repeats of (Serine-Glycine-Aspartic Acid)n, (Serine-Aspartic Acid)n, (Aspartic Acid)n. In some embodiments, the recognition motif comprising a portion of ssrA, a Prokaryotic Ubiquitin-like Protein, SulA, peroxisomal membrane protein (Pex15), or combinations thereof. In some embodiments, a sequence of the recognition motif comprises one or more of SEQ ID NOs: 201-206.

In some embodiments, the leader construct is attached to a C-terminal or a N-terminal of the non-nucleic acid based polymer analyte. In some embodiments, the non-nucleic acid based polymer analyte comprises a polypeptide, wherein the leader construct is added to a N terminus of the polypeptide. In some embodiments, the non-nucleic acid based polymer analyte comprises a polypeptide, wherein the leader construct is added to a C terminus of the polypeptide. In some embodiments, the non-nucleic acid based polymer analyte comprises a second leader construct.

In some embodiments, the first solution and the second solution are configured to generate an electro-osmotic force across the membrane. In some embodiments, the first solution comprises a first concentration of a solute and the second solution comprises a second concentration of a solute. In some embodiments, the solute comprises an ion or an osmolyte. In some embodiments, a difference between the first concentration of the solute and the second concentration of the solute is configured to generate the electro-osmotic force. In some embodiments, the electro-osmotic force comprises a net ionic current flow from the cis side to the trans side of the membrane. In some embodiments, the electro-osmotic force is modulated by a pH, a type of a salt, a concentration of a salt, an osmotic pressure across the membrane of the system, a modification of the nanopore, or any combinations thereof. In some embodiments, the electro-osmotic force is modulated by modification of a charge of the nanopore. In some embodiments, the electro-osmotic force is modulated by an asymmetric salt distribution between the cis side and trans side of the membrane.

In some embodiments, the system further comprises a pair of electrodes comprising a first electrode and a second electrode. In some embodiments, the first electrode is disposed on the cis side of the fluidic chamber and the second electrode is disposed on the trans side of the fluidic chamber. In some embodiments, the pair of electrodes are configured to provide an applied voltage to generate an electrophoretic force across the membrane in an opposing direction to the electro-osmotic force. In some embodiments, the electro-osmotic force is strong enough to translocate the non-nucleic acid based polymer analyte through the nanopore against the electrophoretic force. In some embodiments, the applied voltage is a negative voltage on the trans side. In some embodiments, the applied voltage is a positive voltage on the trans side. In some embodiments, a magnitude of the applied voltage is less than 300 mV. In some embodiments, a magnitude of the applied voltage is greater than 20 mV. In some embodiments, an absolute relative net electro-osmotic current over the applied voltage is greater than about 0.10 pA/mV.

In another aspect, the present disclosure provides a method comprising: providing: a nanopore system, wherein the nanopore system comprises a fluidic chamber and; (2) a membrane comprising a nanopore, wherein the membrane separates the fluidic chamber into a cis side and a trans side; and a non-nucleic acid based polymer analyte; and translocating the non-nucleic acid based polymer analyte from the cis side to the trans side of the fluidic chamber, wherein the nanopore comprises an adaptor, wherein at least a portion of the adaptor is within a channel of the nanopore.

In some embodiments, the adaptor is configured to modify a geometry of the channel of the nanopore. In some embodiments, the adaptor is configured to constrict the channel of the nanopore. In some embodiments, the adaptor is configured to modify a charge of the channel of the nanopore. In some embodiments, the adaptor is configured to modify the channel of the nanopore or a portion thereof to have a positive net charge. In some embodiments, the adaptor is configured to modify the channel of the nanopore or a portion thereof to have a negative net charge. In some embodiments, the adaptor comprises a proteinaceous adaptor or a chemical adaptor. In some embodiments, the proteinaceous adaptor comprises a CsgF subunit, a CsgF subunit truncation, or a CsgF subunit homolog, paralog or ortholog. In some embodiments, the chemical adaptor comprises cyclodextrin, cucurbituril, crown ethers, calixarenes, porphyrins, cyclosporines, cyclems, or cyclams. In some embodiments, the adaptor is coupled to the channel of the nanopore. In some embodiments, the adaptor is coupled to the channel of the nanopore via a covalent bond. In some embodiments, the adaptor is coupled to the channel of the nanopore via a non-covalent bond. In some embodiments, the adaptor is coupled to the channel of the nanopore via a linker. In some embodiments, the nanopore system comprises a cis side to trans side electro-osmotic force resulting from a net ionic current flow cis side to trans side.

In some embodiments, the method further comprises: providing an electrophoretic force acting in an opposite direction to the cis side to trans side electro-osmotic force. In some embodiments, the cis side to trans side electro-osmotic force is strong enough to push the non-nucleic acid based polymer analyte through the nanopore against the electrophoretic force. In some embodiments, the non-nucleic acid based polymer analyte is translocated through the nanopore using an electro-osmotic force.

In some embodiments, the method further comprises: providing an electrophoretic force acting in an opposite direction to the electro-osmotic force. In some embodiments, the electro-osmotic force pushes the non-nucleic acid based polymer analyte through the nanopore against the electrophoretic force. In some embodiments, the electro-osmotic force comprises a net ionic current flow cis side-to-trans side. In some embodiments, the electro-osmotic force is modulated by a pH, a type of a salt, a concentration of a salt, an osmotic pressure across the membrane of the nanopore system, a modification of the nanopore, or any combinations thereof. In some embodiments, the electro-osmotic force is modulated by modification of a charge of the nanopore. In some embodiments, the electro-osmotic force is modulated by an asymmetric salt distribution between the cis side and trans side of the membrane.

In some embodiments, the nanopore system further comprises a pair of electrodes. In some embodiments, the pair of electrodes are configured to provide an applied voltage to generate an electrophoretic force. In some embodiments, the applied voltage is a negative voltage on the trans side. In some embodiments, the applied voltage is a positive voltage on the trans side. In some embodiments, a magnitude of the applied voltage is less than 300 mV. In some embodiments, a magnitude of the applied voltage is greater than 20 mV. In some embodiments, an absolute relative net electro-osmotic current over the applied voltage is greater than about 0.10 pA/mV.

In some embodiments, the non-nucleic acid based polymer analyte is translocated using a translocase. In some embodiments, the translocase comprises an ATP-driven unfoldase. In some embodiments, the translocase comprises an NTP-driven unfoldase. In some embodiments, the translocase comprises an AAA+ enzyme. In some embodiments, the AAA+ enzyme is selected from the group consisting of ClpX, ClpA, Pan, LON, VAT, AMA, 854, MBA, SAMP, ClpC, ClpE, HsIU, ClpY, LonA, LonB, FtsH, Mpa, Cpa, Msp1, SecA, and functional homologs, orthologs, paralogs thereof.

In another aspect, the present disclosure provides a system comprising: a fluidic chamber; and a membrane comprising a nanopore, wherein the membrane separates the fluidic chamber into a cis side comprising a first solution and a trans side comprising a second solution, wherein the first solution and the second solution are configured to translocate a non-nucleic acid based polymer analyte; wherein the nanopore comprises an adapter within a channel of the nanopore.

In some embodiments, the adaptor comprises a proteinaceous adapter or a chemical adaptor. In some embodiments, the proteinaceous adaptor comprises a CsgF subunit, a CsgF subunit truncation, or a CsgF subunit homolog, paralog or ortholog. In some embodiments, the chemical adaptor comprises cyclodextrin, cucurbituril, crown ethers, calixarenes, porphyrins, cyclosporines, cyclems, or cyclams. In some embodiments, the adaptor is coupled to the channel of the nanopore. In some embodiments, the adaptor is coupled to the channel of the nanopore via a covalent bond. In some embodiments, the adaptor is coupled to the channel of the nanopore via a non-covalent bond. In some embodiments, the adaptor is coupled to the channel of the nanopore via a linker.

In some embodiments, the first solution comprises a first concentration of a solute and the second solution comprises a second concentration of the solute. In some embodiments, the solute comprises an ion or an osmolyte. In some embodiments, a difference between the first concentration of the solute and the second concentration of the solute is configured to generate an electro-osmotic force. In some embodiments, the first solution and the second solution are configured to generate an electro-osmotic force across the membrane. In some embodiments, the electro-osmotic force results from a net ionic current flow from the cis side to the trans side of the membrane.

In some embodiments, the system further comprises an electrophoretic force acting in an opposite direction to the electro-osmotic force, wherein the electro-osmotic force is strong enough to push the non-nucleic acid based polymer analyte through the nanopore against the electrophoretic force. In some embodiments, the electro-osmotic force is modulated by a pH, a type of a salt, a concentration of a salt, an osmotic pressure across the membrane of the system, a modification of the nanopore, or any combinations thereof. In some embodiments, the electro-osmotic force is modulated by modification of a charge of the nanopore. In some embodiments, the electro-osmotic force is modulated by an asymmetric salt distribution between the cis side and trans side of the membrane.

In some embodiments, the system further comprises a pair of electrodes. In some embodiments, a first electrode of the pair of electrodes is disposed on the cis side and a second electrode of the pair of electrodes is disposed on the trans side of the membrane. In some embodiments, the pair of electrodes is configured to detect a signal during a translocation of a non-nucleic acid based polymer analyte. In some embodiments, the signal is associated with a characteristic of the non-nucleic acid based polymer analyte. In some embodiments, the pair of electrodes is configured to provide an applied voltage to generate an electrophoretic force. In some embodiments, the applied voltage is a negative voltage on the trans side. In some embodiments, the applied voltage is a positive voltage on the trans side. In some embodiments, a magnitude of the applied voltage is less than 300 mV. In some embodiments, a magnitude of the applied voltage is greater than 20 mV. In some embodiments, an absolute relative net electro-osmotic current over the applied voltage is greater than about 0.10 pA/mV.

In another aspect, the present disclosure provides a method comprising: (a) providing: a nanopore system, wherein the nanopore system comprises a fluidic chamber and a membrane comprising a nanopore, wherein the membrane separates the fluidic chamber into a cis side and a trans side; (b) adding a combined solution to the cis side of the fluidic chamber, wherein the combined solution comprises a non-nucleic acid based polymer analyte and a preloading solution; and (c) translocating the non-nucleic acid based polymer analyte from the cis side to the trans side of the fluidic chamber.

In some embodiments, prior to (b), further comprising combining a sample comprising a non-nucleic acid based polymer analyte with a preloading solution. In some embodiments, the preloading solution comprises a translocase. In some embodiments, the non-nucleic acid based polymer analyte is translocated using the translocase. In some embodiments, the translocase comprises an ATP-driven unfoldase. In some embodiments, the translocase comprises an NTP-driven unfoldase. In some embodiments, the translocase comprises an AAA+ enzyme. In some embodiments, the AAA+ enzyme is selected from the group consisting of ClpX, ClpA, Pan, LON, VAT, AMA, 854, MBA, SAMP, ClpC, ClpE, HsIU, ClpY, LonA, LonB, FtsH, Mpa, Cpa, Msp1, SecA, and functional homologs, orthologs, paralogs thereof.

In some embodiments, combining the sample and the preloading solution forms a non-nucleic acid based polymer analyte-translocase complex. In some embodiments, the combining the sample and the preloading solution forms a non-nucleic acid based polymer analyte-leader construct complex. In some embodiments, the preloading solution comprises a leader construct. In some embodiments, the preloading solution comprises a chemical that enhances a binding of the non-nucleic acid based polymer analyte to a component of the preloading solution. In some embodiments, the binding of the non-nucleic acid based polymer analyte to a component of the preloading solution is higher than a binding of the non-nucleic acid based polymer analyte to a component in the fluidic chamber. In some embodiments, the preloading solution comprises one or more cofactors. In some embodiments, the one or more cofactors comprise NTP, $M^{2+}$, NblA/B, ClpS, ClpF, Hsp10, Hsp60, calnexin, ERp29, ERp57, polyethylene glycol, dextran, Ficoll, iron manganese, cobalt, copper, penicillamine, trientine, sodium calcium edetate, or ethylenediaminetetraacetic acid.

In some embodiments, the non-nucleic acid based polymer analyte is translocated using an electro-osmotic force. In some embodiments, the translocating comprises providing an electrophoretic force acting in an opposite direction to the electro-osmotic force. In some embodiments, the electro-osmotic force pushes the non-nucleic acid based polymer analyte through the nanopore against the electrophoretic force. In some embodiments, the electro-osmotic force comprises a net ionic current flow cis side-to-trans side.

In some embodiments, the electro-osmotic force is modulated by a pH, a type of a salt, a concentration of a salt, an osmotic pressure across the membrane of the nanopore system, a modification of the nanopore, or any combinations thereof. In some embodiments, the electro-osmotic force is modulated by modification of a charge of the nanopore. In some embodiments, the electro-osmotic force is modulated by an asymmetric salt distribution between the cis side and trans side of the membrane.

In some embodiments, the nanopore system further comprises a pair of electrodes. In some embodiments, the pair of electrodes are configured to provide an applied voltage to generate an electrophoretic force. In some embodiments, the applied voltage is a negative voltage on the trans side. In some embodiments, the applied voltage is a positive voltage on the trans side. In some embodiments, a magnitude of the applied voltage is less than 300 mV. In some embodiments, a magnitude of the applied voltage is greater than 20 mV. In some embodiments, an absolute relative net electro-osmotic current over the applied voltage is greater than about 0.10 pA/mV.

In another aspect, the present disclosure provides a system comprising: a fluidic chamber; and a membrane comprising a nanopore, wherein the membrane separates the fluidic chamber into a cis side comprising a first solution and a trans side comprising a second solution, wherein the first solution and the second solution are configured to translocate a non-nucleic acid based polymer analyte across the nanopore; and a preloading solution configured to interact with the non-nucleic acid based polymer analyte.

In some embodiments, the first solution comprises a first concentration of a solute and the second solution comprises a second concentration of the solute. In some embodiments, the solute comprises an ion or an osmolyte. In some embodiments, a difference between the first concentration of the solute and the second concentration of the solute is configured to generate an electro-osmotic force. In some embodiments, the first solution and the second solution are configured to generate an electro-osmotic force across the membrane. In some embodiments, the electro-osmotic force results from a net ionic current flow from the cis side to the trans side of the membrane. In some embodiments, the electro-osmotic force is modulated by a pH, a type of a salt, a concentration of a salt, an osmotic pressure across the membrane of the system, a modification of the nanopore, or any combinations thereof. In some embodiments, the electro-osmotic force is modulated by modification of a charge of the nanopore. In some embodiments, the electro-osmotic force is modulated by an asymmetric salt distribution between the cis side and trans side of the membrane.

In some embodiments, the system further comprises a pair of electrodes disposed on the cis side and trans side of the membrane, wherein the pair of electrodes are configured to provide an applied voltage to generate an electrophoretic force across the membrane in an opposing direction to the electro-osmotic flow. In some embodiments, the applied voltage is a negative voltage on the trans side. In some embodiments, the applied voltage is a positive voltage on the trans side. In some embodiments, a magnitude of the applied voltage is less than 300 mV. In some embodiments, a magnitude of the applied voltage is greater than 300 mV. In some embodiments, an absolute relative net electro-osmotic current over the applied voltage is greater than about 0.10 pA/mV. In some embodiments, the preloading solution comprises one or more cofactors. In some embodiments, the one or more cofactors comprise divalent metal ions, NTP, $M^{2+}$, NblA/B, ClpS, ClpF, Hsp10, Hsp60, calnexin, ERp29, ERp57, polyethylene glycol, dextran, Ficoll, iron manganese, cobalt, copper, penicillamine, trientine, sodium calcium edetate, glycine betaine, or ethylenediaminetetraacetic acid.

In some embodiments, the preloading solution comprises a translocase. In some embodiments, the translocase comprises an ATP-driven unfoldase. In some embodiments, the translocase comprises an NTP-driven unfoldase. In some embodiments, the translocase comprises an AAA+ enzyme. In some embodiments, the AAA+ enzyme is selected from the group consisting of ClpX, ClpA, Pan, LON, VAT, AMA, 854, MBA, SAMP, ClpC, ClpE, HsIU, ClpY, LonA, LonB, FtsH, Mpa, Cpa, Msp1, SecA, or functional homologs, orthologs, or paralogs thereof.

In some embodiments, the preloading solution comprises a leader construct. In some embodiments, the preloading solution comprises chemical that enhances a binding of the non-nucleic acid based polymer analyte to a component of the preloading solution relative to binding in a solution of the cis side of the fluidic chamber. In some embodiments, the nanopore has an ion-selectivity P(+)/P(−) of greater than 2.0. In some embodiments, the nanopore has an ion-selectivity P(+)/P(−) of less than 0.50. In some embodiments, the non-nucleic acid based polymer analyte is an unmodified (label-free) non-nucleic acid based polymer analyte.

In some embodiments, termini of the non-nucleic acid based polymer analyte lack a three-dimensional structure. In some embodiments, at least a portion of the non-nucleic acid based polymer analyte is denatured. In some embodiments, the non-nucleic acid based polymer analyte comprises peptide units, saccharide units, water-soluble plastic monomers, or any combination thereof. In some embodiments, the non-nucleic acid based polymer analyte comprises a polypeptide, a polysaccharide, or a water-soluble plastic. In some embodiments, the non-nucleic acid based polymer analyte comprises a polypeptide. In some embodiments, the polypeptide comprises at least 30 peptide units. In some embodiments, the at least 30 peptide units comprise positively charged residues. In some embodiments, the at least 30 peptide units comprise negatively charged residues. In some embodiments, the at least 30 peptide units comprise positively charged residues and negatively charged residues. In some embodiments, the polypeptide is in a denatured state. In some embodiments, the polypeptide is provided in a folded state.

In some embodiments, the method further comprises measuring a signal generated by the translocating of the non-nucleic acid based polymer analyte through the nanopore. In some embodiments, the measuring comprises: measuring a signal for states of (a) an open channel of the nanopore; (b) capture of the non-nucleic acid based polymer analyte by the nanopore; or (c) passage of the non-nucleic acid based polymer analyte through the nanopore. In some embodiments, the measuring comprises detecting differences between states (a), (b) and (c).

In some embodiments, the signal comprises an ionic current, a change in ionic current, or derivations thereof. In some embodiments, the nanopore comprises an inner pore constriction from about 0.5 nm to about 2 nanometers (nm). In some embodiments, the inner pore constriction is from about 1 nm to about 2 nanometers (nm). In some embodiments, the nanopore comprises an alpha-helical oligomeric pore structure. In some embodiments, the nanopore comprise a beta-barrel oligomeric pore structure. In some embodiments, the nanopore comprises a recombinant nanopore. In some embodiments, the nanopore comprises a protein of Aerolysin (Aer), Cytolysin K (CytK), MspA, alpha-hemolysin (aHL), CsgG, Fragaceatoxin C (FraC), Lysenin, OmpF, OmpG, FhuA, phage derived portal proteins, modified variants thereof, or ion-selective mutants thereof.

In some embodiments, the nanopore comprises a biological nanopore. In some embodiments, the biological nanopore is modified to limit passage of one or more ions through a channel of the nanopore. In some embodiments, the biological nanopore limits passage of one or more ions through the channel of the nanopore by modifying a charge of the channel of the nanopore. In some embodiments, a net charge is negative. In some embodiments, a net charge is positive.

In some embodiments, the nanopore is a mutant CytK nanopore. In some embodiments, the mutant CytK comprises one or more amino acid substitutions. In some embodiments, the one or more amino acid substitutions comprises K128D, K128F, K115D, S120D, Q122D, S151D, or any combination thereof. In some embodiments, the one or more amino acid substitutions comprises K128D, K155Q, T116D, S120D, Q122D, S126D, T143D, Q145D, T147D S151D, or any combination thereof. In some embodiments, the mutant CytK nanopore comprises one of the following combinations of amino acid substitutions: (a) K128D and K155D; (b) K128D, K155D and T116D; (c) T147D or S151D; (d) K128D, K155D and S120D; (e) Q122D, T147D or S155D; (f) K128D, K155D, Q145D and S151D; and (g) a combination thereof. In some embodiments, the mutant CytK nanopore comprises one or more of the following combinations of amino acid substitutions: (a) S120D, G122D, or K155D; (b) S120D in combination with K128F/ K128D; (c) Q122D or S151D; (d) K128D or K128F; (e) S120D, K115D and Q122D; (f) K128F, S120D and G122D; (g) K128F, S120D G122D, and K155D; and (h) a combination thereof.

In some embodiments, the nanopore has an ion-selectivity P(+)/P(−) of greater than 2.0. In some embodiments, the nanopore has an ion-selectivity P(+)/P(−) of less than 0.50. In some embodiments, the non-nucleic acid based polymer analyte is an unmodified (label-free) non-nucleic acid based polymer analyte. In some embodiments, termini of the non-nucleic acid based polymer analyte lack a three-dimensional structure. In some embodiments, at least a portion of the non-nucleic acid based polymer analyte is denatured. In some embodiments, the non-nucleic acid based polymer analyte comprises peptide units, saccharide units, water-soluble plastic monomers, or any combination thereof. In some embodiments, the non-nucleic acid based polymer analyte comprises a polypeptide, a polysaccharide, or a water-soluble plastic. In some embodiments, the non-nucleic acid based polymer analyte comprises a polypeptide. In some embodiments, the polypeptide comprises at least 30 peptide units. In some embodiments, the at least 30 peptide units comprise positively charged residues. In some embodiments, the at least 30 peptide units comprise negatively charged residues. In some embodiments, the at least 30 peptide units comprise positively charged residues and negatively charged residues. In some embodiments, the polypeptide is in a denatured state. In some embodiments, the polypeptide is provided in a folded state.

In some embodiments, the system further comprises measuring a signal generated by the translocating of the non-nucleic acid based polymer analyte through the nanopore. In some embodiments, the measuring comprises: measuring a signal for states of (a) an open channel of the nanopore; (b) capture of the non-nucleic acid based polymer analyte by the nanopore; or (c) passage of the non-nucleic acid based polymer analyte through the nanopore. In some embodiments, the measuring comprises detecting differences between states (a), (b) and (c).

In some embodiments, the signal comprises an ionic current, a change in ionic current, or derivations thereof. In some embodiments, the nanopore comprises an inner pore constriction from about 0.5 nm to about 2 nm. In some embodiments, the inner pore constriction is from about 1 nm to about 2 nm. In some embodiments, the nanopore comprises an alpha-helical oligomeric pore structure. In some embodiments, the nanopore comprise a beta-barrel oligomeric pore structure. In some embodiments, the nanopore comprises a recombinant nanopore. In some embodiments, the nanopore comprises a protein of Aerolysin (Aer), Cytolysin K (CytK), MspA, alpha-hemolysin (aHL), CsgG, Fragaceatoxin C (FraC), Lysenin, OmpF, OmpG, FhuA, phage derived portal proteins, modified variants thereof, or ion-selective mutants thereof.

In some embodiments, the nanopore comprises a biological nanopore. In some embodiments, the biological nanopore is modified to limit passage of one or more ions through a channel of the nanopore. In some embodiments, the biological nanopore limits passage of one or more ions through the channel of the nanopore by modifying a charge of the channel of the nanopore. In some embodiments, a net charge is negative. In some embodiments, a net charge is positive.

In some embodiments, the nanopore is a mutant CytK nanopore. In some embodiments, the mutant CytK comprises one or more amino acid substitutions. In some embodiments, the one or more amino acid substitutions comprises K128D, K128F, K115D, S120D, Q122D, S151D, or any combination thereof. In some embodiments, the one or more amino acid substitutions comprises K128D, K155Q, T116D, S120D, Q122D, S126D, T143D, Q145D, T147D S151D, or any combination thereof. In some embodiments, the mutant CytK nanopore comprises one of the following combinations of amino acid substitutions: (a) K128D and K155D; (b) K128D, K155D and T116D; (c) T147D or S151D; (d) K128D, K155D and S120D; (e) Q122D, T147D or S155D; (f) K128D, K155D, Q145D and S151D; and (g) a combination thereof. In some embodiments, the mutant CytK nanopore comprises one or more of the following combinations of amino acid substitutions: (a) S120D, G122D, or K155D; (b) S120D in combination with K128F/ K128D; (c) Q122D or S151D; (d) K128D or K128F; (e) S120D, K115D and Q122D; (f) K128F, S120D and G122D; (g) K128F, S120D G122D, and K155D; and (h) a combination thereof.

In another aspect, the present disclosure provides a device comprising an array of a system comprising the system disclosed herein.

In another aspect, the present disclosure provides a use of any of the methods, kits, or devices disclosed herein for characterizing at least one structural feature of the non-nucleic acid based polymer analyte.

In another aspect, the present disclosure provides a use of any of the methods, kits, or devices disclosed herein for analysis of an amino acid sequence or amino composition of one or more non-nucleic acid based polymer analytes at a single molecule level.

In another aspect, the present disclosure provides a use of any of the systems disclosed herein for characterizing at least one structural feature of the non-nucleic acid based polymer analyte.

In another aspect, the present disclosure provides a use of any of the systems disclosed herein for analysis of an amino acid sequence or amino composition of one or more non-nucleic acid based polymer analytes at a single molecule level.

In another aspect of the present disclosure provides a method for translocating a target protein through a nanopore, the nanopore being comprised in a membrane separating a fluidic chamber of a nanopore system into a cis side and a trans side, comprising: (a) allowing a protein translocase in solution, optionally in the presence of NTP, to capture and form a complex with the target protein to be translocated, (b) contacting the translocase-target protein complex with the cis side of the nanopore and allowing for translocation of the target protein to the trans side, wherein the nanopore system has a cis to trans electro-osmotic force (EOF) resulting from a net ionic current flow cis to trans, so that the target protein is captured in the nanopore with on top of the nanopore the protein translocase controlling the translocation.

In some embodiments, wherein the nanopore system has a cis to trans EOF resulting from a net ionic current flow cis to trans over total ionic current flow ($I_{rel}$) of greater than 0.2 or less than −0.2, greater than 0.3 or less than −0.3, greater than 0.35 or less than −0.35.

In some embodiments of any one of the preceding embodiments, the cis to trans EOF is arranged by modulating the pH, type and/or concentration of a salt and/or osmotic pressure across the membrane of the nanopore system, by modification (e.g. genetic engineering) of the nanopore charge, or any combination thereof, such as by modification of the nanopore and/or an asymmetric salt distribution between the cis and trans side of the chamber.

In some embodiments of any one of the preceding embodiments, the translocase-target protein complex is formed in solution in the cis side of the fluidic chamber.

In some embodiments of any one of the preceding embodiments, the translocase-target protein complex is formed in solution during a separate step prior to adding the complex to the cis side of the fluidic chamber to contact the nanopore.

In some embodiments of any one of the preceding embodiments, the target protein comprises at its N- and/or C-terminus a leader construct to allow for preloading and, optionally stalling, one or more protein translocases. In some embodiments, the leader construct comprises a (i) recognition motif for the protein translocase, further comprising one or more of the following elements: (ii) capture motif; (iii) stall motif; (iv) block motif.

In another aspect of the present disclosure provides a nanopore system for translocating a target protein through a nanopore, comprising: (a) a membrane having nanopore therein, said membrane separating a chamber into a cis side and a trans side, wherein the target protein is to be added to the cis side and translocated through the nanopore to the trans side, (b) on the cis side of said chamber a target protein captured by a protein translocase, which can bind and translocate the target protein through the nanopore in a sequential order, (c) mechanisms for providing a voltage difference between the cis side and the trans side of the membrane, wherein the nanopore system has a cis to trans electro-osmotic force (EOF) resulting from a net ionic current flow cis to trans, so that the target protein is captured in the nanopore with on top of the nanopore the translocase controlling the translocation, wherein the nanopore system has a cis to trans EOF resulting from a net ionic current flow cis-to-trans over total ionic current flow of greater than 0.2 or less than −0.2, greater than 0.3 or less than −0.3, greater than 0.35 or less than −0.35.

In some embodiments, the system further comprises methods for measuring a signal based on ionic current flowing through the nanopore during a period of time of translocation, wherein the measuring methods detects changes in the signal that reflect characteristics of the protein as it is translocated.

In some embodiments of any one of the preceding embodiments, the nanopore system has an ion-selectivity $P_{(+)}/P_{(−)}$ of greater than 2.0 or less than 0.5, greater than 2.5 or less than 0.4, greater than 3.0 or less than 0.33.

In some embodiments of any one of the preceding embodiments, the nanopore is a biological nanopore, having an inner pore constriction in the range of 0.5-2 nm, wherein the nanopore is an alpha-helical or beta-barrel oligomeric pore forming toxin or porin. In some embodiments, the nanopore is selected from the group consisting of Aerolysin (Aer), Cytolysin K (CytK), MspA, alpha-hemolysin (aHL), CsgG, Fragaceatoxin C (FraC), Lysenin, phage derived portal proteins, and modified variants thereof, wherein the nanopore is modified to have a net charge in the lumen facing regions of >21, >28, >35, wherein said net charge is negative. In some embodiments, the nanopore is selected from the group consisting of Aerolysin (Aer), Cytolysin K (CytK), MspA, alpha-hemolysin (aHL), CsgG, Fragaceatoxin C (FraC), Lysenin, phage derived portal proteins, and modified variants thereof, wherein the nanopore is modified to have a net charge in the lumen facing regions of >21, >28, >35, wherein said net charge is positive. In some embodiments, any amino acid residue in a lumen facing region of the nanopore can be mutated. In some cases, the mutated amino acid residue can be mutated to a negatively charged amino acid. In some cases, the mutated amino acid residue can be mutated to a positively charged amino acid. In some cases, the mutated amino acid residue can be mutated to a neutrally charged amino acid.

In some embodiments, the nanopore can be an oligomer. In some cases, the oligomer nanopore can comprise one or more subunits. In some cases, each subunit of the one or more subunits can comprise from about 20 to about 40 charges in the lumen facing regions of the subunit. In some cases, each subunit of the one or more subunits can comprise at least about 20 charges, at least about 21 charges, at least about 22 charges, at least about 23 charges, at least about 24 charges, at least about 25 charges, at least about 26 charges, at least about 27 charges, at least about 28 charges, at least about 29 charges, at least about 30 charges, at least about 31 charges, at least about 32 charges, at least about 33 charges, at least about 34 charges, at least about 35 charges, at least about 36 charges, at least about 37 charges, at least about 38 charges, at least about 39 charges, at least about 40 charges, or more than 40 charges in the lumen facing regions of the subunit. In some cases, each subunit of the one or more subunits can comprise at most about 40 charges, at most about 39 charges, at most about 38 charges, at most about 37 charges, at most about 36 charges, at most about 35 charges, at most about 34 charges, at most about 33 charges, at most about 32 charges, at most about 31 charges, at most about 30 charges, at most about 29 charges, at most about 28 charges, at most about 27 charges, at most about 26 charges, at most about 25 charges, at most about 24 charges, at most about 23 charges, at most about 22 charges, at most about 21 charges, at most about 20 charges, or less than 20 charges in the lumen facing regions of the subunit. In some cases, each subunit of the one or more subunits can comprise about 20 charges, about 21 charges, about 22 charges, about 23 charges, about 24 charges, about 25 charges, about 26 charges, about 27 charges, about 28 charges, about 29 charges, about 30 charges, about 31 charges, about 32 charges, about 33 charges, about 34 charges, about 35 charges, about 36 charges, about 37 charges, about 38 charges, about 39 charges, or about 40 charges in the lumen facing regions of the subunit.

In some embodiments, the nanopore is a mutant CytK nanopore comprising one or more of the amino acid substitutions selected from the group consisting of K128D, K128F, K115D, S120D, Q122D and S151D, comprising one of the following combinations of amino acid substitutions: S120D, G122D and/or K155D; S120D in combination with K128F/K128D, further comprising Q122D or S151D; K128D/K128F, S120D, K115D and Q122D; and K128F, S120D and G122D, optionally in combination with K155D.

In some embodiments of any one of the preceding embodiments, the protein translocase is an NTP-driven Unfoldase, an AAA+ enzyme. In some embodiments, the AAA+ enzyme is selected from the group consisting of ClpX, ClpA, Pan, LON, VAT, AMA, 854, MBA, SAMP, ClpC, ClpE, HsIU, (ClpY), LonA, LonB, FtsH, Mpa, Cpa, Msp1, SecA, and functional homologs, orthologs, or paralogs thereof.

In some embodiments of any one of the preceding embodiments, the nanopore system has an ion-selectivity $P_{(+)}/P_{(-)}$ of greater than 2.0, greater than 2.5, greater than 3.0 wherein there is a negative applied voltage at the trans side. In some embodiments, the system comprises a cation-selective (mutant) nanopore.

One aspect of the present disclosure provides an analytical device comprise an array of nanopore system according to any one of the preceding embodiments.

One aspect of the present disclosure provides a use of a nanopore system or device according to any one of the preceding embodiments for characterizing at least one structural feature of a target protein, for analysis of an amino acid sequence or amino composition of one or more target protein(s) at the single molecule level.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION

The present disclosure relates to systems and methods for analysis of a non-nucleic acid based polymer analyte (e.g., analytes) using nanopore-based sensors. The present disclosure provides nanopore systems, devices and methods for single molecule non-nucleic acid based polymer analyte (e.g., single-molecule protein) analysis and sequencing.

Various studies have demonstrated both freely translocating and motor controlled movement of polypeptides (e.g., proteins that are unfolded during or before translocation through narrow nanopores) through narrow nanopores (typically <2 nm in diameter). However, unlike polynucleotides having a fixed negative charge that can be electrophoretically drawn into nanopores by an electric field from an applied voltage, it remains a challenge to capture and control the movement of peptides of diverse composition. This is because the diverse composition leads to a range of electrical and structural properties (e.g. a mix of positive, negative, neutral, hydrophilic, hydrophobic, aromatic) that prevent simple capture under electrophoretic conditions and translocation in an unfolded state.

It was previously not thought possible to push/feed analytes into pores from the cis side in their native form (e.g. without attaching or conjugating to DNA leaders or adding other (e.g. polyanion) tags to create electrophoretic capture motifs) due to their complex composition. The diverse charge can result in the unfolded peptides are sometimes attracted and sometimes repelled from a nanopore depending on charge and applied voltage, so it is not possible to translocate a diverse repertoire of complex peptides through nanopores by electrophoretic mechanisms alone. Indeed, previous studies have demonstrated translocation of either very short peptides with a contour length shorter than the length of the nanopore channel or of very carefully selected (model) analytes, whose charge, structure or added electrophoretic tags favor capture and translocation through nanopores by electrophoresis. However, in no way is this representative for the broad amino acid composition of proteins that are found in nature. See for example Motone et al. (iScience 24, Sep. 24, 2021) reviewing recent approaches that use a range of techniques aimed at driving protein strands and peptides through nanopores. It is stated therein that nanopore protein sequencing is a challenging frontier that has yet to be realized.

The present disclosure provides a novel approach that may be simple and/or provides robust mechanisms of feeding non-nucleic acid based polymer analyte (e.g., full length proteins) through nanopores (e.g., for the purpose of sequencing and/or characterizing them). In an example the methods and systems disclosed herein may not require additional components (e.g., (protein or polynucleotide) being fused, conjugated and/or otherwise attached to the nanopore.

It was found that these goals can be achieved by using a large and dominant cis-to-trans electro-osmotic flow (EOF), generated by a large cis-to-trans excess of ions flowing through the nanopore, in conjunction with a translocase on the cis side of a nanopore that can controllably feed and pass a wide range of analytes from cis to trans through the nanopore against the direction of the electrophoretic forces (EPFs). In some embodiments, the cis-to-trans osmotic flow can be generated by the flow of ions and solvents from the cis side of the nanopore system to the trans side of the nanopore system.

The present disclosure provides a system that can utilize strong electro-osmotic forces to capture and feed analytes (e.g., peptides, nucleic acid molecules, oligosaccharides, lipids, proteins) from the cis side of a nanopore without coupling the motor translocase to the nanopore. In some embodiments, the forces in the system are sufficient to hold the translocase motor on top of the pore. For example, strong electro-osmotic pores combined with translocase proteins (e.g., molecular motor proteins) on the cis side can first unwind and then feed diverse composition analytes through nanopores, then unbinding and allowing the system to process the next molecule. This may be achieved via the strong EOF pulling on at least a portion of the analyte within or near the nanopore, since the translocase can diffuse away from the nanopore after unbinding for a new complex to bind.

In some embodiments, the strong electro-osmotic forces pull on the analyte as it translocates through the pore, and in turn transmit that force up to the bound translocase motor protein above acting to keep the translocase on top of the pore during controlled translocation of the substrate. In turn, the translocase motor progresses through the analyte under nucleotide triphosphate (NTP) controlled translocase activity, unfolding any three-dimensional structures within the analyte that the translocase encounters, and thereby controlling the movement of the analyte into the nanopore at a speed that enables the changes in current to be measured and characterized.

Accordingly, in one embodiment the present disclosure provides a method for translocating an analyte through a nanopore, the nanopore being comprised in a membrane separating a fluidic chamber of a nanopore system into a cis side and a trans side, comprising:

(a) allowing a protein translocase in solution, optionally in the presence of NTP, to capture and form a complex with the analyte to be translocated;

(b) contacting the translocase-target protein complex with the cis side of the nanopore and allowing for translocation of the analyte to the trans side;

wherein the nanopore system has a cis to trans electro-osmotic force (EOF) resulting from a net ionic current flow cis-to-trans, so that the analyte is captured in the nanopore and the translocase can be located on the top of the nanopore the translocase controlling the translocation.

For example, the nanopore system has a cis to trans EOF resulting from a net ionic current flow cis-to-trans over total ionic current flow (herein also referred to as $I_{rel}$) of greater than 0.2 or less than −0.2, greater than 0.3 or less than −0.3, greater than 0.35 or less than −0.35.

In some embodiments, a cis to trans EOF results from a net ionic current flow cis to trans over a total ionic current flow, also referred to as a relative net current flow cis to trans, of at least about −0.99, at least about −0.95, at least about −0.9, at least about −0.8, at least about −0.7, at least about −0.6, at least about −0.5, at least about −0.4, at least about −0.3, at least about −0.2, at least about −0.1, at least about 0.0, at least about 0.1, at least about 0.2, at least about 0.3, at least about 0.4, at least about 0.5, at least about 0.6, at least about 0.7, at least about 0.8, at least about 0.9, at least about 0.95, about 0.99, or greater than about 0.99. In some embodiments, a cis to trans EOF results from a net ionic current flow cis to trans over a total ionic current flow, also referred to as a relative net current flow cis to trans, of at most about 0.99, at most about 0.9, at most about 0.8, at most about 0.7, at most about 0.6, at most about 0.5, at most about 0.4, at most about 0.3, at most about 0.2, at most about 0.1, at most about 0.0, at most about −0.1, at most about −0.2, at most about −0.3, at most about −0.4, at most about −0.5, at most about −0.6, at most about −0.7, at most about −0.8, at most about −0.9, −0.95, at most about −0.99, or less than about −0.99.

In some embodiments, a cis to trans EOF results from a net ionic current flow cis to trans over a total ionic current flow, also referred to as a relative net current flow cis to trans, from about −0.99 to about 0.99. In some embodiments, a cis to trans EOF results from a net ionic current flow cis to trans over a total ionic current flow, also referred to as a relative net current flow cis to trans, from about −0.99 to about −0.9, about −0.99 to about −0.8, about −0.99 to about −0.6, about −0.99 to about −0.4, about −0.99 to about −0.2, about −0.99 to about 0, about −0.99 to about 0.2, about −0.99 to about 0.4, about −0.99 to about 0.6, about −0.99 to about 0.8, about −0.99 to about 0.99, about −0.9 to about −0.8, about −0.9 to about −0.6, about −0.9 to about −0.4, about −0.9 to about −0.2, about −0.9 to about 0, about −0.9 to about 0.2, about −0.9 to about 0.4, about −0.9 to about 0.6, about −0.9 to about 0.8, about −0.9 to about 0.99, about −0.8 to about −0.6, about −0.8 to about −0.4, about −0.8 to about −0.2, about −0.8 to about 0, about −0.8 to about 0.2, about −0.8 to about 0.4, about −0.8 to about 0.6, about −0.8 to about 0.8, about −0.8 to about 0.99, about −0.6 to about −0.4, about −0.6 to about −0.2, about −0.6 to about 0, about −0.6 to about 0.2, about −0.6 to about 0.4, about −0.6 to about 0.6, about −0.6 to about 0.8, about −0.6 to about 0.99, about −0.4 to about −0.2, about −0.4 to about 0, about −0.4 to about 0.2, about −0.4 to about 0.4, about −0.4 to about 0.6, about −0.4 to about 0.8, about −0.4 to about 0.99, about −0.2 to about 0, about −0.2 to about 0.2, about −0.2 to about 0.4, about −0.2 to about 0.6, about −0.2 to about 0.8, about −0.2 to about 0.99, about 0 to about 0.2, about 0 to about 0.4, about 0 to about 0.6, about 0 to about 0.8, about 0 to about 0.99, about 0.2 to about 0.4, about 0.2 to about 0.6, about 0.2 to about 0.8, about 0.2 to about 0.99, about 0.4 to about 0.6, about 0.4 to about 0.8, about 0.4 to about 0.99, about 0.6 to about 0.8, about 0.6 to about 0.99, or about 0.8 to about 0.99.

In some embodiments, a cis to trans EOF results from a net ionic current flow cis to trans over a total ionic current flow, also referred to as a relative net current flow cis to trans, of about −0.99, about −0.95, about −0.9, about −0.8, about −0.7, about −0.6, about −0.5, about −0.4, about −0.3, about −0.2, about −0.1, about 0.0, about 0.1, about 0.2, about 0.3, about 0.4, about 0.5, about 0.6, about 0.7, about 0.8, about 0.9, about 0.95, or about 0.99.

Suitably, the nanopore system can have an ion-selectivity P(+)/P(−) of greater than 2.0 or less than 0.5, greater than 2.5 or less than 0.4, greater than 3.0 or less than 0.33.

In some embodiments, a pore can comprise a relative ion selectivity P(+)/P(−) of at least about 0.1, at least about 0.2, at least about 0.3, at least about 0.4, at least about 0.5, at least about 0.6, at least about 0.7, at least about 0.8, at least about 0.9, at least about 1, at least about 2, at least about 3, at least about 4, at least about 5, or greater than about 5 under an applied voltage difference across the membrane. In some embodiments, a pore can comprise a relative ion selectivity P(+)/P(−) of at most about 5, at most about 4, at most about 3, at most about 2, at most about 1, at most about 0.9, at most about 0.8, at most about 0.7, at most about 0.6, at most about 0.5, at most about 0.4, at most about 0.3, at most about 0.2, at most about 0.1, or less than about 0.1 under an applied voltage difference across the membrane.

In some embodiments, a pore can comprise a relative ion selectivity P(+)/P(−) from about 0.1 to about 5 under an applied voltage difference across the membrane. In some embodiments, a pore can comprise a relative ion selectivity P(+)/P(−) from about 0.1 to about 0.2, about 0.1 to about 0.3, about 0.1 to about 0.4, about 0.1 to about 0.5, about 0.1 to about 1, about 0.1 to about 1.5, about 0.1 to about 2, about 0.1 to about 2.5, about 0.1 to about 3, about 0.1 to about 4, about 0.1 to about 5, about 0.2 to about 0.3, about 0.2 to about 0.4, about 0.2 to about 0.5, about 0.2 to about 1, about 0.2 to about 1.5, about 0.2 to about 2, about 0.2 to about 2.5, about 0.2 to about 3, about 0.2 to about 4, about 0.2 to about 5, about 0.3 to about 0.4, about 0.3 to about 0.5, about 0.3 to about 1, about 0.3 to about 1.5, about 0.3 to about 2, about 0.3 to about 2.5, about 0.3 to about 3, about 0.3 to about 4, about 0.3 to about 5, about 0.4 to about 0.5, about 0.4 to about 1, about 0.4 to about 1.5, about 0.4 to about 2, about 0.4 to about 2.5, about 0.4 to about 3, about 0.4 to about 4, about 0.4 to about 5, about 0.5 to about 1, about 0.5 to about 1.5, about 0.5 to about 2, about 0.5 to about 2.5, about 0.5 to about 3, about 0.5 to about 4, about 0.5 to about 5, about 1 to about 1.5, about 1 to about 2, about 1 to about 2.5, about 1 to about 3, about 1 to about 4, about 1 to about 5, about 1.5 to about 2, about 1.5 to about 2.5, about 1.5 to about 3, about 1.5 to about 4, about 1.5 to about 5, about 2 to about 2.5, about 2 to about 3, about 2 to about 4, about 2 to about 5, about 2.5 to about 3, about 2.5 to about 4, about 2.5 to about 5, about 3 to about 4, about 3 to about 5, or about 4 to about 5 under an applied voltage difference across the membrane.

In some embodiments, a pore can comprise a relative ion selectivity $P(+)/P(-)$ of about 0.1, about 0.2, about 0.3, about 0.4, about 0.5, about 0.6, about 0.7, about 0.8, about 0.9, about 1, about 2, about 3, about 4, or about 5 under an applied voltage difference across the membrane.

Also provided is a nanopore system for translocating an analyte through a nanopore, comprising:

(a) a membrane having nanopore therein, said membrane separating a chamber into a cis side and a trans side, wherein the analyte is to be added to the cis side and translocated through the nanopore to the trans side;

(b) on the cis side of said chamber an analyte captured by a protein translocase, which can bind and translocate the analyte through the nanopore in a sequential order, (c) mechanisms for providing a voltage difference between the cis side and the trans side of the membrane, wherein the nanopore system has a cis to trans electro-osmotic force (EOF) resulting from a net ionic current flow cis-to-trans, so that the analyte is captured in the nanopore and the nanopore can be located on the top of the nanopore the translocase controlling the translocation, for example resulting from an $I_{rel}$ of greater than 0.2 or less than −0.2, greater than 0.3 or less than −0.3, greater than 0.35 or less than −0.35. In some embodiments, the $I_{rel}$ can be from about −0.4 to about 0.4. In some cases, the $I_{rel}$ can be at least about −0.4, at least about −0.35, at least about −0.3, at least about −0.25, at least about −0.2, at least about −0.15, at least about −0.10, at least about −0.05, at least about 0, at least about 0.05, at least about 0.10, at least about 0.15, at least about 0.20, at least about 0.25, at least about 0.30, at least about 0.35, at least about 0.40, or more than 0.40. In some cases, the $I_{rel}$ can be at most about 0.40, at most about 0.35, at most about 0.30, at most about 0.25, at most about 0.20, at most about 0.15, at most about 0.10, at most about 0.05, at most about 0, at most about −0.05, at most about −0.10, at most about −0.15, at most about −0.20, at most about −0.25, at most about −0.30, at most about −0.35, at most about −0.40, or less than −0.40. In some cases, the $I_{rel}$ can be about −0.4, about −0.35, about −0.30, about −0.25, about −0.20, about −0.15, about −0.10, about −0.05, about 0, about 0.05, about 0.10, about 0.15, about 0.20, about 0.25, about 0.30, about 0.35, or about 0.40.

In a specific aspect, a nanopore system of the present disclosure has an ion-selectivity $P(+)/P(-)$ of greater than 2.0 or less than 0.5, greater than 2.5 or less than 0.4, greater than 3.0 or less than 0.33.

The present disclosure provides a method, system, or device that may rely on a dominant cis-to-trans EOF in conjunction with a translocase on the cis side of a nanopore.

In some cases, EPF may be the dominant process driving capture and translocation in nanopore systems. Hence, all previous demonstrations have either used chosen model polypeptides (having a net charge that aids EPF), or modified the polypeptides with highly charged tags (e.g. adding polyanion tags), so that the EPF forces acting on the polypeptides are in the cis-to-trans direction to drive translocation.

For example, WO2021/111125 relates to methods of characterising a target polypeptide by forming a conjugate of the target polypeptide with a highly charged polynucleotide and using a polynucleotide-handling protein, to control the movement of the conjugate with respect to a nanopore. Hence, in this approach the conjugate including the polypeptide section passes through a nanopore by virtue of a polynucleotide-handling protein, such as a helicase, moving along the polynucleotide extension. The present disclosure provides methods utilizing a protein translocase (in concert with electroosmotic flow). In some cases, the peptides may not couple to a charged moiety.

In some embodiments, the EOF can be employed in the nanopore system of the present disclosure. Where EOF has previously been employed in nanopore systems, it has most often been either in the trans-to-cis direction acting against a cis-to-trans EPF (slowing down the EPF driven translocation), or in the cis-to-trans direction in combination with a cis-to-trans EPF to aid translocation. Some previous studies have shown the capture of neutral or weakly charged small molecules or small polymers in nanopores via weak electro-osmotic forces (https://doi.org/10.1073/pnas.2531778100; https://pubs.acs.org/doi/full/10.1021/ja4026193; https://doi.org/10.1063/1.2723088). The present disclosure provides methods for capturing and/or translocating polymer analytes (e.g., long and/or complex polymers) using cis-to-trans EOF that is capable of overcoming trans-to-cis EPF acting in the opposite direction. The polymer analytes may comprise a contour length greater than the length of the nanopore.

Furthermore, it has heretofore not been considered possible to use a motor protein (e.g., a translocase) in solution on the cis side of a nanopore to controllably feed an analyte into a nanopore, as the strand may not be pulled by the forces and may clog up the nanopore or be ejected back into the cis side of the membrane. The approach may resemble trying to push cooked spaghetti down a plug hole. See for example WO2013/123379 which proposes a nanopore system for translocating a protein from cis to trans through a nanopore, wherein a protein translocase is present on at least one side of the nanopore. Notably however, WO2013/123379 only provides experimental data for systems comprising a translocase on the trans side, which data correspond to Nivala et al. (Nat. Biotechnol. 2013; 31(3):247-250) reporting a nanopore sensor based on alpha-hemolysin (aHL) wherein ClpX translocase is present in the trans solution. The theoretical embodiment proposed WO2013/123379 for having a protein translocase (ClpX) located on the cis side requires fusion of the aHL nanopore to a so-called "docking" protein (ClpP) to allow for non-covalent docking of the translocase onto the nanopore subunits. For this system to work, the axial pores of the translocase and the nanopore can be aligned in the correct orientation. That is, ClpX can be bound to aHL in such a way that as the protein substrate is captured from solution and driven through the ClpX central cavity, it then directly enters into the aHL hemolysin upper lumen and is eventually forced through the entire nanopore.

Thus, the present disclosure provides for the first time an analyte sensing system wherein a translocase functions on top ("top" referring to the entrance side or face of the nanopore on the side of membrane in which the translocase is added) of nanopores without nanopore modification with docking protein(s) or other type of accessory element(s) to translocate a diverse repertoire of complex peptides. Rather, the novel system relies on arranging specific strong electro-osmotic mechanisms in the direction of translocation.

In one embodiment, the present disclosure provides a method for translocating a target protein through a nanopore, comprising:

(a) providing a device comprising a nanopore in a membrane separating a fluidic chamber into a cis side and a trans side;

(b) allowing a protein translocase in solution to capture and form a complex with the target protein to be translocated;

(c) contacting the translocase-target protein complex with the cis side of the nanopore;

(d) wherein the nanopore system has an ion selectivity P+/P− of greater than 3.0 or less than 0.3, so that the target protein is captured in the nanopore with the translocase on top of the nanopore controlling the translocation.

In some embodiments, an electroosmotic flow that generates a force may pull the analyte through the nanopore against any opposing EPF, therein retaining the protein translocase on top of the nanopore until the analyte is released. Presumably, in a method of the present disclosure, an analyte is pulled through the nanopore against any opposing EPF while the protein translocase is retained on top of the nanopore for the duration of the translocation event and then released so that another analyte can bind.

In another aspect of the present disclosure, provided herein is a method comprising: providing a nanopore system. The nanopore system may comprise a membrane comprising a nanopore. In some cases, the membrane may separate the fluidic chamber into a cis side and a trans side. A non-nucleic acid based polymer analyte may also be provided. The non-nucleic acid based polymer analyte may be contacted with a translocase on the cis side of the fluidic chamber. The analyte and the translocase may generate a complex. The non-nucleic acid based polymer analyte may translocate from the cis side to the trans side using a electro-osmotic force. The electro-osmotic force may maintain the translocase of the complex at a cis side entrance of a channel of the nanopore.

In another aspect of the present disclosure, provided herein is a system comprising: providing a nanopore system. The nanopore system may comprise a membrane comprising a nanopore. In some cases, the membrane may separate the fluidic chamber into a cis side and a trans side. A non-nucleic acid based polymer analyte may also be provided. The non-nucleic acid based polymer analyte may be contacted with a translocase on the cis side of the fluidic chamber. The analyte and the translocase may generate a complex. The non-nucleic acid based polymer analyte may translocate from the cis side to the trans side using an electro-osmotic force. The electro-osmotic force may couple the translocase of the complex at a cis side entrance of a channel of the nanopore. In some embodiments, the nanopore can comprise additional structures on the cis side of the membrane. In some embodiments, the nanopore can comprise additional structures on the trans side of the membrane. In some cases, the nanopore can comprise additional structures on the cis side of the membrane and on the trans side of the membrane. In some cases, the additional structures can comprise nucleic acid scaffold molecules. In some cases, the nucleic acid scaffold can be a DNA scaffold. In some cases, the nucleic acid scaffold can be an RNA scaffold. In some cases, the additional structures can comprise proteases. In some cases, the proteases can comprise serine proteases, thrombin, cysteine protease, metalloproteinase, chymotrypsin, trypsin, papain, subtilisin, or any combination thereof. In some cases, the additional structures can comprise docking proteins. In some cases, the docking proteins can comprise ClpP, TatA, TatB, TatC, Tim50, Tim23, Tim17, or any combination thereof.

In one aspect, the translocase-analyte complex is formed in solution in the cis side of the fluidic chamber. Hence, operations b and c may both take place in the cis compartment.

In one embodiment, a net cis-to-trans EOF is achieved by modulating: (i) the pH, (ii) type and/or concentration of a salt and/or osmotic pressure across the membrane of the nanopore system, (iii) by modification (e.g. genetic engineering) or design of the nanopore charge, or any combination thereof. The dominant EOF is arranged by modification of the nanopore and/or asymmetric salt distribution between the cis and trans side of the chamber.

In some embodiments, the system has a cation-based relative current EOF of at least 3.0 in the cis to trans direction. There may be a negative applied voltage at the trans side (e.g., wherein the system comprises a cation-selective (mutant) nanopore).

In another aspect, the translocase-analyte complex is formed in solution during a separate operation prior to adding the complex to the cis side of the fluidic chamber to contact the nanopore. This approach allows for the use of optimal conditions for binding (complex formation) of translocase and analyte. For example, in this pre-mixing (preloading) operation a higher concentration of both components, different salt conditions, temperature, pH, co-factors etc, may be chosen than what is typically used in (the cis chamber of) a nanopore sensor system. The premixture may be part of a kit that can be coupled to analytes of interest. The premixture may be added in a diluted form into the cis chamber.

In one embodiment, the nanopore is a solid state nanopore or a biological nanopore, having an inner pore constriction with a diameter in the range of 0.5-2 nm. In some cases, a solid state nanopore can be a nanopore made from synthetic materials. In some cases, a biological nanopore can be a nanopore found in nature.

In some embodiments, the nanopore may be a biological nanopore. The nanopore may be an alpha-helical or beta-barrel oligomeric pore forming toxin or porin. The nanopore is suitably selected from the group consisting of Aerolysin (Aer), Cytolysin K (CytK), MspA, alpha-hemolysin (aHL), CsgG, Fragaceatoxin C (FraC), Lysenin, phage derived portal proteins (Phi29, G20c, etc) or a mutant thereof. In certain aspects, the nanopore is selected from the mutant CytK nanopores listed in Table 2.

In some cases, the nanopore can be built from elements of existing nanopores (see e.g. WO2021/101378) or developed de novo using predictive protein engineering software (see e.g. Shimizu et al. 2022, Nature Nanotechnology volume 17, pg. 67-75).

In some embodiments, the nanopore system of the present disclosure can utilize any biological nanopore, synthetic nanopore, recombinant nanopore, or any combination thereof. In some cases, the biological nanopore, synthetic nanopore, recombinant nanopore, or any combination thereof can function in the nanopore system of present disclosure without being modified.

In one embodiment, the protein translocase is an NTP-driven Unfoldase, an AAA+ enzyme. The protein translocase may be selected from the group consisting of ATP-dependent Clp protease ATP-binding subunit clpX (ClpX), ATP-dependent Clp protease ATP-binding subunit clpA (ClpA), Pan, LON, VAT, AMA, 854, MBA, SAMP, ATP-dependent Clp protease ATP-binding subunit clpC (ClpC), ATP-dependent Clp protease ATP-binding subunit clpE (ClpE), HsIU, (ClpY), LonA, LonB, FtsH, Mpa, Cpa, Msp1, SecA, and functional homologs, orthologs or paralogs thereof. In some cases, translocases may comprise ClpX and/or ClpA. In some cases, the translocase can comprise a translocase that is specific for peptides, proteins, polypeptides, or any combination thereof. In some cases, the translocase can comprise a translocase that is specific for nucleic acid molecules.

In some embodiments, the non-nucleic acid based polymer analyte may be a target protein or peptide. The analyte may be in its native, unmodified form. For example, translocases that are promiscuous or engineered to remove binding specificity can be mixed with unmodified analytes to enable binding/loading. Such loading methods might lead to a mixture of analyte translocase complexes with some translocases loaded at the C-termini of the analyte and moving in the C-to-N direction, and/or some loading at the N-termini of the analyte moving in the N-to-C direction. The translocase has a binding specificity for either the N- or C-terminus of a analyte, so that complexes have translocases that are moving in a common direction. Translocases acting on unmodified analytes can increase the capture in the nanopore by unfolding the analyte and creating free termini. Complexes based on loading of translocases onto unmodified analytes may have a single translocase or multiple translocases located at random points along the analyte at the time of capture in the nanopore. When the complexes are captured in the nanopore the bound translocase may act to feed the analyte into the nanopore or pull the analyte out of the nanopore depending on which end of the analyte was captured and the orientation of the translocase atop the nanopore.

In another aspect of the present disclosure, provided herein is a method comprising: providing a nanopore system. The nanopore system may comprise a membrane comprising a nanopore. In some cases, the membrane may separate the fluidic chamber into a cis side and a trans side. A non-nucleic acid based polymer analyte may also be provided. The non-nucleic acid based polymer analyte may comprise a leader construct. The leader construct may comprise a stall motif, a block motif, a coupling motif, a recognition motif, a capture motif, or any combination thereof. In some cases, a translocase may also be provided. The non-nucleic acid based polymer analyte may translocate from the cis side to the trans side of the fluidic chamber.

In another aspect of the present disclosure, provided herein is a system comprising: providing a nanopore system. The nanopore system may comprise a membrane comprising a nanopore. In some cases, the membrane may separate the fluidic chamber into a cis side and a trans side. A non-nucleic acid based polymer analyte may also be provided. The non-nucleic acid based polymer analyte may comprise a leader construct. The leader construct may comprise a stall motif, a block motif, a coupling motif, a recognition motif, a capture motif, or any combination thereof. In some cases the leader (or tail) construct/s may comprise a membrane binding motif. In some cases, a translocase may also be provided. The non-nucleic acid based polymer analyte may translocate from the cis side to the trans side of the fluidic chamber.

In another aspect of the present disclosure, provided herein is a system comprising: providing a nanopore system. The nanopore system may comprise a membrane comprising a nanopore. In some cases, the membrane may separate the fluidic chamber into a cis side and a trans side. A non-nucleic acid based polymer analyte may also be provided. In some cases, the cis side can have a first solution. In some cases, the trans side can have a second solution. The first solution and the second solution may be configured to translocate the non-nucleic acid based polymer analyte. The system can further comprise a controller. In some cases, the controller can be operatively coupled to the fluidic chamber and the nanopore. The controller may be configured to detect one or more signals associated with at least one characteristic of a leader construct. The controller may be configured to detect one or more signals associated with at least one characteristic of the non-nucleic acid based polymer analyte. The controller may be configured to detect one of more signals associated with at least one characteristic of a leader construct and one or more signals associated with at least one characteristic of the non-nucleic acid based polymer analyte. In some cases, the one or more signals may be detected during translocation of the non-nucleic acid based polymer analyte. In some cases, the one or more signals may be detected subsequent the translocation of the non-nucleic acid based polymer analyte. In some cases, the one or more signals may be detected during or subsequent the translocation of the non-nucleic acid based polymer analyte. In some cases, the leader construct can be coupled to the non nucleic acid based polymer analyte. In some cases, the non-nucleic acid based polymer analyte can translocate through the nanopore using a nanopore. In some cases, the leader construct can comprise a stall motif, a block motif, a coupling motif, a recognition motif, a capture motif, or any combination thereof.

In other embodiments of the present disclosure the analyte comprises "leader" and/or "tail" extensions at the termini of the protein. In certain aspects of the present disclosure, the analyte comprises a leader construct that can preload, and/or optionally stall, a protein translocase. For example, preloading is performed outside of the (cis chamber of) the nanopore system, after which the analyte-translocase complex is introduced in the cis chamber. In another embodiment the analyte can be coupled to a leader construct that can load, and/or optionally stall, a protein translocase when the two are mixed together in the cis chamber of the system. In some embodiments, the analyte can be coupled to a leader construct that can load, and/or optionally stall, a protein translocase when the two are mixed together in the trans chamber of the system. The leader construct may be an exogenous sequence. It comprises (i) a recognition motif for the protein translocase to direct binding to a specific location, and/or to enable more efficient binding and loading. It may further comprise one or more of the following elements: (ii) capture motif; (iii) stall motif; (iv) block motif; (v) coupling motif.

In another embodiment the translocase is coupled to the nanopore. In the system of the present disclosure the translocase may not be coupled to the top of the nanopore to optimally feed the analyte into the nanopore. Instead the strong cis-to-trans EOF of the present disclosure enables the portion of an analyte extruded from the translocase to be captured into the nanopore and translocated, which will in turn pull the translocase atop the pore, whereupon it will continue to control the movement of the extruded analyte. In this embodiment the analyte may not have stall or capture motifs due to the proximity of the extruded analyte to the nanopore entrance.

A method according to present disclosure may further comprise measuring ionic current changes caused by translocation of the analyte through the nanopore. Current changes may be measured for states of (i) open channel, (ii) capture of the analyte by the nanopore, and/or (iii) passage of an analyte from (ii) through the nanopore. For example, the method of measuring ionic current changes comprises detecting differences between states (i), (ii) and (iii). In a specific aspect, the measuring comprises measuring differences during state (iii) caused by amino acid composition or structure of the analyte passing through the nanopore. The method suitably comprises taking one or more measurements characteristic of the analyte. The one or more measurements may be characteristic of one, two, three, four or five or more characteristics of the analyte. One or more characteristics are selected from (i) length of the analyte; (ii) analyte identity; (iii) analyte sequence; (iv) secondary or tertiary structures of the analyte; and (v) whether the analyte was modified or not. Any combination of (i) to (v) may be measured in accordance with the present disclosure.

A further embodiment of the present disclosure relates to a nanopore system for translocating an analyte through a nanopore, comprising:

(a) a membrane having nanopore therein, said membrane separating a chamber into a cis side and a trans side, wherein the analyte is to be added to the cis side and translocated through the nanopore to the trans side; (b) on the cis side of said chamber an analyte captured by a protein translocase, which can bind and translocate the analyte through the nanopore in a sequential order; and (c) element for providing a voltage difference between the cis side and the trans side of the membrane. In some cases, the element in (c) can comprise a pair of electrodes.

In some embodiments, the nanopore system is further characterized by a cis to trans electro-osmotic force (EOF) resulting from a net ionic current flow cis-to-trans, so that the analyte is captured in the nanopore with on top of the nanopore the translocase controlling the translocation. The nanopore system has a cis to trans EOF resulting from a net ionic current flow cis-to-trans over total ionic current flow of greater than 0.2 or less than −0.2, more greater than 0.3 or less than −0.3, greater than 0.35 or less than −0.35.

In a specific aspect, the nanopore system has an ion-selectivity $P_{(+)}/P_{(-)}$ of greater than 2.0 or less than 0.5, greater than 2.5 or less than 0.4, greater than 3.0 or less than 0.33, or even greater than 3.5 or less than 0.2.

In some embodiments, a voltage difference can be provided in various ways, for example one circuit can both apply the voltage and measure the current; or the system contains a first circuit to apply a voltage and a second circuit to measure the current. It is also possible to create a voltage difference with an asymmetric salt across the membrane. For example, the device comprises a circuit for providing a voltage between the cis side and the trans side and for measuring ionic current flowing through the nanopore. See FIG. 1. A negative voltage is applied on the trans side.

In some embodiments, the system may further comprise methods for measuring a signal based on ionic current flowing through the nanopore during a period of time of translocation. These measuring mechanisms are set up to detect changes in the signal that reflect characteristics of the analyte as it is translocated. In some embodiments, the analyte measured can be a protein. In some cases, the characteristic of the protein measured can comprise an amino acid sequence of the protein, one or more post-translational modifications of the protein, amino acid mutations in the sequence of the protein, domain structures of the protein, length of the protein, net charge of the protein, or conformation of the protein. In some embodiments, the analyte measured can be a nucleic acid molecule. In some cases, the characteristic of the nucleic acid molecule measured can comprise a nucleotide sequence of the nucleic acid molecule, nucleotide mutations in the sequence of the nucleic acid molecule, methylation of the nucleic acid molecule, acetylation of the nucleic acid molecule, length of the nucleic acid molecule, net charge of the nucleic acid molecule, or conformation of the nucleic acid molecule. In some embodiments, the analyte measured can be an oligosaccharide. In some cases, the characteristic of the oligosaccharide measured can comprise a sequence of the oligosaccharide, the length of the oligosaccharide, the net charge of the oligosaccharide, presence or absence of coupled lipids, presence or absence of coupled peptides, or structure of the oligosaccharide. In some embodiments, the analyte measured can be a lipid molecule. In some cases, the characteristic of the lipid measured can comprise length of the lipid, the net charge of the lipid, or a structure of a lipid.

The system may employ alternative mechanisms of measuring the voltage-current properties of the nanopore system, such as those that employ fluorescence probes of ionic flux or field effect transistor systems than measure changes in voltage. However, there are also other suitable detection methods, such as tunneling, surface enhanced raman, plasmonics, and other spectroscopic methods that do not measure the ionic current and instead measure the properties of the analyte in the nanopore directly.

Also provided is an analytical device comprising one or more nanopore systems as herein disclosed, e.g. in the form of an array.

A further embodiment relates the use of a method, nanopore system or device according to the present disclosure for characterizing at least one feature of an analyte, for detection and analysis of one or more analyte(s) at the single molecule level. In one aspect, the use comprises of characterizing the amino acid sequence of a non-denatured analyte or a mixture of different non-denatured analytes.

In some embodiments, methods are provided relating to the analysis of an analyte.

In some embodiments, methods are provided relating to the analysis of an analyte.

In some embodiments, a change in ionic current can be measured while the analyte translocates through the nanopore. In some cases, the change in ionic current can be measured by a voltage based chip. In some cases, the voltage based chip can measure the voltage and/or change in current across the nanopore. In some cases, the voltage based chip can be a trans electrode (e.g. electrodes adjacent to the membrane/nanopore to measure the voltage across the nanopore).

The characterisation methods may involve measuring the ion current flow through the pore, typically by measurement of a current. Alternatively, the ion flow through the pore may be measured optically, such as disclosed by Heron et al: J. Am. Chem. Soc. 9 Vol. 131, No. 5, 2009. Therefore the apparatus may also comprise an electrical circuit capable of applying a potential and measuring an electrical signal across the membrane and pore. The characterisation methods may be carried out using a patch clamp or a voltage clamp. The characterization methods can involve the use of a voltage clamp.

In some embodiments, an analyte comprises a polymer analyte. The analyte can comprise a nucleic acid based polymer analyte or a non-nucleic acid based polymer analyte. The analyte can be of synthetic, semi-synthetic, or biological origin. For example, a synthetic analyte may comprise an analyte constructed by a non-biological chemical process, such as polyethylene glycol (PEG), or a synthetically constructed DNA molecule. For example, a synthetic analyte may comprise an analyte constructed by a non-biological chemical process, such as polyethylene glycol (PEG), synthetically constructed peptides of proteins, or a synthetically constructed DNA molecule. A biological analyte can comprise an analyte produced by a biological process, such as a protein produced by a cell or by systems employing cellular (or cellular derived) components (e.g. enzymatic in vitro translation systems). A biological analyte can comprise an analyte produced by a biological process, such as a protein produced by a cell. A semi-synthetic analyte can comprise portions created by biological and non-biological origins, for example, a biologically-produced protein conjugated to a PEG molecule. Possible electrical measurements can include current measurements, impedance measurements, tunneling, electron tunneling measurements (Ivanov A P et al., Nano Lett. 2011 Jan. 12; 11(1): 279-85), FET measurements (International Application WO2005/124888), voltage FET measurements, or any combination thereof. In some embodiments, the signal may be electron tunneling across a solid state nanopore or a voltage FET measurement across a solid state nanopore.

The characterisation methods may involve measuring the ion current flow through the pore, by measurement of a current. Alternatively, the ion flow through the pore may be measured optically, such as disclosed by Heron et al: J. Am. Chem. Soc. 9 Vol. 131, No. 5, 2009. Therefore the apparatus may also comprise an electrical circuit capable of applying a potential and measuring an electrical signal across the membrane and pore. The characterisation methods may be carried out using a patch clamp or a voltage clamp. The characterisation methods preferably involve the use of a voltage clamp.

The characterisation methods may be carried out on an array of nanopores or wells where each array comprises 128, 256, 512, 1024, 2000, 3000, 4000, 6000, 10000, 12000, 15000 or more nanopores or wells.

The characterisation methods may involve the measuring of a current flowing through the pore. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, 20 mV, +50 mV, +100 mV, +150 mV, +200 mV, +300 mV and +400 mV. The voltage used is more preferably in the range 20 mV to 240 mV and most preferably in the range of 120 mV to 220 mV. It is possible to increase discrimination between different characteristics of the analyte by a pore by using an increased applied potential.

In some embodiments, an analyte comprises a polymer analyte. The analyte can comprise a nucleic acid based polymer analyte or a non-nucleic acid based polymer analyte. The analyte can be of synthetic, semi-synthetic, or biological origin. For example, a synthetic analyte may comprise an analyte constructed by a non-biological chemical process, such as polyethylene glycol (PEG), or a synthetically constructed DNA molecule. A biological analyte can comprise an analyte produced by a biological process, such as a protein produced by a cell. A semi-synthetic analyte can comprise portions created by biological and non-biological origins, for example, a biologically-produced protein conjugated to a PEG molecule.

In some embodiments, an analyte comprises a protein (e.g., a polypeptide) or peptide. A protein or peptide can comprise a folded state, an unfolded state, or intermediate states thereof (e.g., a partially unfolded state). A folded state comprises a state of a protein or peptide in which the polymer is at a low-energy state such that the protein or peptide maintains a two or three dimensional structure. This low-energy state can be based on the interactions of the amino acids of the peptide or protein with each other. An unfolded state can comprise a state of a protein or peptide in which the polymer is at a high-energy state such that the protein or peptide does not maintain a two or three dimensional structure. An intermediate state between a folded and unfolded state can be an energy state at which a portion or portions of the peptide or protein may maintain a two or three dimensional structure, and other portions of the peptide or protein may not maintain a two or three dimensional structure. In some embodiments, a protein (e.g., polypeptide) can comprise a folded protein structure. In some embodiments, a peptide can comprise a linear structure. In some cases, a peptide can comprise a portion of a protein.

In some embodiments, the analyte can comprise a nucleic acid molecule. In some cases, the nucleic acid molecule can be a DNA molecule. In some cases, the DNA molecule can be genomic DNA, mitochondrial DNA, or any combination thereof. In some cases, the nucleic acid molecule can be a RNA molecule. In some cases, the RNA molecule can be transfer RNA (tRNA), messenger RNA (mRNA), ribosomal RNA (rRNA), small nuclear RNA (snRNA), snoRNA (small nucleolar RNA (snoRNA), piwi-interacting RNA (piRNA), small interfering RNA (siRNA), micro RNA (miRNA), or any combination thereof. In some embodiments, the analyte can comprise a lipid. In some cases, the lipid can be oleic acid, linoleic acid, palmitic acid, docosahexaenoic acid, eicosapentaenoic acid, or any combination thereof. In some embodiments, the analyte can comprise an oligosaccharide. In some cases, the oligosaccharide can be a glycoprotein, inulin, lactose, mannose, sucrose, fructooligosaccharide, monosaccharide, carbohydrate, maltose, prebiotics, galactooligosaccharides, glycan, chitosan, pentasaccharide, or any combination thereof. In some embodiments, the analyte can comprise a polysaccharide. In some cases, the polysaccharide can be starch, glycogen, galactogen, inulin, arabinoxylans, cellulose, chitin, pectins, or any combination thereof.

In some embodiments, the analyte can comprise a non-nucleic acid based polymer analyte. In some embodiments, a portion of non-nucleic acid based polymer analyte can comprise a nucleic acid molecule. In some cases, the portion of the non-nucleic acid polymer analyte can be from 0% to about 100% of the non-nucleic acid polymer analyte. In some cases, the portion of the non-nucleic acid polymer analyte can be at least about 0%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% of the non-nucleic acid polymer analyte. In some cases, the portion of the non-nucleic acid polymer analyte can be at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, or at most about 0% of the non-nucleic acid polymer analyte. In some cases, the portion of the non-nucleic acid polymer analyte can be about 0%, about 5%, about 10%, about 15%, about 20%, about 25%, about 30%, about 35%, about 40%, about 45%, about 50%, about 55%, about 60%, about 65%, about 75%, about 80%, about 85%, about 90%, about 95%, or about 100% of the non-nucleic acid polymer analyte.

In some embodiments, a portion of non-nucleic acid based polymer analyte can comprise an oligosaccharide molecule. In some cases, the portion of the non-nucleic acid polymer analyte can be from 0% to about 100% of the non-nucleic acid polymer analyte. In some cases, the portion of the non-nucleic acid polymer analyte can be at least about 0%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% of the non-nucleic acid polymer analyte. In some cases, the portion of the non-nucleic acid polymer analyte can be at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, or at most about 0% of the non-nucleic acid polymer analyte. In some cases, the portion of the non-nucleic acid polymer analyte can be about 0%, about 5%, about 10%, about 15%, about 20%, about 25%, about 30%, about 35%, about 40%, about 45%, about 50%, about 55%, about 60%, about 65%, about 75%, about 80%, about 85%, about 90%, about 95%, or about 100% of the non-nucleic acid polymer analyte.

The analyte can comprise a contour length. The analyte can comprise a linear length. The linear length can be the length of an analyte in an unfolded state. An analyte in an unfolded state may or may not comprise secondary structure elements. Secondary structure elements may include α-helices, β-helices, coils, or β-sheets. Helices may be left handed or right handed. An analyte may in an unfolded state may be fully or partially unfolded (e.g., an intermediate state of unfolding). The contour length can be the length of a polymer analyte when two termini of the polymer analyte are fully extended from each other. In some embodiments, an analyte can comprise a structured portion, an unstructured portion, a denatured portion, a partially denatured portion, or combinations thereof. In some embodiments, an analyte can comprise between about 1 to about 6 termini. In some embodiments, an analyte can comprise at least about 1, at least about 2, at least about 3, at least about 4, at least about 5, or at least about 6 termini, or more. In some embodiments, the analyte can comprise at most about 6 termini, at most about 5 termini, at most about 4 termini, at most about 3 termini, at most about 2 termini, at most about 1 terminus, or less. In some embodiments, the analyte can comprise about 1 terminus, about 2 termini, about 3 termini, about 4 termini, about 5 termini, or about 6 termini. In some embodiments, a terminus of an analyte can comprise a structured portion, an unstructured portion, a denatured portion, a partially denatured portion, or combinations thereof.

The analyte can comprise repeating units. The units can comprise peptide units, saccharide units, lipid units, nucleotide units, water-soluble plastic monomers, or combinations thereof. The analyte can comprise a polypeptide, a polysaccharide, a nucleic acid, a water-soluble plastic, or combinations thereof. In some embodiments, the analyte can comprise a charge. The charge can be positive or negative. The charge can be distributed evenly or unevenly across the analyte. In some embodiments, the charge can be the result of an amino acid residue. The amino acid residue can be a natural or mutated residue. In some cases, a mutated amino acid residue can comprise one or more additional chemical groups compared to a natural amino acid. In some embodiments the analyte can comprise a peptide. A peptide can comprise a polypeptide or protein. A protein can be a full length protein or a truncated protein. A truncated protein can be a protein that is shorter in length than when the protein was first made. For example, the protein can be shorter due to cleavage (e.g., by a peptidase) or degradation (e.g., due to acidic or basic conditions). A protein can comprise a sequence that is a native protein sequence or a modified protein sequence. The sequence can be modified by mutation, deletion, or insertion of a sequence. A sequence can be a combination of sequences. For example, first native sequence can be appended to or inserted into a second native sequence to form a third sequence that is a combination of the first and second sequences.

In some embodiments an analyte comprises a protein. In some embodiments an analyte comprises a peptide or polypeptide (e.g., protein). In some embodiments a peptide, polypeptide, or protein can be targeted. A targeted analyte may be a target-peptide, target-polypeptide, or target-protein. A targeted analyte can be an analyte that is combined with a translocase. An analyte can be combined with a translocase to form a complex (e.g., a translocase-analyte complex).

In some embodiments, the analyte and the translocase can be located on the cis side of the membrane. In some cases, the analyte and the translocase can form the complex on the cis side of the membrane. In some embodiments, the analyte and the translocase can form the complex in the nanopore system.

In some embodiments, the analyte and the translocase can be located on the trans side of the membrane. In some cases, the analyte and the translocase can form the complex on the trans side of the membrane.

In some embodiments, the analyte can be contacted with the translocase outside of the nanopore system. In some cases, the analyte and the translocase can form the complex in a separate container from the nanopore system. In some cases, the analyte and translocase complex can be added to the nanopore system.

In some embodiments, the analyte can be a target analyte. In some cases, the target analyte can be a protein. In some cases, the target analyte can be a polypeptide. In some cases, the target analyte can be a peptide. In some cases, the target analyte can be a nucleic acid molecule. In some instances, the nucleic acid molecule can be an RNA molecule. In some instances, the nucleic acid molecule can be an DNA molecule. In some cases, the target analyte can be a polysaccharide. Non-limiting examples of polysaccharides include cellulose, chitin, amylopectin, chitosan, dextran, galactans, lentinan, amylose, amylopectin, starch, hemicellulose, alginic acid, glycosaminoglycan, gellan gum, carrageenan, glycogen, pectins, glucans, inulin, homopolysaccharide, fucoidan, and polydextrose. In some cases, the target analyte can be an oligosaccharide. Non-limiting examples of oligosaccharides include lactose, maltose, sucrose, cellobiose, nigerotriose, maltotriose, melezitose, maltotriulose, raffinose, kestose, nigerotetraose, maltotetraose, lychnose, nystose, sesamose, stachyose, pentasaccharides, fructooligosaccharides, galactooligosaccharides, hexasaccharides, and heptasaccharides. In some embodiments, the target analyte can be a glycosylation. In some cases, the glycosylation can be a N-linked oligosaccharide. In some cases, the glycosylation can be a O-linked oligosaccharide.

In some embodiments, an electro-osmotic flow (also termed an electro-osmotic force, EOF) acts across the membrane in a cis to trans direction or a trans to cis direction. An electro-osmotic flow can be the flow that results from a net flow of a mobile layer of ions along a surface as induced by an applied potential (e.g., applied voltage potential). For example, a charged surface may form a static layer of oppositely charged mobile ions. Under an applied potential the charged mobile ions may be induced to move in the direction of higher potential if negative, or in the direction of lower potential if positive. The flow of charged ions can create a drag on the surrounding solvent (e.g., water) molecules, which in turn can result in a net flow that exerts a force acting on the surrounding molecules, both charged and neutral. For example, in a negatively charged nanopore lumen, an electroosmotic flow can result from a net flow of positive ions in a cis to trans direction (e.g., due to a lower potential on the trans side) causing the surrounding water to flow cis to trans and exert a force on surrounding molecules. The amount of ion flow and the corresponding magnitude of the electroosmotic flow can be influenced by parameters including an ion concentration difference across the membrane, a difference in potential, a net charge of a nanopore lumen, a geometry of a nanopore lumen, or any combinations thereof.

In some embodiments, an electro-osmotic flow can be the flow that results from one or more constrictions present in a nanopore channel. For example, constrictions in a nanopore can affect the flow of some ions (e.g. larger hydrated ions) more than other ions (e.g. smaller hydrated ions). In some embodiments, an electro-osmotic flow can be the flow that results from a net flow of mobile ions along a surface as induced by an applied potential and one or more constrictions present in a nanopore channel.

In some embodiments, an electro-osmotic flow can be created or modified by a difference between a solution on a cis side of a membrane and a solution on a trans side of a membrane. In some cases, the solution on the cis side of the membrane can be a first solution. In some cases, the solution on the trans side of the membrane can be a second solution. The difference can be a difference in concentration of a molecule, including an ion, an electrolyte or an osmolyte.

In some embodiments, a difference between solutions can be a salt asymmetry or an ion asymmetry, wherein one side of a membrane (e.g. a cis side) comprises a different concentration of an ion than the other side (e.g. a trans side). An ion asymmetry can influence an ionic current across a membrane, as described by the Goldman-Hodgkin-Katz equation.

$$I_{(s)} = P_{(S)}z_s^2 * \frac{V_m F^2}{RT} \frac{[S]_{trans} - [S]_{cis} * e^{-z_s \frac{V_m F}{RT}}}{1 - e^{-z_s \frac{V_m F}{RT}}}$$

Where the ionic current ($I(S)$) ion species S across the membrane as a function of the applied potential (Vm): where $P_{(S)}$ is the membrane permeability of ion species S, $z_s$ the valency of the ion, F the Faraday constant, R the gas constant, T the temperature and $[S]_{cis}$ and $[S]_{trans}$ the cis and trans concentrations of an ion species S, respectively. As the difference in concentration of the ions on the cis and trans sides impacts the ionic flux, the combined ionic flux of different species can thus influence an electro-osmotic force as ions flow in different directions across the membrane. This can be used to strengthen or weaken an electro-osmotic force by having a difference in ion concentration between the cis and trans sides that minimizes or maximizes a contribution of the ionic current of the species S to the net ionic flux.

A difference in a concentration of a molecule between two sides of a membrane can modify an electro-osmotic flux by providing a competing or assisting osmotic flux. A difference in concentration across a membrane can create an osmotic gradient, wherein a solvent (e.g., water) may diffuse across a membrane in the direction of a higher concentration of the molecule so as to minimize the difference in concentration between the sides of the membrane. The osmotic gradient can be oriented so as to drive a water flow in the same direction as the electro-osmotic force, or in a different direction. For example, a high ion concentration on a cis side relative to a trans side can create an osmotic gradient that competes with a cis to trans electro-osmotic force, as the osmotic gradient can drive water flow in a trans to cis direction. The ion concentrations may support a cis to trans electro-osmotic flow even if they also provide an osmotic gradient.

In some embodiments, the EOF can be generated by an asymmetric salt distribution between the cis side of the membrane and the trans side of the membrane. In some cases, the concentration of one or more salts on the cis side of the membrane can be different from the concentration of the one or more salts on the trans side of the membrane. In some cases, the concentration of one or more salts on the cis side of the membrane can be higher than the concentration of the one or more salts on the trans side of the membrane. In some cases, the concentration of one or more salts on the cis side of the membrane can be lower than the concentration of one or more salts on the trans side of the membrane. In some cases, the concentration of one or more salts on the trans side of the membrane can be higher than the concentration of the one or more salts on the cis side of the membrane. In some cases, the concentration of one or more salts on the trans side of the membrane can be lower than the concentration of the one or more salts on the cis side of the membrane.

In some cases, the concentration of one or more salts on the cis side of the membrane can be between about 1 nanomolar (nM) to about 1,000 nM. In some instances, the concentration of one or more salts on the cis side of the membrane can be between about 1 nM to about 10 nM, between about 10 nM to about 100 nM, or between about 100 nM to about 1,000 nM. In some cases, the concentration of one or more salts on the cis side of the membrane can be at least about 1 nM, at least about 5 nM, at least about 10 nM, at least about 15 nM, at least about 20 nM, at least about 25 nM, at least about 30 nM, at least about 35 nM, at least about 40 nM, at least about 45 nM, at least about 50 nM, at least about 55 nM, at least about 60 nM, at least about 65 nM, at least about 70 nM, at least about 75 nM, at least about 80 nM, at least about 85 nM, at least about 90 nM, at least about 95 nM, at least about 100 nM, at least about 150 nM, at least about 200 nM, at least about 250 nM, at least about 300 nM, at least about 350 nM, at least about 400 nM, at least about 450 nM, at least about 500 nM, at least about 550 nM, at least about 600 nM, at least about 650 nM, at least about 700 nM, at least about 750 nM, at least about 800 nM, at least about 850 nM, at least about 900 nM, at least about 950 nM, at least about 1,000 nM, or more than 1,000 nM. In some cases, the concentration of one or more salts on the cis side of the membrane can at most about 1,000 nM, at most about 950 nM, at most about 900 nM, at most about 850 nM, at most about 800 nM, at most about 750 nM, at most about 700 nM, at most about 650 nM, at most about 600 nM, at most about 550 nM, at most about 500 nM, at most about 450 nM, at most about 400 nM, at most about 350 nM, at most about 300 nM, at most about 250 nM, at most about 200 nM, at most about 150 nM, at most about 100 nM, at most about 95 nM, at most about 90 nM, at most about 85 nM, at most about 80 nM, at most about 75 nM, at most about 70 nM, at most about 65 nM, at most about 60 nM, at most about 55 nM, at most about 45 nM, at most about 40 nM, at most about 35 nM, at most about 30 nM, at most about 25 nM, at most about 20 nM, at most about 15 nM, at most about 10 nM, at most about 5 nM, at most about 1 nM, or less than 1 nM. In some cases, the concentration of one or more salts on the cis side of the membrane can about 1 nM, about 5 nM, about 10 nM, about 15 nM, about 20 nM, about 25 nM, about 30 nM, about 35 nM, about 40 nM, about 45 nM, about 50 nM, about 55 nM, about 60 nM, about 65 nM, about 70 nM, about 75 nM, about 80 nM, about 85 nM, about 90 nM, about 95 nM, about 100 nM, about 150 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about 850 nM, about 900 nM, about 950 nM, or about 1,000 nM.

In some embodiments, a salt, ion, osmolyte, or electrolyte concentration on the cis side can be at least about 0.01 M, at least about 0.05 M, at least about 0.10 M, at least about 0.20 M, at least about 0.30 M, at least about 0.40 M, at least about 0.50 M, at least about 0.60 M, at least about 0.70 M, at least about 0.80 M, at least about 0.90 M, at least about 1.00 M, at least about 1.10 M, at least about 1.25 M, at least about 1.50 M, at least about 1.75 M, at least about 2 M, at least about 2.5 M, at least about 3 M, at least about 3.5 M, at least about 4 M, at least about 4.5 M, at least about 5 M, or greater than about 5 M. In some embodiments, a salt, ion, osmolyte, or electrolyte concentration on the cis side can be at most about 5 M, at most about 4.5 M, at most about 4 M, at most about 3.5 M, at most about 3 M, at most about 2.5 M, at most about 2 M, at most about 1.75 M, at most about 1.50 M, at most about 1.25 M, at most about 1 M, at most about 0.90 M, at most about 0.80 M, at most about 0.70 M, at most about 0.60 M, at most about 0.50 M, at most about 0.40 M, at most about 0.30 M, at most about 0.20 M, at most about 0.10 M, at most about 0.05 M, at most about 0.01 M, or less than about 0.01 M.

In some embodiments, a salt, ion, osmolyte, or electrolyte concentration on the cis side can be from about 0.01 M to about 5 M. In some embodiments, a salt, ion, osmolyte, or electrolyte concentration on the cis side can be from about 0.01 M to about 0.1 M, about 0.01 M to about 0.5 M, about 0.01 M to about 1 M, about 0.01 M to about 1.5 M, about 0.01 M to about 2 M, about 0.01 M to about 2.5 M, about 0.01 M to about 3 M, about 0.01 M to about 3.5 M, about 0.01 M to about 4 M, about 0.01 M to about 4.5 M, about 0.01 M to about 5 M, about 0.1 M to about 0.5 M, about 0.1 M to about 1 M, about 0.1 M to about 1.5 M, about 0.1 M to about 2 M, about 0.1 M to about 2.5 M, about 0.1 M to about 3 M, about 0.1 M to about 3.5 M, about 0.1 M to about 4 M, about 0.1 M to about 4.5 M, about 0.1 M to about 5 M, about 0.5 M to about 1 M, about 0.5 M to about 1.5 M, about 0.5 M to about 2 M, about 0.5 M to about 2.5 M, about 0.5 M to about 3 M, about 0.5 M to about 3.5 M, about 0.5 M to about 4 M, about 0.5 M to about 4.5 M, about 0.5 M to about 5 M, about 1 M to about 1.5 M, about 1 M to about 2 M, about 1 M to about 2.5 M, about 1 M to about 3 M, about 1 M to about 3.5 M, about 1 M to about 4 M, about 1 M to about 4.5 M, about 1 M to about 5 M, about 1.5 M to about 2 M, about 1.5 M to about 2.5 M, about 1.5 M to about 3 M, about 1.5 M to about 3.5 M, about 1.5 M to about 4 M, about 1.5 M to about 4.5 M, about 1.5 M to about 5 M, about 2 M to about 2.5 M, about 2 M to about 3 M, about 2 M to about 3.5 M, about 2 M to about 4 M, about 2 M to about 4.5 M, about 2 M to about 5 M, about 2.5 M to about 3 M, about 2.5 M to about 3.5 M, about 2.5 M to about 4 M, about 2.5 M to about 4.5 M, about 2.5 M to about 5 M, about 3 M to about 3.5 M, about 3 M to about 4 M, about 3 M to about 4.5 M, about 3 M to about 5 M, about 3.5 M to about 4 M, about 3.5 M to about 4.5 M, about 3.5 M to about 5 M, about 4 M to about 4.5 M, about 4 M to about 5 M, or about 4.5 M to about 5 M.

In some embodiments, a salt, ion, osmolyte, or electrolyte concentration on the cis side can be about 0.01 M, about 0.05 M, about 0.10 M, about 0.20 M, about 0.30 M, about 0.40 M, about 0.50 M, about 0.60 M, about 0.70 M, about 0.80 M, about 0.90 M, about 1.00 M, about 1.10 M, about 1.25 M, about 1.50 M, about 1.75 M, about 2 M, about 2.5 M, about 3 M, about 3.5 M, about 4 M, about 4.5 M, or about 5 M.

In some cases, the concentration of one or more salts on the trans side of the membrane can be between about 1 nanomolar (nM) to about 1,000 nM. In some instances, the concentration of one or more salts on the trans side of the membrane can be between about 1 nM to about 10 nM, between about 10 nM to about 100 nM, or between about 100 nM to about 1,000 nM. In some cases, the concentration of one or more salts on the trans side of the membrane can be at least about 1 nM, at least about 5 nM, at least about 10 nM, at least about 15 nM, at least about 20 nM, at least about 25 nM, at least about 30 nM, at least about 35 nM, at least about 40 nM, at least about 45 nM, at least about 50 nM, at least about 55 nM, at least about 60 nM, at least about 65 nM, at least about 70 nM, at least about 75 nM, at least about 80 nM, at least about 85 nM, at least about 90 nM, at least about 95 nM, at least about 100 nM, at least about 150 nM, at least about 200 nM, at least about 250 nM, at least about 300 nM, at least about 350 nM, at least about 400 nM, at least about 450 nM, at least about 500 nM, at least about 550 nM, at least about 600 nM, at least about 650 nM, at least about 700 nM, at least about 750 nM, at least about 800 nM, at least about 850 nM, at least about 900 nM, at least about 950 nM, at least about 1,000 nM, or more than about 1,000 nM. In some cases, the concentration of one or more salts on the trans side of the membrane can at most about 1,000 nM, at most about 950 nM, at most about 900 nM, at most about 850 nM, at most about 800 nM, at most about 750 nM, at most about 700 nM, at most about 650 nM, at most about 600 nM, at most about 550 nM, at most about 500 nM, at most about 450 nM, at most about 400 nM, at most about 350 nM, at most about 300 nM, at most about 250 nM, at most about 200 nM, at most about 150 nM, at most about 100 nM, at most about 95 nM, at most about 90 nM, at most about 85 nM, at most about 80 nM, at most about 75 nM, at most about 70 nM, at most about 65 nM, at most about 60 nM, at most about 55 nM, at most about 45 nM, at most about 40 nM, at most about 35 nM, at most about 30 nM, at most about 25 nM, at most about 20 nM, at most about 15 nM, at most about 10 nM, at most about 5 nM, at most about 1 nM, or less than 1 nM. In some cases, the concentration of one or more salts on the trans side of the membrane can about 1 nM, about 5 nM, about 10 nM, about 15 nM, about 20 nM, about 25 nM, about 30 nM, about 35 nM, about 40 nM, about 45 nM, about 50 nM, about 55 nM, about 60 nM, about 65 nM, about 70 nM, about 75 nM, about 80 nM, about 85 nM, about 90 nM, about 95 nM, about 100 nM, about 150 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about 850 nM, about 900 nM, about 950 nM, or about 1,000 nM.

In some embodiments, a salt, ion, osmolyte, or electrolyte concentration on the trans side can be at least about 0.01 M, at least about 0.05 M, at least about 0.10 M, at least about 0.20 M, at least about 0.30 M, at least about 0.40 M, at least about 0.50 M, at least about 0.60 M, at least about 0.70 M, at least about 0.80 M, at least about 0.90 M, at least about 1.00 M, at least about 1.10 M, at least about 1.25 M, at least about 1.50 M, at least about 1.75 M, at least about 2 M, at least about 2.5 M, at least about 3 M, at least about 3.5 M, at least about 4 M, at least about 4.5 M, at least about 5 M, or greater than about 5 M. In some embodiments, a salt, ion, osmolyte, or electrolyte concentration on the trans side can be at most about 5 M, at most about 4.5 M, at most about 4 M, at most about 3.5 M, at most about 3 M, at most about 2.5 M, at most about 2 M, at most about 1.75 M, at most about 1.50 M, at most about 1.25 M, at most about 1 M, at most about 0.90 M, at most about 0.80 M, at most about 0.70 M, at most about 0.60 M, at most about 0.50 M, at most about 0.40 M, at most about 0.30 M, at most about 0.20 M, at most about 0.10 M, at most about 0.05 M, at most about 0.01 M, or less than about 0.01 M.

In some embodiments, a salt, ion, osmolyte, or electrolyte concentration on the trans side can be from about 0.01 M to about 5 M. In some embodiments, a salt, ion, osmolyte, or electrolyte concentration on the cis side can be from about 0.01 M to about 0.1 M, about 0.01 M to about 0.5 M, about 0.01 M to about 1 M, about 0.01 M to about 1.5 M, about 0.01 M to about 2 M, about 0.01 M to about 2.5 M, about 0.01 M to about 3 M, about 0.01 M to about 3.5 M, about 0.01 M to about 4 M, about 0.01 M to about 4.5 M, about 0.01 M to about 5 M, about 0.1 M to about 0.5 M, about 0.1 M to about 1 M, about 0.1 M to about 1.5 M, about 0.1 M to about 2 M, about 0.1 M to about 2.5 M, about 0.1 M to about 3 M, about 0.1 M to about 3.5 M, about 0.1 M to about 4 M, about 0.1 M to about 4.5 M, about 0.1 M to about 5 M, about 0.5 M to about 1 M, about 0.5 M to about 1.5 M, about 0.5 M to about 2 M, about 0.5 M to about 2.5 M, about 0.5 M to about 3 M, about 0.5 M to about 3.5 M, about 0.5 M to about 4 M, about 0.5 M to about 4.5 M, about 0.5 M to about 5 M, about 1 M to about 1.5 M, about 1 M to about 2 M, about 1 M to about 2.5 M, about 1 M to about 3 M, about 1 M to about 3.5 M, about 1 M to about 4 M, about 1 M to about 4.5 M, about 1 M to about 5 M, about 1.5 M to about 2 M, about 1.5 M to about 2.5 M, about 1.5 M to about 3 M, about 1.5 M to about 3.5 M, about 1.5 M to about 4 M, about 1.5 M to about 4.5 M, about 1.5 M to about 5 M, about 2 M to about 2.5 M, about 2 M to about 3 M, about 2 M to about 3.5 M, about 2 M to about 4 M, about 2 M to about 4.5 M, about 2 M to about 5 M, about 2.5 M to about 3 M, about 2.5 M to about 3.5 M, about 2.5 M to about 4 M, about 2.5 M to about 4.5 M, about 2.5 M to about 5 M, about 3 M to about 3.5 M, about 3 M to about 4 M, about 3 M to about 4.5 M, about 3 M to about 5 M, about 3.5 M to about 4 M, about 3.5 M to about 4.5 M, about 3.5 M to about 5 M, about 4 M to about 4.5 M, about 4 M to about 5 M, or about 4.5 M to about 5 M.

In some embodiments, a salt, ion, osmolyte, or electrolyte concentration on the trans side can be about 0.01 M, about 0.05 M, about 0.10 M, about 0.20 M, about 0.30 M, about 0.40 M, about 0.50 M, about 0.60 M, about 0.70 M, about 0.80 M, about 0.90 M, about 1.00 M, about 1.10 M, about 1.25 M, about 1.50 M, about 1.75 M, about 2 M, about 2.5 M, about 3 M, about 3.5 M, about 4 M, about 4.5 M, or about 5 M.

In some embodiments, a difference in salt, ion, or electrolyte concentrations between the cis and trans sides can be at least about 0.01 M, at least about 0.05, at least about 0.10, at least about 0.20, at least about 0.30, at least about 0.40, at least about 0.50, at least about 0.60, at least about 0.70, at least about 0.80, at least about 0.90, at least about 1.00, at least about 1.10, at least about 1.25, at least about 1.50, at least about 1.75, at least about 2, at least about 2.5, at least about 3, at least about 3.5, at least about 4, at least about 4.5, at least about 5 M, or greater than about 5 M. In some embodiments, a difference in salt, ion, or electrolyte concentrations between the cis and trans sides can be at most about 5 M, at most about 4.5 M, at most about 4 M, at most about 3.5 M, at most about 3 M, at most about 2.5 M, at most about 2 M, at most about 1.75 M, at most about 1.50 M, at most about 1.25 M, at most about 1 M, at most about 0.90 M, at most about 0.80 M, at most about 0.70 M, at most about 0.60 M, at most about 0.50 M, at most about 0.40 M, at most about 0.30 M, at most about 0.20 M, at most about 0.10 M, at most about 0.05 M, at most about 0.01 M, or less than about 0.01 M.

In some embodiments, a difference in salt, ion, or electrolyte concentrations between the cis and trans sides can be from about 0.01 M to about 5 M. In some embodiments, a difference in salt, ion, or electrolyte concentrations between the cis and trans sides can be from about 0.01 M to about 0.1 M, about 0.01 M to about 0.5 M, about 0.01 M to about 1 M, about 0.01 M to about 1.5 M, about 0.01 M to about 2 M, about 0.01 M to about 2.5 M, about 0.01 M to about 3 M, about 0.01 M to about 3.5 M, about 0.01 M to about 4 M, about 0.01 M to about 4.5 M, about 0.01 M to about 5 M, about 0.1 M to about 0.5 M, about 0.1 M to about 1 M, about 0.1 M to about 1.5 M, about 0.1 M to about 2 M, about 0.1 M to about 2.5 M, about 0.1 M to about 3 M, about 0.1 M to about 3.5 M, about 0.1 M to about 4 M, about 0.1 M to about 4.5 M, about 0.1 M to about 5 M, about 0.5 M to about 1 M, about 0.5 M to about 1.5 M, about 0.5 M to about 2 M, about 0.5 M to about 2.5 M, about 0.5 M to about 3 M, about 0.5 M to about 3.5 M, about 0.5 M to about 4 M, about 0.5 M to about 4.5 M, about 0.5 M to about 5 M, about 1 M to about 1.5 M, about 1 M to about 2 M, about 1 M to about 2.5 M, about 1 M to about 3 M, about 1 M to about 3.5 M, about 1 M to about 4 M, about 1 M to about 4.5 M, about 1 M to about 5 M, about 1.5 M to about 2 M, about 1.5 M to about 2.5 M, about 1.5 M to about 3 M, about 1.5 M to about 3.5 M, about 1.5 M to about 4 M, about 1.5 M to about 4.5 M, about 1.5 M to about 5 M, about 2 M to about 2.5 M, about 2 M to about 3 M, about 2 M to about 3.5 M, about 2 M to about 4 M, about 2 M to about 4.5 M, about 2 M to about 5 M, about 2.5 M to about 3 M, about 2.5 M to about 3.5 M, about 2.5 M to about 4 M, about 2.5 M to about 4.5 M, about 2.5 M to about 5 M, about 3 M to about 3.5 M, about 3 M to about 4 M, about 3 M to about 4.5 M, about 3 M to about 5 M, about 3.5 M to about 4 M, about 3.5 M to about 4.5 M, about 3.5 M to about 5 M, about 4 M to about 4.5 M, about 4 M to about 5 M, or about 4.5 M to about 5 M.

In some embodiments, a difference in salt, ion, or electrolyte concentrations between the cis and trans sides can be about 0.01 M, about 0.05 M, about 0.10 M, about 0.20 M, about 0.30 M, about 0.40 M, about 0.50 M, about 0.60 M, about 0.70 M, about 0.80 M, about 0.90 M, about 1.00 M, about 1.10 M, about 1.25 M, about 1.50 M, about 1.75 M, about 2 M, about 2.5 M, about 3 M, about 3.5 M, about 4 M, about 4.5 M, or about 5 M.

In some embodiments, the one or more salts can comprise sodium chloride, sodium carbonate, ammonium chloride, sodium acetate, potassium cyanide, zinc chloride hydroxide, potassium chlorate, calcium phosphate, sodium nitrate, potassium cerium fluoride, Mohr's salt, sodium potassium sulphate, potassium permanganate, tetra amino cupric sulphate, zinc chloride hydroxide monohydrate, monosodium glutamate, copper sulfate, calcium chloride, potassium chloride, magnesium sulfate, magnesium chloride, sodium acetate, magnesium nitrate, potassium glutamate, sodium ferricyanide, sodium ferrocyanide, potassium ferricyanide, potassium ferrocyanide, or any combination thereof.

In some embodiments, the one or more salts on the cis side of the membrane can comprise sodium chloride, sodium carbonate, ammonium chloride, sodium acetate, potassium cyanide, zinc chloride hydroxide, potassium chlorate, calcium phosphate, sodium nitrate, potassium cerium fluoride, Mohr's salt, sodium potassium sulphate, potassium permanganate, tetra amino cupric sulphate, zinc chloride hydroxide monohydrate, monosodium glutamate, copper sulfate, calcium chloride, potassium chloride, magnesium sulfate, magnesium chloride, sodium acetate, magnesium nitrate, or any combination thereof. In some embodiments, the one or more salts on the trans side of the membrane can comprise sodium chloride, sodium carbonate, ammonium chloride, sodium acetate, potassium cyanide, zinc chloride hydroxide, potassium chlorate, calcium phosphate, sodium nitrate, potassium cerium fluoride, Mohr's salt, sodium potassium sulphate, potassium permanganate, tetra amino cupric sulphate, zinc chloride hydroxide monohydrate, monosodium glutamate, copper sulfate, calcium chloride, potassium chloride, magnesium sulfate, magnesium chloride, sodium acetate, magnesium nitrate, or any combination thereof.

In some embodiments, the one or more salts on the cis side of the membrane can be the same as the one or more salts on the trans side of the membrane. In some cases, the one or more salts on the cis side of the membrane can be the same types of salt on the trans side of the membrane. In some embodiments, one or more salts on the cis side of the membrane can be different from the one or more salts on the trans side of the membrane. In some cases, the one or more types of salts on the cis side of the membrane can be different types of salts than the one or more salts on the trans side of the membrane.

In some embodiments, the one or more salts can comprise between about one type of salt to about ten types of salts. In some cases, the one or more salts can comprise at least about one type of salt, at least about two types of salts, at least about three types of salts, at least about four types of salts, at least about five types of salts, at least about six types of salts, at least about seven types of salts, at least about eight types of salts, at least about nine types of salts, at least about ten types of salts, or more than ten types of salt. In some cases, the one or more salts can comprise at most about ten types of salts, at most about nine types of salts, at most about eight types of salts, at most about seven types of salts, at most about six types of salts, at most about five types of salts, at most about four types of salts, at most about three types of salts, at most about two types of salts, at most about one type of salt, or less than one type of salt. In some cases, the one or more salts can comprise one type of salt, about two types of salts, about three types of salts, about four types of salts, about five types of salts, about six types of salts, about seven types of salts, about eight types of salts, about nine types of salts, or about ten types of salts.

In some embodiments, the one or more salts on the cis side membrane can be the same types of salts as the one or more salts on the trans side of the membrane. In some cases, the same types of salts present on the cis side and the trans side of the membrane can be present in the same concentrations. In some cases, the same type of salts present on the cis side and the trans side of the membrane can be present in different concentrations.

In some embodiments, the one or more salts on the cis side membrane can be different salt types than the one or more salts on the trans side of the membrane. In some embodiments, the different types of salts present on the cis side and the trans side of the membrane can be present in the same concentrations. In some cases, the different types of salt present on the cis side and the trans side of the membrane can be present in different concentrations.

In some embodiments, the concentration of one or more salts on the cis side of the membrane can be between about 0.1% to about 500% higher than the concentration of one or more salts on the trans side of the membrane. In some cases, the concentration of one or more salts on the cis side of the membrane can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% higher than the concentration of one or more salts on the trans side of the membrane.

In some cases, the concentration of one or more salts on the cis side of the membrane can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% higher than the concentration of one or more salts on the trans side of the membrane.

In some cases, the concentration of one or more salts on the cis side of the membrane can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% higher than the concentration of one or more salts on the trans side of the membrane.

In some cases, the concentration of one or more salts on the cis side of the membrane can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% higher than the concentration of one or more salts on the trans side of the membrane.

In some embodiments, the concentration of one or more salts on the cis side of the membrane can be between about 0.1% to about 500% lower than the concentration of one or more salts on the trans side of the membrane. In some cases, the concentration of one or more salts on the cis side of the membrane can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% lower than the concentration of one or more salts on the trans side of the membrane.

In some cases, the concentration of one or more salts on the cis side of the membrane can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% lower than the concentration of one or more salts on the trans side of the membrane.

In some cases, the concentration of one or more salts on the cis side of the membrane can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% lower than the concentration of one or more salts on the trans side of the membrane.

In some cases, the concentration of one or more salts on the cis side of the membrane can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% lower than the concentration of one or more salts on the trans side of the membrane.

In some embodiments, the concentration of one or more salts on the trans side of the membrane can be between about 0.1% to about 500% higher than the concentration of one or more salts on the cis side of the membrane. In some cases, the concentration of one or more salts on the trans side of the membrane can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% higher than the concentration of one or more salts on the cis side of the membrane.

In some cases, the concentration of one or more salts on the trans side of the membrane can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% higher than the concentration of one or more salts on the cis side of the membrane.

In some cases, the concentration of one or more salts on the trans side of the membrane can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% higher than the concentration of one or more salts on the cis side of the membrane.

In some cases, the concentration of one or more salts on the trans side of the membrane can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% higher than the concentration of one or more salts on the cis side of the membrane.

In some embodiments, the concentration of one or more salts on the trans side of the membrane can be between about 0.1% to about 500% lower than the concentration of one or more salts on the cis side of the membrane. In some cases, the concentration of one or more salts on the trans side of the membrane can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% lower than the concentration of one or more salts on the cis side of the membrane.

In some cases, the concentration of one or more salts on the trans side of the membrane can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% lower than the concentration of one or more salts on the cis side of the membrane.

In some cases, the concentration of one or more salts on the trans side of the membrane can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% lower than the concentration of one or more salts on the cis side of the membrane.

In some cases, the concentration of one or more salts on the trans side of the membrane can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% lower than the concentration of one or more salts on the cis side of the membrane.

In some embodiments, the EOF can be generated by asymmetric salt distribution. An asymmetric salt distribution may be when the concentration of the one or more salts on the cis side of the membrane is greater or less than the concentration of the one or more salts on the trans side of the membrane.

Alternatively, the EOF can be generated by a symmetric salt distribution between the cis side of the membrane and the trans side of the membrane. Symmetric salt distribution may be when the concentration of the one or more salts on the cis side of the membrane is the same as the concentration of the one or more salts on the trans side of the membrane. In some embodiments, the concentration of one or more salts on the cis side of the membrane can be the same as the concentration of the one or more salts on the trans side of the membrane.

In some embodiments, the EOF can be generated by an asymmetric ion distribution between the cis side of the membrane and the trans side of the membrane. Asymmetric ion distribution may be when the concentration of the one or more ions on the cis side of the membrane is greater or less than the concentration of the one or more ions on the trans side of the membrane. In some cases, the concentration of one or more ions on the cis side of the membrane can be greater or less than the concentration of the one or more ions on the trans side of the membrane. In some cases, the concentration of one or more ions on the cis side of the membrane can be higher than the concentration of the one or more ions on the trans side of the membrane. In some cases, the concentration of one or more ions on the cis side of the membrane can be lower than the concentration of one or more ions on the trans side of the membrane. In some cases, the concentration of one or more ions on the trans side of the membrane can be higher than the concentration of the one or more ions on the cis side of the membrane. In some cases, the concentration of one or more ions on the trans side of the membrane can be lower than the concentration of one or more ions on the cis side of the membrane.

In some cases, the concentration of one or more ions on the cis side of the membrane can be between about 1 nanomolar (nM) to about 1,000 nM. In some instances, the concentration of one or more ions on the cis side of the membrane can be between about 1 nM to about 10 nM, between about 10 nM to about 100 nM, or between about 100 nM to about 1,000 nM. In some cases, the concentration of one or more ions on the cis side of the membrane can be at least about 1 nM, at least about 5 nM, at least about 10 nM, at least about 15 nM, at least about 20 nM, at least about 25 nM, at least about 30 nM, at least about 35 nM, at least about 40 nM, at least about 45 nM, at least about 50 nM, at least about 55 nM, at least about 60 nM, at least about 65 nM, at least about 70 nM, at least about 75 nM, at least about 80 nM, at least about 85 nM, at least about 90 nM, at least about 95 nM, at least about 100 nM, at least about 150 nM, at least about 200 nM, at least about 250 nM, at least about 300 nM, at least about 350 nM, at least about 400 nM, at least about 450 nM, at least about 500 nM, at least about 550 nM, at least about 600 nM, at least about 650 nM, at least about 700 nM, at least about 750 nM, at least about 800 nM, at least about 850 nM, at least about 900 nM, at least about 950 nM, at least about 1,000 nM, or more than 1,000 nM. In some cases, the concentration of one or more ions on the cis side of the membrane can at most about 1,000 nM, at most about 950 nM, at most about 900 nM, at most about 850 nM, at most about 800 nM, at most about 750 nM, at most about 700 nM, at most about 650 nM, at most about 600 nM, at most about 550 nM, at most about 500 nM, at most about 450 nM, at most about 400 nM, at most about 350 nM, at most about 300 nM, at most about 250 nM, at most about 200 nM, at most about 150 nM, at most about 100 nM, at most about 95 nM, at most about 90 nM, at most about 85 nM, at most about 80 nM, at most about 75 nM, at most about 70 nM, at most about 65 nM, at most about 60 nM, at most about 55 nM, at most about 45 nM, at most about 40 nM, at most about 35 nM, at most about 30 nM, at most about 25 nM, at most about 20 nM, at most about 15 nM, at most about 10 nM, at most about 5 nM, at most about 1 nM, or less than 1 nM. In some cases, the concentration of salt on the cis side of the membrane can about 1 nM, about 5 nM, about 10 nM, about 15 nM, about 20 nM, about 25 nM, about 30 nM, about 35 nM, about 40 nM, about 45 nM, about 50 nM, about 55 nM, about 60 nM, about 65 nM, about 70 nM, about 75 nM, about 80 nM, about 85 nM, about 90 nM, about 95 nM, about 100 nM, about 150 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about 850 nM, about 900 nM, about 950 nM, or about 1,000 nM.

In some cases, the concentration of one or more ions on the trans side of the membrane can be between about 1 nanomolar (nM) to about 1,000 nM. In some instances, the concentration of one or more ions on the trans side of the membrane can be between about 1 nM to about 10 nM, between about 10 nM to about 100 nM, or between about 100 nM to about 1,000 nM. In some cases, the concentration of one or more ions on the trans side of the membrane can be at least about 1 nM, at least about 5 nM, at least about 10 nM, at least about 15 nM, at least about 20 nM, at least about 25 nM, at least about 30 nM, at least about 35 nM, at least about 40 nM, at least about 45 nM, at least about 50 nM, at least about 55 nM, at least about 60 nM, at least about 65 nM, at least about 70 nM, at least about 75 nM, at least about 80 nM, at least about 85 nM, at least about 90 nM, at least about 95 nM, at least about 100 nM, at least about 150 nM, at least about 200 nM, at least about 250 nM, at least about 300 nM, at least about 350 nM, at least about 400 nM, at least about 450 nM, at least about 500 nM, at least about 550 nM, at least about 600 nM, at least about 650 nM, at least about 700 nM, at least about 750 nM, at least about 800 nM, at least about 850 nM, at least about 900 nM, at least about 950 nM, at least about 1,000 nM, or more than 1,000 nM. In some cases, the concentration of one or more ions on the trans side of the membrane can at most about 1,000 nM, at most about 950 nM, at most about 900 nM, at most about 850 nM, at most about 800 nM, at most about 750 nM, at most about 700 nM, at most about 650 nM, at most about 600 nM, at most about 550 nM, at most about 500 nM, at most about 450 nM, at most about 400 nM, at most about 350 nM, at most about 300 nM, at most about 250 nM, at most about 200 nM, at most about 150 nM, at most about 100 nM, at most about 95 nM, at most about 90 nM, at most about 85 nM, at most about 80 nM, at most about 75 nM, at most about 70 nM, at most about 65 nM, at most about 60 nM, at most about 55 nM, at most about 45 nM, at most about 40 nM, at most about 35 nM, at most about 30 nM, at most about 25 nM, at most about 20 nM, at most about 15 nM, at most about 10 nM, at most about 5 nM, at most about 1 nM, or less than 1 nM. In some cases, the concentration of one or more ions on the trans side of the membrane can about 1 nM, about 5 nM, about 10 nM, about 15 nM, about 20 nM, about 25 nM, about 30 nM, about 35 nM, about 40 nM, about 45 nM, about 50 nM, about 55 nM, about 60 nM, about 65 nM, about 70 nM, about 75 nM, about 80 nM, about 85 nM, about 90 nM, about 95 nM, about 100 nM, about 150 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about 850 nM, about 900 nM, about 950 nM, or about 1,000 nM.

In some embodiments, the one or more ions can comprise chloride, carbonate, chlorite, chlorate, phosphate, bicarbonate, bromide, ammonium sulfate, ammonium, sulfate, sulfide, calcium, fluoride, hydroxide, aluminum, barium, bismuth, cadmium, cesium, chromium, cobalt, copper, hydrogen, iron, lead, lithium, magnesium, mercury, nickel, potassium, rubidium, silver, sodium, strontium, tin, zinc, iodide, nitride, oxide, or any combinations thereof.

In some embodiments, the one or more ions on the cis side of the membrane can comprise chloride, carbonate, chlorite, chlorate, phosphate, bicarbonate, bromide, ammonium sulfate, ammonium, sulfate, sulfide, calcium, fluoride, hydroxide, aluminum, barium, bismuth, cadmium, cesium, chromium, cobalt, copper, hydrogen, iron, lead, lithium, magnesium, mercury, nickel, potassium, rubidium, silver, sodium, strontium, tin, zinc, iodide, nitride, oxide, or any combinations thereof.

In some embodiments, the one or more ions on the trans side of the membrane can comprise chloride, carbonate, chlorite, chlorate, phosphate, bicarbonate, bromide, ammonium sulfate, ammonium, sulfate, sulfide, calcium, fluoride, hydroxide, aluminum, barium, bismuth, cadmium, cesium, chromium, cobalt, copper, hydrogen, iron, lead, lithium, magnesium, mercury, nickel, potassium, rubidium, silver, sodium, strontium, tin, zinc, iodide, nitride, oxide, or any combinations thereof.

In some embodiments, the one or more ions on the cis side of the membrane can be the same types of ions as the one or more ions on the trans side of the membrane. In some embodiments, one or more ions on the cis side of the membrane can be different types of ions from the one or more ions on the trans side of the membrane.

In some embodiments, the one or more ions can comprise between about one ion to about ten ions. In some cases, the one or more ions can comprise at least about one ion, at least about two ions, at least about three ions, at least about four ions, at least about five ions, at least about six ions, at least about seven ions, at least about eight ions, at least about nine ions, at least about ten ions, or more than ten ions. In some cases, the one or more ions can comprise at most about ten ions, at most about nine ions, at most about eight ions, at most about seven ions, at most about six ions, at most about five ions, at most about four ions, at most about three ions, at most about two ions, at most about one ion, or less than one ion. In some cases, the one or more ions can comprise about one ion, about two ions, about three ions, about four ions, about five ions, about six ions, about seven ions, about eight ions, about nine ions, or about ten ions.

In some embodiments, the one or more ions on the cis side of the membrane can be present in the same concentration as the one or more ions on the trans side of the membrane. In some cases, the one or more ions on the cis side of the membrane can be present in different concentrations as the one or more ions on the trans side of the membrane.

In some embodiments, the concentration of one or more ions on the cis side of the membrane can be between about 0.1% to about 500% higher than the concentration of one or more ions on the trans side of the membrane. In some cases, the concentration of one or more ions on the cis side of the membrane can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% higher than the concentration of one or more ions on the trans side of the membrane.

In some cases, the concentration of one or more ions on the cis side of the membrane can beat least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% higher than the concentration of one or more ions on the trans side of the membrane.

In some cases, the concentration of one or more ions on the cis side of the membrane can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% higher than the concentration of one or more ions on the trans side of the membrane.

In some cases, the concentration of one or more ions on the cis side of the membrane can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% higher than the concentration of one or more ions on the trans side of the membrane.

In some embodiments, the concentration of one or more ions on the cis side of the membrane can be between about 0.1% to about 500% lower than the concentration of one or more ions on the trans side of the membrane. In some cases, the concentration of one or more ions on the cis side of the membrane can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% lower than the concentration of one or more ions on the trans side of the membrane.

In some cases, the concentration of one or more ions on the cis side of the membrane can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% lower than the concentration of one or more ions on the trans side of the membrane.

In some cases, the concentration of one or more ions on the cis side of the membrane can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% lower than the concentration of one or more ions on the trans side of the membrane.

In some cases, the concentration of one or more ions on the cis side of the membrane can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% lower than the concentration of one or more ions on the trans side of the membrane.

In some embodiments, the concentration of one or more ions on the trans side of the membrane can be between about 0.1% to about 500% higher than the concentration of salt on the cis side of the membrane. In some cases, the concentration of salt on the trans side of the membrane can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% higher than the concentration of one or more ions on the cis side of the membrane.

In some cases, the concentration of one or more ions on the trans side of the membrane can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% higher than the concentration of one or more ions on the cis side of the membrane.

In some cases, the concentration of one or more ions on the trans side of the membrane can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% higher than the concentration of one or more ions on the cis side of the membrane.

In some cases, the concentration of one or more ions on the trans side of the membrane can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% higher than the concentration of one or more ions on the cis side of the membrane.

In some embodiments, the concentration of one or more ions on the trans side of the membrane can be between about 0.1% to about 500% lower than the concentration of one or more ions on the cis side of the membrane. In some cases, the concentration of one or more ions on the trans side of the membrane can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% lower than the concentration of one or more ions on the cis side of the membrane.

In some cases, the concentration of one or more ions on the trans side of the membrane can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% lower than the concentration of one or more ions on the cis side of the membrane.

In some cases, the concentration of one or more ions on the trans side of the membrane can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% lower than the concentration of one or more ions on the cis side of the membrane.

In some cases, the concentration of one or more ions on the trans side of the membrane can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% lower than the concentration of one or more ions on the cis side of the membrane.

Alternatively, the EOF can be generated by a symmetric ion distribution between the cis side of the membrane and the trans side of the membrane. A symmetric ion distribution may be when the concentration of the one or more ions on the cis side of the membrane can be the same concentration of the one or more ions on the trans side of the membrane. In some cases, the concentration of the one or more ions on the cis side of the membrane is the same as the concentration of the one or more ions on the trans side of the membrane.

In some embodiments, the EOF can be generated by an asymmetric concentration of one or more salts and an asymmetric concentration of one or more ions between the cis side of the membrane and the trans side of the membrane.

In some embodiments an electro-osmotic force can act in the same direction as an electrophoretic force or in an opposing direction to an electrophoretic force. In some embodiments, the electro-osmotic force can be greater than the electrophoretic force. In some embodiments, the electro-osmotic force can be less than the electrophoretic force.

In some embodiments, a cis to trans EOF can comprise a net ionic current flow from the cis side of the membrane to the trans side of the membrane. In some embodiments, a trans to cis EOF can comprise a net ionic current flow from the trans side of the membrane to the cis side of the membrane. In some cases, the nanopore system can comprise a total ionic current flow. In some instances, the net ionic current flow can comprise the flow of less than all of the total ions in the nanopore system. In some cases, the net ionic current flow can comprise the flow of less than all of the total ions in the nanopore system in a specific direction. In some cases, the specific direction can be from the cis side of the membrane to the trans side of the membrane. In some cases, the specific direction can be from the trans side of the membrane to the cis side of the membrane. In some cases, the total ionic current flow can comprise the total flow of all ions in the nanopore system. In some cases, the total flow of all ions in the nanopore system can be from the cis side of the membrane to the trans side of the membrane. In some cases, the total flow of all ions in the nanopore system can be from the trans side of the membrane to the cis side of the membrane. In some cases, the total ionic current flow can comprise the total flow of all ions in the nanopore system in a specific direction. In some cases, the specific direction can from the cis side of the membrane to the trans side of the membrane. In some cases, the specific direction can from the trans side of the membrane to the cis side of the membrane.

In some embodiments, the net ionic current flow can comprise between about 0.001% to about 100% of the total ionic current flow. In some cases, the net ionic current flow can comprise between about 0.001% to about 0.01%, between about 0.01% to about 0.1%, between about 0.1% to about 1%, between about 1% to about 10%, or between about 10% to about 100% of the total ionic current flow. In some cases, the net ionic current flow can comprise at least about 0.001%, at least about 0.005%, at least about 0.01%, at least about 0.05%, at least about 0.1%, at least about 0.5%, at least about 1%, at least about 5%, at least about 10%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, at least about 99.5%, or at least about 100% of the total ionic current flow. In some instances, the net ionic current flow can comprise at most about 100%, at most about 99.5%, at most about 99%, at most about 98%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, at most about 0.05%, at most about 0.01%, at most about 0.005%, at most about 0.001%, or less than 0.001% of the total ionic current flow. In some cases, the net ionic current flow can comprise about 0.001%, about 0.005%, about 0.01%, about 0.05%, about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98%, about 99%, about 99.5%, or about 100% of the total ionic current flow.

In some embodiments, a cis to trans EOF results from a net ionic current flow cis to trans over a total ionic current flow, also referred to as a relative net current flow cis to trans, of greater than about 0.0, greater than about 0.1, greater than about 0.2, greater than about 0.3, greater than about 0.4, greater than about 0.5, greater than about 0.6, greater than about 0.7, greater than about 0.8, greater than about 0.9, greater than about 0.95, or greater than about 0.99. In some embodiments, a cis to trans EOF results from a net ionic current flow trans to cis over a total ionic current flow, also referred to as a relative net current flow cis to trans, of less than about 0.0, less than about −0.1, less than about −0.2, less than about −0.3, less than about −0.4, less than about −0.5, less than about −0.6, less than about −0.7, less than about −0.8, less than about −0.9, less than about −0.95, or less than about −0.99.

In some embodiments, the absolute relative net electro-osmotic current over applied voltage ($I_{relV}$), is greater than about 0.01, greater than about 0.02, greater than about 0.03, greater than about 0.04, greater than about 0.05, greater than about 0.06, greater than about 0.07, greater than about 0.08, greater than about 0.09, greater than about 0.10, greater than about 0.15, greater than about 0.2, greater than about 0.3, greater than about 0.4, greater than about 0.5, greater than about 0.6, greater than about 0.7, greater than about 0.8, greater than about 0.9, or greater than about 1 picoampere per millivolt (pA/mV). In some embodiments, the absolute relative net electro-osmotic current over applied voltage ($I_{relV}$), is less than about 0.01, less than about 0.02, less than about 0.03, less than about 0.04, less than about 0.05, less than about 0.06, less than about 0.07, less than about 0.08, less than about 0.09, less than about 0.10, less than about 0.15, less than about 0.2, less than about 0.3, less than about 0.4, less than about 0.5, less than about 0.6, less than about 0.7, less than about 0.8, less than about 0.9, or less than about 1 pA/mV.

In some embodiments, the system can comprise a translocase. A translocase can comprise a molecular motor (e.g., an unfoldase). In some embodiments, the molecular motor can move an analyte through the translocase. In some cases, the translocase can move an analyte through the translocase and into a nanopore. In some cases, the translocase can move an analyte through the translocase, into a nanopore, and through a nanopore channel. The molecular motor can be NTP-driven, ATP-driven, or neither. A translocase can comprise an unfoldase. An unfoldase can be an AAA+ enzyme. A translocase can comprise a molecular motor (e.g., an unfoldase). A translocase can comprise ClpX, ClpA, Pan, LON, VAT, AMA, 854, MBA, SAMP, ClpC, ClpE, HsIU, (ClpY), LonA, LonB, FtsH, Mpa, Cpa, Msp1, SecA, functional homologs, orthologs, or paralogs, or any combination thereof. A translocase can bind to or form a complex with analyte, (e.g. a translocase-analyte complex). A translocase can push an analyte through the translocase. A translocase can translocate an analyte through a nanopore. Pushing the analyte through the translocase can disrupt (e.g., unfold) a quaternary, tertiary, or secondary structure of an analyte (e.g., a protein). The disruption of the quaternary, tertiary, or secondary structure can assist in the translocation of the analyte through a nanopore. A translocase may form a complex at the N-terminus or C-terminus of an analyte (e.g., a peptide, a protein). A translocase may form a translocase-analyte complex with an analyte on a cis side of a fluidic chamber. The translocase-analyte complex can be formed outside of the fluidic chamber, or in the fluidic chamber (e.g. on the cis side of the fluidic chamber). The translocase-analyte complex can be formed prior to addition to the cis side of the fluidic chamber (e.g. by preloading with a pre-loading solution). A translocase can control a rate of translocation. The translocase's rate of translocation can be modulated. Modulation can be done by changing a concentration of an energy source for a translocase (e.g. NTP, ATP).

In some embodiments, the translocase can be capable to moving an analyte. In some embodiments, the translocase may not be capable of separating the strands of double-stranded nucleic acids. In some cases, the translocase may not be a helicase. In some embodiments, the translocase may not be capable of replicating nucleic acids. In some cases, the translocase may not be a nucleic acid polymerase. In some cases, the translocase may not be an DNA polymerase or an RNA polymerase. In some embodiments, the translocase may not be involved in nucleic acid replication. In some embodiments, the translocase may not be capable of cleaving the analyte. In some embodiments, the translocases may not be topoisomerase.

In some embodiments, the translocase may be coupled to a nanopore. The translocase may be coupled covalently (e.g., genetically fused) or non-covalently (e.g., by a recognition element).

In some embodiments, the translocase may not be coupled to the nanopore. In some cases, the translocase may not be coupled to the opening of the nanopore. In some cases, the translocase may not be coupled to the membrane adjacent to the nanopore.

In some embodiments the translocase may not be bound to the nanopore. In some cases, the translocase may not be bound to the opening of the nanopore. In some case, the translocase may not be bound to the membrane adjacent to the nanopore.

In some embodiments, the electro-osmotic force can capture a translocase-analyte complex (e.g., a translocase-analyte complex. The capture can be the result of pulling a portion of the analyte that is not within the translocase of the translocase-analyte complex into the nanopore. The capture of a portion of the analyte by the nanopore channel can cause a portion of the analyte of the translocate-analyte complex to be translocated through the nanopore as the analyte may be pulled further into the nanopore channel by the electro-osmotic force. The translocation may occur in opposition to an electrophoretic force, or in conjunction with an electrophoretic force. The translocation of the analyte portion can bring the translocase of the translocase-analyte complex adjacent to the nanopore channel as portion of the analyte being translocated approaches the portion of the analyte within the translocase. The translocase can be brought adjacent to the nanopore on the cis side of the nanopore channel if the electro-osmotic force is acting in a cis to trans direction or the trans side of the nanopore channel if the electro-osmotic force is acting in a trans to cis direction. The electro-osmotic force can hold the translocase of the translocase-analyte complex adjacent to the nanopore of the nanopore channel, for example by continuing to draw the analyte through the nanopore and transferring the force of the electro-osmotic force to the attached translocase. Adjacent to the nanopore channel can be at an opening of the nanopore channel, also referred to as "on top" of the nanopore, or near the portion of the nanopore that is not within the membrane.

In some embodiments, the EOF can hold the translocase on the top of the nanopore without an analyte. In some cases, a portion of the translocase can be captured in the nanopore. In some cases, a portion of the translocase can be captured in the nanopore due to the electro-osmotic force. In some cases, a portion of the translocase can be captured in the nanopore due to the electrophoretic force. In some cases, a portion of the translocase can be captured in the nanopore due to the electro-osmotic force and the electrophoretic force. In some cases, the portion of the translocase captured in the nanopore can be a charged linker or a peptide extension of the translocase.

When held adjacent to a nanopore channel, the translocase of the translocase-analyte complex can be held oriented such that a channel of the translocase is adjacent to the channel of the nanopore. This orientation may be provided by the analyte being drawn into the nanopore by the electro-osmotic force, which can bring the point of connection of the analyte to the translocase (e.g., the translocase channel) adjacent to the nanopore channel and the translocase channel are aligned. In some embodiments, the translocase can control the rate of analyte translocation. The rate of translocation can be the result of the translocase acting on the analyte as a molecular motor. In some embodiments, the rate of translocation can be from about 0.1 amino acids per second (aa/s) to about 1,000 aa/s. In some cases, the rate of translocation can be at least about 0.1 aa/s, at least about 0.5 aa/s, at least about 1 aa/s, at least about 5 aa/s, at least about 10 aa/s, at least about 50 aa/s, at least about 100 aa/s, at least about 500 aa/s, at least about 1,000 aa/s, or more than 1,000 aa/s. In some cases, the rate of translocation can at least most about 1,000 aa/s, at most about 500 aa/s, at most about 100 aa/s, at most about 50 aa/s, at most about 10 aa/s, at most about 5 aa/s, at most about 1 aa/s, at most about 0.5 aa/s, at most about 0.1 aa/s, or less than 0.1 aa/s. In some cases, the rate of translocation can be about 0.1 aa/s, about 0.5 aa/s, about 1 aa/s, about 5 aa/s, about 10 aa/s, about 50 aa/s, about 100 aa/s, about 500 aa/s, or about 1,000 aa/s.

The translocation orientation can be such that a feed direction of the translocase aligns with the channel of the nanopore. The feed direction can be oriented cis to trans or trans to cis. There may or may not be a gap between the lumen of the translocase channel and the lumen of the nanopore channel. The translocase can be held such that the translocase can feed the analyte through the nanopore in the direction of the electro-osmotic force, or it can be held such that the translocase pulls the analyte through the nanopore against the electro-osmotic force.

The translocase can feed the analyte through the nanopore in the direction of the electroosmotic force such that it translocates at a rate faster or slower than the analyte that translocates with the electro-osmotic force alone.

In some embodiments, the rate of translocation of the analyte through the nanopore with the translocase can be faster than a rate of translocation of the analyte through the nanopore without the translocase. In some cases, the rate of translocation of the analyte through the nanopore with the translocase can be between about 0.1% to about 500% faster than a rate of translocation of the analytes through the nanopore without the translocase. In some cases, the rate of translocation of the analyte through the nanopore with the translocase can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% faster than a rate of translocation of the analytes through the nanopore without the translocase.

In some cases, the rate of translocation of the analyte through the nanopore with the translocase can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% faster than a rate of translocation of the analytes through the nanopore without the translocase. In some cases, the rate of translocation of the analyte through the nanopore with the translocase can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% faster than a rate of translocation of the analytes through the nanopore without the translocase. In some cases, the rate of translocation of the analyte through the nanopore with the translocase can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% faster than a rate of translocation of the analytes through the nanopore without the translocase.

In some embodiments, the rate of translocation of the analyte through the nanopore with the translocase can be slower than a rate of translocation of the analyte through the nanopore without the translocase. In some cases, the rate of translocation of the analyte through the nanopore with the translocase can be between about 0.1% to about 500% slower than a rate of translocation of the analytes through the nanopore without the translocase. In some cases, the rate of translocation of the analyte through the nanopore with the translocase can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% slower than a rate of translocation of the analytes through the nanopore without the translocase.

In some cases, the rate of translocation of the analyte through the nanopore with the translocase can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% slower than a rate of translocation of the analytes through the nanopore without the translocase. In some cases, the rate of translocation of the analyte through the nanopore with the translocase can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% slower than a rate of translocation of the analytes through the nanopore without the translocase. In some cases, the rate of translocation of the analyte through the nanopore with the translocase can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% slower than a rate of translocation of the analytes through the nanopore without the translocase.

In some embodiments, the main force in the translocation of the analyte through the nanopore can be the EOF. In some embodiments, the translocation of the analyte through the nanopore can occur using the EOF. In some cases, the translocation of the analyte through the nanopore can occur in the absence of a translocase. In some cases, the translocation of the analyte through the nanopore can occur using the EOF and in the absence of a translocase.

In some embodiments, the translocation of the analyte through the nanopore may not occur in the absence of the EOF. In some cases, the translocation of the analyte through the nanopore may not occur in the presence of a translocase. In some cases, the translocation of the analyte through the nanopore may not occur in the absence of the EOF and in the presence of a translocase.

The translocase can be held at the cis or trans side of the nanopore without needing to be coupled to the nanopore. The electro-osmotic force can hold the translocase adjacent to the nanopore without additional coupling to the nanopore channel. The electro-osmotic force can hold the translocase adjacent to the nanopore so that the nanopore can couple with the translocase. The translocase can be held adjacent to the nanopore channel while the analyte translocates through the nanopore. After the analyte has fully translocate through the nanopore, the translocase may continue to be held adjacent to the nanopore, or the translocase may be released from the position adjacent to the nanopore. A released translocase may then form a translocase-analyte complex with another analyte. In some embodiments, the translocase may not be coupled to the nanopore. In some cases, the translocase may not be coupled adjacent to the nanopore. In some cases, the translocase may not be coupled to the membrane adjacent to the nanopore.

Alternatively, in some embodiments, the translocase can be coupled to the cis side or the trans side of the nanopore. In some cases, the translocase can be coupled to the nanopore via a covalent bond. In some instances, the covalent bond is a polar covalent bond. In some instances, the covalent bond is a non-polar covalent bond. In some cases, the translocase can be coupled to the nanopore via a non-covalent bond. In some cases, the non-covalent bonds can comprise electrostatic interactions, hydrogens bonds, van der Waals interactions, hydrophobic interactions, or any combination thereof. In some cases, the translocase can be coupled to the nanopore via a linker. In some cases, the linkers can comprise (GGGGS)$_3$ (SEQ ID NO: 1), (GGGGS)$_n$ (SEQ ID NO: 2), (SG)$_n$, (Gly)$_8$ (SEQ ID NO: 3), (Gly)$_6$ (SEQ ID NO: 4), (EAAAK)$_3$ (SEQ ID NO: 5), (EAAAK)$_n$ (SEQ ID NO: 6), VSQTSKLTRAETVFPDV (SEQ ID NO: 7), PLGLWA (SEQ ID NO: 8), RVLAEA (SEQ ID NO: 9), EDVVCCSNSY (SEQ ID NO: 10), GGIEGRGS (SEQ ID NO: 11), TRHRQPRGWE (SEQ ID NO: 12), AGNRVRRSVG (SEQ ID NO: 13), RRRRRRRRR (SEQ ID NO: 14), GFLG (SEQ ID NO: 15), A(EAAAK)$_4$ALEA(EAAAK)$_4$A (SEQ ID NO: 16), PAPAP (SEQ ID NO: 17), AEAAAKEAAAKA (SEQ ID NO: 18), (Ala-Pro)$_n$, disulfide bond, cysteine linkages, or any combination thereof. In some embodiments, a linker can comprise any combination of amino acids. In some cases, the amino acids can be canonical amino acids. In some cases, the canonical amino acids can comprise alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or any combination thereof. In some cases, the amino acids can be non-natural amino acids. In some cases, the non-natural amino acids can comprise hydroproline, beta-alanine, citrulline, ornithine, norleucine, 3-nitrotyrosine, nitroarginine, pyroglutamic acid, naphtylalanine, Abu, DAB, methionine sulfoxide, methionine sulfone, α-amino-n-butyric acid, norvaline, alloisoleucine, t-leucine, α-amino-n-heptanoic acid, pipecolic acid, allothreonine, homocysteine, homoserine, α,β-diaminopropionic acid, α,γ-diaminobutyric acid, β-alanine, β-amino-n-butyric acid, β-aminoisobutyric acid, β-aminoisobutyric acid, γ-aminobutyric acid, α-aminoisobutyric acid, isovaline, sarcosine, N-ethylglycine, N-propylglycine, N-isopropylglycine, N-methylalanine, N-ethylalanine, N-methyl-β-alanine, N-ethyl-β-alanine, isoserine, α-hydroxy-γ-aminobbutyric acid, or any combinations thereof. In some cases, the linker can comprise any combination of canonical amino acids and non-natural amino acids. In some cases, the linker can be ethylene glycol. In some cases, the linker can be polyethylene glycol. In some cases, the linker can be biotin. In some cases, the linker can be streptavidin. In some cases, the linker can be cysteine linkages. In some case the linker can be formed using Spytag/Spycatcher, Halo-tag, Snap-tag or other bioconjugation methods. In some cases the linker can be formed from click chemistry. In some cases the linker attaches to non-natural amino acids.

In some embodiments, a method comprises providing a system. In some embodiments, the system comprises a fluidic chamber. In some embodiments, the system comprises a membrane. The membrane can divide the fluidic chamber into two or more sides. The membrane can divide the fluidic chamber into a cis side and a trans side. The cis side can comprise a first fluidic solution. The trans side can comprises a second fluidic solution. In some embodiments, a solution or solutions on either the cis side or the trans side of the fluidic chamber may be configured to have a set pH. The solution or solutions may have a pH of greater than about 1, greater than about 2, greater than about 3, greater than about 3.8, greater than about 4, greater than about 4.5, greater than about 6, greater than about 7, greater than about 8, greater than about 9, greater than about 10, greater than about 10.5, greater than about 11, greater than about 12, greater than about 13, or greater than about 14 can be employed. The solution or solutions may have a pH of less than about 1, less than about 2, less than about 3, less than about 3.8, less than about 4, less than about 4.5, less than about 6, less than about 7, less than about 8, less than about 9, less than about 10, less than about 10.5, less than about 11, less than about 12, less than about 13, or less than about 14 can be employed.

In some embodiments, the first solution and the second solution can be different solutions. In some embodiments, the first solution and the second solution can be different solutions and can have different concentrations of one or more types of ions. In some embodiments, the first solution and the second solution can be different solutions and can have different concentrations of one or more types of salts. In some embodiments, the first solution and the second solution can be different solutions and can have different concentrations of one or more types of salts and different concentrations of one or more types of ions.

Alternatively, in some embodiments, the first solution and the second solution can be the different solutions and can have the same concentration of one or more types of salts. In some embodiments, the first solution and the second solution can be the different solutions and can have the same concentration of one or more types of ions. In some embodiments, the first solution and the second solution can be the different solutions and can have the same concentration of one or more types of ions and the same concentration of one or more types of salts.

In some embodiments, the first solution and the second solution can be the same solution. In some embodiments, the first solution and the second solution can be the same solution and can have different concentrations of one or more types of ions. In some embodiments, the first solution and the second solution can be the same solution and can have different concentrations of one or more types of salts. In some embodiments, the first solution and the second solution can be the same solution and can have different concentrations of one or more types of ions and different concentrations of one or more types of salts.

Alternatively, in some embodiments, the first solution and the second solution can be the same solution and can have the same concentration of one or more types of salts. In some embodiments, the first solution and the second solution can be the same solution and can have the same concentration of one or more types of ions. In some embodiments, the first solution and the second solution can be the same solution and can have the same concentration of one or more types of ions and the same concentration of one or more types of salts.

The fluidic solutions can be configured to provide an electro-osmotic flow, also termed an electro-osmotic force. In some embodiments, the electro-osmotic flow can be generated by having an asymmetric distribution of one or more salts between the cis side of the membrane and the trans side of the membrane. In some embodiments, the electro-osmotic flow can be generated by having an asymmetric distribution of one or more ions between the cis side of the membrane and the trans side of the membrane. In some embodiments, the electro-osmotic flow can be generated by having an asymmetric distribution of one or more ions and one or more salts between the cis side of the membrane and the trans side of the membrane. The electro-osmotic force can act across the membrane. In some embodiments, the membrane comprises a nanopore. In some embodiments a pair of electrodes is provided. The pair of electrodes can be disposed with one electrode on a cis side of the fluidic chamber, and the other electrode on the trans side of the fluidic chamber. In some embodiments, a pair of electrodes can be configured to provide an applied voltage.

The applied voltage can be across a membrane. The applied voltage can result in an electrophoretic force. In some embodiments a pair of electrodes can be configured to provide an electrophoretic force across a membrane. The pair of electrodes can be configured to measure a signal.

In some embodiments, the applied voltage across the membrane can be at least about 1, at least about 5, at least about 10, at least about 20, at least about 30, at least about 40, at least about 50, at least about 60, at least about 70, at least about 80, at least about 90, at least about 100, at least about 150, at least about 200, at least about 250, at least about 300, at least about 350, at least about 400, at least about 450, at least about 500, at least about 600, at least about 700, at least about 800, at least about 900, or at least about 1000 millivolts (mV) in magnitude. The applied voltage can be at most about 1, at most about 5, at most about 10, at most about 20, at most about 30, at most about 40, at most about 50, at most about 60, at most about 70, at most about 80, at most about 90, at most about 100, at most about 150, at most about 200, at most about 250, at most about 300, at most about 350, at most about 400, at most about 450, at most about 500, at most about 600, at most about 700, at most about 800, at most about 900, or at most about 1000 mV in magnitude. In some embodiments, the voltage is negative cis to trans. In some embodiments the voltage is positive cis to trans.

In some embodiments, the translocation of the analyte through the nanopore occurs in a cis to trans direction. In some embodiments, the translocation of the analyte through the nanopore occurs in a trans to cis direction. In some embodiments, the translocation of the analyte through the nanopore occurs in the direction of the electro-osmotic force (EOF). In some embodiments, the translocation of the analyte through the nanopore occurs in the opposite direction of the electrophoretic force (EPF). In some embodiments, the translocation of the analyte through the nanopore occurs in the direction of the EOF and opposite the direction of the EPF.

In some embodiments, the EOF can be greater than the EPF. In some cases, the EOF is between about 0.1% to about 500% greater than the EPF. In some cases, the EOF is between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% longer greater than the EPF.

In some cases, the EOF can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% greater than the EPF.

In some cases, the EOF can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% greater than the EPF.

In some cases, the EOF can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% greater than the EPF.

In some embodiments, the translocation of the analyte through the nanopore occurs in the direction of the EOF. In some embodiments, the translocation of the analyte through the nanopore occurs in the direction of the EPF. In some embodiments, the translocation of the analyte through the nanopore occurs in the direction of the EOF and the direction of the EPF.

Alternatively, in some embodiments, the translocation of the analyte through the nanopore occurs in the direction of the EPF. In some embodiments, the translocation of the analyte through the nanopore occurs in the opposite direction of the EOF. In some embodiments, the translocation of the analyte through the nanopore occurs in the direction of the EPF and opposite the direction of the EOF.

Alternatively, in some embodiments, the EPF can be greater than the EOF. In some embodiments, the EPF can be greater than the EOF. In some cases, the EPF is between about 0.1% to about 500% greater than the EOF. In some cases, the EPF is between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% longer greater than the EOF.

In some cases, the EPF can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% greater than the EOF.

In some cases, the EPF can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% greater than the EOF.

In some cases, the EPF can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% greater than the EOF.

In some embodiments a signal is measured. The signal can comprise an electrical signal. The signal can be related to or caused by the translocation of an analyte. The signal can comprise an ionic current, or a change in ionic current.

The signal can comprise a measurement of a current change between states of a nanopore. The states of a nanopore can comprise an open channel, a capture of an analyte by the nanopore, or a passage of a polymer from a captured state through the nanopore. In some embodiments, measuring the signal can comprise comparing the signal during different states of the nanopore.

In some embodiments, an electrophoretic force is provided. In some embodiments, the method comprises translocating an analyte through the nanopore. The translocation can be assisted by the electro-osmotic force, the electrophoretic force, or combinations thereof. The translocation can be opposed by the electro-osmotic force, the electrophoretic force, or combinations thereof. In some embodiments, the analyte is in a pre-denatured state prior to translocation. In some embodiments, the method comprises measuring a signal. The signal can be caused or influenced by the translocation of the analyte. In some embodiments, one or more analytes are translocated. The signals of one or more translocated analytes may be measured. In some embodiments, multiple analytes may be measured. The signal or signals from the multiple analytes may be used to characterize them. In some embodiments, at least about 2, at least about 3, at least about 4, at least about 5, at least about 6, at least about 7, at least about 8, at least about 9, at least about 10, at least about 20, at least about 30, at least about 50, at least about 100, at least about 200, at least about 300, at least about 400, at least about 500, at least about 600, at least about 700, at least about 800, at least about 900, at least about 1000, at least about 1500, at least about 2000, at least about 2500, at least about 3500, at least about 4000, at least about 4500, at least about 5000, at least about 5500, at least about 6000, at least about 6500, at least about 7000, at least about 7500, at least about 8000, at least about 8500, at least about 9000, at least about 9500, or at least about 10000 analytes may be characterized. In some embodiments, at most about 2, at most about 3, at most about 4, at most about 5, at most about 6, at most about 7, at most about 8, at most about 9, at most about 10, at most about 20, at most about 30, at most about 50, at most about 100, at most about 200, at most about 300, at most about 400, at most about 500, at most about 600, at most about 700, at most about 800, at most about 900, at most about 1000, at most about 1500, at most about 2000, at most about 2500, at most about 35 00, at most about 4000, at most about 4500, at most about 5000, at most about 5500, at most about 6000, at most about 6500, at most about 7000, at most about 7500, at most about 8000, at most about 8500, at most about 9000, at most about 9500, or at most about 10000 analytes may be characterized.

In some embodiments, the solutions on the cis side and trans side of the fluidic chamber are configured to generate an electro-osmic force. The electro-osmic force can be generated due to a difference in concentration of a solute between the solution on the cis side and the solution on the cis side. The solute can be an ion or an osmolyte. These ions or osmolytes can flow across the membrane through the nanopore. These ions can be high mobility ions or low mobility ions.

In some embodiments an electrophoretic force can act in a cis to trans direction or a trans to cis direction. An electrophoretic force can act in the same direction as an electro-osmotic force or in an opposing direction to an electro-osmotic force. An electrophoretic force can exert a greater or lesser force on an analyte than an electro-osmotic force. The electrophoretic force can assist or oppose a translocation of an analyte.

In some embodiments, the high mobility ions may comprise less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the salt content on the side of the membrane from which they flow through the nanopore. In some embodiments, the high mobility ions may comprise greater than about 1%, greater than about 2%, greater than about 3%, greater than about 4%, greater than about 5%, greater than about 6%, greater than about 7%, greater than about 8%, greater than about 9%, greater than about 10%, greater than about 15%, greater than about 20%, greater than about 25%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, or greater than about 95% of the salt content on the side of the membrane from which they flow through the nanopore.

In some embodiments, the low mobility ions may comprise less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the salt content on the side of the membrane from which they flow through the nanopore. In some embodiments, the low mobility ions may comprise greater than about 1%, greater than about 2%, greater than about 3%, greater than about 4%, greater than about 5%, greater than about 6%, greater than about 7%, greater than about 8%, greater than about 9%, greater than about 10%, greater than about 15%, greater than about 20%, greater than about 25%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, or greater than about 95% of the salt content on the side of the membrane from which they flow through the nanopore.

In some embodiments, a salt, ion, osmolyte, or electrolyte concentration on the cis side is greater than about 0.01, 0.05, 0.10, 0.20, 0.30, 0.40, 0.50, 0.60, 0.70, 0.80, 0.90, 1.00, 1.10, 1.25, 1.50, 1.75, 2, 2.5, 3, 3.5, 4, 4.5 or about 5 M. In some embodiments, a difference in salt, ion, or electrolyte concentrations between the cis and trans sides is greater than about 0.01, 0.05, 0.10, 0.20, 0.30, 0.40, 0.50, 0.60, 0.70, 0.80, 0.90, 1.00, 1.10, 1.25, 1.50, 1.75, 2, 2.5, 3, 3.5, 4, 4.5 or about 5 M.

In some embodiments, the concentration of the solute is greater on the cis side than the trans side. In some embodiments, the concentration of the solute is greater on the trans side than the cis side.

In some embodiments, an analyte is an unmodified analyte. In some embodiments, an analyte is a label-free or tag-free analyte. In some embodiments, an analyte comprises a leader construct. A leader construct can comprise a molecule conjugated or coupled to an analyte. The conjugation or coupling of the molecule to the analyte can improve a performance characteristic of the provided methods for analyte characterization. A performance characteristic can comprise a read length, a throughput, a processing speed, a sequence accuracy, a sequence coverage, or combinations thereof. A leader construct can comprise a label, a barcode, or combinations thereof. In some embodiments, a leader construct can be configured to modify a characteristic of an analyte. The leader construct can be configured to modify analyte binding to a translocase, analyte binding to an unfoldase, analyte binding to a membrane, analyte capture by a nanopore, or combinations thereof. In some embodiments, the leader construct can be configured to couple the analyte with the translocase. In some cases, the leader construct can be configured to bind the analyte with the translocase. In some instances, the leader construct can be bound to the analyte via a covalent bond. In some instances, the leader construct can be configured to bind the analyte via a non-covalent bond. In some instances, the leader construct can be configured to bind the analyte via a linker. In some embodiments, the leader construct can be configured to couple the analyte with the unfoldase. In some embodiments, the leader construct may not be configured to couple to the nanopore. In some cases, the leader construct may not couple with the nanopore. In some instances, the leader construct may not bind to the nanopore. In some cases, the leader construct may not be configured to assist in the capture of the analyte by the nanopore.

In some embodiments, the leader construct can comprise nucleic acids. In some cases, the nucleic acids can comprise DNA, RNA, locked nucleic acid (LNA), peptide nucleic acid (PNA), bridged nucleic acid (BNA), glycol nucleic acid (GNA), threose nucleic acid (TNA), hexitol nucleic acid (HNA), or any combination thereof. In some embodiments, the leader construct can comprise one or more peptides or proteins. In some embodiments, the leader construct can comprise nucleic acids, proteins, peptides, or any combination thereof.

In some embodiments, the leader construct can be present in a 5' to a 3' orientation. In some embodiment, the leader construct can be present in a N-terminal to a C-terminal orientation.

In some embodiments, the leader construct can comprise the following 5' to 3' orientation: a coupling motif, a stall motif, a block motif, a recognition motif, and a capture motif. In some embodiments, the leader construct can comprise the following N-terminal to C-terminal orientation: a coupling motif, a stall motif, a block motif, a recognition motif, and a capture motif.

In some embodiments, the leader construct can comprise the following 5' to 3' orientation: a coupling motif, a stall motif, a block motif, a capture motif, and a recognition motif. In some embodiments, the leader construct can comprise the following N-terminal to C-terminal orientation: a coupling motif, a stall motif, a block motif, a capture motif, and a recognition motif.

In some embodiments, the leader construct can comprise the following 5' to 3' orientation: a coupling motif, a stall motif, a recognition motif, a block motif, and a capture motif. In some embodiments, the leader construct can comprise the following N-terminal to C-terminal orientation: a coupling motif, a stall motif, a block motif, a capture motif, and a recognition motif.

In some embodiments, the leader construct can comprise the following 5' to 3' orientation: a coupling motif, a stall motif, a recognition motif, a capture motif, and a block motif. In some embodiments, the leader construct can comprise the following N-terminal to C-terminal orientation: a coupling motif, a stall motif, a block motif, a capture motif, and a recognition motif.

In some embodiments, the leader construct can comprise the following 5' to 3' orientation: a coupling motif, a stall motif, a capture motif, a block motif, and a recognition motif. In some embodiments, the leader construct can comprise the following N-terminal to C-terminal orientation: a coupling motif, a stall motif, a capture motif, a block motif, and a recognition motif.

In some embodiments, the leader construct can comprise the following 5' to 3' orientation: a coupling motif, a stall motif, a capture motif, a recognition motif, and a block motif. In some embodiments, the leader construct can comprise the following N-terminal to C-terminal orientation: a coupling motif, a stall motif, a capture motif, a recognition motif, and a block motif.

In some embodiments, the leader construct can comprise the following 5' to 3' orientation: a coupling motif, a block motif, a stall motif, a recognition motif, and a capture motif. In some embodiments, the leader construct can comprise the following N-terminal to C-terminal orientation: a coupling motif, a block motif, a stall motif, a recognition motif, and a capture motif.

In some embodiments, the leader construct can comprise the following 5' to 3' orientation: a coupling motif, a block motif, a stall motif, a capture motif, and a recognition motif. In some embodiments, the leader construct can comprise the following N-terminal to C-terminal orientation: a coupling motif, a block motif, a stall motif, a capture motif, and a recognition motif.

In some embodiments, the leader construct can comprise the following 5' to 3' orientation: a coupling motif, a block motif, a recognition motif, a stall motif, and a capture motif. In some embodiments, the leader construct can comprise the following N-terminal to C-terminal orientation: a coupling motif, a block motif, a recognition motif, a stall motif, and a capture motif.

In some embodiments, the leader construct can comprise the following 5' to 3' orientation: a coupling motif, a block motif, a recognition motif, a capture motif, and a stall motif. In some embodiments, the leader construct can comprise the following N-terminal to C-terminal orientation: a coupling motif, a block motif, a recognition motif, a capture motif, and a stall motif.

In some embodiments, the leader construct can comprise the following 5' to 3' orientation: a coupling motif, a block motif, a capture motif, a recognition motif, and a stall motif. In some embodiments, the leader construct can comprise the following N-terminal to C-terminal orientation: a coupling motif, a block motif, a capture motif, a recognition motif, and a stall motif.

In some embodiments, the leader construct can comprise the following 5' to 3' orientation: a coupling motif, a block motif, a capture motif, a stall motif, and a recognition motif. In some embodiments, the leader construct can comprise the following N-terminal to C-terminal orientation: a coupling motif, a block motif, a capture motif, a stall motif, and a recognition motif.

In some embodiments, the leader construct can comprise the following 5' to 3' orientation: a coupling motif, a recognition motif, a capture motif, a stall motif, and a block motif. In some embodiments, the leader construct can comprise the following N-terminal to C-terminal orientation: a coupling motif, a recognition motif, a capture motif, a stall motif, and a block motif.

In some embodiments, the leader construct can comprise the following 5' to 3' orientation: a coupling motif, a recognition motif, a capture motif, a block motif, and a stall motif. In some embodiments, the leader construct can comprise the following N-terminal to C-terminal orientation: a coupling motif, a recognition motif, a capture motif, a block motif, and a stall motif.

In some embodiments, the leader construct can comprise the following 5' to 3' orientation: a coupling motif, a recognition motif, a stall motif, a block motif, and a capture motif. In some embodiments, the leader construct can comprise the following N-terminal to C-terminal orientation: a coupling motif, a recognition motif, a stall motif, a block motif, and a capture motif.

In some embodiments, the leader construct can comprise the following 5' to 3' orientation: a coupling motif, a recognition motif, a stall motif, capture motif, and block motif. In some embodiments, the leader construct can comprise the following N-terminal to C-terminal orientation: a coupling motif, a recognition motif, a stall motif, capture motif, and block motif.

In some embodiments, the leader construct can comprise the following 5' to 3' orientation: a coupling motif, a recognition motif, a block motif, a stall motif, and a capture motif. In some embodiments, the leader construct can comprise the following N-terminal to C-terminal orientation: a coupling motif, a recognition motif, a block motif, a stall motif, and a capture motif.

In some embodiments, the leader construct can comprise the following 5' to 3' orientation: a coupling motif, a recognition motif, a block motif, a capture motif, and a stall motif. In some embodiments, the leader construct can comprise the following N-terminal to C-terminal orientation: a coupling motif, a recognition motif, a block motif, a capture motif, and a stall motif.

In some embodiments, the leader construct can comprise the following 5' to 3' orientation: a coupling motif, a capture motif, a block motif, a stall motif, and a recognition motif. In some embodiments, the leader construct can comprise the following N-terminal to C-terminal orientation: a coupling motif, a capture motif, a block motif, a stall motif, and a recognition motif.

In some embodiments, the leader construct can comprise the following 5' to 3' orientation: a coupling motif, a capture motif, a block motif, a recognition motif, and a stall motif. In some embodiments, the leader construct can comprise the following N-terminal to C-terminal orientation: a coupling motif, a capture motif, a block motif, a recognition motif, and a stall motif.

In some embodiments, the leader construct can comprise the following 5' to 3' orientation: a coupling motif, a capture motif, a recognition motif, a block motif, and a stall motif. In some embodiments, the leader construct can comprise the following N-terminal to C-terminal orientation: a coupling motif, a capture motif, a recognition motif, a block motif, and a stall motif.

In some embodiments, the leader construct can comprise the following 5' to 3' orientation: a coupling motif, a capture motif, a recognition motif, a stall motif, and a block motif. In some embodiments, the leader construct can comprise the following N-terminal to C-terminal orientation: a coupling motif, a capture motif, a recognition motif, a stall motif, and a block motif.

In some embodiments, the leader construct can comprise the following 5' to 3' orientation: a coupling motif, a capture motif, a stall motif, a block motif, and a recognition motif. In some embodiments, the leader construct can comprise the following N-terminal to C-terminal orientation: a coupling motif, a capture motif, a stall motif, a block motif, and a recognition motif.

In some embodiments, the leader construct can comprise the following 5' to 3' orientation: a coupling motif, a capture motif, a stall motif, recognition motif, and a block motif. In some embodiments, the leader construct can comprise the following N-terminal to C-terminal orientation: a coupling motif, a capture motif, a stall motif, recognition motif, and a block motif.

In some embodiments, the leader construct can comprise the following 5' to 3' orientation: a stall motif, a block motif, a recognition motif, a capture motif, and a coupling motif. In some embodiments, the leader construct can comprise the following N-terminal to C-terminal orientation: a stall motif, a block motif, a recognition motif, a capture motif, and a coupling motif.

In some embodiments, the leader construct can comprise the following 5' to 3' orientation: a stall motif, a block motif, a recognition motif, a coupling motif, and a capture motif. In some embodiments, the leader construct can comprise the following N-terminal to C-terminal orientation: a stall motif, a block motif, a recognition motif, a coupling motif, and a capture motif.

In some embodiments, the leader construct can comprise the following 5' to 3' orientation: a stall motif, a block motif, a capture motif, a recognition motif, and a coupling motif. In some embodiments, the leader construct can comprise the following N-terminal to C-terminal orientation: a stall motif, a block motif, a capture motif, a recognition motif, and a coupling motif.

In some embodiments, the leader construct can comprise the following 5' to 3' orientation: a stall motif, a block motif, a capture motif, a coupling motif, and a recognition motif. In some embodiments, the leader construct can comprise the following N-terminal to C-terminal orientation: a stall motif, a block motif, a capture motif, a coupling motif, and a recognition motif.

In some embodiments, the leader construct can comprise the following 5' to 3' orientation: a stall motif, a block motif, a coupling motif, a recognition motif, and a capture motif. In some embodiments, the leader construct can comprise the following N-terminal to C-terminal orientation: a stall motif, a block motif, a coupling motif, a recognition motif, and a capture motif.

In some embodiments, the leader construct can comprise the following 5' to 3' orientation: a stall motif, a block motif, a coupling motif, a capture motif, and a recognition motif. In some embodiments, the leader construct can comprise the following N-terminal to C-terminal orientation: a stall motif, a block motif, a coupling motif, a capture motif, and a recognition motif.

In some embodiments, the leader construct can comprise the following 5' to 3' orientation: a stall motif, a recognition motif, a block motif, a capture motif, and a coupling motif. In some embodiments, the leader construct can comprise the following N-terminal to C-terminal orientation: a stall motif, a recognition motif, a block motif, a capture motif, and a coupling motif.

In some embodiments, the leader construct can comprise the following 5' to 3' orientation: a stall motif, a recognition motif, a block motif, a coupling motif, and a capture motif. In some embodiments, the leader construct can comprise the following N-terminal to C-terminal orientation: a stall motif, a recognition motif, a block motif, a coupling motif, and a capture motif.

In some embodiments, the leader construct can comprise the following 5' to 3' orientation: a stall motif, a recognition motif, a capture motif, a block motif, and coupling motif. In some embodiments, the leader construct can comprise the following N-terminal to C-terminal orientation: a stall motif, a recognition motif, a capture motif, a block motif, and coupling motif.

In some embodiments, the leader construct can comprise the following 5' to 3' orientation: a stall motif, a recognition motif, a capture motif, a coupling motif, and a block motif. In some embodiments, the leader construct can comprise the following N-terminal to C-terminal orientation: a stall motif, a recognition motif, a capture motif, a coupling motif, and a block motif.

In some embodiments, the leader construct can comprise the following 5' to 3' orientation: a stall motif, a recognition motif, a coupling motif, a block motif, and a capture motif. In some embodiments, the leader construct can comprise the following N-terminal to C-terminal orientation: a stall motif, a recognition motif, a coupling motif, a block motif, and a capture motif.

In some embodiments, the leader construct can comprise the following 5' to 3' orientation: a stall motif, a recognition motif, a coupling motif, a capture motif, and a block motif. In some embodiments, the leader construct can comprise the following N-terminal to C-terminal orientation: a stall motif, a recognition motif, a coupling motif, a capture motif, and a block motif.

In some embodiments, the leader construct can comprise the following 5' to 3' orientation: a stall motif, a capture motif, a block motif, a recognition motif, and a coupling motif. In some embodiments, the leader construct can comprise the following N-terminal to C-terminal orientation: a stall motif, a capture motif, a block motif, a recognition motif, and a coupling motif.

In some embodiments, the leader construct can comprise the following 5' to 3' orientation: a stall motif, a capture motif, a block motif, a coupling motif, and a recognition motif. In some embodiments, the leader construct can comprise the following N-terminal to C-terminal orientation: a stall motif, a capture motif, a block motif, a coupling motif, and a recognition motif.

In some embodiments, the leader construct can comprise the following 5' to 3' orientation: a stall motif, a capture motif, a recognition motif, a block motif, and a coupling motif. In some embodiments, the leader construct can comprise the following N-terminal to C-terminal orientation: a stall motif, a capture motif, a recognition motif, a block motif, and a coupling motif.

In some embodiments, the leader construct can comprise the following 5' to 3' orientation: a stall motif, a capture motif, a recognition motif, a coupling motif, and a block motif. In some embodiments, the leader construct can comprise the following N-terminal to C-terminal orientation: a stall motif, a capture motif, a recognition motif, a coupling motif, and a block motif.

In some embodiments, the leader construct can comprise the following 5' to 3' orientation: a stall motif, a capture motif, a coupling motif, a block motif, and a recognition motif. In some embodiments, the leader construct can comprise the following N-terminal to C-terminal orientation: a stall motif, a capture motif, a coupling motif, a block motif, and a recognition motif.

In some embodiments, the leader construct can comprise the following 5' to 3' orientation: a stall motif, a capture motif, a coupling motif, a recognition motif, and a block motif. In some embodiments, the leader construct can comprise the following N-terminal to C-terminal orientation: a stall motif, a capture motif, a coupling motif, a recognition motif, and a block motif.

In some embodiments, the leader construct can comprise the following 5' to 3' orientation: a stall motif, a coupling motif, a block motif, a recognition motif, and a capture motif. In some embodiments, the leader construct can comprise the following N-terminal to C-terminal orientation: a stall motif, a coupling motif, a block motif, a recognition motif, and a capture motif.

In some embodiments, the leader construct can comprise the following 5' to 3' orientation: a stall motif, a coupling motif, a block motif, a capture motif, and a recognition motif. In some embodiments, the leader construct can comprise the following N-terminal to C-terminal orientation: a stall motif, a coupling motif, a block motif, a capture motif, and a recognition motif.

In some embodiments, the leader construct can comprise the following 5' to 3' orientation: a stall motif, a coupling motif, a recognition motif, a capture motif, and a block motif. In some embodiments, the leader construct can comprise the following N-terminal to C-terminal orientation: a stall motif, a coupling motif, a recognition motif, a capture motif, and a block motif.

In some embodiments, the leader construct can comprise the following 5' to 3' orientation: a stall motif, a coupling motif, a recognition motif, a block motif, and a capture motif. In some embodiments, the leader construct can comprise the following N-terminal to C-terminal orientation: a stall motif, a coupling motif, a recognition motif, a block motif, and a capture motif.

In some embodiments, the leader construct can comprise the following 5' to 3' orientation: a stall motif, a coupling motif, a capture motif, a recognition motif, and a block motif. In some embodiments, the leader construct can comprise the following N-terminal to C-terminal orientation: a stall motif, a coupling motif, a capture motif, a recognition motif, and a block motif.

In some embodiments, the leader construct can comprise the following 5' to 3' orientation: a stall motif, a coupling motif, a capture motif, a block motif, and a recognition motif. In some embodiments, the leader construct can comprise the following N-terminal to C-terminal orientation: a stall motif, a coupling motif, a capture motif, a block motif, and a recognition motif.

In some embodiments, the leader construct can comprise the following 5' to 3' orientation: a block motif, a stall motif, a recognition motif, a capture motif, and a coupling motif. In some embodiments, the leader construct can comprise the following N-terminal to C-terminal orientation: a block motif, a stall motif, a recognition motif, a capture motif, and a coupling motif.

In some embodiments, the leader construct can comprise the following 5' to 3' orientation: a block motif, a stall motif, a recognition motif, a coupling motif, and a capture motif. In some embodiments, the leader construct can comprise the following N-terminal to C-terminal orientation: a block motif, a stall motif, a recognition motif, a coupling motif, and a capture motif.

In some embodiments, the leader construct can comprise the following 5' to 3; orientation: a block motif, a stall motif, a capture motif, a recognition motif, and a coupling motif. In some embodiments, the leader construct can comprise the following N-terminal to C-terminal orientation: a block motif, a stall motif, a capture motif, a recognition motif, and a coupling motif.

In some embodiments, the leader construct can comprise the following 5' to 3' orientation: a block motif, a stall motif, a capture motif, a coupling motif, and a recognition motif. In some embodiments, the leader construct can comprise the following N-terminal to C-terminal orientation: a block motif, a stall motif, a capture motif, a coupling motif, and a recognition motif.

In some embodiments, the leader construct can comprise the following 5' to 3; orientation: a block motif, a stall motif, a coupling motif, a recognition motif, and a capture motif. In some embodiments, the leader construct can comprise the following N-terminal to C-terminal orientation: a block motif, a stall motif, a coupling motif, a recognition motif, and a capture motif.

In some embodiments, the leader construct can comprise the following 5' to 3; orientation: a block motif, a stall motif, a coupling motif, a capture motif, and a recognition motif. In some embodiments, the leader construct can comprise the following N-terminal to C-terminal orientation: a block motif, a stall motif, a coupling motif, a capture motif, and a recognition motif.

In some embodiments, the leader construct can comprise the following 5' to 3' orientation: a block motif, a recognition motif, a stall motif, a capture motif, and a coupling motif. In some embodiments, the leader construct can comprise the following N-terminal to C-terminal orientation: a block motif, a recognition motif, a stall motif, a capture motif, and a coupling motif.

In some embodiments, the leader construct can comprise the following 5' to 3' orientation: a block motif, a recognition motif, a stall motif, a coupling motif, and a capture motif. In some embodiments, the leader construct can comprise the following N-terminal to C-terminal orientation: a block motif, a recognition motif, a stall motif, a coupling motif, and a capture motif.

In some embodiments, the leader construct can comprise the following 5' to 3' orientation: a block motif, a recognition motif, a capture motif, a stall motif, and a coupling motif. In some embodiments, the leader construct can comprise the following N-terminal to C-terminal orientation: a block motif, a recognition motif, a capture motif, a stall motif, and a coupling motif.

In some embodiments, the leader construct can comprise the following 5' to 3' orientation: a block motif, a recognition motif, a capture motif, a coupling motif, and a stall motif. In some embodiments, the leader construct can comprise the following N-terminal to C-terminal orientation: a block motif, a recognition motif, a capture motif, a coupling motif, and a stall motif.

In some embodiments, the leader construct can comprise the following 5' to 3' orientation: a block motif, a recognition motif, a coupling motif, a stall motif, and a capture motif. In some embodiments, the leader construct can comprise the following N-terminal to C-terminal orientation: a block motif, a recognition motif, a coupling motif, a stall motif, and a capture motif.

In some embodiments, the leader construct can comprise the following 5' to 3' orientation: a block motif, a recognition motif, a coupling motif, a capture motif, and a stall motif. In some embodiments, the leader construct can comprise the following N-terminal to C-terminal orientation: a block motif, a recognition motif, a coupling motif, a capture motif, and a stall motif.

In some embodiments, the leader construct can comprise the following 5' to 3' orientation: a block motif, a capture motif, a stall motif, a recognition motif, and a coupling motif. In some embodiments, the leader construct can comprise the following N-terminal to C-terminal orientation: a block motif, a capture motif, a stall motif, a recognition motif, and a coupling motif.

In some embodiments, the leader construct can comprise the following 5' to 3' orientation: a block motif, a capture motif, a stall motif, a coupling motif, and a recognition motif. In some embodiments, the leader construct can comprise the following N-terminal to C-terminal orientation: a block motif, a capture motif, a stall motif, a coupling motif, and a recognition motif.

In some embodiments, the leader construct can comprise the following 5' to 3' orientation: a block motif, a capture motif, a recognition motif, a stall motif, and a coupling motif. In some embodiments, the leader construct can comprise the following N-terminal to C-terminal orientation: a block motif, a capture motif, a recognition motif, a stall motif, and a coupling motif.

In some embodiments, the leader construct can comprise the following 5' to 3' orientation: a block motif, a capture motif, a recognition motif, a coupling motif, and a stall motif. In some embodiments, the leader construct can comprise the following N-terminal to C-terminal orientation: a block motif, a capture motif, a recognition motif, a coupling motif, and a stall motif.

In some embodiments, the leader construct can comprise the following 5' to 3' orientation: a block motif, a capture motif, a coupling motif, a stall motif, and a recognition motif. In some embodiments, the leader construct can comprise the following N-terminal to C-terminal orientation: a block motif, a capture motif, a coupling motif, a stall motif, and a recognition motif.

In some embodiments, the leader construct can comprise the following 5' to 3' orientation: a block motif, a capture motif, a coupling motif, a recognition motif, and a stall motif. In some embodiments, the leader construct can comprise the following N-terminal to C-terminal orientation: a block motif, a capture motif, a coupling motif, a recognition motif, and a stall motif.

In some embodiments, the leader construct can comprise the following 5' to 3' orientation: a block motif, a coupling motif, a capture motif, a stall motif, and a recognition motif. In some embodiments, the leader construct can comprise the following N-terminal to C-terminal orientation: a block motif, a coupling motif, a capture motif, a stall motif, and a recognition motif.

In some embodiments, the leader construct can comprise the following 5' to 3' orientation: a block motif, a coupling motif, a capture motif, a recognition motif, and a stall motif. In some embodiments, the leader construct can comprise the following N-terminal to C-terminal orientation: a block motif, a coupling motif, a capture motif, a recognition motif, and a stall motif.

In some embodiments, the leader construct can comprise the following 5' to 3' orientation: a block motif, a coupling motif, a stall motif, a recognition motif, and a capture motif. In some embodiments, the leader construct can comprise the following N-terminal to C-terminal orientation: a block motif, a coupling motif, a stall motif, a recognition motif, and a capture motif.

In some embodiments, the leader construct can comprise the following 5' to 3' orientation: a block motif, a coupling motif, a stall motif, a capture motif, and a recognition motif. In some embodiments, the leader construct can comprise the following N-terminal to C-terminal orientation: a block motif, a coupling motif, a stall motif, a capture motif, and a recognition motif.

In some embodiments, the leader construct can comprise the following 5' to 3' orientation: a block motif, a coupling motif, a recognition motif, a stall motif, and a capture motif. In some embodiments, the leader construct can comprise the following N-terminal to C-terminal orientation: a block motif, a coupling motif, a recognition motif, a stall motif, and a capture motif.

In some embodiments, the leader construct can comprise the following 5' to 3' orientation: a block motif, a coupling motif, a recognition motif, a capture motif, and a stall motif. In some embodiments, the leader construct can comprise the following N-terminal to C-terminal orientation: a block motif, a coupling motif, a recognition motif, a capture motif, and a stall motif.

In some embodiments, the leader construct can comprise the following 5' to 3' orientation: a recognition motif, a stall motif, a block motif, a capture motif, and a coupling motif. In some embodiments, the leader construct can comprise the following N-terminal to C-terminal orientation: a recognition motif, a stall motif, a block motif, a capture motif, and a coupling motif.

In some embodiments, the leader construct can comprise the following 5' to 3' orientation: a recognition motif, a stall motif, a block motif, a coupling motif, and a capture motif. In some embodiments, the leader construct can comprise the following N-terminal to C-terminal orientation: a recognition motif, a stall motif, a block motif, a coupling motif, and a capture motif.

In some embodiments, the leader construct can comprise the following 5' to 3' orientation: a recognition motif, a stall motif, a capture motif, a block motif, and a coupling motif. In some embodiments, the leader construct can comprise the following N-terminal to C-terminal orientation: a recognition motif, a stall motif, a capture motif, a block motif, and a coupling motif.

In some embodiments, the leader construct can comprise the following 5' to 3' orientation: a recognition motif, a stall motif, a capture motif, a coupling motif, and a block motif. In some embodiments, the leader construct can comprise the following N-terminal to C-terminal orientation: a recognition motif, a stall motif, a capture motif, a coupling motif, and a block motif.

In some embodiments, the leader construct can comprise the following 5' to 3' orientation: a recognition motif, a stall motif, a coupling motif, a block motif, and a capture motif. In some embodiments, the leader construct can comprise the following N-terminal to C-terminal orientation: a recognition motif, a stall motif, a coupling motif, a block motif, and a capture motif.

In some embodiments, the leader construct can comprise the following 5' to 3' orientation: a recognition motif, a stall motif, a coupling motif, a capture motif, and a block motif. In some embodiments, the leader construct can comprise the following N-terminal to C-terminal orientation: a recognition motif, a stall motif, a coupling motif, a capture motif, and a block motif.

In some embodiments, the leader construct can comprise the following 5' to 3' orientation: a recognition motif, a block motif, a stall motif, a capture motif, and a coupling motif. In some embodiments, the leader construct can comprise the following N-terminal to C-terminal orientation: a recognition motif, a block motif, a stall motif, a capture motif, and a coupling motif.

In some embodiments, the leader construct can comprise the following 5' to 3' orientation: a recognition motif, a block motif, a stall motif, a coupling motif, and a capture motif. In some embodiments, the leader construct can comprise the following N-terminal to C-terminal orientation: a recognition motif, a block motif, a stall motif, a coupling motif, and a capture motif.

In some embodiments, the leader construct can comprise the following 5' to 3' orientation: a recognition motif, a block motif, a capture motif, a stall motif, and a coupling motif. In some embodiments, the leader construct can comprise the following N-terminal to C-terminal orientation: a recognition motif, a block motif, a capture motif, a stall motif, and a coupling motif.

In some embodiments, the leader construct can comprise the following 5' to 3' orientation: a recognition motif, a block motif, a capture motif, a coupling motif, and a stall motif. In some embodiments, the leader construct can comprise the following N-terminal to C-terminal orientation: a recognition motif, a block motif, a capture motif, a coupling motif, and a stall motif.

In some embodiments, the leader construct can comprise the following 5' to 3' orientation: a recognition motif, a block motif, a coupling motif, a stall motif, and a capture motif. In some embodiments, the leader construct can comprise the following N-terminal to C-terminal orientation: a recognition motif, a block motif, a coupling motif, a stall motif, and a capture motif.

In some embodiments, the leader construct can comprise the following 5' to 3' orientation: a recognition motif, a block motif, a coupling motif, a capture motif, and a stall motif. In some embodiments, the leader construct can comprise the following N-terminal to C-terminal orientation: a recognition motif, a block motif, a coupling motif, a capture motif, and a stall motif.

In some embodiments, the leader construct can comprise the following 5' to 3' orientation: a recognition motif, a coupling motif, a block motif, a stall motif, and a capture motif. In some embodiments, the leader construct can comprise the following N-terminal to C-terminal orientation: a recognition motif, a coupling motif, a block motif, a stall motif, and a capture motif.

In some embodiments, the leader construct can comprise the following 5' to 3' orientation: a recognition motif, a coupling motif, a block motif, a capture motif, and a stall motif. In some embodiments, the leader construct can comprise the following N-terminal to C-terminal orientation: a recognition motif, a coupling motif, a block motif, a capture motif, and a stall motif.

In some embodiments, the leader construct can comprise the following 5' to 3' orientation: a recognition motif, a coupling motif, a stall motif, a block motif, and a capture motif. In some embodiments, the leader construct can comprise the following N-terminal to C-terminal orientation: a recognition motif, a coupling motif, a stall motif, a block motif, and a capture motif.

In some embodiments, the leader construct can comprise the following 5' to 3' orientation: a recognition motif, a coupling motif, a stall motif, a capture motif, and a block motif. In some embodiments, the leader construct can comprise the following N-terminal to C-terminal orientation: a recognition motif, a coupling motif, a stall motif, a capture motif, and a block motif.

In some embodiments, the leader construct can comprise the following 5' to 3' orientation: a recognition motif, a coupling motif, a capture motif, a block motif, and a stall motif. In some embodiments, the leader construct can comprise the following N-terminal to C-terminal orientation: a recognition motif, a coupling motif, a capture motif, a block motif, and a stall motif.

In some embodiments, the leader construct can comprise the following 5' to 3' orientation: a recognition motif, a coupling motif, a capture motif, a stall motif, and a block motif. In some embodiments, the leader construct can comprise the following N-terminal to C-terminal orientation: a recognition motif, a coupling motif, a capture motif, a stall motif, and a block motif.

In some embodiments, the leader construct can comprise the following 5' to 3' orientation: a recognition motif, a capture motif, a block motif, a stall motif, and a coupling motif. In some embodiments, the leader construct can comprise the following N-terminal to C-terminal orientation: a recognition motif, a capture motif, a block motif, a stall motif, and a coupling motif.

In some embodiments, the leader construct can comprise the following 5' to 3' orientation: a recognition motif, a capture motif, a block motif, a coupling motif, and a stall motif. In some embodiments, the leader construct can comprise the following N-terminal to C-terminal orientation: a recognition motif, a capture motif, a block motif, a coupling motif, and a stall motif.

In some embodiments, the leader construct can comprise the following 5' to 3' orientation: a recognition motif, a capture motif, a stall motif, a block motif, and a coupling motif. In some embodiments, the leader construct can comprise the following N-terminal to C-terminal orientation: a recognition motif, a capture motif, a stall motif, a block motif, and a coupling motif.

In some embodiments, the leader construct can comprise the following 5' to 3' orientation: a recognition motif, a capture motif, a stall motif, a coupling motif, and a block motif. In some embodiments, the leader construct can comprise the following N-terminal to C-terminal orientation: a recognition motif, a capture motif, a stall motif, a coupling motif, and a block motif.

In some embodiments, the leader construct can comprise the following 5' to 3' orientation: a recognition motif, a capture motif, a coupling motif, a stall motif, and a block motif. In some embodiments, the leader construct can comprise the following N-terminal to C-terminal orientation: a recognition motif, a capture motif, a coupling motif, a stall motif, and a block motif.

In some embodiments, the leader construct can comprise the following 5' to 3' orientation: a recognition motif, a capture motif, a coupling motif, a block motif, and a stall motif. In some embodiments, the leader construct can comprise the following N-terminal to C-terminal orientation: a recognition motif, a capture motif, a coupling motif, a block motif, and a stall motif.

In some embodiments, the leader construct can comprise the following 5' to 3' orientation: a capture motif, a recognition motif, a stall motif, a block motif, and a coupling motif. In some embodiments, the leader construct can comprise the following N-terminal to C-terminal orientation: a capture motif, a recognition motif, a stall motif, a block motif, and a coupling motif.

In some embodiments, the leader construct can comprise the following 5' to 3' orientation: a capture motif, a recognition motif, a stall motif, a coupling motif, and a block motif. In some embodiments, the leader construct can comprise the following N-terminal to C-terminal orientation: a capture motif, a recognition motif, a stall motif, a coupling motif, and a block motif.

In some embodiments, the leader construct can comprise the following 5' to 3' orientation: a capture motif, a recognition motif, a block motif, a stall motif, and a coupling motif. In some embodiments, the leader construct can comprise the following N-terminal to C-terminal orientation: a capture motif, a recognition motif, a block motif, a stall motif, and a coupling motif.

In some embodiments, the leader construct can comprise the following 5' to 3' orientation: a capture motif, recognition motif, a block motif, a coupling motif, and a stall motif. In some embodiments, the leader construct can comprise the following N-terminal to C-terminal orientation: a capture motif, recognition motif, a block motif, a coupling motif, and a stall motif.

In some embodiments, the leader construct can comprise the following 5' to 3' orientation: a capture motif, a recognition motif, a coupling motif, a stall motif, and a block motif. In some embodiments, the leader construct can comprise the following N-terminal to C-terminal orientation: a capture motif, a recognition motif, a coupling motif, a stall motif, and a block motif.

In some embodiments, the leader construct can comprise the following 5' to 3' orientation: a capture motif, a recognition motif, a coupling motif, a block motif, and a stall motif. In some embodiments, the leader construct can comprise the following N-terminal to C-terminal orientation: a capture motif, a recognition motif, a coupling motif, a block motif, and a stall motif.

In some embodiments, the leader construct can comprise the following 5' to 3' orientation: a capture motif, a stall motif, a block motif, a recognition motif, and a coupling motif. In some embodiments, the leader construct can comprise the following N-terminal to C-terminal orientation: a capture motif, a stall motif, a block motif, a recognition motif, and a coupling motif.

In some embodiments, the leader construct can comprise the following 5' to 3' orientation: a capture motif, a stall motif, a block motif, a coupling motif, and a recognition motif. In some embodiments, the leader construct can comprise the following N-terminal to C-terminal orientation: a capture motif, a stall motif, a block motif, a coupling motif, and a recognition motif.

In some embodiments, the leader construct can comprise the following 5' to 3' orientation: a capture motif, the stall motif, the recognition motif, a block motif, and a coupling motif. In some embodiments, the leader construct can comprise the following N-terminal to C-terminal orientation: a capture motif, the stall motif, the recognition motif, a block motif, and a coupling motif.

In some embodiments, the leader construct can comprise the following 5' to 3' orientation: a capture motif, a stall motif, a recognition motif, a coupling motif, and a block motif. In some embodiments, the leader construct can comprise the following N-terminal to C-terminal orientation: a capture motif, a stall motif, a recognition motif, a coupling motif, and a block motif.

In some embodiments, the leader construct can comprise the following 5' to 3' orientation: a capture motif, a stall motif, a coupling motif, a block motif, and a recognition motif. In some embodiments, the leader construct can comprise the following N-terminal to C-terminal orientation: a capture motif, a stall motif, a coupling motif, a block motif, and a recognition motif.

In some embodiments, the leader construct can comprise the following 5' to 3' orientation: a capture motif, a stall motif, a coupling motif, a recognition motif, and a block motif. In some embodiments, the leader construct can comprise the following N-terminal to C-terminal orientation: a capture motif, a stall motif, a coupling motif, a recognition motif, and a block motif.

In some embodiments, the leader construct can comprise the following 5' to 3' orientation: a capture motif, a block motif, a stall motif, a recognition motif, and a coupling motif. In some embodiments, the leader construct can comprise the following N-terminal to C-terminal orientation: a capture motif, a block motif, a stall motif, a recognition motif, and a coupling motif.

In some embodiments, the leader construct can comprise the following 5' to 3' orientation: a capture motif, a block motif, a stall motif, a coupling motif, and a recognition motif. In some embodiments, the leader construct can comprise the following N-terminal to C-terminal orientation: a capture motif, a block motif, a stall motif, a coupling motif, and a recognition motif.

In some embodiments, the leader construct can comprise the following 5' to 3' orientation: a capture motif, a block motif, a recognition motif, a stall motif, and a coupling motif. In some embodiments, the leader construct can comprise the following N-terminal to C-terminal orientation: a capture motif, a block motif, a recognition motif, a stall motif, and a coupling motif.

In some embodiments, the leader construct can comprise the following 5' to 3' orientation: a capture motif, a block motif, a recognition motif, a coupling motif, and a stall motif. In some embodiments, the leader construct can comprise the following N-terminal to C-terminal orientation: a capture motif, a block motif, a recognition motif, a coupling motif, and a stall motif.

In some embodiments, the leader construct can comprise the following 5' to 3' orientation: a capture motif, a block motif, a recognition motif, a stall motif, and a coupling motif. In some embodiments, the leader construct can comprise the following N-terminal to C-terminal orientation: a capture motif, a block motif, a recognition motif, a stall motif, and a coupling motif.

In some embodiments, the leader construct can comprise the following 5' to 3' orientation: a capture motif, a block motif, a recognition motif, a stall motif, and a coupling motif. In some embodiments, the leader construct can comprise the following N-terminal to C-terminal orientation: a capture motif, a block motif, a recognition motif, a stall motif, and a coupling motif.

In some embodiments, the leader construct can comprise the following 5' to 3' orientation: a capture motif, a coupling motif, a stall motif, a block motif, and a recognition motif. In some embodiments, the leader construct can comprise the following N-terminal to C-terminal orientation: a capture motif, a coupling motif, a stall motif, a block motif, and a recognition motif.

In some embodiments, the leader construct can comprise the following 5' to 3' orientation: a capture motif, a coupling motif, a stall motif, a recognition motif, and a block motif. In some embodiments, the leader construct can comprise the following N-terminal to C-terminal orientation: a capture motif, a coupling motif, a stall motif, a recognition motif, and a block motif.

In some embodiments, the leader construct can comprise the following 5' to 3' orientation: a capture motif, a coupling motif, a block motif, a stall motif, and a recognition motif. In some embodiments, the leader construct can comprise the following N-terminal to C-terminal orientation: a capture motif, a coupling motif, a block motif, a stall motif, and a recognition motif.

In some embodiments, the leader construct can comprise the following 5' to 3' orientation: a capture motif, a coupling motif, a block motif, a recognition motif, and a stall motif.

In some embodiments, the leader construct can comprise the following N-terminal to C-terminal orientation: a capture motif, a coupling motif, a block motif, a recognition motif, and a stall motif.

In some embodiments, the leader construct can comprise the following 5' to 3' orientation: a capture motif, a coupling motif, a recognition motif, a stall motif, and a block motif. In some embodiments, the leader construct can comprise the following N-terminal to C-terminal orientation: a capture motif, a coupling motif, a recognition motif, a stall motif, and a block motif.

In some embodiments, the leader construct can comprise the following 5' to 3' orientation: a capture motif, a coupling motif, a recognition motif, a block motif, and a stall motif. In some embodiments, the leader construct can comprise the following N-terminal to C-terminal orientation: a capture motif, a coupling motif, a recognition motif, a block motif, and a stall motif.

In some embodiments, the leader construct can be configured to couple the analyte to one or more translocases. In some embodiments, the leader construct can be coupled to the analyte via the coupling motif. In some embodiments, the capture motif can be configured to couple the analyte with one or more translocases.

In some embodiments the leader construct can be configured to slow or speed up the progression or translocation of an analyte through a translocase, an unfoldase, or a nanopore. The leader construct can stall or unstall a molecular motor. The leader construct can be configured to identify the leader construct from another leader construct. A leader construct can comprise a recognition motif, a capture motif, a stall motif, a block motif, a coupling motif, a barcode motif, a membrane binding motif, or combinations thereof. A leader construct can comprise polymeric molecules, reactive groups, inert groups, or combinations thereof. A leader motif can comprise natural or non-natural amino acids, nucleic acids (e.g., DNA, RNA), water soluble polymers (e.g. polyethylene glycol), peptides, proteins, lipids, saccharides, enzymes, fluorescent tags, inorganic components, or combinations thereof. In some embodiments, the leader construct can comprise a stall motif. In some cases, the stall motif can comprise nucleic acids. In some cases, the nucleic acids can comprise DNA, RNA, LNA, PNA, BNA, GNA, TNA, HNA, or any combination thereof. In some cases, the stall motif can comprise one or more peptides or proteins. In some cases, the stall motif can comprise nucleic acids, proteins, peptides, or any combination thereof.

In some embodiments, the leader construct can comprise a block motif. In some cases, the block motif can comprise nucleic acids. In some cases, the nucleic acids can comprise DNA, RNA, LNA, PNA, BNA, GNA, TNA, HNA, or any combination thereof. In some cases, the block motif can comprise one or more peptides or proteins. In some cases, the block motif can comprise nucleic acids, proteins, peptides, or any combination thereof.

In some embodiments, the leader construct can comprise a coupling motif. In some cases, the coupling motif can comprise nucleic acids. In some cases, the nucleic acids can comprise DNA, RNA, LNA, PNA, BNA, GNA, TNA, HNA, or any combination thereof. In some cases, the coupling motif can comprise one or more peptides or proteins. In some cases, the coupling motif can comprise nucleic acids, proteins, peptides, or any combination thereof.

In some embodiments, the leader construct can comprise a recognition motif. In some cases, the recognition motif can comprise nucleic acids. In some cases, the nucleic acids can comprise DNA, RNA, LNA, PNA, BNA, GNA, TNA, HNA, or any combination thereof. In some cases, the recognition motif can comprise one or more peptides or proteins. In some cases, the recognition motif can comprise nucleic acids, proteins, peptides, or any combination thereof. In some embodiments, the recognition motif can be configured to bind to one or more translocases.

In some embodiments, the leader construct can comprise a capture motif. In some cases, the capture motif can comprise nucleic acids. In some cases, the nucleic acids can comprise DNA, RNA, LNA, PNA, BNA, GNA, TNA, HNA, or any combination thereof. In some cases, the capture motif can comprise one or more peptides or proteins. In some cases, the capture motif can comprise nucleic acids, proteins, peptides, or any combination thereof.

In some cases, the leader construct can comprise a stall motif and a block motif. In some cases, the leader construct can comprise a stall motif and a coupling motif. In some cases, the leader construct can comprise a stall motif and a recognition motif. In some cases, the leader construct can comprise a stall motif and a capture motif. In some cases, the leader construct can comprise a block motif and a coupling motif. In some cases, the leader construct can comprise a block motif and a recognition motif. In some cases, the leader construct can comprise a block motif and a capture motif. In some cases, the leader construct can comprise a coupling motif and a recognition motif. In some cases, the leader construct can comprise a coupling motif and a capture motif. In some cases, the leader construct can comprise a recognition motif and a capture motif. In some instances, the leader construct can comprise a block motif, a stall motif, and a coupling motif. In some instances, the leader construct can comprise a block motif, a stall motif, and a recognition motif. In some instances, the leader construct can comprise a block motif, a stall motif, and a capture motif. In some instances, the leader construct can comprise a block motif, a coupling motif, and a recognition motif. In some instances, the leader construct can comprise a block motif, a coupling motif, and a capture motif. In some instances, the leader construct can comprise a block motif, a recognition motif, and a capture motif. In some instances, the leader construct can comprise a stall motif, a coupling motif, and a recognition motif. In some instances, the leader construct can comprise a stall motif, a coupling motif, and a capture motif. In some instances, the leader construct can comprise a stall motif, a recognition motif, and a capture motif. In some instances, the leader construct can comprise a coupling motif, a recognition motif, and a capture motif. In some cases, the leader construct can comprise a block motif, a stall motif, a coupling motif, and a recognition motif. In some cases, the leader construct can comprise a block motif, a stall motif, a coupling motif, and a capture motif. In some cases, the leader construct can comprise a stall motif, a coupling motif, a recognition motif, and a capture motif. In some cases, the leader construct can comprise a block motif, a coupling motif, a recognition motif, and a capture motif. In some cases, the leader construct can comprise a block motif, a stall motif, a recognition motif, and a capture motif. In some cases, the leader construct can comprise a block motif, a stall motif, a coupling motif, and a capture motif. In some embodiments, the capture motif can comprise a block motif, a stall motif, a coupling motif, a recognition motif, and a capture motif.

In some embodiments, the leader construct can be greater than about 30 repeating units in length. In some cases, the repeating units can be amino acid residues, nucleotides, oligosaccharides, lipids, or any combination thereof. In some cases, the leader construct can be greater than about 30 repeating units, greater than about 35 repeating units, greater than about 40 repeating units, greater than about 45 repeating units, greater than about 50 repeating units, greater than about 55 repeating units, greater than about 60 repeating units, greater than about 65 repeating units, greater than about 70 repeating units, greater than about 75 repeating units, greater than about 80 repeating units, greater than about 85 repeating units, greater than about 90 repeating units, greater than about 95 repeating units, greater than about 100 repeating units, or more than 100 repeating units in length. In some the leader construct can comprise about 30 repeating units, about 35 repeating units, about 40 repeating units, about 45 repeating units, about 50 repeating units, about 55 repeating units, about 60 repeating units, about 65 repeating units, about 70 repeating units, about 75 repeating units, about 80 repeating units, about 85 repeating units, about 90 repeating units, about 95 repeating units, or about 100 repeating units in length. In some embodiments, the leader construct can be at most about 30 repeating units in length. In some cases, the leader construct can be at least about one repeating unit, at least about two repeating units, at least about three repeating units, at least about four repeating units, at least about five repeating units, at least about six repeating units, at least about seven repeating units, at least about eight repeating units, at least about nine repeating units, at least about ten repeating units, at least about 11 repeating units, at least about 12 repeating units, at least about 13 repeating units, at least about 14 repeating units, at least about 15 repeating units, at least about 16 repeating units, at least about 17 repeating units, at least about 18 repeating units, at least about 19 repeating units, at least about 20 repeating units, at least about 21 repeating units, at least about 22 repeating units, at least about 23 repeating units, at least about 24 repeating units, at least about 25 repeating units, at least about 26 repeating units, at least about 27 repeating units, at least about 28 repeating units, at least about 29 repeating units, at least about 30 repeating units, or more than 30 repeating units in length. In some cases, the leader construct can be at most about 30 repeating units, at most about 29 repeating units, at most about 28 repeating units, at most about 27 repeating units, at most about 26 repeating units, at most about 25 repeating units, at most about 24 repeating units, at most about 23 repeating units, at most about 22 repeating units, at most about 21 repeating units, at most about 20 repeating units, at most about 19 repeating units, at most about 18 repeating units, at most about 17 repeating units, at most about 16 repeating units, at most about 15 repeating units, at most about 14 repeating units, at most about 13 repeating units, at most about 12 repeating units, at most about 11 repeating units, at most about 10 repeating units, at most about nine repeating units, at most about eight repeating units, at most about seven repeating units, at most about six repeating units, at most about five repeating units, at most four repeating units, at most about three repeating units, at most about two repeating units, at most about one repeating unit, or less than one repeating unit in length. In some cases, the leader construct can be about one repeating unit, about two repeating units, about three repeating units, about four repeating units, about five repeating units, about six repeating units, about seven repeating units, about eight repeating units, about nine repeating units, about ten repeating units, about 11 repeating units, about 12 repeating units, about 13 repeating units, about 14 repeating units, about 15 repeating units, about 16 repeating units, about 17 repeating units, about 18 repeating units, about 19 repeating units, about 20 repeating units, about 21 repeating units, about 22 repeating units, about 23 repeating units, about 24 repeating units, about 25 repeating units, about 26 repeating units, about 27 repeating units, about 28 repeating units, about 29 repeating units, or about 30 repeating units in length.

In some embodiments, a leader construct comprises a recognition motif. A recognition motif can comprise a peptide tag, a recognition element, or modified variants thereof. A recognition motif can be a peptide sequence that binds to a protein, or assists in binding to a protein. The protein can be a translocase, an unfoldase, a nanopore, or any combination thereof. In some embodiments, the recognition sequence can comprise a nucleic acid sequence. In some cases, the recognition sequence can comprise a peptide sequence. In some cases, the recognition sequence can comprise a nucleic acid sequence and a peptide sequence. The peptide sequence can be natural, mutated, or created de novo. In some embodiments, a corresponding translocase, unfoldase, or nanopore may be mutated or evolved to bind a recognition motif. In some embodiments, evolution comprises directed evolution. In some embodiments, a recognition motif may be created or discovered to bind a translocase, an unfoldase, or a nanopore. A recognition motif may be created for example by peptide screening. Known recognition motifs, mutants of recognition motifs, variants of recognition motifs, random libraries of peptide sequences, or combinations thereof can be screened for binding to a translocase, an unfoldase, or a nanopore.

In some embodiments, the recognition motif can comprise between about one repeating unit to about 30 repeating units. In some cases, the recognition motif can comprise between about on repeating unit to about 5 repeating units, between about 5 repeating units to about 10 repeating units, between about 10 repeating units to about 15 repeating units, between about 15 repeating units to about 20 repeating units, between about 20 repeating units to about 25 repeating units, or between about 25 repeating units. In some cases, the recognition motif can comprise at least about one repeating unit, at least about 2 repeating units, at least about 3 repeating units, at least about 4 repeating units, at least about 5 repeating units, at least about 6 repeating units, at least about 7 repeating units, at least about 8 repeating units, at least about 9 repeating units, at least about 10 repeating units, at least about 11 repeating units, at least about 12 repeating units, at least about 13 repeating units, at least about 14 repeating units, at least about 15 repeating units, at least about 16 repeating units, at least about 17 repeating units, at least about 18 repeating units, at least about 19 repeating units, at least about 20 repeating units, at least about 21 repeating units, at least about 22 repeating units, at least about 23 repeating units, at least about 24 repeating units, at least about 25 repeating units, at least about 26 repeating units, at least about 27 repeating units, at least about 28 repeating units, at least about 29 repeating units, at least about 30 repeating units, or more than 30 repeating units. In some cases, the recognition motif can comprise at most about 30 repeating units, at most about 29 repeating units, at most about 28 repeating units, at most about 27 repeating units, at most about 26 repeating units, at most about 25 repeating units, at most about 24 repeating units, at most about 23 repeating units, at most about 22 repeating units, at most about 21 repeating units, at most about 20 repeating units, at most about 19 repeating units, at most about 18 repeating units, at most about 17 repeating units, at most about 16 repeating units, at most about 15 repeating units, at most about 14 repeating units, at most about 13 repeating units, at most about 12 repeating units, at most about 11 repeating units, at most about 10 repeating units, at most about 9 repeating units, at most about 8 repeating units, at most about 7 repeating units, at most about 6 repeating units, at most about 5 repeating units, at most about 4 repeating units, at most about 3 repeating units, at most about 2 repeating units, at most about one repeating unit, or less than one repeating unit. In some cases, the recognition motif can comprise about one repeating unit, about two repeating units, about 3 repeating units, about 4 repeating units, about 5 repeating units, about 6 repeating units, about 7 repeating units, about 8 repeating units, about 9 repeating units, about 10 repeating units, about 11 repeating units, about 12 repeating units, about 13 repeating units, about 14 repeating units, about 15 repeating units, about 16 repeating units, about 17 repeating units, about 18 repeating units, about 19 repeating units, about 20 repeating units, about 21 repeating units, about 22 repeating units, about 23 repeating units, about 24 repeating units, about 25 repeating units, about 26 repeating units, about 27 repeating units, about 28 repeating units, about 29 repeating units, or about 30 repeating units.

In some embodiments, a leader construct comprises a capture motif. The capture motif can comprise a combination of a recognition motif and a pore-capture motif. The capture motif may promote capture of the leader construct or the analyte by a pore. In some embodiments, capture of the analyte by the nanopore can be promoted by a net charge of the capture motif. The net charge may be attracted to, or repelled by, an applied voltage. The applied voltage may be applied to the opposite side of the membrane in which the analyte or leader construct is contained. For example, a capture motif comprising a net positive charge may enhance capture when a negative applied voltage is applied, or a capture motif comprising a net negative charge may enhance capture when a positive applied voltage is applied. The capture motif may comprise repeated amino acids, or repeated amino acid groups. The capture motif may comprise repeated nucleotides, or repeated nucleotide groups. An amino acid or amino acid group may comprise a charged amino acid. A nucleotide or nucleotide group may have a negative charge or a positive charge. The charged amino acid may have a negative charge or a positive charge. In some cases, a positively charged amino acid can comprise lysine, arginine, or any combination thereof. In some cases, a negatively charged amino acid can comprise aspartic acid, glutamic acid, or any combination thereof. The capture motif may comprise a polyanion or a polycation. In some embodiments, the capture motif may comprise one or more units of (SGX)n, (SX)n, or (X)n, wherein n is an integer, and X comprises a positive or negatively charged amino acid. For example, the capture motif may comprise one or more units of (SGD)n, (SD)n, (D)n, (SGR)n, (SR)n, (R)n, wherein n is an integer. In some embodiments, n can be greater than about 1, greater than about 2, greater than about 3, greater than about 4, greater than about 5, greater than about 6, greater than about 7, greater than about 8, greater than about 9, greater than about 10, greater than about 11, greater than about 12, greater than about 13, greater than about 14, greater than about 15, greater than about 16, greater than about 17, greater than about 18, greater than about 19, greater than about 20, greater than about 25, greater than about 30, greater than about 40, greater than about 45, or greater than about 50. In some embodiments, n is less than about 2, less than about 3, less than about 4, less than about 5, less than about 6, less than about 7, less than about 8, less than about 9, less than about 10, less than about 11, less than about 12, less than about 13, less than about 14, less than about 15, less than about 16, less than about 17, less than about 18, less than about 19, less than about 20, less than about 25, less than about 30, less than about 40, less than about 45, or less than about less than about 50.

In some embodiments, the capture motif can comprise between about one repeating unit to about 30 repeating units. In some cases, the capture motif can comprise between about on repeating unit to about 5 repeating units, between about 5 repeating units to about 10 repeating units, between about 10 repeating units to about 15 repeating units, between about 15 repeating units to about 20 repeating units, between about 20 repeating units to about 25 repeating units, or between about 25 repeating units. In some cases, the capture motif can comprise at least about one repeating unit, at least about 2 repeating units, at least about 3 repeating units, at least about 4 repeating units, at least about 5 repeating units, at least about 6 repeating units, at least about 7 repeating units, at least about 8 repeating units, at least about 9 repeating units, at least about 10 repeating units, at least about 11 repeating units, at least about 12 repeating units, at least about 13 repeating units, at least about 14 repeating units, at least about 15 repeating units, at least about 16 repeating units, at least about 17 repeating units, at least about 18 repeating units, at least about 19 repeating units, at least about 20 repeating units, at least about 21 repeating units, at least about 22 repeating units, at least about 23 repeating units, at least about 24 repeating units, at least about 25 repeating units, at least about 26 repeating units, at least about 27 repeating units, at least about 28 repeating units, at least about 29 repeating units, at least about 30 repeating units, or more than 30 repeating units. In some cases, the capture motif can comprise at most about 30 repeating units, at most about 29 repeating units, at most about 28 repeating units, at most about 27 repeating units, at most about 26 repeating units, at most about 25 repeating units, at most about 24 repeating units, at most about 23 repeating units, at most about 22 repeating units, at most about 21 repeating units, at most about 20 repeating units, at most about 19 repeating units, at most about 18 repeating units, at most about 17 repeating units, at most about 16 repeating units, at most about 15 repeating units, at most about 14 repeating units, at most about 13 repeating units, at most about 12 repeating units, at most about 11 repeating units, at most about 10 repeating units, at most about 9 repeating units, at most about 8 repeating units, at most about 7 repeating units, at most about 6 repeating units, at most about 5 repeating units, at most about 4 repeating units, at most about 3 repeating units, at most about 2 repeating units, at most about one repeating unit, or less than one repeating unit. In some cases, the capture motif can comprise about one repeating unit, about two repeating units, about 3 repeating units, about 4 repeating units, about 5 repeating units, about 6 repeating units, about 7 repeating units, about 8 repeating units, about 9 repeating units, about 10 repeating units, about 11 repeating units, about 12 repeating units, about 13 repeating units, about 14 repeating units, about 15 repeating units, about 16 repeating units, about 17 repeating units, about 18 repeating units, about 19 repeating units, about 20 repeating units, about 21 repeating units, about 22 repeating units, about 23 repeating units, about 24 repeating units, about 25 repeating units, about 26 repeating units, about 27 repeating units, about 28 repeating units, about 29 repeating units, or about 30 repeating units.

In some embodiments, a leader construct comprises a stall motif. A stall motif can be configured to disrupt interaction of a translocase with a polymer analyte. A stall motif may be configured to encourage slipping of a translocase on a polymer analyte. In some embodiments, a stall motif can comprise a region of low traction for a translocase. The low traction area can be due to small side chains, no side chains, or side chains that do not interact favorably with a translocase. The lack of favorable interaction can be due to an inability of the translocase to exert force on the stall motif. In some embodiments, at least a portion of a stall motif comprises a region that does not interact favorably with a paddle of a translocase. In some embodiments, the paddles of the translocase may be unable to grasp the analyte-leader construct complex at the stall motif. In some cases, the translocase may not be able to move the analyte through the translocase and the nanopore when the translocase is unable to grasp the analyte-leader construct complex.

In some embodiments, amino acids with no side chains can include glycine. In some embodiments, amino acids with small side chains can include alanine, serine, cysteine, valine, threonine, leucine, isoleucine, or any combination thereof.

In some embodiments, the stall motif can comprise any combination of amino acids with no side chains or amino acids with small side chains. In some embodiments, the stall motif can comprise any combination of amino acids with no side chains or amino acids with small side chains. In some cases, the stall motif can comprise glycine. In some embodiments, the stall motif can comprise alanine. In some embodiments, the stall motif can comprise serine. In some embodiments, the stall motif can comprise cysteine. In some embodiments, the stall motif can comprise valine. In some embodiments, the stall motif can comprise threonine. In some embodiments, the stall motif can comprise leucine. In some embodiments, the stall motif can comprise isoleucine. In Some embodiments, the stall motif can comprise glycine, alanine, serine, cysteine, valine, threonine, leucine, isoleucine, or any combination thereof.

A stall motif can comprise a region of amino acid residues including at least one of glycine, alanine, valine, or serine. In some embodiments, the stall motif comprises a region comprising n repeats of glycine ((G)n), alanine, ((A)n), or valine, ((V)n). In some embodiments, the stall motif can comprise n repeats of glycine. In some embodiments, the stall motif can comprise n repeats of alanine. In some embodiments, the stall motif can comprise n repeats of valine. In some cases, the stall motif can comprise n repeats of glycine and n repeats of alanine. In some cases, the stall motif can comprise n repeats of alanine and n repeats of valine. In some cases, the stall motif can comprise n repeats of glycine and n repeats of valine. In some cases, the stall motif can comprise n repeats of glycine, n repeats of alanine, and n repeats of valine.

In some embodiments, the stall motif comprises a region comprising n repeats of glycine-serine ((GS)n), serine-glycine ((SG)n), alanine-serine ((AS)n), serine-alanine ((SA)n), valine-serine ((VS)n), or serine-valine ((SV)n).

In some embodiments, n can be between about 1 to about 50. In some cases, n can be between about 1 to about 5, between about 5 to about 10, between about 10 to about 15, between about 15 to about 20, between about 20 to about 25, between about 25 to about 30, between about 30 to about 35, between about 35 to about 40, between about 40 to about 45, or between about 45 to about 50.

In some embodiments, n is greater than about 1, greater than about 2, greater than about 3, greater than about 4, greater than about 5, greater than about 6, greater than about 7, greater than about 8, greater than about 9, greater than about 10, greater than about 11, greater than about 12, greater than about 13, greater than about 14, greater than about 15, greater than about 16, greater than about 17, greater than about 18, greater than about 19, greater than about 20, greater than about 21, greater than about 22, greater than about 23, greater than about 24, greater than about 25, greater than about 26, greater than about 27, greater than about 28, greater than about 29, greater than about 30, greater than about 31, greater than about 32, greater than about 33, greater than about 34, greater than about 35, greater than about 36, greater than about 37, greater than about 38, greater than about 39, greater than about 40, greater than about 41, greater than about 42, greater than about 43, greater than about 44, greater than about 45, greater than about 50, or more.

In some embodiments, n is less than about 50, less than about 49, less than about 48, less than about 47, less than about 46, less than about 45, less than about 44, less than about 43, less than about 42, less than about 41, less than about 40, less than about 39, less than about 38, less than about 37, less than about 36, less than about 35, less than about 34, less than about 33, less than about 32, less than about 31, less than about 30, less than about 29, less than about 28, less than about 27, less than about 26, less than about 25, less than about 24, less than about 23, less than about 22, less than about 21, less than about 20, less than about 19, less than about 18, less than about 17, less than about 16, less than about 15, less than about 14, less than about 13, less than about 12, less than about 11, less than about 10, less than about 9, less than about 8, less than about 7, less than about 6, less than about 5, less than about 4, less than about 3, less than about 2, less than about 1, or less. In some embodiments, n is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50.

In some embodiments, the stall motif comprises a region comprising a non-amino acid chemistry. In some cases, the stall motif can comprise a region of one or more nucleotides. In some cases, the stall motif can comprise a region of one or more polymeric molecules. In some cases, the one or more polymeric molecules can comprise polyethylene glycol, ethylene, polystyrene, vinyl chloride, polyethylene, polypropylene, polycarbonates, polytetrafluoroethylene, polyamide, silicone based polymers, PMOXA polymers, polyglycans, polyacrylamide polymers, polyacrylic acid polymers, polyamines, polyethyleneimines, quaternaray ammonium polymers, polyvinyl alcohol polymers, pluronic polymers, ethylene oxide polymers, propylene oxide polymers, polyvinylpyrrolidone polymers, carboxypolymethylene polymers, or any combination thereof. In some embodiments, the stall motif can comprise a region of one or more nucleic acid molecules. In some cases, the one or more nucleic acid comprises can comprise DNA, RNA, or any combination thereof. In some cases, the stall motif can comprise a region of one or more nucleic acid molecule analogues. In some cases, the one or more nucleic acid molecule analogues can comprise PNA, LNA, BNA, GNA, TNA, HNA, or any combination thereof.

In some embodiments, the stall motif can be coupled to the leader construct. In some cases, the stall motif can be coupled to the leader construct via a covalent bond. In some cases, the stall motif can be coupled to the leader construct via a noncovalent bond. In some cases, the stall motif can be coupled to the leader construct via a linker. In some cases, the stall motif can be coupled to the leader construct via Click chemistry.

In some embodiments, the stall motif can comprise between about one repeating unit to about 30 repeating units. In some cases, the stall motif can comprise between about on repeating unit to about 5 repeating units, between about 5 repeating units to about 10 repeating units, between about 10 repeating units to about 15 repeating units, between about 15 repeating units to about 20 repeating units, between about 20 repeating units to about 25 repeating units, or between about 25 repeating units. In some cases, the stall motif can comprise at least about one repeating unit, at least about 2 repeating units, at least about 3 repeating units, at least about 4 repeating units, at least about 5 repeating units, at least about 6 repeating units, at least about 7 repeating units, at least about 8 repeating units, at least about 9 repeating units, at least about 10 repeating units, at least about 11 repeating units, at least about 12 repeating units, at least about 13 repeating units, at least about 14 repeating units, at least about 15 repeating units, at least about 16 repeating units, at least about 17 repeating units, at least about 18 repeating units, at least about 19 repeating units, at least about 20 repeating units, at least about 21 repeating units, at least about 22 repeating units, at least about 23 repeating units, at least about 24 repeating units, at least about 25 repeating units, at least about 26 repeating units, at least about 27 repeating units, at least about 28 repeating units, at least about 29 repeating units, at least about 30 repeating units, or more than 30 repeating units. In some cases, the stall motif can comprise at most about 30 repeating units, at most about 29 repeating units, at most about 28 repeating units, at most about 27 repeating units, at most about 26 repeating units, at most about 25 repeating units, at most about 24 repeating units, at most about 23 repeating units, at most about 22 repeating units, at most about 21 repeating units, at most about 20 repeating units, at most about 19 repeating units, at most about 18 repeating units, at most about 17 repeating units, at most about 16 repeating units, at most about 15 repeating units, at most about 14 repeating units, at most about 13 repeating units, at most about 12 repeating units, at most about 11 repeating units, at most about 10 repeating units, at most about 9 repeating units, at most about 8 repeating units, at most about 7 repeating units, at most about 6 repeating units, at most about 5 repeating units, at most about 4 repeating units, at most about 3 repeating units, at most about 2 repeating units, at most about one repeating unit, or less than one repeating unit. In some cases, the stall motif can comprise about one repeating unit, about two repeating units, about 3 repeating units, about 4 repeating units, about 5 repeating units, about 6 repeating units, about 7 repeating units, about 8 repeating units, about 9 repeating units, about 10 repeating units, about 11 repeating units, about 12 repeating units, about 13 repeating units, about 14 repeating units, about 15 repeating units, about 16 repeating units, about 17 repeating units, about 18 repeating units, about 19 repeating units, about 20 repeating units, about 21 repeating units, about 22 repeating units, about 23 repeating units, about 24 repeating units, about 25 repeating units, about 26 repeating units, about 27 repeating units, about 28 repeating units, about 29 repeating units, or about 30 repeating units.

In some embodiments, a leader construct comprises a block motif. A block motif can be configured to prevent or oppose a translocase translocating past or through the block motif by providing a steric obstruction or blockade to analyte translocation. A block motif can be placed downstream or upstream of a stall motif. A block motif may be placed after a stall motif in order of procession by a translocase. In some embodiments, a block motif is configured to prevent movement of a translocase past a stall motif. In some cases, the block motif can be placed after a stall motif to provide a barrier to translocase. In some embodiments, a translocase cannot overcome a block motif. In some embodiments, the translocase may not be capable of translocating past the block motif. In some cases, the translocase may translocate past the block motif once a portion of the analyte moves through the nanopore. In some cases, the movement of the analyte through the nanopore can assist the translocase in translocating past the block motif. In some cases, the movement of the analyte through the nanopore can unfold the block motif. In some cases, the unfolded block motif can be translocated by the translocase.

A steric obstruction can prevent a translocase from pulling the analyte through the translocase by providing a physical barrier to the translocase.

In some embodiments, the block motif can be larger than the opening of the channel of the nanopore. In some cases, the block motif may not be able to enter the opening of the channel of the nanopore. In some cases, the block motif may not be able to enter the channel of the nanopore. In some embodiments, the block motif can be between about 0.1% to about 500% larger than the opening of the channel of the nanopore. In some cases, the block motif can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% larger than the opening of the channel of the nanopore.

In some cases, the block motif can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% larger than the opening of the channel of the nanopore.

In some cases, the block motif can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% larger than the opening of the channel of the nanopore.

In some cases, the block motif can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% larger than the opening of channel of the nanopore.

In some embodiments, the block motif may not be larger than the opening of the channel of the nanopore. In some embodiments, the block motif can enter into the channel of the nanopore in the absence of a translocase. In some embodiments, the block motif may not enter into the channel of the nanopore in the absence of a translocase.

A steric obstruction or blockade can be formed by a folded protein or a bulky side chain. A folded protein may be difficult to unfold, or unfolding-resistant. In some embodiments, the steric obstruction can be one or more bulky amino acids. In some cases, the one or more bulky amino acids can comprise histidine, phenylalanine, tyrosine, tryptophan, or any combination thereof. In some embodiments, the steric obstruction can have between about 1 to about 20 bulky amino acids. In some embodiments, the steric obstruction can have between about 1 to about 5 bulky amino acids, between about 5 to about 10 bulky amino acids, between about 10 to about 15 bulky amino acids, or between about 15 to about 20 bulky amino acids. In some cases, the steric obstruction can have at least about 1 bulky amino acid, at least about 2 bulky amino acids, at least about 3 bulky amino acids, at least about 4 bulky amino acids, at least about 5 bulky amino acids, at least about 6 bulky amino acids, at least about 7 bulky amino acids, at least about 8 bulky amino acids, at least about 9 bulky amino acids, at least about 10 bulky amino acids, at least about 11 bulky amino acids, at least about 12 bulky amino acids, at least about 13 bulky amino acids, at least about 14 bulky amino acids, at least about 15 bulky amino acids, at least about 16 bulky amino acids, at least about 17 bulky amino acids, at least about 18 bulky amino acids, at least about 19 bulky amino acids, at least about 20 bulky amino acids, or more than 20 bulky amino acids. In some cases, the steric obstruction can have at most about 20 bulky amino acids, at most about 19 bulky amino acids, at most about 18 bulky amino acids, at most about 17 bulky amino acids, at most about 16 bulky amino acids, at most about 15 bulky amino acids, at most about 14 bulky amino acids, at most about 13 bulky amino acids, at most about 12 bulky amino acids, at most about 11 bulky amino acids, at most about 10 bulky amino acids, at most about 9 bulky amino acids, at most about 8 bulky amino acids, at most about 7 bulky amino acids, at most about 6 bulky amino acids, at most about 5 bulky amino acids, at most about 4 bulky amino acids, at most about 3 bulky amino acids, at most about 2 bulky amino acids, at most about 1 bulky amino acid, or less than 1 bulky amino acid. In some cases, the steric obstruction can have about 1 bulky amino acid, about 2 bulky amino acids, about 3 bulky amino acids, about 4 bulky amino acids, about 5 bulky amino acids, about 6 bulky amino acids, about 7 bulky amino acids, about 8 bulky amino acids, about 9 bulky amino acids, about 10 bulky amino acids, about 11 bulky amino acids, about 12 bulky amino acids, about 13 bulky amino acids, about 14 bulky amino acids, about 15 bulky amino acids, about 16 bulky amino acids, about 17 bulky amino acids, about 18 bulky amino acids, about 19 bulky amino acids, or about 20 bulky amino acids. In some cases, the steric obstruction can have any combination of bulky amino acids disclosed herein.

In some embodiments, a translocase may unfold an analyte with a three-dimensional structure by pulling at the analyte's backbone with such a force to overcome the energetic bonds that maintain the three-dimensional structure of the analyte and thereby disassemble (e.g., unfold) a steric obstruction in the analyte. In some embodiments, the analyte can be a protein with a three-dimensional structure. In some cases, a translocase may unfold the protein by pulling at the peptide backbone with such force as to overcome the energetic bonds that maintain the three dimensional structure, and thereby disassemble a steric obstruction.

To prevent this from occurring, a block motif can comprise a protein may be unfolding-resistant so as to prevent the translocase from disassembling the steric obstruction provided by the protein. In some embodiments, an unfolding-resistant protein can comprise a protein that does not naturally unfold. In some cases, the unfolding-resistant protein may require additional energy in order to be unfolded. In some cases, the additional energy can comprise the movement of the unfolding resistant protein by a translocase. In some cases, the additional energy can comprise the movement of the analyte through the nanopore. In some cases, the additional energy can comprise the movement of the unfolding resistant protein by a translocase and the movement of the analyte through the nanopore.

In some embodiments, the unfolding resistant protein can be a protein that is coupled to a cognate partner. In some cases, the protein coupled to a cognate partner can have a higher melting temperature than a protein not coupled to a cognate partner. In some cases, the protein coupled to a cognate partner can have a melting temperature that is from 0.1% to about 500% higher than a protein not coupled to a cognate partner. In some cases, the protein coupled to a cognate partner can have a melting temperature that is from about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% higher than a protein not coupled to a cognate partner.

In some cases, the protein coupled to a cognate partner can have a melting temperature that is at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more than 500% higher than a protein not coupled to a cognate partner.

In some cases, the protein coupled to a cognate partner can have a melting temperature that is at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less than 0.1% higher than a protein not coupled to a cognate partner.

In some cases, the protein coupled to a cognate partner can have a melting temperature that is about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% higher than a protein not coupled to a cognate partner.

In some cases, the cognate partner can be a small molecule. In some instances, the small molecule can comprise sugars, lipids, fatty acids, phenolic compounds, alkaloids, or any combination thereof. In some cases, the cognate partner can be one or more metal salts. In some instances, the one or more metal salts can comprise aluminum sulfate, sodium aluminate, ferric chloride, ferric sulfate, ferrous sulfate, ferrous chloride, or any combinations thereof. In some cases, the cognate partner can be a peptide. In some cases, the peptide can comprise amino acid residues. In some instances, the peptide cognate residue can comprise from about one amino acid residue to about 20 amino acid residues. In some instances, the peptide can comprise at least about one amino acid residue, at least about 5 amino acid residues, at least about 10 amino acid residues, at least about 15 amino acid residues, at least about 20 amino acid residues, or more than 20 amino acid residues, In some instances, the peptide can comprise at most about 20 amino acid residues, at most about 15 amino acid residues, at most about 10 amino acid residues, at most about 5 amino acid residues, at most about one amino acid residues, or less than one amino acid residue. In some instances, the peptide can comprise about one amino acid residue, about 5 amino acid residues, about 10 amino acid residues, about 15 amino acid residues, or about 20 amino acid residues. In some cases, the peptide cognate partner can comprise a fluorophore. In some cases, the cognate partner can be a whole protein. In some cases, the cognate partner can be cross-linked peptides. In some cases, the cognate partner can be an aptamer. In some cases, the cognate partner can be an antibody. In some instances, the antibody can comprise anti-fluorophore antibody. In some cases, the cognate partner can be a nanobody. In some cases, the cognate partner can be biotin. In some cases, the cognate partner can be a monobody. In some cases, the cognate partner can be an affimer. In some cases, the cognate partner can be an avidin molecule. In some cases, the cognate partner can be a darpin.

In some cases, the protein can be coupled to from about one cognate partner to about 20 cognate partners. In some cases, the protein can be coupled to at least about one cognate partner, at least about two cognate partners, at least about three cognate partners, at least about four cognate partners, at least about five cognate partners, at least about six cognate partners, at least about seven cognate partners, at least about eight cognate partners, at least about nine cognate partners, at least about ten cognate partners, at least about 11 cognate partners, at least about 12 cognate partners, at least about 13 cognate partners, at least about 14 cognate partners, at least about 15 cognate partners, at least about 16 cognate partners, at least about 17 cognate partners, at least about 18 cognate partners, at least about 19 cognate partners, at least about 20 cognate partners, or more. In some cases, the protein can be coupled to at most about 20 cognate partners, at most about 19 cognate partners, at most about 18 cognate partners, at most about 17 cognate partners, at most about 16 cognate partners, at most about 15 cognate partners, at most about 14 cognate partners, at most about 13 cognate partners, at most about 12 cognate partners, at most about 11 cognate partners, at most about 10 cognate partners, at most about 9 cognate partners, at most about 8 cognate partners, at most about 7 cognate partners, at most about 6 cognate partners, at most about 5 cognate partners, at most about 4 cognate partners, at most about 3 cognate partners, at most about 2 cognate partners, at most about 1 cognate partner, or less. In some cases, the protein can be coupled to about 1 cognate partner, about 2 cognate partners, about 3 cognate partners, about 4 cognate partners, about 5 cognate partners, about 6 cognate partners, about 7 cognate partners, about 8 cognate partners, about 9 cognate partners, about 10 cognate partners, about 11 cognate partners, about 12 cognate partners, about 13 cognate partners, about 14 cognate partners, about 15 cognate partners, about 16 cognate partners, about 17 cognate partners, about 18 cognate partners, about 19 cognate partners, or about 20 cognate partners.

In some embodiments, the protein can be coupled to the cognate partner via a non-covalent bond. In some embodiments, the protein can be coupled to the cognate partner via a linker.

A protein can be unfolding-resistant by comprising stabilizing bonds such that a translocase may not be able to exert sufficient energy to disrupt the bonds. In some cases, a stabilizing bond can be a disulfide bridge between cysteine residues, wherein the energy of the bond is greater than the energy exerted by the translocase. An unfolding-resistant protein may be a protein that has been cross-linked to form multiple stabilizing bonds. A protein may be cross-linked multiple stabilizing bonds. In some cases, the stabilizing bond can be a disulfide bridge, a desmosine bond, an ionic bond, a hydrogen bond, hydrophobic interactions, van der Waals forces, or combinations thereof.

A protein may be unfolding-resistant due to a stabilizing ligand. A stabilizing ligand can comprise a molecule that binds to the protein. The stabilizing ligand may bind exclusively in the folded state. The binding of the stabilizing ligand may provide an additional energetic barrier to protein unfolding by lowering the energy state of the protein, which provides an additional energetic barrier for the translocase to overcome in order to remove the steric obstruction provided by the protein in a block motif. The binding of the stabilizing ligand may provide an additional kinetic barrier to protein unfolding by adding an additional kinetic operation to overcome to reach an unfolded state and remove the steric blockade provided by the protein. In some embodiments, the stabilizing ligand can comprise one or more internal bonds within the unfolding-resistant protein. In some cases, the one or more internal bonds can comprise disulfide bonds, ionic bonds, hydrogen bonds, metallic bonds, a polar covalent bond, a non-polar covalent bond, or any combination thereof. In some embodiments, the stabilizing ligand can comprise one or more ligands. In some cases, the one or more ligands can connect two or more locations on the unfolding resistant protein. In some cases, the binding of the one or more ligands to the two or more locations on the unfolding resistant protein can increase the stabilization of the unfolding resistant protein. In some cases, increasing the stabilization of unfolding resistant protein may require additional energy to unfold the unfolding resistant protein. In some embodiments, the one or more ligands can comprise one or more peptide ligands. In some embodiments, the one or more ligands can comprise one or more nucleic acid ligands. In some cases, the one or more nucleic acid ligands can comprise DNA molecules, RNA molecules, nucleic acid analog molecules, or any combination thereof. In some embodiments, the one or more ligands can comprise one or more oligosaccharide ligands. In some cases, the one or more oligosaccharide ligands can comprise mannose, galactose, glucose, lactose, or any combination thereof. In some embodiments, the one or more ligands can comprise one or more lipid ligands. In some cases, the one or more lipid ligands can comprise tricylglycerols, phospholipids, sterols, or any combination thereof. In some embodiments, the one or more ligands can comprise one or more chemical ligands. In some cases, the one or more chemical ligands can comprise anilinonapththalene sulfonate derivatives, iodide, bromide, sulfide, thiocyanate, chloride, nitrate, azide, fluoride, hydroxide, oxalate, water, nitrite, isothiocyanate, acetonitrile, pyridine, ammonia, ethylenediamine, 2,2'-bipyridine, 1,10-phenanthroline, nitrite, triphenylphosphine, cyanide, carbon monoxide, or any combination thereof. In some cases, the one or more ligands can comprise one or more stabilizing molecules. In some cases, the one or more stabilizing ligands can comprise Barstar, methotrexate, biotin, streptavidin, or any combination thereof.

In some embodiments, the stabilizing ligand can comprise at least one portion of an unfolding-resistant protein. In some cases, an unfolding-resistant protein can comprise a protein that requires additional energy in order for the protein to be unfolded. In some cases, the at least one portion of the unfolding-resistant protein can be a region of the unfolding-resistant protein.

An unfolding-resistant protein may comprise Maltose Binding Protein (MBP), Titin, dihydrofolate reductase, barnase, mNeonGreen, dihydrofolate reductase, streptavidin, or any combination thereof. In some embodiments, the stabilizing ligand can comprise between about one portion to about ten portions of an unfolding-resistant protein. In some cases, the stabilizing ligand can comprise at least about one portion, at least about two portions, at least about three portions, at least about four portions, at least about five portions, at least about six portions, at least about seven portions, at least about eight portions, at least about nine portions, at least about ten portions, or more of an unfolding-resistant protein. In some cases, the stabilizing ligand can comprise at most about ten portions, at most about nine portions, at most about eight portions, at most about seven portions, at most about six portions, at most about five portions, at most about four portions, at most about three portions, at most about two portions, at most about one portions, or less of an unfolding-resistant protein. In some cases, the stabilizing ligand can comprise about one portion, about two portions, about three portions, about four portions, about five portions, about six portions, about seven portions, about eight portions, about nine portions, or about ten portions of an unfolding-resistant protein. In some embodiments, the stabilizing ligand can comprise any combinations of portions of unfolding-resistant proteins disclosed herein.

In some embodiments, the unfolding resistant protein can comprise at least about 1 stabilizing ligand, at least about 2 stabilizing ligands, at least about 3 stabilizing ligands, at least about 4 stabilizing ligands, at least about 5 stabilizing ligands, at least about 6 stabilizing ligands, at least about 7 stabilizing ligands, at least about 8 stabilizing ligands, at least about 9 stabilizing ligands, at least about 10 stabilizing ligands, at least about 12 stabilizing ligands, at least about 15 stabilizing ligands, at least about 18 stabilizing ligands, at least about 20 stabilizing ligands, at least about 25 stabilizing ligands, at least about 30 stabilizing ligands, at least about 35 stabilizing ligands, at least about 40 stabilizing ligands, at least about 45 stabilizing ligands, at least about 50 stabilizing ligands, or greater than about 50 stabilizing ligands. In some embodiments, the unfolding resistant protein can comprise at most about 50 stabilizing ligands, at most about 45 stabilizing ligands, at most about 40 stabilizing ligands, at most about 35 stabilizing ligands, at most about 30 stabilizing ligands, at most about 25 stabilizing ligands, at most about 20 stabilizing ligands, at most about 18 stabilizing ligands, at most about 15 stabilizing ligands, at most about 12 stabilizing ligands, at most about 10 stabilizing ligands, at most about 9 stabilizing ligands, at most about 8 stabilizing ligands, at most about 7 stabilizing ligands, at most about 6 stabilizing ligands, at most about 5 stabilizing ligands, at most about 4 stabilizing ligands, at most about 3 stabilizing ligands, at most about 2 stabilizing ligands, at most about 1 stabilizing ligand, or less than about 1 stabilizing ligand.

In some embodiments, the unfolding resistant protein can comprise from about 1 stabilizing ligand to about 50 stabilizing ligands. In some embodiments, the unfolding resistant protein can comprise from about 1 stabilizing ligand to about 2 stabilizing ligands, about 1 stabilizing ligand to about 3 stabilizing ligands, about 1 stabilizing ligand to about 4 stabilizing ligands, about 1 stabilizing ligand to about 5 stabilizing ligands, about 1 stabilizing ligand to about 10 stabilizing ligands, about 1 stabilizing ligand to about 15 stabilizing ligands, about 1 stabilizing ligand to about 20 stabilizing ligands, about 1 stabilizing ligand to about 25 stabilizing ligands, about 1 stabilizing ligand to about 30 stabilizing ligands, about 1 stabilizing ligand to about 40 stabilizing ligands, about 1 stabilizing ligand to about 50 stabilizing ligands, about 2 stabilizing ligands to about 3 stabilizing ligands, about 2 stabilizing ligands to about 4 stabilizing ligands, about 2 stabilizing ligands to about 5 stabilizing ligands, about 2 stabilizing ligands to about 10 stabilizing ligands, about 2 stabilizing ligands to about 15 stabilizing ligands, about 2 stabilizing ligands to about 20 stabilizing ligands, about 2 stabilizing ligands to about 25 stabilizing ligands, about 2 stabilizing ligands to about 30 stabilizing ligands, about 2 stabilizing ligands to about 40 stabilizing ligands, about 2 stabilizing ligands to about 50 stabilizing ligands, about 3 stabilizing ligands to about 4 stabilizing ligands, about 3 stabilizing ligands to about 5 stabilizing ligands, about 3 stabilizing ligands to about 10 stabilizing ligands, about 3 stabilizing ligands to about 15 stabilizing ligands, about 3 stabilizing ligands to about 20 stabilizing ligands, about 3 stabilizing ligands to about 25 stabilizing ligands, about 3 stabilizing ligands to about 30 stabilizing ligands, about 3 stabilizing ligands to about 40 stabilizing ligands, about 3 stabilizing ligands to about 50 stabilizing ligands, about 4 stabilizing ligands to about 5 stabilizing ligands, about 4 stabilizing ligands to about 10 stabilizing ligands, about 4 stabilizing ligands to about 15 stabilizing ligands, about 4 stabilizing ligands to about 20 stabilizing ligands, about 4 stabilizing ligands to about 25 stabilizing ligands, about 4 stabilizing ligands to about 30 stabilizing ligands, about 4 stabilizing ligands to about 40 stabilizing ligands, about 4 stabilizing ligands to about 50 stabilizing ligands, about 5 stabilizing ligands to about 10 stabilizing ligands, about 5 stabilizing ligands to about 15 stabilizing ligands, about 5 stabilizing ligands to about 20 stabilizing ligands, about 5 stabilizing ligands to about 25 stabilizing ligands, about 5 stabilizing ligands to about 30 stabilizing ligands, about 5 stabilizing ligands to about 40 stabilizing ligands, about 5 stabilizing ligands to about 50 stabilizing ligands, about 10 stabilizing ligands to about 15 stabilizing ligands, about 10 stabilizing ligands to about 20 stabilizing ligands, about 10 stabilizing ligands to about 25 stabilizing ligands, about 10 stabilizing ligands to about 30 stabilizing ligands, about 10 stabilizing ligands to about 40 stabilizing ligands, about 10 stabilizing ligands to about 50 stabilizing ligands, about 15 stabilizing ligands to about 20 stabilizing ligands to about 25 stabilizing ligands, about 15 stabilizing ligands to about 30 stabilizing ligands, about 15 stabilizing ligands to about 40 stabilizing ligands, about 15 stabilizing ligands to about 50 stabilizing ligands, about 20 stabilizing ligands to about 25 stabilizing ligands, about 20 stabilizing ligands to about 30 stabilizing ligands, about 20 stabilizing ligands to about 40 stabilizing ligands, about 20 stabilizing ligands to about 50 stabilizing ligands, about 25 stabilizing ligands to about 30 stabilizing ligands, about 25 stabilizing ligands to about 40 stabilizing ligands, about 25 stabilizing ligands to about 50 stabilizing ligands, about 30 stabilizing ligands to about 40 stabilizing ligands, about 30 stabilizing ligands to about 50 stabilizing ligands, or about 40 stabilizing ligands to about 50 stabilizing ligands.

In some embodiments, the unfolding resistant protein can comprise about 1 stabilizing ligand, about 2 stabilizing ligands, about 3 stabilizing ligands, about 4 stabilizing ligands, about 5 stabilizing ligands, about 6 stabilizing ligands, about 7 stabilizing ligands, about 8 stabilizing ligands, about 9 stabilizing ligands, about 10 stabilizing ligands, about 12 stabilizing ligands, about 15 stabilizing ligands, about 18 stabilizing ligands, about 20 stabilizing ligands, about 25 stabilizing ligands, about 30 stabilizing ligands, about 35 stabilizing ligands, about 40 stabilizing ligands, about 45 stabilizing ligands, or about 50 stabilizing ligands.

In some embodiments, the stabilizing ligand can be removed from the unfolding resistant protein. In some cases, the removal of one or more stabilizing ligands can decrease the stability of the unfolding resistant protein. In some cases, the removal of one or more stabilizing ligands can result in unfolding of the unfolding resistant protein. In some embodiments, the one or more stabilizing ligands can be removed by the translocase. In some cases, the translocase can remove the one or more stabilizing ligands as the translocase contacts the one or more stabilizing ligands on the unfolding-resistant protein. In some cases, the paddle on the translocase can remove the one or more stabilizing ligands. In some embodiments, the one or more stabilizing ligands can be removed by a removal agent. In some cases, the removal agent is a chemical. In some cases, the chemical removal agent can be dimercaptonol, dimercaprol, ethylenediaminetetraacetic acid, penicillamine, trientine, zinc, deferasirox, deferiprone, deferoxamine, or any combination thereof. In some cases, the removal agent is an enzyme. In some cases, the enzymatic removal agent can be a serine protease, a cysteine protein, chymotrypsin, subtilisin, pepsin, cathepsin, threonine protein, kallikrein, metalloproteinase, papain, urokinase, aspartic protein, elastase, rennin, thermolysin, trypsin, thrombin, bromelain, plasmin, renin, aminopeptidase, caplpain, RNases, DNases, topoisomerases, recombinases, ribozymes, RNA splicing enzymes, bile salt-dependent lipase, pancreatic lipase, lysosomal lipase, hepatic lipase, lipoprotein lipase, hormone-sensitive lipase, gastric lipase, endothelial lipase, pancreatic lipase related protein 2, pancreatic lipase related protein 1, lingual lipase, lactase, O-GlcNcase, amplase, hyaluronidase, sucrose, maltase, or any combination thereof.

In some embodiments, the steric obstruction can comprise a molecule bound to the block motif. In some cases, the molecule can be incorporated into the backbone of the block motif. In some cases, the molecule can be streptavidin or biotin. In some cases, the molecule can be avidins. In some cases, the molecule can be an antibody. In some instances, the antibody can be an anti-fluorophore antibody. In some cases, the molecule can be a fluorophore. In some cases, the molecule can be a monobody. In some cases, the molecule can be a affimer. In some cases, the molecule can be a nanobody. In some cases, the molecule can be a darpin. In some cases, the molecule can couple to a binder element. In some cases, the molecule can be coupled to the binder element via a non-covalent bond. In some cases, the molecule can be coupled to the binder element via a linker. In some cases, the binder element can be a peptide. In some cases, the binder element can be a protein. In some cases, the binder element can be a nucleic acid. In some cases, the binder element can be a lipid. In some cases, the binder element can be a carbohydrate. In some cases, the carbohydrate can comprise a monosaccharide, a disaccharide, an oligosaccharide, a polysaccharide, or any combination thereof. In some cases, the binder element can be an oligosaccharide. In some embodiments, the binder element can comprise a polymeric molecule. In some cases, the binder elements can include a carbohydrate, a multi-ring molecule, a branched dextran, biotin, streptavidin, an antigen element, a nanobody, an antibody, or any combination thereof. In some cases, one or more binder elements can be coupled together. In some cases, the one or more binder elements can be coupled together via a non-covalent bond. In some cases, the one or more binder elements can be displaced by the translocase. In some cases, the one or more binder elements may or may not be displaced when a molecular motor proceeds through the block motif. A block motif may be adjacent to a stall motif. In some cases, the block motif may not be adjacent to the stall motif.

In some embodiments, the one or more binder elements can be removed from the block motif. In some cases, the one or more binder elements can be removed from the block motif by the translocase. In some cases, the translocase can remove the one or more binder elements as the translocase contacts the one or more binder elements as the translocase contacts the one or more binder elements on the block motif. In some cases, the paddle translocase can remove the one or more binder elements.

In some embodiments, the block motif can comprise between about one repeating unit to about 30 repeating units. In some cases, the block motif can comprise between about on repeating unit to about 5 repeating units, between about 5 repeating units to about 10 repeating units, between about 10 repeating units to about 15 repeating units, between about 15 repeating units to about 20 repeating units, between about 20 repeating units to about 25 repeating units, or between about 25 repeating units. In some cases, the block motif can comprise at least about one repeating unit, at least about 2 repeating units, at least about 3 repeating units, at least about 4 repeating units, at least about 5 repeating units, at least about 6 repeating units, at least about 7 repeating units, at least about 8 repeating units, at least about 9 repeating units, at least about 10 repeating units, at least about 11 repeating units, at least about 12 repeating units, at least about 13 repeating units, at least about 14 repeating units, at least about 15 repeating units, at least about 16 repeating units, at least about 17 repeating units, at least about 18 repeating units, at least about 19 repeating units, at least about 20 repeating units, at least about 21 repeating units, at least about 22 repeating units, at least about 23 repeating units, at least about 24 repeating units, at least about 25 repeating units, at least about 26 repeating units, at least about 27 repeating units, at least about 28 repeating units, at least about 29 repeating units, at least about 30 repeating units, or more than 30 repeating units. In some cases, the block motif can comprise at most about 30 repeating units, at most about 29 repeating units, at most about 28 repeating units, at most about 27 repeating units, at most about 26 repeating units, at most about 25 repeating units, at most about 24 repeating units, at most about 23 repeating units, at most about 22 repeating units, at most about 21 repeating units, at most about 20 repeating units, at most about 19 repeating units, at most about 18 repeating units, at most about 17 repeating units, at most about 16 repeating units, at most about 15 repeating units, at most about 14 repeating units, at most about 13 repeating units, at most about 12 repeating units, at most about 11 repeating units, at most about 10 repeating units, at most about 9 repeating units, at most about 8 repeating units, at most about 7 repeating units, at most about 6 repeating units, at most about 5 repeating units, at most about 4 repeating units, at most about 3 repeating units, at most about 2 repeating units, at most about one repeating unit, or less than one repeating unit. In some cases, the block motif can comprise about one repeating unit, about two repeating units, about 3 repeating units, about 4 repeating units, about 5 repeating units, about 6 repeating units, about 7 repeating units, about 8 repeating units, about 9 repeating units, about 10 repeating units, about 11 repeating units, about 12 repeating units, about 13 repeating units, about 14 repeating units, about 15 repeating units, about 16 repeating units, about 17 repeating units, about 18 repeating units, about 19 repeating units, about 20 repeating units, about 21 repeating units, about 22 repeating units, about 23 repeating units, about 24 repeating units, about 25 repeating units, about 26 repeating units, about 27 repeating units, about 28 repeating units, about 29 repeating units, or about 30 repeating units.

In some embodiments, a leader construct comprises a coupling motif. A coupling motif can be configured to couple a leader construct to an analyte. In some cases, the coupling motif can couple to the analyte via a covalent bond. In some cases, the coupling motif can couple to the analyte via a non-covalent bond. In some cases, the coupling motif can couple to the analyte via a linker. In some cases, the coupling motif can couple to the analyte via click chemistry reactions. In some cases, the click chemistry reactions can comprise cycloaddition reactions, hetero Diels-Alder reactions, nucleophilic ring-opening reaction, carbonyl chemistry, epoxidation, dihydroxylation, azide-phosphine coupling, or any combination thereof. In some cases, the click chemistry reactions can involve one or more click reagents. In some cases, the one or more click reagents can include 1,3-dipolar families, epoxides, aziridines, cyclic sulfates, epoxides, aziridines, cyclic sulfates, oxine ethers, hydrazones, aromatic heterocycles, or any combination thereof. In some cases, the coupling motif can couple to the analyte via a cysteine amino acid residue of the analyte. In some examples, the coupling motif can couple to a cysteine amino acid residue via a sulfide based conjugative reaction. In some cases, the coupling motif can couple to the analyte via an ester reaction. In some cases, the coupling motif can couple to the analyte via a thioester reaction. In some cases, the coupling motif can couple to the analyte via an amide reaction. In some cases, the coupling motif can couple to the analyte via a native chemical ligation reaction. In some cases, the native chemical ligation reaction can comprise reacting a peptide thioester with a cysteinyl peptide. In some cases, the coupling motif can couple to the analyte via a bioconjugation reaction. In some instances, the bioconjugation reaction can comprise reacting lysine with a N-hydroxysuccinimidyl (NHS) ester, a lysine acylation reaction, reacting lysine with isocyanates, reacting lysine with isothiocyanates, reacting lysine with benzoyl fluorides, reacting cysteine with maleimides, reacting cysteine with iodoacetamides, reacting cysteine with 2-thiopyridine, reacting cysteine with 3-arylpropiolonitrile, an electrophilic aromatic substitution reactions, reacting tyrosine with diazonium salts, reacting tyrosine with 4-phenyl-1,2,4-triazole-3,5-di-one (PTAD), a mannich reaction, reacting a N-terminal serine or threonine with $NaIO_4$, reacting N-terminal cysteine with iodoacetamides, reacting N-terminal of analyte with pyridoxal phosphate, staudinger ligation with azides, huisgen cyclization of azides, strain promoted huisgen cyclization of azides, cysteine or Tryptophan RH-catalyzed alkylation, lysine or N-terminal Ir-catalyzed alkylation, tyrosine Pd-catalyzed O-alkylation. cysteine Au-catalyzed alkylation, tryptophan arylation, cysteine arylation, lysine arylation, or any combination thereof.

In some embodiments, the coupling motif can selectively couple to the N-terminal of the analyte. In some cases, the coupling motif can selectively couple to the N-terminal of the analyte via a N-terminal specific reaction. In some cases, the N-terminal specific reaction can comprise transamination reaction, an azolation reaction, a condensation reaction, an oxidation reaction, an acylation reaction, an alkylation imine formation reaction, or any combination thereof. In some embodiments, the coupling motif can selectively couple to the C-terminal of the analyte. In some cases, the coupling motif can selectively couple to the N-terminal of the analyte via a C-terminal specific reaction. In some cases, the C-terminal specific reaction can comprise decarboxylative photoredox alkylation, thioacid/azide amidation, C-terminal bioconjugation with asparaginyl endopeptides, or any combination thereof.

In some embodiments, the analyte can comprise a nucleic acid molecule. In some cases, the coupling motif can couple to the 5' end of the nucleic acid molecule. In some instances, the coupling motif can selectively couple to the 5' end of the nucleic acid molecule over the 3' end of the nucleic acid molecule. In some cases, the coupling motif can couple to the 3' end of the nucleic acid molecule. In some instances, the coupling motif can selectively couple to the 3' end of the nucleic acid molecule over the 5' end of the nucleic acid molecule. In some embodiments, the coupling motif can non-selectively couple to the 3' end or the 5' end of the nucleic acid molecule. In some cases, the coupling motif can couple to both the 3' end and the 5' end of the nucleic acid molecule.

In some embodiments, the coupling motif can couple to a repeating unit near the N-terminal of the analyte. In some cases, the coupling motif can couple to a repeating unit that is one repeating unit away from the N-terminal. In some cases, the coupling motif can couple to a repeating unit that is two repeating units away from the N-terminal. In some cases, the coupling motif can couple to a repeating unit that is three repeating units away from the N-terminal. In some cases, the coupling motif can couple to a repeating unit that is four repeating units away from the N-terminal. In some cases, the coupling motif can couple to a repeating unit that is five repeating units away from the N-terminal. In some cases, the coupling motif can couple to a repeating unit that is six repeating units away from the N-terminal.

In some embodiments, the coupling motif can couple to a repeating unit near the C-terminal of the analyte. In some cases, the coupling motif can couple to a repeating unit that is one repeating unit away from the C-terminal. In some cases, the coupling motif can couple to a repeating unit that is two repeating units away from the C-terminal. In some cases, the coupling motif can couple to a repeating unit that is three repeating units away from the C-terminal. In some cases, the coupling motif can couple to a repeating unit that is four repeating units away from the C-terminal. In some cases, the coupling motif can couple to a repeating unit that is five repeating units away from the C-terminal. In some cases, the coupling motif can couple to a repeating unit that is six repeating units away from the C-terminal.

In some embodiments, the analyte can comprise a protein, polypeptide, or peptide. In some cases, the coupling motif can couple to the N-terminus of the protein, polypeptide, or peptide. In some cases, the coupling motif can couple to the C-terminus of the protein. In some cases, the coupling motif can selectively couple to the N-terminal of the protein, polypeptide, or peptide over the C-terminal of the protein, polypeptide, or peptide. In some cases, the coupling motif can selectively couple to the C-terminal of the protein, polypeptide, or peptide over the N-terminal of the protein, polypeptide, or peptide. In some embodiments, the coupling motif can non-selectively couple to the N-terminus or the C-terminus of the protein, polypeptide, or peptide. In some cases, the coupling motif can couple to both the N-terminus and the C-terminus of the protein, polypeptide, or peptide.

In some embodiments, the coupling motif can couple to a particular end of the analyte. In some instances, the particular end can comprise the N-terminus of the analyte. In some instances, the particular end can comprise the C-terminus of the analyte. In some instances, the particular end can comprise the 5' end of the analyte. In some instances, the particular end can comprise the 3' end of the analyte.

A coupling motif can comprise a chemical group. The chemical group can react with a portion of an analyte to covalently couple the leader construct to the analyte. The chemical group can react with proteins. The chemical group can react with amino acid groups, including cysteines, lysines, tyrosine, tryptophan, arginine, methionine, N-terminal residues, C-terminal residues, or any combination thereof. In some cases, a maleimide chemical group can react with cysteine. In some cases, an iodoacetamide chemical group can react with cysteine. In some cases, a 2-thiopyridine group can react with cysteine. In some cases, a 3-arylpropiolonitrile can react with cysteine. In some cases, an NHS-ester group can react with lysine. In some cases, an isocyanate group can react with lysine. In some cases, an isothiocyanate group can react with lysine. In some cases, a benzoyl fluoride group can react with lysine. In some cases, a diazonium salt can react with tyrosine. In some cases, PTAD can react with tyrosine. In some cases, tyrosine can overgo a Mannich reaction. In some cases, a N-terminal serine or a N-terminal threonine can react with a $NaIO_4$ group. In some cases, a N-terminal cysteine can react with an iodoacetamide group. In some cases, an N-terminal residue can react with PLP.

A coupling motif can couple a leader construct to an analyte via enzymatic activity. In some embodiments, the coupling motif can comprise an enzyme coupling region. In some cases, an enzyme can couple to the enzyme coupling region of the coupling motif. A coupling motif can comprise a portion for binding or loading of an enzyme. In some cases, the enzyme can have peptide ligase activity. In some embodiments, the enzyme can comprise peptiligase, omniligase, sortase, butelase, trypsiligase, peptide amidase, asparaginyl endopeptidase, or any combination thereof.

A coupling motif may comprise a recognition sequence. The recognition sequence may help the enzyme target an N-terminus or a C-terminus of the analyte. The recognition sequence may help the enzyme target a 3' end or a 5' end of the analyte. In some embodiments, a leader construct couples to an N-terminus, a C-terminus or both a N-terminus and C-terminus of an analyte. In some embodiments, the leader construct can couple to a 3' end of the analyte, the 5' end of the analyte, or both the 3' end and the 5' end of the analyte. An analyte with a leader construct on both the N-terminus and C-terminus can be translocated N-to-C or C-to-N. An analyte with a leader construct on both the 3' end and the 5' end can be translocated 5' to 3' or 3' to 5'. The direction of translocation can depend on what end the captured leader was attached. In some embodiments, the end of the analyte with the leader construct can enter into the channel before the end of the analyte without the leader construct. In some embodiments, the end of the analyte without the leader construct can enter into the channel before the end of the analyte with the leader construct. Coupling can occur prior to an analyte complexing with a translocase or after complexing with a translocase.

In some embodiments, the coupling motif can comprise between about one repeating unit to about 30 repeating units. In some cases, the coupling motif can comprise between about on repeating unit to about 5 repeating units, between about 5 repeating units to about 10 repeating units, between about 10 repeating units to about 15 repeating units, between about 15 repeating units to about 20 repeating units, between about 20 repeating units to about 25 repeating units, or between about 25 repeating units. In some cases, the coupling motif can comprise at least about one repeating unit, at least about 2 repeating units, at least about 3 repeating units, at least about 4 repeating units, at least about 5 repeating units, at least about 6 repeating units, at least about 7 repeating units, at least about 8 repeating units, at least about 9 repeating units, at least about 10 repeating units, at least about 11 repeating units, at least about 12 repeating units, at least about 13 repeating units, at least about 14 repeating units, at least about 15 repeating units, at least about 16 repeating units, at least about 17 repeating units, at least about 18 repeating units, at least about 19 repeating units, at least about 20 repeating units, at least about 21 repeating units, at least about 22 repeating units, at least about 23 repeating units, at least about 24 repeating units, at least about 25 repeating units, at least about 26 repeating units, at least about 27 repeating units, at least about 28 repeating units, at least about 29 repeating units, at least about 30 repeating units, or more than 30 repeating units. In some cases, the coupling motif can comprise at most about 30 repeating units, at most about 29 repeating units, at most about 28 repeating units, at most about 27 repeating units, at most about 26 repeating units, at most about 25 repeating units, at most about 24 repeating units, at most about 23 repeating units, at most about 22 repeating units, at most about 21 repeating units, at most about 20 repeating units, at most about 19 repeating units, at most about 18 repeating units, at most about 17 repeating units, at most about 16 repeating units, at most about 15 repeating units, at most about 14 repeating units, at most about 13 repeating units, at most about 12 repeating units, at most about 11 repeating units, at most about 10 repeating units, at most about 9 repeating units, at most about 8 repeating units, at most about 7 repeating units, at most about 6 repeating units, at most about 5 repeating units, at most about 4 repeating units, at most about 3 repeating units, at most about 2 repeating units, at most about one repeating unit, or less than one repeating unit. In some cases, the coupling motif can comprise about one repeating unit, about two repeating units, about 3 repeating units, about 4 repeating units, about 5 repeating units, about 6 repeating units, about 7 repeating units, about 8 repeating units, about 9 repeating units, about 10 repeating units, about 11 repeating units, about 12 repeating units, about 13 repeating units, about 14 repeating units, about 15 repeating units, about 16 repeating units, about 17 repeating units, about 18 repeating units, about 19 repeating units, about 20 repeating units, about 21 repeating units, about 22 repeating units, about 23 repeating units, about 24 repeating units, about 25 repeating units, about 26 repeating units, about 27 repeating units, about 28 repeating units, about 29 repeating units, or about 30 repeating units.

Electro-Osmotic Force (EOF)

In some embodiments, the nanopore system has a cis-to-trans electro-osmotic flow, or vice versa, which creates a drag on the particles dispersed in the solution (independent of their charge) that is often termed an electro-osmotic force (EOF). The EOF arises from a net flow of ions (e.g. cis to trans) that creates a strong force on the solvent itself (water) sufficient to move the fluid (Chinappi et al., 2020, ACS Nano, 14, 11, pg. 15816-15828), which imposes a significant force on any molecules within the flux. Electroosmosis can either compete or cooperate with electrophoresis (EPF).

In some embodiments, the nanopore system has a cis-to-trans electro-osmotic flow with an EOF that dominates over EPF. A dominant cis-to-trans EOF enables capture and translocation of complex and charged analyte s against EPF acting in a trans-to-cis direction. This selected high and dominant EOF is believed to capture and retain the analyte in the nanopore. The EOF pulls on the analyte and/or the translocase directly, pulling the analyte through the nanopore and in turn through transferred force keeps the translocase pinned to the top of the nanopore, whereupon the translocase can then control the translocation of the analyte through the nanopore. Without an EOF, the entire complex may be ejected in cases where the charge on the analyte section within the nanopore was of a polarity such that the net EPF repelled the analyte from the trans side-to-the cis side. Alternatively, in cases where the analyte has net neutral charge (i.e. a balance of negative and positive residues) or no charged residues, without EOF the analyte may most likely become stuck in the nanopore, while the translocase above the nanopore may continue to move along the analyte and away from the top of the nanopore, thus no longer controlling the movement of the analyte in any manner. Analytes can have a diversity of positive, negative and neutral sections, it is not possible to control translocation without a dominant EOF.

In some embodiments, the cis side is meant to indicate the compartment of the sensor system to which analyte(s) is added and/or the nanopore is added in the case of a biologically derived nanopore (and assuming vectorial insertion as most nanopores have a selective insertion orientation based on which compartment they are inserted from). However, it is to be noted that the terms "trans" and "cis" are used herein as the common convention determined by electronics/voltage polarity at the trans electrode. For example, without wishing to be bound to any one type of electrical circuit as many options are possible, the cis chamber is at ground and the applied transmembrane potential is given as the potential on the trans side i.e. the trans potential minus the cis potential. A positive current is one in which positive charge (e.g. K ions) moves through the nanopore from the trans to the cis side, or negative charge (e.g. Cl ions) from the cis to the trans side (see e.g. Maglia et al. Methods Enzymol. 2010; 475:591-623).

In some embodiments, the direction of the EOF may be dependent on the polarity of the applied voltage and the relative conditions in the cis and trans compartments in combination with any ion selectivity of the nanopore. Further, the present disclosure teaches that the direction of the EOF (be it cis-to-trans or trans-to-cis) dictates the direction of the net forces acting to translocate the analyte across the nanopore, and thus dictates to which side the analyte and translocase are added within the context of the methods described herein. Thus, for example, it is also possible within the context of the present disclosure to add the analyte to the trans side of the membrane to enable trans-to-cis threading for a system where the EOF is created in a trans-to-cis direction. A person of skill will also understand that while it is conventional to insert biological nanopores from the cis compartment, it will also be possible to insert them from the trans compartment, and that both orientations of the nanopore relative to the EOF can be employed.

In some embodiments, a core principle underlying the present disclosure is the generation of a net ion flux in one direction across the nanopore to create a dominant EOF that enables capture and transport of analytes. Ion selective ion flux across membranes can be described by the Goldman-Hodgkin-Katz (GHK) flux equation (Bertil Hille, 2001, Ion channels of excitable membranes, 3rd ed.), which is used to determine the ionic current ($I_{(S)}$) ion species S across the membrane as a function of the applied potential ($V_m$):

$$I_{(s)} = P_{(S)} z_s^2 * \frac{V_m F^2}{RT} \frac{[S]_{trans} - [S]_{cis} * e^{-z_s \frac{V_m F}{RT}}}{1 - e^{-z_s \frac{V_m F}{RT}}}$$

where $P_{(S)}$ is the membrane permeability of ion species S, $z_s$ the valency of the ion, F the Faraday constant, R the gas constant, T the temperature and $[S]_{cis}$ and $[S]_{trans}$ the cis and trans concentrations of ion species S, respectively. The GHK flux equation can therefore be used to determine the separate current flow contributions (e.g. $I_{(S1)}$, $I_{(S2)}$, $I_{(S3)}$, etc) of all the ion species (e.g. S1, S2, S3, etc) in the system, flowing either in a cis-to-trans direction or a trans-to-cis direction.

In some embodiments, the separate ionic current contributions can be combined to determine the measured current (I) (which accounts for the direction of the ionic flows relative to the polarity of the applied voltage):

$$I = I_{(s1)} + I_{(s2)} + I_{(s3)} \ldots$$

which will approximately match the ionic current that is measured experimentally across the nanopore system under an applied voltage (ignoring any access resistance from the bulk solution).

In some embodiments, the total absolute ionic current ($I_{total}$) flowing through the nanopore regardless of direction is given by the sum of absolute component currents:

$$I_{total} = |I_{(s1)}| + |I_{(s2)}| + |I_{(s3)}| \ldots$$

When accounting for direction of flow, the separate ionic currents (e.g. $I_{(S1)}$, $I_{(S2)}$, $I_{(S3)}$, etc) can also be combined to determine the separate components of the net ionic current flowing cis-to-trans ($I_{c \to t}$) and net ionic current flowing trans-to-cis ($I_{t \to c}$).

$$I_{c \to t} = -1 \times \sum_{I_{(Sn)} < I} I_{(s1)} + I_{(s2)} + I_{(s3)} \ldots$$

$$I_{t \to c} = \sum_{I_{(Sn)} > I} I_{(s1)} + I_{(s2)} + I_{(s3)} \ldots$$

These in turn can be used to determine the net ion current flow cis-to-trans ($I_{\Delta c \to t}$):

$$I_{\Delta c \to t} = I_{c \to t} - I_{t \to c}$$

In some embodiments, to understand the relative magnitude of the net current flow cis-to-trans as a proportion of the total current flowing through the nanopore, the net cis-to-trans is divided by the total amount of current flowing to obtain:

$$I_{rel} = \frac{I_{c \to t} - I_{t \to c}}{I_{c \to t} + I_{t \to c}} = \frac{I_{\Delta c \to t}}{I_{total}}$$

where $I_{rel}$ is the relative net current flow can be in the cis-to-trans direction.

In some embodiments, in a balanced nanopore system, under an applied voltage the cis-to-trans current ($I_{c \to t}$) is typically balanced by an equal trans-to-cis current ($I_{t \to c}$), so that $I_{\Delta c \to t} \approx 0$ and $I_{rel} \approx 0$. In a nanopore system where the net current flowing is cis-to-trans then $I_{rel} > 0$ up to a maximum of $I_{rel} = 1$ when all the current is flowing in a cis-to-trans direction. Vice versa, in a nanopore system where the net current flowing can be trans-to-cis then $I_{rel} < 0$ to a maximum of $I_{rel} = -1$. Therefore, $I_{rel}$ varies between −1 and 1, and the further away from 0 the stronger the net current flowing through the nanopore in one direction is, and hence the stronger the resulting EOF is in that direction.

According to the present disclosure, analyte capture and translocation is enabled in a nanopore system with a large net cis-to-trans current $I_{\Delta c \to t} \gg 0$ arising from a large relative difference between the cis-to-trans current and the trans-to-cis current ($I_{\Delta t \to c}$), or vice versa ($I_{\Delta t \to c} \gg 0$ from $I_{rel} < 1$). Suitable $I_{rel}$ are greater than 0.2 or less than −0.2, greater than 0.3 or less than −0.3, greater than 0.4 or less than −0.4.

Thus, the GHK flux equation can indicate how to create a large net cis-to-trans current by altering one or more of the nanopore system variables, including the system ion-selectivity, the mixtures of salts used, the salt concentrations and salt asymmetries, and the applied voltage. At least three methods can generate a net total ion flux across the membrane: 1) an asymmetry in electrolyte concentration (e.g. 1 M KCl buffer in cis and 0.1 M KCl buffer in trans), 2) an asymmetry in electrolyte compositions with different permeabilities (e.g. 1 M KCl in cis and 1 M KGlutamate (KGlu) in trans), 3) or the use of ion-selective membrane channels. These methods can be used as such or in any combination.

According to the present disclosure, creating a highly ion-selective nanopore system is one method of creating a directional net flow of water (the EOF) across a membrane, even in a system where there is no salt asymmetry. Nanopores can be ion selective due to the electrostatic effect that charge (in particular charge in the inner surface of the central water-filled channel) has on the nearby ions flowing through the constrained dimensions of the central channel. The ion-selectivity (the specificity for translocating one ion species over another) is reflected in the GHK flux equation by the ion-permeability of each ion species.

The ion selectivity of a nanopore system can be quantified by methods of measuring the current-voltage (I-V) relationship under asymmetric electrolyte conditions. Under asymmetric electrolyte conditions, a net flow of ions will occur when no voltage is applied ($V_m=0$ mV). However, when a specific reversal potential ($V_r$) is applied, the flux of positive and negative ions is equal in magnitude and direction and no net current is measured across the system, enabling the GHK flux equation to be solved at 0 pA for both species of ions to discover the ion-selectivity ratio:

$$\frac{P_{(X+)}}{P_{(Y-)}} = \frac{[a_{Y^-}]_{trans} - [a_{Y^-}]_{cis} * e^{\frac{V_r F}{RT}}}{[a_{X^+}]_{trans} * e^{\frac{V_r F}{RT}} - [a_{X^+}]_{cis}}$$

wherein $P_{(X+)}$ and $P_{(Y-)}$ denote the permeability of the nanopore system for cation species X and anion species Y respectively. $[a_{Y^-}]$ and $[a_{X^-}]$ are the activity of ion Y and X respectively in the indicated compartment, and can be calculated by multiplying the concentration with the mean ion activity coefficient (known and tabulated for most electrolytes (Lide, D. R., 2003, CRC handbook of chemistry and physics, 84th edition, Handb. Chem. Phys. 53, 2616)). The latter is to correct for the presence of other ions in concentrated electrolyte solutions. The empirical ion-selectivity ratio ($P_{(X+)}/P_{(Y-)}$) can inserted back into the GHK flux equations in combination with experimental measurements of ionic current versus applied voltage (I-V curves) for a nanopore system containing the XY salts on both cis and trans to determine the absolute values of $P_{(X+)}$ and $P_{(Y-)}$. Thus, permeability $P_{(S)}$ can be determined for any ion species S employed in the nanopore system of the present disclosure, and then used in the GHK flux equations to determine the underlying ionic current flows for nanopore systems containing a mixtures of two or more ion species (e.g. asymmetric salts types).

In some embodiments, under symmetric salt conditions, in a system comprised primarily of two ions X+ and Y− in both compartments, the ion-selectivity ratio ($P_{(X+)}/P_{(Y-)}$) determines the relative ion flux that will flow across the membrane in a cis-to-trans direction and a trans-to-cis direction. Thus, if $P_{(X+)}/P_{(Y-)}>1$, the cation species dominate the ion flux and the EOF is directed towards the negative electrode, whereas the EOF is directed towards the positive electrode when $P_{(X+)}/P_{(Y-)}<1$. Pores with larger ($P_{(X+)}/P_{(Y-)}$) ratios will have a larger net ion flux and hence a larger EOF.

In some cases, when mixtures of salts are employed, to a first approximation the ion-selectivity ratio is given by:

$$\frac{\overline{P_{(+)}}}{\overline{P_{(-)}}} = \frac{\overline{P_{(+)}}cis}{\overline{P_{(-)}}trans} \text{ for } V \ll 0; \quad \frac{\overline{P_{(+)}}}{\overline{P_{(-)}}} = \frac{\overline{P_{(+)}}trans}{\overline{P_{(-)}}cis} \text{ for } V \gg 0$$

where $\overline{P_{()}}$ is the average permeability of the indicated polarity ions in the indicated compartment, where average permeability is calculated using $\overline{P_{()}}=(P_{(1)}[P_{(1)}]+P_{(2)}[P_{(2)}]+ \ldots)/[total]$ for the indicated polarity ions in the indicated compartment, where $P_{(s)}$ and $[P_{(s)}]$ are the permeability and concentration respectively for species S=1, 2, . . . etc in given compartment, and [total] is the total concentration of the same ions.

According to the present disclosure, it has been discovered that an ion-selectivity ratio $\overline{P_{(+)}}/\overline{P_{(-)}}>2.0$ or $<0.5, >2.5$ or $<0.4,>3.0$ or $<0.33,>3.5$ or $<0.29$, in combination with a symmetrical salt system is sufficient to drive capture and translocation of complex analytes against any prevailing EPF under an applied voltage across the membrane of 20 mV to 1 V, 50 mV to 300 mV, 75 mV to 200 mV.

In some embodiments, a pore can comprise a relative ion selectivity $P_{(+)}/P_{(-)}$ of at least about 0.1, at least about 0.2, at least about 0.3, at least about 0.4, at least about 0.5, at least about 0.6, at least about 0.7, at least about 0.8, at least about 0.9, at least about 1, at least about 2, at least about 3, at least about 4, at least about 5, or greater than about 5 under an applied voltage difference across the membrane. In some embodiments, a pore can comprise a relative ion selectivity $P_{(+)}/P_{(-)}$ of at most about 5, at most about 4, at most about 3, at most about 2, at most about 1, at most about 0.9, at most about 0.8, at most about 0.7, at most about 0.6, at most about 0.5, at most about 0.4, at most about 0.3, at most about 0.2, at most about 0.1, or less than about 0.1 under an applied voltage difference across the membrane.

In some embodiments, a pore can comprise a relative ion selectivity $P_{(+)}/P_{(-)}$ from about 0.1 to about 5 under an applied voltage difference across the membrane. In some embodiments, a pore can comprise a relative ion selectivity $P_{(+)}/P_{(-)}$ from about 0.1 to about 0.2, about 0.1 to about 0.3, about 0.1 to about 0.4, about 0.1 to about 0.5, about 0.1 to about 1, about 0.1 to about 1.5, about 0.1 to about 2, about 0.1 to about 2.5, about 0.1 to about 3, about 0.1 to about 4, about 0.1 to about 5, about 0.2 to about 0.3, about 0.2 to about 0.4, about 0.2 to about 0.5, about 0.2 to about 1, about 0.2 to about 1.5, about 0.2 to about 2, about 0.2 to about 2.5, about 0.2 to about 3, about 0.2 to about 4, about 0.2 to about 5, about 0.3 to about 0.4, about 0.3 to about 0.5, about 0.3 to about 1, about 0.3 to about 1.5, about 0.3 to about 2, about 0.3 to about 2.5, about 0.3 to about 3, about 0.3 to about 4, about 0.3 to about 5, about 0.4 to about 0.5, about 0.4 to about 1, about 0.4 to about 1.5, about 0.4 to about 2, about 0.4 to about 2.5, about 0.4 to about 3, about 0.4 to about 4, about 0.4 to about 5, about 0.5 to about 1, about 0.5 to about 1.5, about 0.5 to about 2, about 0.5 to about 2.5, about 0.5 to about 3, about 0.5 to about 4, about 0.5 to about 5, about 1 to about 1.5, about 1 to about 2, about 1 to about 2.5, about 1 to about 3, about 1 to about 4, about 1 to about 5, about 1.5 to about 2, about 1.5 to about 2.5, about 1.5 to about 3, about 1.5 to about 4, about 1.5 to about 5, about 2 to about 2.5, about 2 to about 3, about 2 to about 4, about 2 to about 5, about 2.5 to about 3, about 2.5 to about 4, about 2.5 to about 5, about 3 to about 4, about 3 to about 5, or about 4 to about 5 under an applied voltage difference across the membrane.

In some embodiments, a pore can comprise a relative ion selectivity $P_{(+)}/P_{(-)}$ of about 0.1, about 0.2, about 0.3, about 0.4, about 0.5, about 0.6, about 0.7, about 0.8, about 0.9, about 1, about 2, about 3, about 4, or about 5 under an applied voltage difference across the membrane.

In some embodiments, the applied voltage across the membrane can be at least about 1 mV, at least about 5 mV, at least about 10 mV, at least about 20 mV, at least about 30 mV, at least about 40 mV, at least about 50 mV, at least about 60 mV, at least about 70 mV, at least about 80 mV, at least about 90 mV, at least about 100 mV, at least about 150 mV, at least about 200 mV, at least about 250 mV, at least about 300 mV, at least about 350 mV, at least about 400 mV, at least about 450 mV, at least about 500 mV, at least about 600 mV, at least about 700 mV, at least about 800 mV, at least about 900 mV, at least about 1000 mV, or greater than about 1000 mV in magnitude. In some embodiments, the applied voltage across the membrane can be at least about 1000 mV, at most about 900 mV, at most about 800 mV, at most about 700 mV, at most about 600 mV, at most about 500 mV, at most about 450 mV, at most about 400 mV, at most about 350 mV, at most about 300 mV, at most about 250 mV, at most about 200 mV, at most about 150 mV, at most about 100 mV, at most about 90 mV, at most about 80 mV, at most about 70 mV, at most about 60 mV, at most about 50 mV, at most about 40 mV, at most about 30 mV, at most about 20 mV, at most about 10 mV, at most about 5 mV, at most about 1 mV, or less than about 1 mV in magnitude.

In some embodiments, the applied voltage across the membrane can be from about 1 mV to about 100 mV in magnitude. In some embodiments, the applied voltage across the membrane can be from about 1 mV to about 5 mV, about 1 mV to about 10 mV, about 1 mV to about 20 mV, about 1 mV to about 30 mV, about 1 mV to about 40 mV, about 1 mV to about 50 mV, about 1 mV to about 60 mV, about 1 mV to about 70 mV, about 1 mV to about 80 mV, about 1 mV to about 90 mV, about 1 mV to about 100 mV, about 5 mV to about 10 mV, about 5 mV to about 20 mV, about 5 mV to about 30 mV, about 5 mV to about 40 mV, about 5 mV to about 50 mV, about 5 mV to about 60 mV, about 5 mV to about 70 mV, about 5 mV to about 80 mV, about 5 mV to about 90 mV, about 5 mV to about 100 mV, about 10 mV to about 20 mV, about 10 mV to about 30 mV, about 10 mV to about 40 mV, about 10 mV to about 50 mV, about 10 mV to about 60 mV, about 10 mV to about 70 mV, about 10 mV to about 80 mV, about 10 mV to about 90 mV, about 10 mV to about 100 mV, about 20 mV to about 30 mV, about 20 mV to about 40 mV, about 20 mV to about 50 mV, about 20 mV to about 60 mV, about 20 mV to about 70 mV, about 20 mV to about 80 mV, about 20 mV to about 90 mV, about 20 mV to about 100 mV, about 30 mV to about 40 mV, about 30 mV to about 50 mV, about 30 mV to about 60 mV, about 30 mV to about 70 mV, about 30 mV to about 80 mV, about 30 mV to about 90 mV, about 30 mV to about 100 mV, about 40 mV to about 50 mV, about 40 mV to about 60 mV, about 40 mV to about 70 mV, about 40 mV to about 80 mV, about 40 mV to about 90 mV, about 40 mV to about 100 mV, about 50 mV to about 60 mV, about 50 mV to about 70 mV, about 50 mV to about 80 mV, about 50 mV to about 90 mV, about 50 mV to about 100 mV, about 60 mV to about 70 mV, about 60 mV to about 80 mV, about 60 mV to about 90 mV, about 60 mV to about 100 mV, about 70 mV to about 80 mV, about 70 mV to about 90 mV, about 70 mV to about 100 mV, about 80 mV to about 90 mV, about 80 mV to about 100 mV, or about 90 mV to about 100 mV in magnitude.

In some embodiments, the applied voltage across the membrane can be from about 100 mV to about 1,000 mV in magnitude. In some embodiments, the applied voltage across the membrane can be from about 100 mV to about 150 mV, about 100 mV to about 200 mV, about 100 mV to about 250 mV, about 100 mV to about 300 mV, about 100 mV to about 400 mV, about 100 mV to about 500 mV, about 100 mV to about 600 mV, about 100 mV to about 700 mV, about 100 mV to about 800 mV, about 100 mV to about 900 mV, about 100 mV to about 1,000 mV, about 150 mV to about 200 mV, about 150 mV to about 250 mV, about 150 mV to about 300 mV, about 150 mV to about 400 mV, about 150 mV to about 500 mV, about 150 mV to about 600 mV, about 150 mV to about 700 mV, about 150 mV to about 800 mV, about 150 mV to about 900 mV, about 150 mV to about 1,000 mV, about 200 mV to about 250 mV, about 200 mV to about 300 mV, about 200 mV to about 400 mV, about 200 mV to about 500 mV, about 200 mV to about 600 mV, about 200 mV to about 700 mV, about 200 mV to about 800 mV, about 200 mV to about 900 mV, about 200 mV to about 1,000 mV, about 250 mV to about 300 mV, about 250 mV to about 400 mV, about 250 mV to about 500 mV, about 250 mV to about 600 mV, about 250 mV to about 700 mV, about 250 mV to about 800 mV, about 250 mV to about 900 mV, about 250 mV to about 1,000 mV, about 300 mV to about 400 mV, about 300 mV to about 500 mV, about 300 mV to about 600 mV, about 300 mV to about 700 mV, about 300 mV to about 800 mV, about 300 mV to about 900 mV, about 300 mV to about 1,000 mV, about 400 mV to about 500 mV, about 400 mV to about 600 mV, about 400 mV to about 700 mV, about 400 mV to about 800 mV, about 400 mV to about 900 mV, about 400 mV to about 1,000 mV, about 500 mV to about 600 mV, about 500 mV to about 700 mV, about 500 mV to about 800 mV, about 500 mV to about 900 mV, about 500 mV to about 1,000 mV, about 600 mV to about 700 mV, about 600 m V to about 800 mV, about 600 mV to about 900 mV, about 600 mV to about 1,000 mV, about 700 mV to about 800 mV, about 700 mV to about 900 mV, about 700 mV to about 1,000 mV, about 800 mV to about 900 mV, about 800 mV to about 1,000 mV, or about 900 mV to about 1,000 mV in magnitude.

In some embodiments, the applied voltage across the membrane can be about 1 mV, about 5 mV, about 10 mV, about 20 mV, about 30 mV, about 40 mV, about 50 mV, about 60 mV, about 70 mV, about 80 mV, about 90 mV, about 100 mV, about 150 mV, about 200 mV, about 250 mV, about 300 mV, about 350 mV, about 400 mV, about 450 mV, about 500 mV, about 600 mV, about 700 mV, about 800 mV, about 900 mV, or about 1000 mV in magnitude.

In some embodiments, mechanisms of controlling the EOF by inducing a strong net flow of ions in one direction across the nanopore are known in the art. In some embodiments, the EOF can be controlled by inducing a strong net flow of ion ions in one direction across the nanopore. The EOF can be controlled by modifying of the nanopore, applying specific electrolyte asymmetries and concentrations, or any combination thereof.

For example, mechanisms of controlling or arranging the EOF including the genetic engineering (e.g. mutating) of the inner channel of the nanopore to alter the steric and/or the electrostatic conditions, to in turn adjust the specificity for translocating one ion over another. For example, the net charge of the inner channel of the nanopore can be increased so as to electrostatically limit the flux of one of the ions from one direction across the nanopore, while retaining/enhancing the flux of the oppositely charged ion flowing in the opposite direction under an applied voltage. Creating a strong EOF is enhanced by creating a strong overlap between the Debye layers (alternatively termed the Stern layer, the Gouy-Chapman diffuse layer or the electric double layer) from adjacent walls within a nanopore (Chinappi et al., 2020, ACS Nano, 14, 11, pg. 15816-15828). The EOF can be enhanced by either adding more charges to the residues lining the walls of the channel, or narrowing the channel dimensions, or a combination thereof.

In some embodiments, a nanopore lumen comprises a net charge of at least about 2 coulombs, at least about 3 coulombs, at least about 4 coulombs, at least about 5 coulombs, at least about 10 coulombs, at least about 15 coulombs, at least about 20 coulombs, at least about 25 coulombs, at least about 30 coulombs, at least about 35 coulombs, at least about 40 coulombs, at least about 45 coulombs, at least about 50 coulombs, at least about 55 coulombs, at least about 60 coulombs, at least about 70 coulombs, at least about 80 coulombs, at least about 90 coulombs, at least about 100 coulombs, at least about 150 coulombs, at least about 200 coulombs, or greater than about 200 coulombs. In some embodiments coulombs, a nanopore lumen comprises a net charge of at most about 200 coulombs, at most about 150 coulombs, at most about 100 coulombs, at most about 90 coulombs, at most about 80 coulombs, at most about 70 coulombs, at most about 60 coulombs, at most about 55 coulombs, at most about 50 coulombs, at most about 45 coulombs, at most about 40 coulombs, at most about 35 coulombs, at most about 30 coulombs, at most about 25 coulombs, at most about 20 coulombs, at most about 15 coulombs, at most about 10 coulombs, at most about 5 coulombs, at most about 4 coulombs, at most about 3 coulombs, at most about 2 coulombs, or less than about 2 coulombs.

In some embodiments, a nanopore lumen comprises a net charge from about 2 to about 200 coulombs. In some embodiments, a nanopore lumen comprises a net charge from at most about 200. In some embodiments, a nanopore lumen comprises a net charge from about 2 to about 5, about 2 to about 10, about 2 to about 20, about 2 to about 30, about 2 to about 40, about 2 to about 50, about 2 to about 75, about 2 to about 100, about 2 to about 125, about 2 to about 150, about 2 to about 200, about 5 to about 10, about 5 to about 20, about 5 to about 30, about 5 to about 40, about 5 to about 50, about 5 to about 75, about 5 to about 100, about 5 to about 125, about 5 to about 150, about 5 to about 200, about 10 to about 20, about 10 to about 30, about 10 to about 40, about 10 to about 50, about 10 to about 75, about 10 to about 100, about 10 to about 125, about 10 to about 150, about 10 to about 200, about 20 to about 30, about 20 to about 40, about 20 to about 50, about 20 to about 75, about 20 to about 100, about 20 to about 125, about 20 to about 150, about 20 to about 200, about 30 to about 40, about 30 to about 50, about 30 to about 75, about 30 to about 100, about 30 to about 125, about 30 to about 150, about 30 to about 200, about 40 to about 50, about 40 to about 75, about 40 to about 100, about 40 to about 125, about 40 to about 150, about 40 to about 200, about 50 to about 75, about 50 to about 100, about 50 to about 125, about 50 to about 150, about 50 to about 200, about 75 to about 100, about 75 to about 125, about 75 to about 150, about 75 to about 200, about 100 to about 125, about 100 to about 150, about 100 to about 200, about 125 to about 150, about 125 to about 200, or about 150 to about 200 coulombs.

In some embodiments coulombs, a nanopore lumen comprises a net charge of about 2 coulombs, about 3 coulombs, about 4 coulombs, about 5 coulombs, about 10 coulombs, about 15 coulombs, about 20 coulombs, about 25 coulombs, about 30 coulombs, about 35 coulombs, about 40 coulombs, about 45 coulombs, about 50 coulombs, about 55 coulombs, about 60 coulombs, about 70 coulombs, about 80 coulombs, about 90 coulombs, about 100 coulombs, about 150 coulombs, about 200 coulombs.

In some embodiments, a lumen of the nanopore can comprise a net positive charge to create the EOF. In some embodiments, a lumen of the nanopore can comprise a net negative charge to create the EOF. In some embodiments, the nanopore lumen can comprise a net charge from about −20 to about +20 for a single subunit of an oligomeric nanopore. This net charge can be multiplied up to e.g. 5, 6, 7, 8, 9, 10 or more times in the final pore, thus it is possible to have >100 charges in the lumen of the final nanopore which can comprise oligomeric pores, monomeric pores or fusion pores wherein all monomers are genetically fused into a single pore.

The net charge of the lumen/channel of the nanopore as defined herein can be combined with any charge on the remainder of the nanopore protein e.g. there can be positive and/or negative charges on the outside of the pore.

In some cases, the nanopore lumen can comprise a net charge of at least about −20, at least about −19, at least about −18, at least about −17, at least about −16, at least about −15, at least about −14, at least about −13, at least about −12, at least about −11, at least about −10, at least about −9, at least about −8, at least about −7, at least about −6, at least about −5, at least about −4, at least about −3, at least about −2, at least about −1, at least about 0, at least about +1, at least about +2, at least about +3, at least about +4, at least about +5, at least about +6, at least about +7, at least about +8, at least about +9, at least about +10, at least about +11, at least about +12, at least about +13, at least about +14, at least about +15, at least about +16, at least about +17, at least about +18, at least about +19, at least about +20, or more than +20 for a single nanopore subunit. In some cases, the nanopore lumen can comprise a net charge of at most about +20, at most about +19, at most about +18, at most about +17, at most about +16, at most about +15, at most about +14, at most about +13, at most about +12, at most about +11, at most about +10, at most about +9, at most about +8, at most about +7, at most about +6, at most about +5, at most about +4, at most about +3, at most about +2, at most about +1, at most about 0, at most about −1, at most about −2, at most about −3, at most about −4, at most about −5, at most about −6, at most about −7, at most about −8, at most about −9, at most about −10, at most about −11, at most about −12, at most about −13, at most about −14, at most about −15, at most about −16, at most about −17, at most about −18, at most about −19, at most about −20, or less than −20 for a single nanopore subunit. In some cases, the nanopore lumen can comprise a net charge of about −20, about-19, about −18, about −17, about −16, about −15, about −14, about −13, about −12, about −11, about −10, about −9, about −8, about −7, about −6, about −5, about −4, about −3, about −2, about −1, about 0, about +1, about +2, about +3, about +4, about +5, about +6, about +7, about +8, about +9, about +10, about +11, about +12, about +13, about +14, about +15, about +16, about +17, about +18, about +19, or about +20 for a single nanopore subunit.

In some embodiments, the nanopore can comprise one or more subunits. In some cases, each subunit of the one or more subunits can comprise from one to 20 charged amino acids. In some embodiments, the number of charged amino acids in each subunit of the one or more subunits that may be distributed evenly within the lumen can be at least about 1 charged amino acids, at least about 2 charged amino acids, at least about 3 charged amino acids, at least about 4 charged amino acids, at least about 5 charged amino acids, at least about 6 charged amino acids, at least about 7 charged amino acids, at least about 8 charged amino acids, at least about 10 charged amino acids, at least about 11 charged amino acids, at least about 12 charged amino acids, at least about 13 charged amino acids, at least about 14 charged amino acids, at least about 15 charged amino acids, at least about 16 charged amino acids, at least about 17 charged amino acids, at least about 18 charged amino acids, at least about 19 charged amino acids, at least about 20 charged amino acids, or greater than about 20 charged amino acids. In some embodiments charged amino acids, the number of charged amino acids in each subunit of the one or more subunits may be distributed evenly within the lumen can be at most about 20 charged amino acids, at most about 19 charged amino acids, at most about 18 charged amino acids, at most about 17 charged amino acids, at most about 16 charged amino acids, at most about 15 charged amino acids, at most about 14 charged amino acids, at most about 13 charged amino acids, at most about 12 charged amino acids, at most about 11 charged amino acids, at most about 10 charged amino acids, at most about 9 charged amino acids, at most about 8 charged amino acids, at most about 7 charged amino acids, at most about 6 charged amino acids, at most about 5 charged amino acids, at most about 4 charged amino acids, at most about 3 charged amino acids, at most about 2 charged amino acids, at most about 1 charged amino acids, or less than about 1 charged amino acids.

In some embodiments, the number of charged amino acids in each subunit of the one or more subunits may be distributed evenly within the lumen can be from about 1 to about 20 charged amino acids. In some embodiments, the number of amino acids that may be distributed evenly within the lumen can be from about 1 to about 2, about 1 to about 3, about 1 to about 4, about 1 to about 5, about 1 to about 8, about 1 to about 9, about 1 to about 10, about 1 to about 12, about 1 to about 15, about 1 to about 18, about 1 to about 20, about 2 to about 3, about 2 to about 4, about 2 to about 5, about 2 to about 8, about 2 to about 9, about 2 to about 10, about 2 to about 12, about 2 to about 15, about 2 to about 18, about 2 to about 20, about 3 to about 4, about 3 to about 5, about 3 to about 8, about 3 to about 9, about 3 to about 10, about 3 to about 12, about 3 to about 15, about 3 to about 18, about 3 to about 20, about 4 to about 5, about 4 to about 8, about 4 to about 9, about 4 to about 10, about 4 to about 12, about 4 to about 15, about 4 to about 18, about 4 to about 20, about 5 to about 8, about 5 to about 9, about 5 to about 10, about 5 to about 12, about 5 to about 15, about 5 to about 18, about 5 to about 20, about 8 to about 9, about 8 to about 10, about 8 to about 12, about 8 to about 15, about 8 to about 18, about 8 to about 20, about 9 to about 10, about 9 to about 12, about 9 to about 15, about 9 to about 18, about 9 to about 20, about 10 to about 12, about 10 to about 15, about 10 to about 18, about 10 to about 20, about 12 to about 15, about 12 to about 18, about 12 to about 20, about 15 to about 18, about 15 to about 20, or about 18 to about 20 charged amino acids.

In some embodiments, the number of charged amino acids in each subunit of the one or more subunits may be distributed evenly within the lumen can be about 1 amino acid, about 2 amino acids, about 3 amino acids, about 4 amino acids, about 5 amino acids, about 6 amino acids, about 7 amino acids, about 8 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, or about 20 charged amino acids.

In some embodiments, a nanopore lumen may comprise at least about 1, at least about 2, at least about 3, at least about 4, at least about 5, at least about 6, at least about 7, at least about 8, at least about 10, at least about 11, at least about 12, at least about 13, at least about 14, at least about 15, at least about 16, at least about 17, at least about 18, at least about 19, at least about 20, or greater than about 20 separate sets of charges. In some embodiments, a nanopore may comprise at most about 20, at most about 19, at most about 18, at most about 17, at most about 16, at most about 15, at most about 14, at most about 13, at most about 12, at most about 11, at most about 10, at most about 9, at most about 8, at most about 7, at most about 6, at most about 5, at most about 4, at most about 3, at most about 2, at most about 1, or less than about 1 separate set of charges.

In some embodiments, a nanopore lumen may comprise from about 1 to about 20 separate sets of charges. In some embodiments, a nanopore may comprise from about 1 to about 2, about 1 to about 3, about 1 to about 4, about 1 to about 5, about 1 to about 8, about 1 to about 9, about 1 to about 10, about 1 to about 12, about 1 to about 15, about 1 to about 18, about 1 to about 20, about 2 to about 3, about 2 to about 4, about 2 to about 5, about 2 to about 8, about 2 to about 9, about 2 to about 10, about 2 to about 12, about 2 to about 15, about 2 to about 18, about 2 to about 20, about 3 to about 4, about 3 to about 5, about 3 to about 8, about 3 to about 9, about 3 to about 10, about 3 to about 12, about 3 to about 15, about 3 to about 18, about 3 to about 20, about 4 to about 5, about 4 to about 8, about 4 to about 9, about 4 to about 10, about 4 to about 12, about 4 to about 15, about 4 to about 18, about 4 to about 20, about 5 to about 8, about 5 to about 9, about 5 to about 10, about 5 to about 12, about 5 to about 15, about 5 to about 18, about 5 to about 20, about 8 to about 9, about 8 to about 10, about 8 to about 12, about 8 to about 15, about 8 to about 18, about 8 to about 20, about 9 to about 10, about 9 to about 12, about 9 to about 15, about 9 to about 18, about 9 to about 20, about 10 to about 12, about 10 to about 15, about 10 to about 18, about 10 to about 20, about 12 to about 15, about 12 to about 18, about 12 to about 20, about 15 to about 18, about 15 to about 20, or about 18 to about 20 separate sets of charges.

In some embodiments, a nanopore lumen may comprise about 1, about 2, about 3, about 4, about 5, about 6, about 7, about 8, about 10, about 11, about 12, about 13, about 14, about 15, about 16, about 17, about 18, about 19, or about 20 separate sets of charges.

In some embodiments, the sets of charges may each be spaced at least about 0.1 nanometers, at least about 0.2 nanometers, at least about 0.3 nanometers, at least about 0.4 nanometers, at least about 0.5 nanometers, at least about 0.6 nanometers, at least about 0.7 nanometers, at least about 0.8 nanometers, at least about 0.9 nanometers, at least about 1 nanometers, at least about 2 nanometers, at least about 3 nanometers, at least about 4 nanometers, at least about 5 nanometers, or greater than about 5 nanometers apart from each other along the longitudinal length of the channel. In some embodiments, the sets of charges may each be spaced at most about 5 nanometers, at most about 4 nanometers, at most about 3 nanometers, at most about 2 nanometers, at most about 1 nanometers, at most about 0.9 nanometers, at most about 0.8 nanometers, at most about 0.7 nanometers, at most about 0.6 nanometers, at most about 0.5 nanometers, at most about 0.4 nanometers, at most about 0.3 nanometers, at most about 0.2 nanometers, at most about 0.1 nanometers, or less than about 0.1 nanometer apart from each other along the longitudinal length of the channel.

In some embodiments, the sets of charges may each be spaced from about 0.1 nanometers to about 5 nanometers apart from each other along the longitudinal length of the channel. In some embodiments, the sets of charges may each be spaced from about 0.1 nanometers to about 0.2 nanometers, about 0.1 nanometers to about 0.3 nanometers, about 0.1 nanometers to about 0.4 nanometers, about 0.1 nanometers to about 0.5 nanometers, about 0.1 nanometers to about 1 nanometer, about 0.1 nanometers to about 1.5 nanometers, about 0.1 nanometers to about 2 nanometers, about 0.1 nanometers to about 2.5 nanometers, about 0.1 nanometers to about 3 nanometers, about 0.1 nanometers to about 4 nanometers, about 0.1 nanometers to about 5 nanometers, about 0.2 nanometers to about 0.3 nanometers, about 0.2 nanometers to about 0.4 nanometers, about 0.2 nanometers to about 0.5 nanometers, about 0.2 nanometers to about 1 nanometer, about 0.2 nanometers to about 1.5 nanometers, about 0.2 nanometers to about 2 nanometers, about 0.2 nanometers to about 2.5 nanometers, about 0.2 nanometers to about 3 nanometers, about 0.2 nanometers to about 4 nanometers, about 0.2 nanometers to about 5 nanometers, about 0.3 nanometers to about 0.4 nanometers, about 0.3 nanometers to about 0.5 nanometers, about 0.3 nanometers to about 1 nanometer, about 0.3 nanometers to about 1.5 nanometers, about 0.3 nanometers to about 2 nanometers, about 0.3 nanometers to about 2.5 nanometers, about 0.3 nanometers to about 3 nanometers, about 0.3 nanometers to about 5 nanometers, about 0.4 nanometers to about 0.5 nanometers, about 0.4 nanometers to about 1 nanometer, about 0.4 nanometers to about 1.5 nanometers, about 0.4 nanometers to about 2 nanometers, about 0.4 nanometers to about 2.5 nanometers, about 0.4 nanometers to about 3 nanometers, about 0.4 nanometers to about 4 nanometers, about 0.4 nanometers to about 5 nanometers, about 0.5 nanometers to about 1 nanometer, about 0.5 nanometers to about 1.5 nanometers, about 0.5 nanometers to about 2 nanometers, about 0.5 nanometers to about 2.5 nanometers, about 0.5 nanometers to about 3 nanometers, about 0.5 nanometers to about 4 nanometers, about 0.5 nanometers to about 5 nanometers, about 1 nanometer to about 1.5 nanometers, about 1 nanometer to about 2 nanometers, about 1 nanometer to about 2.5 nanometers, about 1 nanometer to about 3 nanometers, about 1 nanometer to about 4 nanometers, about 1 nanometer to about 5 nanometers, about 1.5 nanometers to about 2 nanometers, about 1.5 nanometers to about 2.5 nanometers, about 1.5 nanometers to about 3 nanometers, about 1.5 nanometers to about 4 nanometers, about 1.5 nanometers to about 5 nanometers, about 2 nanometers to about 2.5 nanometers, about 2 nanometers to about 3 nanometers, about 2 nanometers to about 4 nanometers, about 2 nanometers to about 5 nanometers, about 2.5 nanometers to about 3 nanometers, about 2.5 nanometers to about 4 nanometers, about 2.5 nanometers to about 5 nanometers, about 3 nanometers to about 4 nanometers, about 3 nanometers to about 5 nanometers, or about 4 nanometers to about 5 nanometers apart from each other along the longitudinal length of the channel.

In some embodiments, the sets of charges may each be spaced about 0.1 nanometers, about 0.2 nanometers, about 0.3 nanometers, about 0.4 nanometers, about 0.5 nanometers, about 0.6 nanometers, about 0.7 nanometers, about 0.8 nanometers, about 0.9 nanometers, about 1 nanometers, about 2 nanometers, about 3 nanometers, about 4 nanometers, or about 5 nanometers apart from each other along the longitudinal length of the channel.

For example, a nanopore may be engineered to contain regions of at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, or greater than about 20 separate rings of charges along the longitudinal length of the channel. A nanopore may be engineered to contain regions of at most about 20, at most about 19, at most about 18, at most about 17, at most about 16, at most about 15, at most about 14, at most about 13, at most about 12, at most about 11, at most about 10, at most about 9, at most about 8, at most about 7, at most about 6, at most about 5, at most about 4, at most about 3, at most about 2, or less than about 2 separate rings of charges along the longitudinal length of the channel.

A nanopore may be engineered to contain regions from about 2 to about 20 separate rings of charges along the longitudinal length of the channel. A nanopore may be engineered to contain regions from about 2 to about 3, about 2 to about 4, about 2 to about 5, about 2 to about 6, about 2 to about 7, about 2 to about 8, about 2 to about 9, about 2 to about 10, about 2 to about 15, about 2 to about 20, about 3 to about 4, about 3 to about 5, about 3 to about 6, about 3 to about 7, about 3 to about 8, about 3 to about 9, about 3 to about 10, about 3 to about 15, about 3 to about 20, about 4 to about 5, about 4 to about 6, about 4 to about 7, about 4 to about 8, about 4 to about 9, about 4 to about 10, about 4 to about 15, about 4 to about 20, about 5 to about 6, about 5 to about 7, about 5 to about 8, about 5 to about 9, about 5 to about 10, about 5 to about 15, about 5 to about 20, about 6 to about 7, about 6 to about 8, about 6 to about 9, about 6 to about 10, about 6 to about 15, about 6 to about 20, about 7 to about 8, about 7 to about 9, about 7 to about 10, about 7 to about 15, about 7 to about 20, about 8 to about 9, about 8 to about 10, about 8 to about 15, about 8 to about 20, about 9 to about 10, about 9 to about 15, about 9 to about 20, about 10 to about 15, about 10 to about 20, or about 15 to about 20 separate rings of charges along the longitudinal length of the channel.

A nanopore may be engineered to contain regions of about 2, about 3, about 4, about 5, about 6, about 7, about 8, about 9, about 10, about 11, about 12, about 13, about 14, about 15, about 16, about 17, about 18, about 19, or about 20 separate rings of charges along the longitudinal length of the channel.

In some embodiments, the rings of charges may each be spaced at least about 0.1 nanometers, at least about 0.2 nanometers, at least about 0.3 nanometers, at least about 0.4 nanometers, at least about 0.5 nanometers, at least about 0.6 nanometers, at least about 0.7 nanometers, at least about 0.8 nanometers, at least about 0.9 nanometers, at least about 1 nanometers, at least about 2 nanometers, at least about 3 nanometers, at least about 4 nanometers, at least about 5 nanometers, at least about 6 nanometers, at least about 7 nanometers, at least about 8 nanometers, at last about 9 nanometers, or greater than about 10 nanometers apart from each other along the longitudinal length of the channel. In some embodiments, the rings of charges may each be spaced at most about 10 nanometers, at most about 9 nanometers, at most about 8 nanometers, at most about 7 nanometers, at most about 6 nanometers, at most about 5 nanometers, at most about 4 nanometers, at most about 3 nanometers, at most about 2 nanometers, at most about 1 nanometers, at most about 0.9 nanometers, at most about 0.8 nanometers, at most about 0.7 nanometers, at most about 0.6 nanometers, at most about 0.5 nanometers, at most about 0.4 nanometers, at most about 0.3 nanometers, at most about 0.2 nanometers, at most about 0.1 nanometers, or less than about 0.1 nanometer apart from each other along the longitudinal length of the channel.

In some embodiments, the rings of charges may each be spaced from about 0.1 nanometers to about 5 nanometers apart from each other along the longitudinal length of the channel. In some embodiments, the rings of charges may each be spaced from about 0.1 nanometers to about 0.2 nanometers, about 0.1 nanometers to about 0.3 nanometers, about 0.1 nanometers to about 0.4 nanometers, about 0.1 nanometers to about 0.5 nanometers, about 0.1 nanometers to about 1 nanometer, about 0.1 nanometers to about 1.5 nanometers, about 0.1 nanometers to about 2 nanometers, about 0.1 nanometers to about 2.5 nanometers, about 0.1 nanometers to about 3 nanometers, about 0.1 nanometers to about 4 nanometers, about 0.1 nanometers to about 5 nanometers, about 0.2 nanometers to about 0.3 nanometers, about 0.2 nanometers to about 0.4 nanometers, about 0.2 nanometers to about 0.5 nanometers, about 0.2 nanometers to about 1 nanometer, about 0.2 nanometers to about 1.5 nanometers, about 0.2 nanometers to about 2 nanometers, about 0.2 nanometers to about 2.5 nanometers, about 0.2 nanometers to about 3 nanometers, about 0.2 nanometers to about 4 nanometers, about 0.2 nanometers to about 5 nanometers, about 0.3 nanometers to about 0.4 nanometers, about 0.3 nanometers to about 0.5 nanometers, about 0.3 nanometers to about 1 nanometer, about 0.3 nanometers to about 1.5 nanometers, about 0.3 nanometers to about 2 nanometers, about 0.3 nanometers to about 2.5 nanometers, about 0.3 nanometers to about 3 nanometers, about 0.3 nanometers to about 4 nanometers, about 0.3 nanometers to about 5 nanometers, about 0.4 nanometers to about 0.5 nanometers, about 0.4 nanometers to about 1 nanometer, about 0.4 nanometers to about 1.5 nanometers, about 0.4 nanometers to about 2 nanometers, about 0.4 nanometers to about 2.5 nanometers, about 0.4 nanometers to about 3 nanometers, about 0.4 nanometers to about 4 nanometers, about 0.4 nanometers to about 5 nanometers, about 0.5 nanometers to about 1 nanometer, about 0.5 nanometers to about 1.5 nanometers, about 0.5 nanometers to about 2 nanometers, about 0.5 nanometers to about 2.5 nanometers, about 0.5 nanometers to about 3 nanometers, about 0.5 nanometers to about 4 nanometers, about 0.5 nanometers to about 5 nanometers, about 1 nanometer to about 1.5 nanometers, about 1 nanometer to about 2 nanometers, about 1 nanometer to about 2.5 nanometers, about 1 nanometer to about 3 nanometers, about 1 nanometer to about 4 nanometers, about 1 nanometer to about 5 nanometers, about 1.5 nanometers to about 2 nanometers, about 1.5 nanometers to about 2.5 nanometers, about 1.5 nanometers to about 3 nanometers, about 1.5 nanometers to about 4 nanometers, about 1.5 nanometers to about 5 nanometers, about 2 nanometers to about 2.5 nanometers, about 2 nanometers to about 3 nanometers, about 2 nanometers to about 4 nanometers, about 2 nanometers to about 5 nanometers, about 2.5 nanometers to about 3 nanometers, about 2.5 nanometers to about 4 nanometers, about 2.5 nanometers to about 5 nanometers, about 3 nanometers to about 4 nanometers, about 3 nanometers to about 5 nanometers, about 4 nanometers to about 5 nanometers, about 5 nanometers to about 6 nanometers, about 6 nanometers to about 7 nanometers, about 7 nanometers to about 8 nanometers, about 8 nanometers to about 9 nanometers, or about 9 nanometers to about 10 nanometers apart from each other along the longitudinal length of the channel.

In some embodiments, the rings of charges may each be spaced about 0.1 nanometers, about 0.2 nanometers, about 0.3 nanometers, about 0.4 nanometers, about 0.5 nanometers, about 0.6 nanometers, about 0.7 nanometers, about 0.8 nanometers, about 0.9 nanometers, about 1 nanometers, about 2 nanometers, about 3 nanometers, about 4 nanometers, about 5 nanometers, about 6 nanometers, about 7 nanometers, about 8 nanometers, about 9 nanometers, or about 10 nanometers apart from each other along the longitudinal length of the channel.

In some embodiments, a nanopore lumen comprises a net charge of at least about 2, at least about 3, at least about 4, at least about 5, at least about 10, at least about 15, at least about 20, at least about 25, at least about 30, at least about 35, at least about 40, at least about 45, at least about 50, at least about 55, at least about 60, at least about 70, at least about 80, at least about 90, at least about 100, at least about 150, at least about 200, or greater than about 200. In some embodiments, a nanopore lumen comprises a net charge of at most about 200, at most about 150, at most about 100, at most about 90, at most about 80, at most about 70, at most about 60, at most about 55, at most about 50, at most about 45, at most about 40, at most about 35, at most about 30, at most about 25, at most about 20, at most about 15, at most about 10, at most about 5, at most about 4, at most about 3, at most about 2, or less than about 2.

In some embodiments, a nanopore lumen comprises a net charge from about 2 to about 200. In some embodiments, a nanopore lumen comprises a net charge from at most about 200. In some embodiments, a nanopore lumen comprises a net charge from about 2 to about 5, about 2 to about 10, about 2 to about 20, about 2 to about 30, about 2 to about 40, about 2 to about 50, about 2 to about 75, about 2 to about 100, about 2 to about 125, about 2 to about 150, about 2 to about 200, about 5 to about 10, about 5 to about 20, about 5 to about 30, about 5 to about 40, about 5 to about 50, about 5 to about 75, about 5 to about 100, about 5 to about 125, about 5 to about 150, about 5 to about 200, about 10 to about 20, about 10 to about 30, about 10 to about 40, about 10 to about 50, about 10 to about 75, about 10 to about 100, about 10 to about 125, about 10 to about 150, about 10 to about 200, about 20 to about 30, about 20 to about 40, about 20 to about 50, about 20 to about 75, about 20 to about 100, about 20 to about 125, about 20 to about 150, about 20 to about 200, about 30 to about 40, about 30 to about 50, about 30 to about 75, about 30 to about 100, about 30 to about 125, about 30 to about 150, about 30 to about 200, about 40 to about 50, about 40 to about 75, about 40 to about 100, about 40 to about 125, about 40 to about 150, about 40 to about 200, about 50 to about 75, about 50 to about 100, about 50 to about 125, about 50 to about 150, about 50 to about 200, about 75 to about 100, about 75 to about 125, about 75 to about 150, about 75 to about 200, about 100 to about 125, about 100 to about 150, about 100 to about 200, about 125 to about 150, about 125 to about 200, or about 150 to about 200.

In some embodiments, a nanopore lumen comprises a net charge of about 2, about 3, about 4, about 5, about 10, about 15, about 20, about 25, about 30, about 35, about 40, about 45, about 50, about 55, about 60, about 70, about 80, about 90, about 100, about 150, about 200.

In some embodiments, the number of negatively charged amino acids that may be distributed evenly within the lumen can be at least about 1 amino acid, at least about 2 amino acids, at least about 3 amino acids, at least about 4 amino acids, at least about 5 amino acids, at least about 6 amino acids, at least about 7 amino acids, at least about 8 amino acids, at least about 10 amino acids, at least about 11 amino acids, at least about 12 amino acids, at least about 13 amino acids, at least about 14 amino acids, at least about 15 amino acids, at least about 16 amino acids, at least about 17 amino acids, at least about 18 amino acids, at least about 19 amino acids, at least about 20 amino acids, or greater than about 20 charged amino acids. In some embodiments, the number of negatively charged amino acids that may be distributed evenly within the lumen can be at most about 20 amino acids, at most about 19 amino acids, at most about 18 amino acids, at most about 17 amino acids, at most about 16 amino acids, at most about 15 amino acids, at most about 14 amino acids, at most about 13 amino acids, at most about 12 amino acids, at most about 11 amino acids, at most about 10 amino acids, at most about 9 amino acids, at most about 8 amino acids, at most about 7 amino acids, at most about 6 amino acids, at most about 5 amino acids, at most about 4 amino acids, at most about 3 amino acids, at most about 2 amino acids, at most about 1 amino acid, or less than about 1 charged amino acid.

In some embodiments, the number of negatively charged amino acids that may be distributed evenly within the lumen can be from about 1 to about 20 charged amino acids. In some embodiments, the number of amino acids that may be distributed evenly within the lumen can be from about 1 to about 2, about 1 to about 3, about 1 to about 4, about 1 to about 5, about 1 to about 8, about 1 to about 9, about 1 to about 10, about 1 to about 12, about 1 to about 15, about 1 to about 18, about 1 to about 20, about 2 to about 3, about 2 to about 4, about 2 to about 5, about 2 to about 8, about 2 to about 9, about 2 to about 10, about 2 to about 12, about 2 to about 15, about 2 to about 18, about 2 to about 20, about 3 to about 4, about 3 to about 5, about 3 to about 8, about 3 to about 9, about 3 to about 10, about 3 to about 12, about 3 to about 15, about 3 to about 18, about 3 to about 20, about 4 to about 5, about 4 to about 8, about 4 to about 9, about 4 to about 10, about 4 to about 12, about 4 to about 15, about 4 to about 18, about 4 to about 20, about 5 to about 8, about 5 to about 9, about 5 to about 10, about 5 to about 12, about 5 to about 15, about 5 to about 18, about 5 to about 20, about 8 to about 9, about 8 to about 10, about 8 to about 12, about 8 to about 15, about 8 to about 18, about 8 to about 20, about 9 to about 10, about 9 to about 12, about 9 to about 15, about 9 to about 18, about 9 to about 20, about 10 to about 12, about 10 to about 15, about 10 to about 18, about 10 to about 20, about 12 to about 15, about 12 to about 18, about 12 to about 20, about 15 to about 18, about 15 to about 20, or about 18 to about 20 charged amino acids.

In some embodiments, the number of negatively charged amino acids that may be distributed evenly within the lumen can be about 1 amino acid, about 2 amino acids, about 3 amino acids, about 4 amino acids, about 5 amino acids, about 6 amino acids, about 7 amino acids, about 8 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, or about 20 charged amino acids.

In some embodiments, the channel of the nanopore can be narrowed. In some cases, the channel of the nanopore can be narrowed from about 0.1% to about 500%. In some cases, the channel of the nanopore can be narrowed from between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500%.

In some cases, the channel of the nanopore can be narrowed by at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more.

In some cases, the channel of the nanopore can be narrowed by at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less.

In some cases, the channel of the nanopore can be narrowed by about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500%.

In some embodiments, the net charges as defined herein above relate to the charge in the narrowest region (constriction) of the nanopore channel. The net charge of the constriction region will dominate due to the electrostatic dependence on Debye length e.g. under the salty conditions. In some embodiments, there can be positive charges on the wide part of the nanopore lumen (5 nm diameter for example) and negative charges at a constriction part (0.5 nm diameter for example). In other embodiments, there can be negative charges on the wide part of the nanopore lumen and positive charges at a constriction part of the nanopore lumen.

In some embodiments, mutating the pore suitably comprises one or more amino acid substitution(s), mutating one or more lumen-facing residues. Mutations may also employ non-naturally occurring amino-acids to further control the magnitude and position of the charge relative to the amino-acid backbone of the nanopore. Mutating the pore involves mutating the narrowest regions of the inner channel of the nanopore (the constriction(s)) to create the highest overlap between Debye double-layers and thus the strongest energy barriers to limit the flow of a specific ion. A person of skill will understand that high salt is advantageous in nanopore systems for creating a large EOF and for creating more signal for characterization of the analyte. However, higher salt concentrations screen the surface charge of the nanopores, reducing the Debye length, and reducing the effective ion-selectivity properties. Therefore, according to the present disclosure, multiple charge mutations are made along the longitudinal axis of the channel cis-to-trans to create multiple sequential energy barriers to limit the flow of a specific ion under high salt conditions (e.g. >0.1 M, >1 M). For example, a nanopore may be engineered to contain regions of 2, 3, 4, 5, 6, or more separate rings of charges along the longitudinal length of the channel each spaced 0.5 nm, 1.0 nm, 1.5 nm, 2.0 nm, 3.0 nm or further from each other. Exemplary high EOF mutant nanopore systems include those listed in table 2.

Charge and/or steric barriers to the flow of specific ions can also be created by chemical modification of the inner lining of a nanopore. For example, cysteine residues can be reacted with derivates of maleimide or iodoacetate. In some embodiments, a wide array of chemical modifications and reaction types can be used in the present disclosure to improve ion selectivity, including but not limited to modification of cysteines, modification of lysines, incorporation of unnatural amino acids, modification of unnatural amino acids with click chemistry groups, and the like.

Charge and/or steric barriers to the flow of specific ions can also be created by use of proteinaceous or chemical adapters inside the nanopore channel. For example, circular chemical adapters such as cyclodextrins or cucurbiturils can be incorporated into the nanopore (Gu et al. Biophys J. 2000 October; 79 (4): 1967-1975). Alternatively, protein based adapters can be employed, such as the CsgF subunit of the CsgG nanopore (Van der Verren et al. 2020 Nature Biotechnology volume 38, pg. 1415-1420), which can separately be mutated and engineered to create steric and electrostatic barriers. The protein or chemical adapters might be attached either by non-covalent docking or by covalent mechanisms.

Charge and/or steric barriers may be engineered into a nanopore channel by the addition of amino acids into the sequence in and around the regions that comprise the channel (e.g. into the beta-barrel transmembrane region of a beta-barrel nanopore such as alpha-hemolysin) to create a loop, turn, constriction or other extrusion that reduces the diameter of the nanopore. Alternatively, charge and/or steric barriers can be created at either the cis or trans entrance to the nanopore channel, and away from the narrowest parts of the nanopore where analyte discrimination is strongest, to create a locally depleted regions of charge that alter the ion-selectivity through the nanopore.

In some embodiments, ion-selectivity biases that create a strong EOF can also be created by altering the system conditions or adding additives that change the properties of the water-facing residues in the channel of the nanopore. For example, the pH of the system can be adjusted, either on both side of the membrane or just one side of the membrane, to change the protonation state of the nanopore. For example, low pH can be employed (e.g. <6.0, <4.0) to increase the net positive charge inside the nanopore, to increase the bias towards anion flow. Alternatively high pH can be used (e.g. >8.0, >10.5) to increase the net negative charge inside the nanopore to increase the bias towards cation flow. Alternatively, additives that interact with the water-facing residues can be added to the solution to change the ionic or steric properties of the water-facing residues inside the nanopore.

Methods for creating and/or enhancing EOF can include the use of selected salt type(s), salt asymmetries, pH, additives such as Guanidinium chloride or guanidine hydrochloride (abbreviated GdmCl and sometimes GdnHCl or GuHCl, GuCl) and osmotics.

In one embodiment, EOF is arranged through type of salts used and how they are distributed on each side of the membrane of the nanopore system. Methods of altering the EOF by adjusting ion-selectivity through choice and/or concentration of salts are known in the art.

For example, according to the GHK flux equations, one method of creating a strong asymmetric ion flow to create a net EOF employs asymmetric salt concentrations on either side of the membrane. Low salt concentration conditions can be used in the compartment from which it is desired to have low ionic transfer, relative to higher salt concentration in the compartment from which high ionic flux is desired. For example, for setting up a system with a strong cis-to-trans EOF, a low concentration of salt can be employed in the trans compartment to limit the flow of ions from the trans side of the membrane to the cis side of the membrane. For example, a nanopore system can be set up with 1 M KGlu (potassium glutamate) in the cis compartment and 0.2 M KGlu in the trans compartment. The salt gradient between the compartments is greater than 0.1 M, 0.2 M, greater than 0.5 M. Under a cis>trans salt concentration asymmetry both cations and anions will flow cis-to-trans at moderate to low applied voltages. Thus, salt applied electro-osmosis can be highly advantageous for creating or enhancing EOF under lower voltages where repulsive EPF effects on the analytes are reduced. High asymmetry salt conditions may be used in combination with nanopores that are engineered with enhanced ion-selectivity.

Salt imbalances across nanopore systems can create strong osmotic gradients, which can either enhance or compete with EOF depending on the relative direction of the fluid flow. For example, for a high-salt-cis low-salt-trans system that is set up to create a net cis-to-trans EOF, the osmotic gradient competes with the EOF. For systems where the osmotic gradient competes with EOF, the low salt compartment also has an osmolyte fully or partially balance the osmotic imbalance created by salt concentration asymmetry. Many common osmolytes are suitable for the present disclosure, including but not limited to non-ionic or zwitterionic solutes such as glycine betaine, glucose, sucrose, glycerol, PEGs, dextrans, etc. For example, a salt imbalance of 0.5 M KCl can be balanced with about 1 M Glycine betaine. Methods for measuring osmolarity of specific osmolytes and balancing with the correct concentration are known in the art. Furthermore, osmolytes can be added either to symmetrical salt concentration or asymmetric salt concentration systems to create an osmotic gradient that acts in the same direction as the EOF (i.e. the fluid flow from both effects moves in the same direction) to enhance the capture and translocation of the analyte. For example, osmolyte (e.g. 1 M glycine betaine) can be added to the trans compartment of an ion-selective nanopore system (e.g. 1 M K Glu cis and 1 M KGlu trans) to enhance the cis-to-trans EOF.

In some embodiments, altering the EOF by methods adjusting the salt asymmetry between the cis and trans compartment can be used in combination with an ion-selective nanopore. In one embodiment, high mobility ions can be used on one side of the membrane and low mobility and/or sterically inhibited counterions on the other side of the membrane. Ionic mobility properties well known in the art can be used to help select for appropriate high mobility and low mobility ions for use in the present disclosure. For example, a salt with a high mobility ion can be used on the cis side of the membrane, and a salt with a low mobility (counter) ion used on the trans side of the membrane to create a stronger cis-to-trans ion-selectivity under the appropriate applied voltage. The low mobility ions might comprise all or part of their respective ionic content in the system. Suitably, the low mobility ions for altering the EOF comprise >50% of the salt content, >90% of the salt content on the side of the membrane from which they flow across the nanopore. The high mobility ions might comprise all or part of their respective ionic content in the system. Suitably, the high mobility ions for altering the EOF comprise >50% of the salt content, more >90% of the salt content on the side of the membrane from which they flow across the nanopore. For a system where the analyte is added to the cis and translocated cis-to-trans via a strong cis-to-trans EOF, the nanopore system is set up with a highly mobile cation salt on the cis (eg. K+, Na+, NH$_4$+) and a low mobility anion salt on the trans (eg. glutamate, acetate, etc), wherein a negative voltage is applied to the trans side of the membrane.

For example, a system can be set up with 1M KCl in the cis compartment and 1M KGlu (potassium glutamate) in trans compartment, so that a greater EOF is achieved cis-to-trans under negative applied voltage to trans than the EOF generated trans-to-cis when a positive voltage is applied to the trans, due to relative lower mobility of glutamate anions versus chloride anions.

According to the present disclosure, immobile and/or sterically hindered ions on one side of the membrane are combined with ion selective nanopores to further limit the flux of one or more of the ions. Due to highly constrained dimensions of a nanopore channel, particularly when filled with analyte, the mobility of a specific ion through the nanopore can differ significantly from that in bulk solution, and this can be enhanced by further mutations that increase the net charge or reduce the diameter of channel. Hence, according to the present disclosure, the ion permeability of large and immobile salts in ion-selective nanopore systems (e.g. based on mutated nanopores) can be determined experimentally using the GHK equation under asymmetric salt conditions, to create a system with a sufficiently large net ion-flux to capture and translocate complex analytes. The system is engineered so that the flux of immobile or sterically hindered ions is effectively zero under an applied voltage, either for the open-pore state and/or the analyte filled state, so that all ionic flux is in one direction (e.g. cis to trans).

According to the present disclosure, small and/or highly mobile ions on one side of the membrane are combined with ion selective nanopores to further increase flux of given ions. For example, small and highly mobile cations (e.g. K+, Na+, NH4+, etc) can be combined with ion-selective nanopores with high internal net negative charge. In such systems the net negative charge inside the pore interacts favorably with the positive cations, acting to increase the absolute flux of the cations relative to the same nanopore with less negative charge. Thus, the increased cation flux increases the relative proportion of net electro-osmotic flux in one direction (e.g cis-to-trans), it also increases the absolute net electro-osmotic flux at a given voltage, which is advantageous for creating a stronger EOF versus EPF.

In some embodiments, the EOF is based on cation biased flux through the nanopore. A cation-biased EOF ($P_{(+)} >> P_{(-)}$) can be created or enhanced by the choice of salts in both the cis and trans compartments. The flux employs high mobility monovalent cations such as K+=NH4+>Na+>Li+>etc. High cation biased EOF can be further enhanced by exploiting salts with large anions that are relatively immobile or otherwise restricted from translocating through the nanopore. Suitable anions are well known in the art, and may include for example high molecular mass inorganic anions (Br, Phosphate, sulphate, FeCN$_6$, etc) or organic anions (Acetate, Glutamate, succinate, maleate, butyrate dextrans, etc) or ionic liquid anions (e.g. tetrafluoroborate (BF4), hexafluorophosphate (PF6), bis-trifluoromethanesulfonimide (NTf2), trifluoromethanesulfonate (OTf), dicyanamide (N(CN)2), hydrogen sulphate (HSO4), and ethyl sulphate (EtOSO3)). For a system where the analyte is added to the cis and translocated cis-to-trans via a strong cis-to-trans cation biased EOF, the system is advantageously set up with a highly mobile cation salt on the cis (eg. K+, Na+, NH4+) and a low mobility anion salt on the trans (eg. glutamate, acetate, FeCN$_6$, etc), wherein a negative voltage is applied to the trans side of the membrane. For example, the cis and trans compartments contain >0.3 M, >0.5 M, >1.0 M or >2.0 M K Glu under and applied voltage of −40 mV to −200 mV. Alternatively the trans compartment contains >0.3 M, >0.5 M, >1.0 M or >2.0 M potassium salts of butyrate, tetrafluoroborate, or ferri- or ferro-cyanide. Suitably, the analyte also contain polycationic tag(s) so that EPF aids in the initial nanopore capture under these conditions.

In some embodiments, the ion selectivity of an unoccupied nanopore system can closely but not example match the state of the nanopore system when translocating the analyte. In some cases, the ion selectivity of an unoccupied nanopore system may not match the state of the nanopore system when translocating the analyte. In some cases, the ion selectivity of an unoccupied nanopore system may match the state of the nanopore system when translocating the analyte. This is in part due to the additional volume the analyte occupies in the nanopore channel (thus creating a further barrier to the passage of larger ions), and partly due to any charges on the analyte that alter the ion-selectivity, and thus varies by amino acid composition. Accordingly, the present disclosure teaches that suitable conditions and ions can be selected to create strong selective conditions, however, experimentation (particularly when employing larger ions that are likely to experience a greater effect from an analyte-filled nanopore) will be able to easily determine if the selectivity is enhanced when carrying out translocation measurements.

According to the present disclosure, the large and dominant net EOF can be created either cis-to-trans or trans-to-cis relative to the convention of stating the polarity of the applied voltage at the trans electrode, and can be either cation biased or anion biased. A person of skill in the art will appreciate that the direction of the net EOF determines to which compartment the analyte and translocase are added according to the methods described herein. According to the present disclosure, the absolute net electro-osmotic flow across the nanopore in any one direction (and hence directly correlated to the magnitude of the force applied to the translocated molecule) is dependent on the applied voltage, varying to a first approximation according to the GHK equations as described herein. Since EPF is also directly correlated to applied voltage (increasing in magnitude as the voltage is increased), a nanopore system can be created with sufficiently large absolute net electro-osmotic flow at relatively low voltages to overcome repulsive EPF forces acting on the analyte. According to the present disclosure, the absolute relative net electro-osmotic current over applied voltage ($I_{relV}$), given by:

$$I_{relV} = \left| \frac{I_{\Delta c \to t}}{V_m} \right|$$

is greater than 0.1 pA/mV, greater than 0.2 pA/mV, greater than 0.3 pA/mV. Therefore, for example, at −80 mV a system according to the present disclosure has >8 pA, >16 pA, greater than 24 pA of net electro-osmotic flow in one direction.

Nanopore

Any suitable nanopore can be used in the disclosed methods, systems and devices. The nanopore can be a solid state artificial nanopore or a biological nanopore. In some embodiments, the solid state artificial nanopore can comprise a nanopore that does not exist in nature. In some embodiments, the biological nanopore can comprise a nanopore that does exist in nature. In one embodiment, the nanopore is a hybrid solid state-biological nanopore such as those described in Cressiot et al. (Nature Comm. Vol. 9, 4652 (2018) or WO2009/020682. For example, many of the biological nanopores discussed herein are suitable candidates for imbedding in a solid state membrane to form a hybrid solid state-biological nanopore. Further, many non-transmembrane toroidal proteins are suitable candidates for imbedding in a solid state membrane to form a hybrid solid state-biological nanopore, for example proteins derived from Phage portal complexes, cellular transmembrane transport complexes, etc.

In some embodiments, the nanopore suitably has an inner pore constriction with a diameter in the range of 0.2 to 10 nm, such as 0.5 to 5 or 0.5-2 nm. The constriction is typically a narrowing in the channel which runs through the nanopore which may determine or control the signal obtained when the target substrate moves with respect to the nanopore. As used herein, both biological and solid state nanopores typically comprise a "constriction".

In some embodiments the nanopore has multiple constrictions along the longitudinal axis of the nanopore channel, for example two constrictions, three constrictions, four constrictions or more. In some embodiments the constrictions are located 1 nm, 2 nm, 3 nm, 5 nm, 7 nm, 10 nm or more apart from each other in the longitudinal direction. In some embodiments the constrictions have about the same inner diameter. In some embodiments the constrictions have different inner diameters. In some embodiments one or more of the multiple constrictions has a net charge to create a strong EOF through the nanopore channel.

In one embodiment the nanopore is a solid state nanopore such as those described in Xue et al., 2020, Nature Reviews Materials, Vol 5, pg. 931-951. In a further embodiment, the system comprises multiple solid state nanopores in sequence that act in concert to control the capture and translocation of the target polymer via a strong EOF (e.g. systems such as those described in Liu et al. 2019, Small, 15, 30). Suitable solid state nanopores included coated and/or multilayered nanopores, where the coating enhances the surface charge and ion-selectivity properties of the nanopores (e.g. Tsutsui et al., 2022, Cell Reports Physical Science, Vol 3, Issue 10, pg. 101065).

In some embodiments, the nanopore is a biological nanopore. In one embodiment, the biological nanopore is partially or wholly comprised on non-proteinaceous organic structure. For example, the nanopore comprised wholly or partly of DNA. In one embodiment the nanopore is formed from DNA origami structures, such as those described in Bell et al., 2014, FEBS Lett., 588, 19, pg. 3564-70. According to the present disclosure, DNA based nanopores are advantageous as they carry a large surface charge that can be used to create strongly ion-selective electro-osmotic gradients. In an alternative embodiment the nanopores are formed from assemblies of cell penetrating molecules, for example cyclic peptides (such as those described in Rodríguez-Vázquez et al., 2014, Curr Top Med Chem., 14, 23, pg. 2647-61) or cell penetrating peptides (such as those described in Krishnan R et al., 2019, J Am Chem Soc, 141, 7, pg. 2949-2959).

In some embodiments, the nanopore is a transmembrane protein pore which is a monomer or an oligomer. The pore is made up of several repeating subunits, such as at least 6, at least 7, at least 8, at least 9, at least 10, at least 11, at least 12, at least 13, at least 14, at least 15, or at least 16 subunits. The pore is a hexameric, heptameric, octameric or nonameric pore. The pore may be a homo-oligomer or a heterooligomer. In one embodiment, the transmembrane protein pore comprises a barrel or channel through which the ions may flow. The subunits of the pore typically surround a central axis and contribute strands to a transmembrane beta-barrel or channel or a transmembrane alpha-helix bundle or channel.

In one embodiment, the nanopore is a transmembrane protein pore derived from beta-barrel pores or alpha-helix bundle pores, beta-barrel pores comprise a barrel or channel that is formed from beta-strands. Suitable beta-barrel pores include, beta-toxins, such as alpha-hemolysin, anthrax toxin and leukocidins, and outer membrane proteins/porins of bacteria, such as *Mycobacterium smegmatis* porin (Msp), for example MspA, MspB, MspC or MspD, CsgG from the *E. coli* curli secretion system, outer membrane porin F (OmpF), outer membrane porin G (OmpG), outer membrane phospholipase A, outer membrane protein FhuA, outer membrane protein A (OmpA) and *Neisseria* autotransporter lipo-protein (NalP) and other pores, such as lysenin, bacterial nucleoside transporter Tsx.

In some embodiments, alpha-helix bundle pores comprise a barrel or channel that is formed from alpha-helices. Suitable alpha-helix bundle pores include inner membrane proteins and outer membrane proteins, such as WZA poly-saccharide transporter and FraC. In a specific embodiment, the nanopore is selected from the group consisting of Aerolysin (Aer), Cytolysin K (CytK), *Mycobacterium smeg-matis* porin A (MspA), alpha-hemolysin (aHL), *E. coli* curli secretion system component CsgG, Fragaceatoxin C (FraC) or an engineered mutant thereof. In one embodiment the nanopore is a transmembrane pore derived from or based on Msp, e.g. MspA, a-hemolysin (a-HL), lysenin, CsgG, ClyA, Spl or haemolytic protein fragaceatoxin C (FraC).

In some embodiments, engineered nanopores as disclosed for example in WO2021/101378 can be used, and variants thereof comprising oligomeric accessory protein coupled to transmembrane domains derived from naturally existing nanopores. Engineered nanopores also includes hybrid sys-tems, such as protein nanopores templated by DNA struc-tures (eg. Spruit et al. Nature Nanotechnology, Vol 13, pg. 739-745). Still further, the nanopore is a de novo nanopores based on de novo alpha-helical or beta-barrel transmem-brane regions (see e.g. Shimizu et al. 2022, Nature Nano-technology volume 17, pg. 67-75; or Scott et al. 2021, Nature Chemistry volume, 13, pg. 643-650; or Vorobieva et al. 2021, Science, Vol 371, Issue 6531)).

In some embodiments, a (mutated) biological nanopore is suitably can be used "as such" i.e. without added structures or components. However, in a method, a device or system of the present disclosure, the nanopore may be coupled or fused to an accessory partner protein that aids the binding and/or functioning of the protein translocase. In one embodiment, the nanopore is coupled to inactive ClpP. It is well known that the protease activity of ClpP can be disabled by muta-tion while retaining its ability to bind ClpX (e.g. Ortega et al., 2000, Mol Cell, 6, pg. 1515-21).

in some embodiments, a nanopore confers or is (geneti-cally) modified to confer the strong and dominant EOF in the direction cis to trans across the membrane of a nanopore system as herein disclosed. These nanopores are herein also referred to as "strong EOF" nanopores. In one aspect, the nanopore is modified to show a relative ion selectivity $P_{(+)}/P_{(-)}$ of greater than 2.0 or less than 0.5, greater than 3.0 or less than 0.33, greater than 3.5 or less than 0.29, under an applied voltage difference across a membrane wherein it is comprised.

In one embodiment, the nanopore lumen is engineered to have a net charge. In some cases, the net charge can be positive. In some cases, the net charge can be negative. In another embodiment, the nanopore is modified to increase the net positive charge of the pore lumen. In one aspect, the pore comprises at least 3, at least 4, negatively charged amino acids pointing towards the lumen of the pore per protomer for an oligomeric nanopore consisting of at least 4 protomers, where the protomers assemble to create the oligomeric nanopore and each protomer contributes to the channel region of the nanopore. Protomers may be separate entities or fused by chemical or genetic mechanisms (Ham-merstein et al., 2011, J Biol Chem., 286, 16, pg. 14324-34 or Pavelenok et al., 2022, Biophys J., 121, 5, pg. 742-754). The protomers that comprise the oligomeric nanopore may be identical or of different sequence (Miles et al., 2006, J Biol Chem., 281, 4: pg. 2205-14). In mixed protomers systems the mutations may be made to one or all of the protomer types that comprise the oligomeric assembly.

In some embodiments, nanopores that have just a single protein (e.g. porins such as OmpF, OmpG, FhuA, etc) multiple mutations can be made along the sequence so as to place charged residues either in rings around the nanopore in plane with the membrane, and/or vertically up the nanopore channel perpendicular to plane of the membrane.

For nanopores with beta-barrel channels the charge muta-tions can be applied on both the "up" strands and the "down" of a beta-strand at positions that co-locate them approxi-mately co-planar so as to further enhance the local electro-static barrier.

Charged amino acids Asp or Glu, Asp, can be readily introduced by single amino acid substitution(s). At least 3 negatively charged amino acids may be distributed evenly within the lumen. At least 1 negatively charged "flanking" residue may be positioned or introduced at pore entry and/or at least 1 negatively charged residue may be positioned or introduced at pore exit. In a specific aspect, the Spacing between Ca atom of the at least 1 internal negatively charged amino acid and the Ca atoms of the negatively charged flanking amino acid is in the range of 7-11 Angstrom, more than 11 Angstrom.

In some embodiments of any one of the preceding embodiments, the nanopore is a biological nanopore, having an inner pore constriction in the range of 0.5-2 nm, wherein the nanopore is an alpha-helical or beta-barrel oligomeric pore forming toxin or porin. In some embodiments, the nanopore is selected from the group consisting of Aerolysin (Aer), Cytolysin K (CytK), MspA, alpha-hemolysin (aHL), CsgG, Fragaceatoxin C (FraC), Lysenin, phage derived portal proteins, and modified variants thereof, wherein the nanopore is modified to have a net charge in the lumen facing regions of >21, >28, >35, wherein said net charge is negative. In some embodiments, the nanopore is selected from the group consisting of Aerolysin (Aer), Cytolysin K (CytK), MspA, alpha-hemolysin (aHL), CsgG, Fragacea-toxin C (FraC), Lysenin, phage derived portal proteins, and modified variants thereof, wherein the nanopore is modified to have a net charge in the lumen facing regions of >21, >28, >35, wherein said net charge is positive. In some embodi-ments, any amino acid residue in a lumen facing region of the nanopore can be mutated. In some cases, the mutated amino acid residue can be mutated to a negatively charged amino acid. In some cases, the mutated amino acid residue can be mutated to a positively charged amino acid. In some cases, the mutated amino acid residue can be mutated to a neutrally charged amino acid.

In some embodiments, the nanopore can be an oligomer. In some cases, the oligomer nanopore can comprise one or more subunits. In some cases, each subunit of the one or more subunits can comprise from about 20 to about 40 charges in the lumen facing regions of the subunit. In some cases, each subunit of the one or more subunits can comprise at least about 20 charges, at least about 21 charges, at least about 22 charges, at least about 23 charges, at least about 24 charges, at least about 25 charges, at least about 26 charges, at least about 27 charges, at least about 28 charges, at least about 29 charges, at least about 30 charges, at least about 31 charges, at least about 32 charges, at least about 33 charges, at least about 34 charges, at least about 35 charges, at least about 36 charges, at least about 37 charges, at least about 38 charges, at least about 39 charges, at least about 40 charges, or more than 40 charges in the lumen facing regions of the subunit. In some cases, each subunit of the one or more subunits can comprise at most about 40 charges, at most about 39 charges, at most about 38 charges, at most about 37 charges, at most about 36 charges, at most about 35 charges, at most about 34 charges, at most about 33 charges, at most about 32 charges, at most about 31 charges, at most about 30 charges, at most about 29 charges, at most about 28 charges, at most about 27 charges, at most about 26 charges, at most about 25 charges, at most about 24 charges, at most about 23 charges, at most about 22 charges, at most about 21 charges, at most about 20 charges, or less than 20 charges in the lumen facing regions of the subunit. In some cases, each subunit of the one or more subunits can comprise about 20 charges, about 21 charges, about 22 charges, about 23 charges, about 24 charges, about 25 charges, about 26 charges, about 27 charges, about 28 charges, about 29 charges, about 30 charges, about 31 charges, about 32 charges, about 33 charges, about 34 charges, about 35 charges, about 36 charges, about 37 charges, about 38 charges, about 39 charges, or about 40 charges in the lumen facing regions of the subunit.

In a embodiment, the nanopore is CytK or a genetically engineered mutant thereof. For example, the mutant CytK comprises one or more of the amino acid substitutions selected from the group consisting of K128D, K128F, K155D, S120D, Q122D and S151D. In one embodiment, mutant CytK comprises S120D, G122D and/or K155D. Mutant cytK comprises S120D in combination with K128F or K128D, further comprising Q122D or S151D. In a specific aspect, mutant CytK comprises mutations K128D or K128F, S120D, K155D and Q122D. In another specific aspect, mutant CytK comprises K128F, S120D and G122D, optionally in combination with K155D.

In some embodiments, the EOF nanopores for use in the present disclosure include mutant nanopores CytK K128D/K155D/S120D/Q122D (CytK 4D2E), CytK-K128F/S120D/Q122D/K155D (CytK_3D1F2E), CytK-K128D/K155D/S120D/S151D (CytK_4D2E_Alt) and CytK-K128F/S120D/Q122D (CytK_2DIF2E). See also Table 2 herein below.

Membrane

According to the present disclosure, the nanopore is comprised in a membrane separating a fluidic chamber of a nanopore system into a cis side and a trans side. The term "membrane" is used herein in its conventional sense to refer to a thin, film-like structure that separates the chamber of the system into a cis side (or cis compartment) and a trans side (trans compartments). The membrane separating the cis and trans compartments comprises at least one nanopore or channel. Membranes can be classified into synthetic membranes and biological membranes. Any membrane may be used in accordance with the present disclosure.

In some embodiments, the membrane is an amphiphilic layer. An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic molecules may be synthetic or naturally occurring. Non-naturally occurring amphiphiles which form a monolayer include, for example, block copolymers (Gonzalez-Perez et al., Langmuir, 2009, 25, 10447-10450).

Also encompassed can be membranes made of a solid state material (eg. SiN). In this context, a nanopore system may comprise a solid state hole or a hybrid pore with a biological pore inserted.

Protein Translocase

As used herein, the term "protein translocase" (e.g., motor protein, unfoldase) refers to a protein which can bind, and translocate along an analyte through the chemical energy provided by NTP(nucleoside triphosphate) hydrolysis, optionally being able to unfold protein structure in the process. Used herein it is able to move along an analyte to feed the analyte through the nanopore in sequential order. In some embodiments, the protein translocase is an NTP-driven unfoldase, such as an AAA+ unfoldase. See for example US2016/0032235 and Dougan et al. (FEBS Letters 529 (2002) 1873-3468) and Olivares et al. 2016, Nature Reviews Microbiology Vol. 14, pg. 33-44.

In some embodiments, members of the AAA+ superfamily have been identified in all organisms studied to date. They are involved in a wide range of cellular events. In bacteria, representatives of this superfamily are involved in functions as diverse as transcription and protein degradation and play an important role in the protein quality control network. Often they employ a common mechanism to mediate an ATP-dependent unfolding/disassembly of protein-protein or DNA-protein complexes. In an increasing number of examples, it appears that the activities of these AAA+ proteins may be modulated by a group of otherwise unrelated proteins, called adaptor proteins.

In some embodiments, protein translocases for use in the present disclosure include ClpX, ClpA, ClpC, ClpE, Mpa, Pan, LON, VAT, Cpa, Msp1, HslU/ClpY, AMA, 854, MBA, SAMP, CDC48, FtsH, SecA, and functional homologs, orthologs, paralogs or fragments thereof. In some cases, for translocases that have a protease domain, the proteolytic activity of the protease components are disabled by mutagenesis, or the entire domain is removed.

For example, the translocase is the prokaryotic AAA+ unfoldase ClpX. ClpX unfolds analytes by ATP-driven translocation of the analyte chain through the central pore of its hexameric assembly. In complex with the ClpP peptidase, ClpX carries out protein degradation by translocating unfolded substrates directly into the ClpP proteolytic chamber (Sauer et al., 2004).

In another embodiment, the protein translocase is the Valosin-containing protein-like ATPase from *Thermoplasma acidophilum* (VAT), or a truncated variant thereof. The AAA+ unfoldase VAT is an ~500-kDa homohexamer, with each monomer containing two tandem AAA+ domains, referred to as D1 and D2, and an N-terminal domain (NTD) distinct from the NTD of other AAA+ enzymes. Both D1 and D2 are homologous to the single AAA+ modules of PAN and Rpt1-6. As is demonstrated herein below, good results can be obtained using a variant VATAN wherein the N-terminal 183 residues are deleted. see Gerega et al. J. Biol. Chem. Vol. 280, Issue 52, 30 Dec. 2005, Pp. 42856-42862), In another embodiment, the proteasome-activating nucleotidase (PAN) from *Methanococcus jannaschii* is used, which is a complex of relative molecular mass 650,000 that is homologous to the ATPases in the eukaryotic 26S proteasome. Other examples include AMA, an AAA protein from *Archaeoglobus* and methanogenic archaea. In a still further embodiment, the translocase is the open reading frame number 854 in the *M. mazei* genome (Forouzan, Dara, et al. "The archaeal proteasome is regulated by a network of AAA ATPases." J. Biological Chemistry 287.46 (2012): 39254-39262). Other suitable translocases for use in the present disclosure include MBA (membrane-bound AAA; Serek-Heuberger, Justyna, et al. "Two unique membrane-bound AAA proteins from *Sulfolobus solfataricus*." (2009): 118-122) and SAMPs (Humbard, Matthew A., et al. "Ubiquitin-like small archaeal modifier proteins (SAMPs) in *Haloferax volcanii*." Nature 463.7277 (2010): 54). Other examples include ClpA, a member of the two-domain AAA ATPases, from *Escherichia coli* (Effantin et al., 2010, J Biol Chem., 285, 19, pg. 14834-40). In another embodiment, the protein translocase is ClpC, an AAA protein from *Staphylococcus aureus* (Frees et al., 2004, Mol Microbiol., 54, 5, pg. 1445-62). Other examples include ClpE, a member of the two-domain AAA ATPases from *Bacillus subtilis* (Miethke et al., 2004, J Bacteriol., 188, 13, pg. 4610-9). Other examples include HslU/ClpY, an AAA protein from *Escherichia coli* (Baytshtok et al., 2016, Structure, 24, 10, pg. 1766-1777). In another embodiment, the protein translocase is Lon, a protease from *Escherichia coli* containing an AAA ATPase domain (Suzuki et al., 2008, Biochim Biophys Acta., 1784 (5): pg. 727-35). In another embodiment, the protein translocase is FtsH, a membrane bound protease from *Escherichia coli* containing an AAA ATPase domain (Langklotz et al., 2012, Biochim Biophys Acta., 1823, 1, pg. 40-8). Other examples include ARC/Mpa (Kavalchuk et al., 2022, Nat Commun., 13, 1, pg. 276), an AAA ATPase from *Mycobacterium tuberculosis*. Other examples include Msp1, a membrane associated AAA ATPase from *Saccharomyces cerevisiae* (Castanzo, 2020, Proc Natl Acad Sci USA., 117, 26, pg. 14970-14977). Other examples include CDC48, an AAA ATPase from *Saccharomyces cerevisiae* (Buchberger, 2013, Subcell Biochem, 66, pg. 195-222). In another embodiment, the protein translocase is Cpa, a CDC48 homologue from actinobacteria (Ziemsky et al., 2018, Elife, pg. 34055). Other examples include SecA, a protein translocase from *Escherichia coli*.

A method of the present disclosure comprises allowing a protein translocase in solution to capture and form a complex with the analyte to be translocated. The ratio translocase to analyte is not critical but it may have some effect on efficiency. Typically, a ~1:1 or slightly greater ratio between translocase and analyte is desired to load one protein translocase per analyte. Too much translocase may lead to the loading of more than one enzyme onto substrate, whereas too little may lead to large amount of free analyte to capture and block in pore. In some embodiments the ratio of translocase to analyte is high so that on average multiple translocases are bound to each analyte in solution. For example, translocases can bind to an analyte and proceed along the analyte, followed by further translocase binding events, so that the analyte has many translocases bound and at different positions along the analyte.

In certain aspects of the present disclosure, a protein translocase, and optionally its accessory protease such as ClpP, is present on both the cis and trans side of the nanopore. In this way the analyte added to the cis compartment is first fed through the nanopore via the translocase on the cis side, and the protein translocase on the trans side aids the progression of the analyte through the nanopore and/or prevents the folding of protein (the latter in particular when combined with an accessory protease unit in the trans that degrades the analyte once it reaches the trans side).

In an alternative embodiment, a protein translocase such as ClpX, and optionally its accessory protease such as ClpP, is present on the trans side of the nanopore, in combination with the defined dominant EOF that is set up to act trans-to-cis according to the present disclosure, wherein the ClpX translocase binds the analyte added to cis compartment after it has been captured and partially translocated through the nanopore cis-to-trans via a polyionic tag that enables electrophoretic capture, and wherein the ClpX translocase then acts to pull the analyte through the nanopore from the cis side of the membrane to the trans side of the membrane. This approach addresses the situation that, while the cis-to-trans EOF can aid the initial movement of the analyte cis-to-trans, it can also be counterproductive, eg. pulling charged and/or unstructured parts of the analyte through the nanopore too quickly. Here the EOF acting against the direction of analyte translocation acts to keep the analyte within the nanopore and stretched as the translocase pulls it out under controlled, thus preventing uncontrolled EPF related slips.

In another embodiment of the present disclosure the translocase is physically attached to the nanopore at either the cis or trans entrance (with respect to the nanopore geometry). The translocase may be coupled tightly to the top of the nanopore so that the translocase assembly is co-planar with the nanopore assembly, such that the central cavity of the translocase is aligned with the entrance to the nanopore channel to optimally feed the analyte into the nanopore. One method of achieving this is to genetically fuse the translocase protomers to the protomers that form the pore. In some cases, the translocase is tethered to the top of the nanopore via a single anchor point that keeps the translocase in the vicinity of the nanopore entrance. Methods of attaching proteins to the top of nanopores are known in the art, including but not limited to chemical attachment (e.g. via cysteines), enzymatic attachment (e.g. Stranges et al. 2016, Proc Natl Acad Sci USA, 113 (44), pg. 6749-E6756), or via hybridization of complementary DNA tags that are attached to the top of the nanopore and the translocase, respectively.

Analytes

In some embodiments, an analyte can comprise a nucleic acid moiety. In some embodiments, the nucleic acid moiety may comprise less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the polymer units. In some embodiments, the nucleic acid moiety may comprise greater than about 1%, greater than about 2%, greater than about 3%, greater than about 4%, greater than about 5%, greater than about 6%, greater than about 7%, greater than about 8%, greater than about 9%, greater than about 10%, greater than about 15%, greater than about 20%, greater than about 25%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, or greater than about 95% of the polymer units.

In some embodiments, the analyte is about 1 to about 4000 kDa. In some embodiments, the polymer analyte is about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 125, about 150, about 175, about 200, about 250, about 300, about 350, about 400, about 450, about 500, about 550, about 600, about 650, about 700, about 750, about 800, about 850, about 900, about 950, about 1000, about 1500, about 2000, about 2500, about 3000, about 3500, or about 4000 kDa. In some embodiments, the analyte is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 125, at least about 150, at least about 175, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950, at least about 1000, at least about 1500, at least about 2000, at least about 2500, at least about 3000, at least about 3500, or at least about 4000 kDa. In some embodiments, the polymer analyte is at most about 1, at most about 2, at most about 3, at most about 4, at most about 5, at most about 6, at most about 7, at most about 8, at most about 9, at most about 10, at most about 15, at most about 20, at most about 25, at most about 30, at most about 35, at most about 40, at most about 45, at most about 50, at most about 55, at most about 60, at most about 65, at most about 70, at most about 75, at most about 80, at most about 85, at most about 90, at most about 95, at most about 100, at most about 125, at most about 150, at most about 175, at most about 200, at most about 250, at most about 300, at most about 350, at most about 400, at most about 450, at most about 500, at most about 550, at most about 600, at most about 650, at most about 700, at most about 750, at most about 800, at most about 850, at most about 900, at most about 950, at most about 1000, at most about 1500, at most about 2000, at most about 2500, at most about 3000, at most about 3500, or at most about 4000 kDa.

In some embodiments, the analyte comprises a polypeptide. In some embodiments, the analyte is about 2 to about 34000 amino acids in length. In some embodiments, the analyte is about 2, about 5, about 10, about 15, about 20, about 30, about 40, about 50, about 60, about 70, about 80, about 90, about 100, about 150, about 200, about 250, about 300, about 350, about 400, about 450, about 500, about 600, about 700, about 800, about 900, about 1000, about 2000, about 3000, about 4000, about 5000, about 6000, about 7000, about 8000, about 9000, about 10000, about 20000, about 30000 or about 34000 amino acids in length. In some embodiments, the analyte is at least about 2, at least about 5, at least about 10, at least about 15, at least about 20, at least about 30, at least about 40, at least about 50, at least about 60, at least about 70, at least about 80, at least about 90, at least about 100, at least about 150, at least about 200, at least about 250, at least about 300, at least about 350, at least about 400, at least about 450, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 20000, at least about 30000 or at least about 34000 amino acids in length. In some embodiments, the analyte is at most about 2, at most about 5, at most about 10, at most about 15, at most about 20, at most about 30, at most about 40, at most about 50, at most about 60, at most about 70, at most about 80, at most about 90, at most about 100, at most about 150, at most about 200, at most about 250, at most about 300, at most about 350, at most about 400, at most about 450, at most about 500, at most about 600, at most about 700, at most about 800, at most about 900, at most about 1000, at most about 2000, at most about 3000, at most about 4000, at most about 5000, at most about 6000, at most about 7000, at most about 8000, at most about 9000, at most about 10000, at most about 20000, at most about 30000 or at most about 34000 amino acids in length.

In some embodiments, the polymer analyte comprises a repeated unit, monomer, or group. In some embodiments, the polymer analyte comprises about 2 to about 34000 repeated units, monomers, or groups. In some embodiments, the polymer analyte comprises about 2, about 5, about 10, about 15, about 20, about 25, about 30, about 35, about 40, about 45, about 50, about 60, about 70, about 80, about 90, about 100, about 150, about 200, about 250, about 300, about 350, about 400, about 450, about 500, about 600, about 700, about 800, about 900, about 1000, about 2000, about 3000, about 4000, about 5000, about 6000, about 7000, about 8000, about 9000, about 10000, about 20000, about 30000 or about 34000 repeated units, monomers, or groups. In some embodiments, the polymer analyte comprises at least about 2, at least about 5, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, at least about 350, at least about 400, at least about 450, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 20000, at least about 30000 or at least about 34000 repeated units, monomers, or groups. In some embodiments, the polymer analyte comprises at most about 2, at most about 5, at most about 10, at most about 15, at most about 20, at most about 25, at most about 30, at most about 35, at most about 40, at most about 45, at most about 50, at most about 60, at most about 70, at most about 80, at most about 90, at most about 100, at most about 150, at most about 200, at most about 250, at most about 300, at most about 350, at most about 400, at most about 450, at most about 500, at most about 600, at most about 700, at most about 800, at most about 900, at most about 1000, at most about 2000, at most about 3000, at most about 4000, at most about 5000, at most about 6000, at most about 7000, at most about 8000, at most about 9000, at most about 10000, at most about 20000, at most about 30000 or at most about 34000 repeated units, monomers, or groups.

In some embodiments, the analyte is longer than the length of a channel of the nanopore. In some embodiments, the polymer analyte is at most 2, at most 3, at most 4, at most 5, at most 6, at most 7, at most 8, at most 9, at most 10, at most 12, at most 13, at most 14, at most 15, at most 16, at most 17, at most 18, at most 19, at most 20, at most 25, at most 30, at most 35, at most 40, at most 45, at most 50, at most 55, at most 60, at most 65, at most 70, at most 75, at most 80, at most 85, at most 90, at most 95, or at most 100 times the channel length of the nanopore. In some embodiments, the analyte is at least about 2, at least about 3, at least about 4, at least about 5, at least about 6, at least about 7, at least about 8, at least about 9, at least about 10, at least about 12, at least about 13, at least about 14, at least about 15, at least about 16, at least about 17, at least about 18, at least about 19, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 times the channel length of the nanopore.

Any suitable analyte can be translocated or characterised in the disclosed methods. In some embodiments the analyte is an unmodified analyte or a portion thereof, or a naturally occurring analyte or a portion thereof. In some embodiments, the analyte is a naturally occurring analyte. In some embodiments analyte fragments can be conjugated to form a longer analyte.

Any number of analytes can be translocated or characterised in the disclosed methods. For instance, the method may comprise characterising 1, 2, 3, 4, 5, 6, 7, 8, 9, 10, 20, 30, 50, 100 or more analytes. If two or more analytes are used, they may be different analyte s or two or more copies of the same analytes. In some embodiments, 1 analyte is characterised.

In some embodiments, at least about 2 analytes, at least about 3 analytes, at least about 4 analytes, at least about 5 analytes, at least about 6 analytes, at least about 7 analytes, at least about 8 analytes, at least about 9 analytes, at least about 10 analytes, at least about 20 analytes, at least about 30 analytes, at least about 40 analytes, at least about 50 analytes, at least about 100 analytes, at least about 200 analytes, at least about 300 analytes, at least about 400 analytes, at least about 500 analytes, at least about 600 analytes, at least about 700 analytes, at least about 800 analytes, at least about 900 analytes, at least about 1000 analytes, at least about 1500 analytes, at least about 2000 analytes, at least about 2500 analytes, at least about 3000 analytes, at least about 3500 analytes, at least about 4000 analytes, at least about 4500 analytes, at least about 5000 analytes, at least about 5500 analytes, at least about 6000 analytes, at least about 6500 analytes, at least about 7000 analytes, at least about 7500 analytes, at least about 8000 analytes, at least about 8500 analytes, at least about 9000 analytes, at least about 9500 analytes, at least about 10000 analytes, or greater than about 10000 analytes may be characterized. In some embodiments analytes, at most about 10000 analytes, at most about 9500 analytes, at most about 9000 analytes, at most about 8500 analytes, at most about 8000 analytes, at most about 7500 analytes, at most about 7000 analytes, at most about 6500 analytes, at most about 6000 analytes, at most about 5500 analytes, at most about 5000 analytes, at most about 4500 analytes, at most about 4000 analytes, at most about 3500 analytes, at most about 3000 analytes, at most about 2500 analytes, at most about 2000 analytes, at most about 1500 analytes, at most about 1000 analytes, at most about 900 analytes, at most about 800 analytes, at most about 700 analytes, at most about 600 analytes, at most about 500 analytes, at most about 400 analytes, at most about 300 analytes, at most about 200 analytes, at most about 100 analytes, at most about 90 analytes, at most about 80 analytes, at most about 70 analytes, at most about 60 analytes, at most about 50 analytes, at most about 40 analytes, at most about 30 analytes, at most about 20 analytes, at most about 10 analytes, at most about 9 analytes, at most about 8 analytes, at most about 7 analytes, at most about 6 analytes, at most about 5 analytes, at most about 4 analytes, at most about 3 analytes, at most about 2 analytes, or less than about 2 analytes may be characterized.

In some embodiments, from about 2 analytes to about 100 analytes may be characterized. In some embodiments, from about 2 analytes to about 5 analytes, about 2 analytes to about 10 analytes, about 2 analytes to about 20 analytes, about 2 analytes to about 30 analytes, about 2 analytes to about 40 analytes, about 2 analytes to about 50 analytes, about 2 analytes to about 60 analytes, about 2 analytes to about 70 analytes, about 2 analytes to about 80 analytes, about 2 analytes to about 90 analytes, about 2 analytes to about 100 analytes, about 5 analytes to about 10 analytes, about 5 analytes to about 20 analytes, about 5 analytes to about 30 analytes, about 5 analytes to about 40 analytes, about 5 analytes to about 50 analytes, about 5 analytes to about 60 analytes, about 5 analytes to about 70 analytes, about 5 analytes to about 80 analytes, about 5 analytes to about 90 analytes, about 5 analytes to about 100 analytes, about 10 analytes to about 20 analytes, about 10 analytes to about 30 analytes, about 10 analytes to about 40 analytes, about 10 analytes to about 50 analytes, about 10 analytes to about 60 analytes, about 10 analytes to about 70 analytes, about 10 analytes to about 80 analytes, about 10 analytes to about 90 analytes, about 10 analytes to about 100 analytes, about 20 analytes to about 30 analytes, about 20 analytes to about 40 analytes, about 20 analytes to about 50 analytes, about 20 analytes to about 60 analytes, about 20 analytes to about 70 analytes, about 20 analytes to about 80 analytes, about 20 analytes to about 90 analytes, about 20 analytes to about 100 analytes, about 30 analytes to about 40 analytes, about 30 analytes to about 50 analytes, about 30 analytes to about 60 analytes, about 30 analytes to about 70 analytes, about 30 analytes to about 80 analytes, about 30 analytes to about 90 analytes, about 30 analytes to about 100 analytes, about 40 analytes to about 50 analytes, about 40 analytes to about 60 analytes, about 40 analytes to about 70 analytes, about 40 analytes to about 80 analytes, about 40 analytes to about 90 analytes, about 40 analytes to about 100 analytes, about 50 analytes to about 60 analytes, about 50 analytes to about 70 analytes, about 50 analytes to about 80 analytes, about 50 analytes to about 90 analytes, about 50 analytes to about 100 analytes, about 60 analytes to about 70 analytes, about 60 analytes to about 80 analytes, about 60 analytes to about 90 analytes, about 60 analytes to about 100 analytes, about 70 analytes to about 80 analytes, about 70 analytes to about 90 analytes, about 70 analytes to about 100 analytes, about 80 analytes to about 90 analytes, about 80 analytes to about 100 analytes, or about 90 analytes to about 100 analytes may be characterized.

In some embodiments, from about 100 analytes to about 10,000 analytes may be characterized. In some embodiments, from about 100 analytes to about 200 analytes, about 100 analytes to about 300 analytes, about 100 analytes to about 400 analytes, about 100 analytes to about 500 analytes, about 100 analytes to about 750 analytes, about 100 analytes to about 1,000 analytes, about 100 analytes to about 2,500 analytes, about 100 analytes to about 5,000 analytes, about 100 analytes to about 7,500 analytes, about 100 analytes to about 10,000 analytes, about 200 analytes to about 300 analytes, about 200 analytes to about 400 analytes, about 200 analytes to about 500 analytes, about 200 analytes to about 750 analytes, about 200 analytes to about 1,000 analytes, about 200 analytes to about 2,500 analytes, about 200 analytes to about 5,000 analytes, about 200 analytes to about 7,500 analytes, about 200 analytes to about 10,000 analytes, about 300 analytes to about 400 analytes, about 300 analytes to about 500 analytes, about 300 analytes to about 750 analytes, about 300 analytes to about 1,000 analytes, about 300 analytes to about 2,500 analytes, about 300 analytes to about 5,000 analytes, about 300 analytes to about 7,500 analytes, about 300 analytes to about 10,000 analytes, about 400 analytes to about 500 analytes, about 400 analytes to about 750 analytes, about 400 analytes to about 1,000 analytes, about 400 analytes to about 2,500 analytes, about 400 analytes to about 5,000 analytes, about 400 analytes to about 7,500 analytes, about 400 analytes to about 10,000 analytes, about 500 analytes to about 750 analytes, about 500 analytes to about 1,000 analytes, about 500 analytes to about 2,500 analytes, about 500 analytes to about 5,000 analytes, about 500 analytes to about 7,500 analytes, about 500 analytes to about 10,000 analytes, about 750 analytes to about 1,000 analytes, about 750 analytes to about 2,500 analytes, about 750 analytes to about 5,000 analytes, about 750 analytes to about 7,500 analytes, about 750 analytes to about 10,000 analytes, about 1,000 analytes to about 2,500 analytes, about 1,000 analytes to about 5,000 analytes, about 1,000 analytes to about 7,500 analytes, about 1,000 analytes to about 10,000 analytes, about 2,500 analytes to about 5,000 analytes, about 2,500 analytes to about 7,500 analytes, about 2,500 analytes to about 10,000 analytes, about 5,000 analytes to about 7,500 analytes, about 5,000 analytes to about 10,000 analytes, or about 7,500 analytes to about 10,000 analytes may be characterized.

In some embodiments, about 2 analytes, about 3 analytes, about 4 analytes, about 5 analytes, about 6 analytes, about 7 analytes, about 8 analytes, about 9 analytes, about 10 analytes, about 20 analytes, about 30 analytes, about 40 analytes, about 50 analytes, about 100 analytes, about 200 analytes, about 300 analytes, about 400 analytes, about 500 analytes, about 600 analytes, about 700 analytes, about 800 analytes, about 900 analytes, about 1000 analytes, about 1500 analytes, about 2000 analytes, about 2500 analytes, about 3000 analytes, about 3500 analytes, about 4000 analytes, about 4500 analytes, about 5000 analytes, about 5500 analytes, about 6000 analytes, about 6500 analytes, about 7000 analytes, about 7500 analytes, about 8000 analytes, about 8500 analytes, about 9000 analytes, about 9500 analytes, or about 10000 analytes may be characterized.

In some embodiments, at least about 2 types of analytes, at least about 3 types of analytes, at least about 4 types of analytes, at least about 5 types of analytes, at least about 6 types of analytes, at least about 7 types of analytes, at least about 8 types of analytes, at least about 9 types of analytes, at least about 10 types of analytes, at least about 20 types of analytes, at least about 30 types of analytes, at least about 40 types of analytes, at least about 50 types of analytes, at least about 100 types of analytes, at least about 200 types of analytes, at least about 300 types of analytes, at least about 400 types of analytes, at least about 500 types of analytes, at least about 600 types of analytes, at least about 700 types of analytes, at least about 800 types of analytes, at least about 900 types of analytes, at least about 1000 types of analytes, at least about 1500 types of analytes, at least about 2000 types of analytes, at least about 2500 types of analytes, at least about 3000 types of analytes, at least about 3500 types of analytes, at least about 4000 types of analytes, at least about 4500 types of analytes, at least about 5000 types of analytes, at least about 5500 types of analytes, at least about 6000 types of analytes, at least about 6500 types of analytes, at least about 7000 types of analytes, at least about 7500 types of analytes, at least about 8000 types of analytes, at least about 8500 types of analytes, at least about 9000 types of analytes, at least about 9500 types of analytes, at least about 10000 types of analytes, or greater than about 10000 types of analytes may be characterized. In some embodiments types of analytes, at most about 10000 types of analytes, at most about 9500 types of analytes, at most about 9000 types of analytes, at most about 8500 types of analytes, at most about 8000 types of analytes, at most about 7500 types of analytes, at most about 7000 types of analytes, at most about 6500 types of analytes, at most about 6000 types of analytes, at most about 5500 types of analytes, at most about 5000 types of analytes, at most about 4500 types of analytes, at most about 4000 types of analytes, at most about 3500 types of analytes, at most about 3000 types of analytes, at most about 2500 types of analytes, at most about 2000 types of analytes, at most about 1500 types of analytes, at most about 1000 types of analytes, at most about 900 types of analytes, at most about 800 types of analytes, at most about 700 types of analytes, at most about 600 types of analytes, at most about 500 types of analytes, at most about 400 types of analytes, at most about 300 types of analytes, at most about 200 types of analytes, at most about 100 types of analytes, at most about 90 types of analytes, at most about 80 types of analytes, at most about 70 types of analytes, at most about 60 types of analytes, at most about 50 types of analytes, at most about 40 types of analytes, at most about 30 types of analytes, at most about 20 types of analytes, at most about 10 types of analytes, at most about 9 types of analytes, at most about 8 types of analytes, at most about 7 types of analytes, at most about 6 types of analytes, at most about 5 types of analytes, at most about 4 types of analytes, at most about 3 types of analytes, at most about 2 types of analytes, or less than about 2 types of analytes may be characterized.

In some embodiments, from about 2 types of analytes to about 100 types of analytes may be characterized. In some embodiments, from about 2 types of analytes to about 5 types of analytes, about 2 types of analytes to about 10 types of analytes, about 2 types of analytes to about 20 types of analytes, about 2 types of analytes to about 30 types of analytes, about 2 types of analytes to about 40 types of analytes, about 2 types of analytes to about 50 types of analytes, about 2 types of analytes to about 60 types of analytes, about 2 types of analytes to about 70 types of analytes, about 2 types of analytes to about 80 types of analytes, about 2 types of analytes to about 90 types of analytes, about 2 types of analytes to about 100 types of analytes, about 5 types of analytes to about 10 types of analytes, about 5 types of analytes to about 20 types of analytes, about 5 types of analytes to about 30 types of analytes, about 5 types of analytes to about 40 types of analytes, about 5 types of analytes to about 50 types of analytes, about 5 types of analytes to about 60 types of analytes, about 5 types of analytes to about 70 types of analytes, about 5 types of analytes to about 80 types of analytes, about 5 types of analytes to about 90 types of analytes, about 5 types of analytes to about 100 types of analytes, about 10 types of analytes to about 20 types of analytes, about 10 types of analytes to about 30 types of analytes, about 10 types of analytes to about 40 types of analytes, about 10 types of analytes to about 50 types of analytes, about 10 types of analytes to about 60 types of analytes, about 10 types of analytes to about 70 types of analytes, about 10 types of analytes to about 80 types of analytes, about 10 types of analytes to about 90 types of analytes, about 10 types of analytes to about 100 types of analytes, about 20 types of analytes to about 30 types of analytes, about 20 types of analytes to about 40 types of analytes, about 20 types of analytes to about 50 types of analytes, about 20 types of analytes to about 60 types of analytes, about 20 types of analytes to about 70 types of analytes, about 20 types of analytes to about 80 types of analytes, about 20 types of analytes to about 90 types of analytes, about 20 types of analytes to about 100 types of analytes, about 30 types of analytes to about 40 types of analytes, about 30 types of analytes to about 50 types of analytes, about 30 types of analytes to about 60 types of analytes, about 30 types of analytes to about 70 types of analytes, about 30 types of analytes to about 80 types of analytes, about 30 types of analytes to about 90 types of analytes, about 30 types of analytes to about 100 types of analytes, about 40 types of analytes to about 50 types of analytes, about 40 types of analytes to about 60 types of analytes, about 40 types of analytes to about 70 types of analytes, about 40 types of analytes to about 80 types of analytes, about 40 types of analytes to about 90 types of analytes, about 40 types of analytes to about 100 types of analytes, about 50 types of analytes to about 60 types of analytes, about 50 types of analytes to about 70 types of analytes, about 50 types of analytes to about 80 types of analytes, about 50 types of analytes to about 90 types of analytes, about 50 types of analytes to about 100 types of analytes, about 60 types of analytes to about 70 types of analytes, about 60 types of analytes to about 80 types of analytes, about 60 types of analytes to about 90 types of analytes, about 60 types of analytes to about 100 types of analytes, about 70 types of analytes to about 80 types of analytes, about 70 types of analytes to about 90 types of analytes, about 70 types of analytes to about 100 types of analytes, about 80 types of analytes to about 90 types of analytes, about 80 types of analytes to about 100 types of analytes, or about 90 types of analytes to about 100 types of analytes may be characterized.

In some embodiments, from about 100 types of analytes to about 10,000 types of analytes may be characterized. In some embodiments, from about 100 types of analytes to about 200 types of analytes, about 100 types of analytes to about 300 types of analytes, about 100 types of analytes to about 400 types of analytes, about 100 types of analytes to about 500 types of analytes, about 100 types of analytes to about 750 types of analytes, about 100 types of analytes to about 1,000 types of analytes, about 100 types of analytes to about 2,500 types of analytes, about 100 types of analytes to about 5,000 types of analytes, about 100 types of analytes to about 7,500 types of analytes, about 100 types of analytes to about 10,000 types of analytes, about 200 types of analytes to about 300 types of analytes, about 200 types of analytes to about 400 types of analytes, about 200 types of analytes to about 500 types of analytes, about 200 types of analytes to about 750 types of analytes, about 200 types of analytes to about 1,000 types of analytes, about 200 types of analytes to about 2,500 types of analytes, about 200 types of analytes to about 5,000 types of analytes, about 200 types of analytes to about 7,500 types of analytes, about 200 types of analytes to about 10,000 types of analytes, about 300 types of analytes to about 400 types of analytes, about 300 types of analytes to about 500 types of analytes, about 300 types of analytes to about 750 types of analytes, about 300 types of analytes to about 1,000 types of analytes, about 300 types of analytes to about 2,500 types of analytes, about 300 types of analytes to about 5,000 types of analytes, about 300 types of analytes to about 7,500 types of analytes, about 300 types of analytes to about 10,000 types of analytes, about 400 types of analytes to about 500 types of analytes, about 400 types of analytes to about 750 types of analytes, about 400 types of analytes to about 1,000 types of analytes, about 400 types of analytes to about 2,500 types of analytes, about 400 types of analytes to about 5,000 types of analytes, about 400 types of analytes to about 7,500 types of analytes, about 400 types of analytes to about 10,000 types of analytes, about 500 types of analytes to about 750 types of analytes, about 500 types of analytes to about 1,000 types of analytes, about 500 types of analytes to about 2,500 types of analytes, about 500 types of analytes to about 5,000 types of analytes, about 500 types of analytes to about 7,500 types of analytes, about 500 types of analytes to about 10,000 types of analytes, about 750 types of analytes to about 1,000 types of analytes, about 750 types of analytes to about 2,500 types of analytes, about 750 types of analytes to about 5,000 types of analytes, about 750 types of analytes to about 7,500 types of analytes, about 750 types of analytes to about 10,000 types of analytes, about 1,000 types of analytes to about 2,500 types of analytes, about 1,000 types of analytes to about 5,000 types of analytes, about 1,000 types of analytes to about 7,500 types of analytes, about 1,000 types of analytes to about 10,000 types of analytes, about 2,500 types of analytes to about 5,000 types of analytes, about 2,500 types of analytes to about 7,500 types of analytes, about 2,500 types of analytes to about 10,000 types of analytes, about 5,000 types of analytes to about 7,500 types of analytes, about 5,000 types of analytes to about 10,000 types of analytes, or about 7,500 types of analytes to about 10,000 types of analytes may be characterized.

In some embodiments, about 2 types of analytes, about 3 types of analytes, about 4 types of analytes, about 5 types of analytes, about 6 types of analytes, about 7 types of analytes, about 8 types of analytes, about 9 types of analytes, about 10 types of analytes, about 20 types of analytes, about 30 types of analytes, about 40 types of analytes, about 50 types of analytes, about 100 types of analytes, about 200 types of analytes, about 300 types of analytes, about 400 types of analytes, about 500 types of analytes, about 600 types of analytes, about 700 types of analytes, about 800 types of analytes, about 900 types of analytes, about 1000 types of analytes, about 1500 types of analytes, about 2000 types of analytes, about 2500 types of analytes, about 3000 types of analytes, about 3500 types of analytes, about 4000 types of analytes, about 4500 types of analytes, about 5000 types of analytes, about 5500 types of analytes, about 6000 types of analytes, about 6500 types of analytes, about 7000 types of analytes, about 7500 types of analytes, about 8000 types of analytes, about 8500 types of analytes, about 9000 types of analytes, about 9500 types of analytes, or about 10000 types of analytes may be characterized.

In some embodiments, the analyte can be at least about 1 kDa, at least about 2 kDa, at least about 3 kDa, at least about 4 kDa, at least about 5 kDa, at least about 6 kDa, at least about 7 kDa, at least about 8 kDa, at least about 9 kDa, at least about 10 kDa, at least about 15 kDa, at least about 20 kDa, at least about 25 kDa, at least about 30 kDa, at least about 35 kDa, at least about 40 kDa, at least about 45 kDa, at least about 50 kDa, at least about 55 kDa, at least about 60 kDa, at least about 65 kDa, at least about 70 kDa, at least about 75 kDa, at least about 80 kDa, at least about 85 kDa, at least about 90 kDa, at least about 95 kDa, at least about 100 kDa, at least about 125 kDa, at least about 150 kDa, at least about 175 kDa, at least about 200 kDa, at least about 250 kDa, at least about 300 kDa, at least about 350 kDa, at least about 400 kDa, at least about 450 kDa, at least about 500 kDa, at least about 550 kDa, at least about 600 kDa, at least about 650 kDa, at least about 700 kDa, at least about 750 kDa, at least about 800 kDa, at least about 850 kDa, at least about 900 kDa, at least about 950 kDa, at least about 1000 kDa, at least about 1500 kDa, at least about 2000 kDa, at least about 2500 kDa, at least about 3000 kDa, at least about 3500 kDa, at least about 4000 kDa, or greater than about 4000 kDa.

In some embodiments, the analyte can be at most about 4000 kDa, at most about 3500 kDa, at most about 3000 kDa, at most about 2500 kDa, at most about 2000 kDa, at most about 1500 kDa, at most about 1000 kDa, at most about 950 kDa, at most about 900 kDa, at most about 850 kDa, at most about 800 kDa, at most about 750 kDa, at most about 700 kDa, at most about 650 kDa, at most about 600 kDa, at most about 550 kDa, at most about 500 kDa, at most about 450 kDa, at most about 400 kDa, at most about 350 kDa, at most about 300 kDa, at most about 250 kDa, at most about 200 kDa, at most about 175 kDa, at most about 150 kDa, at most about 125 kDa, at most about 100 kDa, at most about 95 kDa, at most about 90 kDa, at most about 85 kDa, at most about 80 kDa, at most about 75 kDa, at most about 70 kDa, at most about 65 kDa, at most about 60 kDa, at most about 55 kDa, at most about 50 kDa, at most about 45 kDa, at most about 40 kDa, at most about 35 kDa, at most about 30 kDa, at most about 25 kDa, at most about 20 kDa, at most about 15 kDa, at most about 10 kDa, at most about 9 kDa, at most about 8 kDa, at most about 7 kDa, at most about 6 kDa, at most about 5 kDa, at most about 4 kDa, at most about 3 kDa, at most about 2 kDa, at most about 1 kDa, or less than about 1 kDa.

In some embodiments, the analyte can be from about 1 kDa to about 100 kDa. In some embodiments, the analyte can be from about 1 kDa to about 5 kDa, about 1 kDa to about 10 kDa, about 1 kDa to about 20 kDa, about 1 kDa to about 30 kDa, about 1 kDa to about 40 kDa, about 1 kDa to about 50 kDa, about 1 kDa to about 60 kDa, about 1 kDa to about 70 kDa, about 1 kDa to about 80 kDa, about 1 kDa to about 90 kDa, about 1 kDa to about 100 kDa, about 5 kDa to about 10 kDa, about 5 kDa to about 20 kDa, about 5 kDa to about 30 kDa, about 5 kDa to about 40 kDa, about 5 kDa to about 50 kDa, about 5 kDa to about 60 kDa, about 5 kDa to about 70 kDa, about 5 kDa to about 80 kDa, about 5 kDa to about 90 kDa, about 5 kDa to about 100 kDa, about 10 kDa to about 20 kDa, about 10 kDa to about 30 kDa, about 10 kDa to about 40 kDa, about 10 kDa to about 50 kDa, about 10 kDa to about 60 kDa, about 10 kDa to about 70 kDa, about 10 kDa to about 80 kDa, about 10 kDa to about 90 kDa, about 10 kDa to about 100 kDa, about 20 kDa to about 30 kDa, about 20 kDa to about 40 kDa, about 20 kDa to about 50 kDa, about 20 kDa to about 60 kDa, about 20 kDa to about 70 kDa, about 20 kDa to about 80 kDa, about 20 kDa to about 90 kDa, about 20 kDa to about 100 kDa, about 30 kDa to about 40 kDa, about 30 kDa to about 50 kDa, about 30 kDa to about 60 kDa, about 30 kDa to about 70 kDa, about 30 kDa to about 80 kDa, about 30 kDa to about 90 kDa, about 30 kDa to about 100 kDa, about 40 kDa to about 50 kDa, about 40 kDa to about 60 kDa, about 40 kDa to about 70 kDa, about 40 kDa to about 80 kDa, about 40 kDa to about 90 kDa, about 40 kDa to about 100 kDa, about 50 kDa to about 60 kDa, about 50 kDa to about 70 kDa, about 50 kDa to about 80 kDa, about 50 kDa to about 90 kDa, about 50 kDa to about 100 kDa, about 60 kDa to about 70 kDa, about 60 kDa to about 80 kDa, about 60 kDa to about 90 kDa, about 60 kDa to about 100 kDa, about 70 kDa to about 80 kDa, about 70 kDa to about 90 kDa, about 70 kDa to about 100 kDa, about 80 kDa to about 90 kDa, about 80 kDa to about 100 kDa, or about 90 kDa to about 100 kDa.

In some embodiments, the analyte can be from about 100 kDa to about 4,000 kDa. In some embodiments, the analyte can be from about 100 kDa to about 250 kDa, about 100 kDa to about 500 kDa, about 100 kDa to about 1,000 kDa, about 100 kDa to about 1,500 kDa, about 100 kDa to about 2,000 kDa, about 100 kDa to about 2,500 kDa, about 100 kDa to about 3,000 kDa, about 100 kDa to about 3,500 kDa, about 100 kDa to about 4,000 kDa, about 250 kDa to about 500 kDa, about 250 kDa to about 1,000 kDa, about 250 kDa to about 1,500 kDa, about 250 kDa to about 2,000 kDa, about 250 kDa to about 2,500 kDa, about 250 kDa to about 3,000 kDa, about 250 kDa to about 3,500 kDa, about 250 kDa to about 4,000 kDa, about 500 kDa to about 1,000 kDa, about 500 kDa to about 1,500 kDa, about 500 kDa to about 2,000 kDa, about 500 kDa to about 2,500 kDa, about 500 kDa to about 3,000 kDa, about 500 kDa to about 3,500 kDa, about 500 kDa to about 4,000 kDa, about 1,000 kDa to about 1,500 kDa, about 1,000 kDa to about 2,000 kDa, about 1,000 kDa to about 2,500 kDa, about 1,000 kDa to about 3,000 kDa, about 1,000 kDa to about 3,500 kDa, about 1,000 kDa to about 4,000 kDa, about 1,500 kDa to about 2,000 kDa, about 1,500 kDa to about 2,500 kDa, about 1,500 kDa to about 3,000 kDa, about 1,500 kDa to about 3,500 kDa, about 1,500 kDa to about 4,000 kDa, about 2,000 kDa to about 2,500 kDa, about 2,000 kDa to about 3,000 kDa, about 2,000 kDa to about 3,500 kDa, about 2,000 kDa to about 4,000 kDa, about 2,500 kDa to about 3,000 kDa, about 2,500 kDa to about 3,500 kDa, about 2,500 kDa to about 4,000 kDa, about 3,000 kDa to about 3,500 kDa, about 3,000 kDa to about 4,000 kDa, or about 3,500 kDa to about 4,000 kDa.

In some embodiments, the analyte can be about 1 kDa, about 2 kDa, about 3 kDa, about 4 kDa, about 5 kDa, about 6 kDa, about 7 kDa, about 8 kDa, about 9 kDa, about 10 kDa, about 15 kDa, about 20 kDa, about 25 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, about 100 kDa, about 125 kDa, about 150 kDa, about 175 kDa, about 200 kDa, about 250 kDa, about 300 kDa, about 350 kDa, about 400 kDa, about 450 kDa, about 500 kDa, about 550 kDa, about 600 kDa, about 650 kDa, about 700 kDa, about 750 kDa, about 800 kDa, about 850 kDa, about 900 kDa, about 950 kDa, about 1000 kDa, about 1500 kDa, about 2000 kDa, about 2500 kDa, about 3000 kDa, about 3500 kDa, or about 4000 kDa.

In some embodiments, the analyte can be at least about 2, at least about 5, at least about 10, at least about 15, at least about 20, at least about 30, at least about 40, at least about 50, at least about 60, at least about 70, at least about 80, at least about 90, at least about 100, at least about 150, at least about 200, at least about 250, at least about 300, at least about 350, at least about 400, at least about 450, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 20000, at least about 30000, at least about 34000, or greater than about 34000 repeated units, monomers, or groups. In some embodiments, the analyte can be at most about 34000, at most about 30000, at most about 20000, at most about 10000, at most about 9000, at most about 8000, at most about 7000, at most about 6000, at most about 5000, at most about 4000, at most about 3000, at most about 2000, at most about 1000, at most about 900, at most about 800, at most about 700, at most about 600, at most about 500, at most about 450, at most about 400, at most about 350, at most about 300, at most about 250, at most about 30000, at most about 30000, at most about 200, at most about 150, at most about 100, at most about 90, at most about 80, at most about 70, at most about 60, at most about 50, at most about 40, at most about 30, at most about 20, at most about 15, at most about 10, at most about 5, at most about 2, or less than about 2 repeated units, monomers, or groups.

In some embodiments, the analyte can be from about 2 to about 1,000 repeated units, monomers, or groups. In some embodiments, the analyte can be from about 2 to about 10, about 2 to about 100, about 2 to about 200, about 2 to about 300, about 2 to about 400, about 2 to about 500, about 2 to about 600, about 2 to about 700, about 2 to about 800, about 2 to about 900, about 2 to about 1,000, about 10 to about 100, about 10 to about 200, about 10 to about 300, about 10 to about 400, about 10 to about 500, about 10 to about 600, about 10 to about 700, about 10 to about 800, about 10 to about 900, about 10 to about 1,000, about 100 to about 200, about 100 to about 300, about 100 to about 400, about 100 to about 500, about 100 to about 600, about 100 to about 700, about 100 to about 800, about 100 to about 900, about 100 to about 1,000, about 200 to about 300, about 200 to about 400, about 200 to about 500, about 200 to about 600, about 200 to about 700, about 200 to about 800, about 200 to about 900, about 200 to about 1,000, about 300 to about 400, about 300 to about 500, about 300 to about 600, about 300 to about 700, about 300 to about 800, about 300 to about 900, about 300 to about 1,000, about 400 to about 500, about 400 to about 600, about 400 to about 700, about 400 to about 800, about 400 to about 900, about 400 to about 1,000, about 500 to about 600, about 500 to about 700, about 500 to about 800, about 500 to about 900, about 500 to about 1,000, about 600 to about 700, about 600 to about 800, about 600 to about 900, about 600 to about 1,000, about 700 to about 800, about 700 to about 900, about 700 to about 1,000, about 800 to about 900, about 800 to about 1,000, or about 900 to about 1,000 repeated units, monomers, or groups.

In some embodiments, the analyte can be from about 1,000 to about 34,000 in length. In some embodiments, the analyte can be from about 1,000 to about 2,500, about 1,000 to about 5,000, about 1,000 to about 7,500, about 1,000 to about 10,000, about 1,000 to about 15,000, about 1,000 to about 20,000, about 1,000 to about 25,000, about 1,000 to about 30,000, about 1,000 to about 34,000, about 2,500 to about 5,000, about 2,500 to about 7,500, about 2,500 to about 10,000, about 2,500 to about 15,000, about 2,500 to about 20,000, about 2,500 to about 25,000, about 2,500 to about 30,000, about 2,500 to about 34,000, about 5,000 to about 7,500, about 5,000 to about 10,000, about 5,000 to about 15,000, about 5,000 to about 20,000, about 5,000 to about 25,000, about 5,000 to about 30,000, about 5,000 to about 34,000, about 7,500 to about 10,000, about 7,500 to about 15,000, about 7,500 to about 20,000, about 7,500 to about 25,000, about 7,500 to about 30,000, about 7,500 to about 34,000, about 10,000 to about 15,000, about 10,000 to about 20,000, about 10,000 to about 25,000, about 10,000 to about 30,000, about 10,000 to about 34,000, about 15,000 to about 20,000, about 15,000 to about 25,000, about 15,000 to about 30,000, about 15,000 to about 34,000, about 20,000 to about 25,000, about 20,000 to about 30,000, about 20,000 to about 34,000, about 25,000 to about 30,000, about 25,000 to about 34,000, or about 30,000 to about 34,000 repeated units, monomers, or groups.

In some embodiments, the analyte can be about 2, about 5, about 10, about 15, about 20, about 30, about 40, about 50, about 60, about 70, about 80, about 90, about 100, about 150, about 200, about 250, about 300, about 350, about 400, about 450, about 500, about 600, about 700, about 800, about 900, about 1000, about 2000, about 3000, about 4000, about 5000, about 6000, about 7000, about 8000, about 9000, about 10000, about 20000, about 30000, or about 34000 repeated units, monomers, or groups.

In some embodiments, the analyte can comprise a non-nucleic acid based polymer analyte. In some embodiments, a portion of non-nucleic acid based polymer analyte can comprise a nucleic acid molecule. In some cases, the portion of the non-nucleic acid polymer analyte can be from 0% to about 100% of the non-nucleic acid polymer analyte. In some cases, the portion of the non-nucleic acid polymer analyte can be at least about 0%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% of the non-nucleic acid polymer analyte. In some cases, the portion of the non-nucleic acid polymer analyte can be at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, or at most about 0% of the non-nucleic acid polymer analyte. In some cases, the portion of the non-nucleic acid polymer analyte can be about 0%, about 5%, about 10%, about 15%, about 20%, about 25%, about 30%, about 35%, about 40%, about 45%, about 50%, about 55%, about 60%, about 65%, about 75%, about 80%, about 85%, about 90%, about 95%, or about 100% of the non-nucleic acid polymer analyte.

Analytes can be denatured, partially denatured or non-denatured (conjugated) analytes or a mixture of denatured, partially denatured and/or non-denatured (conjugated) analytes. In one embodiment, the analyte(s) is/are in a native form.

In one embodiment, a method of the present disclosure comprises contacting the protein translocase in solution with a partially denatured or non-denatured (conjugated) analyte or with a mixture of partially denatured and/or non-denatured (conjugated) analytes. In one embodiment, the analyte(s) is/are all in their native form. In another embodiment, the protein translocase may be contacted with a fully denatured analyte. For example, the analyte can be denatured using, for example heating, extreme pH, or chemical denaturants (e.g. urea, guanidinium hydrochloride, detergents, etc.) or a combination thereof. Denatured analyte(s) might then be diluted and contacted with the translocase and added to the cis compartment of the nanopore system under non-denaturing run conditions but remain denatured and unable to refold. In another embodiment, the denatured analytes are added to the nanopore system that retain mild or moderate denaturing conditions to prevent any refolding of the analyte. It is well known that translocases and nanopores can tolerate some level of denaturing conditions, so that some level of denaturing conditions might be employed in the running system to maintain the denatured or partially denatured state of the analytes while retaining the integrity of the translocase and nanopore. For example, nanopores can withstand temperatures up to about 100° C. or urea concentrations up to 4M, and translocases from extremophiles can withstand conditions such as low pH and high temperatures.

In one aspect, the analyte(s) can be contacted with the translocase and added to the nanopore system under denaturing conditions, wherein the denaturing conditions are sufficient to denature analyte in situ while retaining the integrity of the translocase and nanopore.

The analyte may be obtained, isolated or extracted from any organism or microorganism. For instance, it is obtained from a human or animal, e.g. from a bodily fluid, such as urine, lymph, saliva, mucus, seminal fluid or amniotic fluid, or from whole blood, plasma or serum. The analyte may be obtained from a plant e.g. a cereal, legume, ornamental plant, fruit or vegetable, or part thereof including tubers, roots and bulbs.

The analyte can be produced inside (animal) cells such that it can be extracted from cells for characterisation by the disclosed methods. The analyte may comprise the products of cellular expression of a plasmid in a (microbial) host cell. In some embodiments the analyte is secreted from cells.

The analyte can be provided as an impure mixture of one or more analytes and one or more (proteinaceous) impurities. For example, the analyte may be a full length protein and impurities may comprise fragments of the analyte. Impurities may comprise truncated forms of the analyte which are distinct from the "analytes" for characterisation in the disclosed methods. Impurities may also comprise analyte s other than the analytes e.g. which may be co-purified from a cell culture or obtained from a sample.

A analyte may comprise any combination of any amino acids, amino acid analogs and modified amino acids (i.e. amino acid derivatives). Amino acids (and derivatives, analogs etc) in the analyte can be distinguished by their physical size and charge. The amino acids/derivatives/analogs can be naturally occurring or artificial.

In some embodiments, the analyte is modified. In some embodiments, the analyte is modified by a leader construct according to the disclosed methods. In some embodiments, the disclosed methods are for characterising modifications in the analyte. In one aspect, one or more of the amino acids/derivatives/analogs in the analyte is post-translationally modified. Any one or more post-translational modifications may be present in the analyte.

Typical post-translational modifications can include modification with a hydrophobic group, modification with a cofactor, addition of a chemical group, glycation (the non-enzymatic attachment of a sugar), biotinylation and PEGylation. Post-translational modifications can also be non-natural, for instance are chemical modifications introduced in a laboratory for biotechnological or biomedical purposes. This allows for monitoring the levels of post-translational modifications of the laboratory-derived peptide, polypeptide or protein as compared to the natural counterpart. As such, the methods disclosed herein can be used to detect the presence, absence, extent or number of positions of post-translational modifications in a polypeptide.

In some embodiments, post-translational modification with a hydrophobic group include myristoylation, palmitoylation, isoprenylation or prenylation, the attachment of an isoprenoid group; farnesylation, the attachment of a farnesol group; geranylgeranylation, the attachment of a geranylgeraniol group; and glypiation, and glycosylphosphatidylinositol (GPI) anchor formation via an amide bond. Examples of post-translational modification with a cofactor include lipoylation, attachment of a lipoate (Cs) functional group; flavination, attachment of a flavin moiety (e.g. flavin mononucleotide (FMN) or flavin adenine dinucleotide (FAD)); attachment of heme C, for instance via a thioether bond with cysteine; phosphopantetheinylation, the attachment of a 4'-phosphopantetheinyl group; and retinylidene Schiff base formation.

In some embodiments, post-translational modification by addition of a chemical group include acylation, e.g. O-acylation (esters), N-acylation (amides) or S-acylation (thioesters); acetylation, the attachment of an acetyl group for instance to the N-terminus or to lysine; formylation; alkylation, the addition of an alkyl group, such as methyl or ethyl; methylation, the addition of a methyl group for instance to lysine or arginine; amidation; butyrylation; gamma-carboxylation; glycosylation, the enzymatic attachment of a glycosyl group for instance to arginine, asparagine, cysteine, hydroxylysine, serine, threonine, tyrosine or tryptophan; polysialylation, the attachment of polysialic acid; malonylation; hydroxylation; iodination; bromination; citrulination; nucleotide addition, the attachment of any nucleotide such as any of those discussed above, ADP ribosylation; oxidation; phosphorylation, the attachment of a phosphate group for instance to serine, threonine or tyrosine (O-linked) or histidine (N-linked); adenylylation, the attachment of an adenylyl moiety for instance to tyrosine (O-linked) or to histidine or lysine (N-linked); propionylation; pyroglutamate formation; S-glutathionylation; Sumoylation; S-nitrosylation; succinylation, the attachment of a succinyl group for instance to lysine; selenoylation, the incorporation of selenium; and ubiquitinilation, the addition of ubiquitin subunits (N-linked).

In some embodiments, a system provided herein is particularly suitable for the analysis of a analyte, such as a polypeptide, greater than 30 amino acids in length. In some cases, a system of the present disclosure provides for capture and translocation of peptides of 30, 50, 100, 300, 500 or greater than 1000 amino acids in length. In one aspect, the analyte is a protein having a mass in the range of between 200 and 5000 Da, 500 and 1700 Da.

Adaptors

In another aspect of the present disclosure, provided herein is a method comprising: providing a nanopore system. The nanopore system may comprise a membrane comprising a nanopore. In some cases, the membrane may separate the fluidic chamber into a cis side and a trans side. A non-nucleic acid based polymer analyte may also be provided. In some cases, the non-nucleic acid based polymer analyte can be translocated through the nanopore. In some cases, the analyte may be translocated through the nanopore from the cis side of the fluidic chamber to the trans side of the fluidic chamber. The nanopore can further comprise an adaptor. In some cases, at least a portion of the adaptor can be within a channel of the nanopore.

In another aspect of the present disclosure, provided herein is a system comprising: providing a nanopore system. The nanopore system may comprise a membrane comprising a nanopore. In some cases, the membrane may separate the fluidic chamber into a cis side and a trans side. A non-nucleic acid based polymer analyte may also be provided. In some cases, the non-nucleic acid based polymer analyte can be translocated through the nanopore. In some cases, the analyte may be translocated through the nanopore from the cis side of the fluidic chamber to the trans side of the fluidic chamber. The nanopore can further comprise an adaptor. In some cases, at least a portion of the adaptor can be within a channel of the nanopore.

In some embodiments, a nanopore may comprises a steric or electrostatic obstruction. The steric or electrostatic obstruction may be added to a natural or a mutant variant of a biological nanopore. An adaptor can provide a steric or electrostatic obstruction. An adaptor can be a separate entity from the nanopore. An adaptor can provide an additional constriction zone, an additional recognition element, or combinations thereof. An adaptor can be proteinaceous or chemical. An adaptor can comprise at least a portion of a molecule that couples to a nanopore and modifies a steric or electrostatic arrangement of a nanopore channel.

An adaptor can be coupled to a nanopore. The coupling can be covalent or non-covalent. In some cases, the covalent coupling can be a covalent bond. In some instances, the covalent bound can be a polar covalent bond or a nonpolar covalent bond. In some cases, the noncovalent coupling can be a noncovalent bond. Non-limiting examples of noncovalent bond include hydrogen bonds, electrostatic interactions, van der Waals interactions, hydrophobic interactions, and cysteine bonds. In some cases, the adaptor can be coupled to the channel of the nanopore via a cysteine bond, a hydrogen bond, an electrostatic interaction, or combinations thereof. In some cases, the adaptor is coupled to the nanopore via a linker. Non-limiting examples of linkers include $(GGGGS)_3$ (SEQ ID NO: 1), $(SG)_n$, $(GGGGS)_n$ (SEQ ID NO: 2), $(Gly)_8$ (SEQ ID NO: 3), $(Gly)_6$ (SEQ ID NO: 4), $(EAAAK)_3$ (SEQ ID NO: 5), $(EAAAK)_n$ (SEQ ID NO: 6), VSQTSKLTRA-ETVFPDV (SEQ ID NO: 7), PLGLWA (SEQ ID NO: 8), RVLAEA (SEQ ID NO: 9), EDVVCCSNSY (SEQ ID NO: 10), GGIEGRGS (SEQ ID NO: 11), TRHRQPRGWE (SEQ ID NO: 12), AGNRVRRSVG (SEQ ID NO: 13), RRRRRRRRR (SEQ ID NO: 14), GFLG (SEQ ID NO: 15), $A(EAAAK)_4ALEA(EAAAK)_4A$ (SEQ ID NO: 16), PAPAP (SEQ ID NO: 17), AEAAAKEAAAKA (SEQ ID NO: 18), $(Ala-Pro)_n$, disulfide bond, cysteine linkages, and any combination thereof. In some embodiments, a linker can comprise any combination of amino acids. In some cases, the amino acids can be canonical amino acids. In some cases, the amino acids can be non-natural amino acids. In some cases, the linker can comprise any combination of canonical amino acids and non-natural amino acids. In some cases, the linker can be ethylene glycol. In some cases, the linker can be polyethylene glycol. In some cases, the linker can be a cysteine linkage.

In some embodiments, the adaptor can be a separate entity from the nanopore channel. In some examples, the adaptor can be a protein coupled to the channel of the nanopore. In some cases, the adaptor may not be a portion of the amino acid sequence of the nanopore channel. In some cases, the adaptor may not modify the sequence of the nanopore channel. In some examples, the adaptor may not modify the amino acid residue sequence of the nanopore channel.

An adaptor can be coupled to a subunit, a monomer, a dimer, a trimer, a tetramer, a pentamer, a hexamer, a heptamer, an octamer, or a nonamer of a nanopore.

In some embodiments, at least one adaptor can be coupled to a nanopore. In some embodiments, between about one adaptor to about 10 adaptors can be coupled to a nanopore. In some cases, at least about one adaptor, at least two about adaptors, at least about three adaptors, at least about four adaptors, at least about five adaptors, at least about six adaptors, at least about seven adaptors, at least about eight adaptors, at least about nine adaptors, or more can be coupled to a nanopore. In some cases, at most about nine adaptors, at most about eight adaptor, at most about seven adaptors, at most about six adaptors, at most about five adaptors, at most about four adaptors, at most about three adaptors, at most about two adaptors, at most about one adaptor, or less can be coupled to a nanopore. In some cases, about one adaptor, about two adaptors, about three adaptors, about four adaptors, about five adaptors, about six adaptors, about seven adaptors, about eight adaptors, or about nine adaptors can be coupled to a nanopore.

An adaptor can comprise one or multiple proteinaceous subunits. In some cases, the adaptor protein can be a protein complex. In some cases, the protein complex can comprise one or more proteins (e.g., proteinaceous subunits). In some embodiments, the adaptor can comprise between about one to about 50 proteinaceous subunits. In some embodiments, the adaptor can comprise between about one to about five proteinaceous subunits, between about five to about 10 proteinaceous subunits, between about 10 to about 15 proteinaceous subunits, between about 15 to about 20 proteinaceous subunits, between about 20 to about 25 proteinaceous subunits, between about 25 to about 30 proteinaceous subunits, between about 30 to about 35 proteinaceous subunits, between about 35 to about 40 proteinaceous subunits, between about 40 to about 45 proteinaceous subunits, or between about 45 to about 50 proteinaceous subunits. In some cases, the adaptor can comprise at least about one proteinaceous subunit, at least about five proteinaceous subunits, at least about ten proteinaceous subunits, at least about 15 proteinaceous subunits, at least about 20 proteinaceous subunits, at least about 25 proteinaceous subunits, at least about 30 proteinaceous subunits, at least about 35 proteinaceous subunits, at least about 40 proteinaceous subunits, at least about 45 proteinaceous subunits, at least about 50 proteinaceous subunits, or more. In some cases, the adaptor can comprise at most about 50 proteinaceous subunits, at most about 45 proteinaceous subunits, at most about 40 proteinaceous subunits, at most about 35 proteinaceous subunits, at most about 30 proteinaceous subunits, at most about 25 proteinaceous subunits, at most about 20 proteinaceous subunits, at most about 15 proteinaceous subunits, at most about 10 proteinaceous subunits, at most about 5 proteinaceous subunits, at most about one proteinaceous subunit.

An adaptor can provide a steric obstruction, an electrostatic change, or combinations thereof. An adaptor can obstruct flow of an analyte through a channel of the nanopore. An adaptor can selectively obstruct flow through a nanopore. In some cases, an adaptor can obstruct flow through the nanopore by modifying a charge of a nanopore or a geometry of a nanopore. In some examples, the adaptor can obstruct flow of the analyte through the channel nanopore by decreasing the circumference of the channel. In some examples, the adaptor can obstruct flow of the analyte through the channel nanopore by causing the nanopore channel to have a net negative charge. An adaptor can narrow a portion of the channel of the nanopore so as to selectively obstruct larger molecules from passing through the nanopore channel by providing a steric barrier. The selectivity can be based at least in part on a charge characteristic of the adaptor. In some examples, the adaptor can prevent translocation of a nucleic acid analyte by causing the nanopore channel to have a net negative charge. In some cases, an adaptor can increase a positive net charge so as to decrease a flow of positively charged molecules, such as cations, by providing an electrostatic barrier. In some cases, an adaptor can increase a positive net charge so as to increase a flow of negatively charged molecules, such as anions, by creating attractive electrostatic interactions. In some cases, an adaptor can decrease a positive net charge as to increase a flow of positively charged molecule by providing an electrostatic barrier. In some cases, an adaptor can increase a negative net charge so as to decrease a flow of negatively charged molecules, such as anions or nucleic acid molecules, by providing an electrostatic barrier. In some cases, an adaptor can increase a negative net charge so as to increase a flow of positively charged molecules, such as cations, by creating attractive electrostatic interactions. In some cases, an adaptor can decrease a negative net charge so as to increase a flow of negatively charged molecules by providing an electrostatic barrier. A charge characteristic can be positive, negative, or neutral.

In some cases, the adaptor can modify a net charge of the channel of the nanopore. In some cases, the adaptor can modify a net charge of the channel of the nanopore to be a positive net charge. In some examples, the adaptor can comprise surface exposed positively charge amino acid residues (e.g., lysine, arginine). In some cases, the adaptor can modify a net charge of the channel of the nanopore to be a negative net charge. In some examples, the adaptor can comprise surface exposed negatively charge amino acid residues (e.g., aspartic acid, glutamic acid).

In some embodiments, the adaptor can increase the positive charge of the nanopore or the channel of the nanopore. In some cases, the adaptor can increase the positive charge of the nanopore or the channel of the nanopore by between about 0.1% to about 500%. In some cases, the adaptor can increase the positive charge of the nanopore or the channel of the nanopore by between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500%.

In some cases, the adaptor can increase the positive charge of the nanopore or the channel of the nanopore by at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more.

In some cases, the adaptor can increase the positive charge of the nanopore or the channel of the nanopore by at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less.

In some cases, the adaptor can increase the positive charge of the nanopore or the channel of the nanopore by about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500%.

In some embodiments, the adaptor can decrease the positive charge of the nanopore or the channel of the nanopore. In some cases, the adaptor can decrease the positive charge of the nanopore or the channel of the nanopore by between about 0.1% to about 500%. In some cases, the adaptor can decrease the positive charge of the nanopore or the channel of the nanopore by between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500%.

In some cases, the adaptor can decrease the positive charge of the nanopore or the channel of the nanopore by at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more.

In some cases, the adaptor can decrease the positive charge of the nanopore or the channel of the nanopore by at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less.

In some cases, the adaptor can decrease the positive charge of the nanopore or the channel of the nanopore by about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500%.

In some embodiments, the adaptor can increase the negative charge of the nanopore or the channel of the nanopore. In some cases, the adaptor can increase the negative charge of the nanopore or the channel of the nanopore by between about 0.1% to about 500%. In some cases, the adaptor can increase the negative charge of the nanopore or the channel of the nanopore by between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500%.

In some cases, the adaptor can increase the negative charge of the nanopore or the channel of the nanopore by at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more.

In some cases, the adaptor can increase the negative charge of the nanopore or the channel of the nanopore by at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less.

In some cases, the adaptor can increase the negative charge of the nanopore or the channel of the nanopore by about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500%.

In some embodiments, the adaptor can decrease the negative charge of the nanopore or the channel of the nanopore. In some cases, the adaptor can decrease the negative charge of the nanopore or the channel of the nanopore by between 0.1% to about 500%. In some cases, the adaptor can decrease the negative charge of the nanopore or the channel of the nanopore by between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500%.

In some cases, the adaptor can decrease the negative charge of the nanopore or the channel of the nanopore by at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more.

In some cases, the adaptor can decrease the negative charge of the nanopore or the channel of the nanopore by at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less.

In some cases, the adaptor can decrease the negative charge of the nanopore or the channel of the nanopore by about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500%.

An adaptor can be coupled within the channel of a nanopore, or external to a channel of a nanopore. An adaptor can modify or generate an electro-osmotic force. For example, an adaptor can modify a nanopore comprising a weak electro-osmotic force due to low ion selectivity so as to have a greater electro-osmotic force by increasing the ion selectivity. In some cases, the adaptor can increase the ion selectivity for anions by the adaptor comprising surface exposed positively charged amino acid residues. In some cases, the adaptor can increase the ion selectivity for cations by the adaptor comprising surface exposed negatively charged amino acid residues. The ion selectivity can be increased, for example, by increasing a net charge of the nanopore. The increase in charge can be negative or positive depending on the desired direction of the electro-osmotic flow.

In some embodiments, the adaptor can comprise one or more charged chemical molecules. In some cases, the one or more charged chemical molecules can comprise chloride, carbonate, chlorite, chlorate, phosphate, bicarbonate, bromide, ammonium sulfate, ammonium, sulfate, sulfide, calcium, fluoride, hydroxide, aluminum, barium, bismuth, cadmium, cesium, chromium, cobalt, copper, hydrogen, iron, lead, lithium, magnesium, mercury, nickel, potassium, rubidium, silver, sodium, strontium, tin, zinc, iodide, nitride, oxide, or any combinations thereof.

In some embodiments, the adaptor can comprise between about one to about 100 charged chemical molecules. In some cases, the adaptor can comprise from about one charged chemical molecule to about 10 charged chemical molecules, from about 10 charged chemical molecules to about 20 charged chemical molecules, from about 20 charged chemical molecules to about 30 charged chemical molecules, from about 30 charged chemical molecules to about 40 charged chemical molecules, from about 40 charged chemical molecules to about 50 charged chemical molecules, from about 50 charged chemical molecules to about 60 charged chemical molecules, from about 60 charged chemical molecules to about 70 charged chemical molecules, from about 70 charged chemical molecules to about 80 charged chemical molecules, from about 80 charged chemical molecules to about 90 charged chemical molecules, or from about 90 charged chemical molecules to about 100 charged chemical molecules. In some cases, the adaptor can comprise at least about one charged chemical molecule, at least about five charged chemical molecules, at least about 10 charged chemical molecules, at least about 15 charged chemical molecules, at least about 20 charged chemical molecules, at least about 25 charged chemical molecules, at least about 30 charged chemical molecules, at least about 35 charged chemical molecules, at least about 40 charged chemical molecules, at least about 45 charged chemical molecules, at least about 50 charged chemical molecules, at least about 55 charged chemical molecules, at least about 60 charged chemical molecules, at least about 65 charged chemical molecules, at least about 70 charged chemical molecules, at least about 75 charged chemical molecules, at least about 80 charged chemical molecules, at least about 85 charged chemical molecules, at least about 90 charged chemical molecules, at least about 95 charged chemical molecules, at least about 100 charged chemical molecules, or more than 100 charged chemical molecules. In some cases, the adaptor can comprise at most about 100 charged chemical molecules, at most about 95 charged chemical molecules, at most about 90 charged chemical molecules, at most about 85 charged chemical molecules, at most about 80 charged chemical molecules, at most about 75 charged chemical molecules, at most about 70 charged chemical molecules, at most about 65 charged chemical molecules, at most about 60 charged chemical molecules, at most about 55 charged chemical molecules, at most about 50 charged chemical molecules, at most about 45 charged chemical molecules, at most about 40 charged chemical molecules, at most about 35 charged chemical molecules, at most about 30 charged chemical molecules, at most about 25 charged chemical molecules, at most about 20 charged chemical molecules, at most about 15 charged chemical molecules, at most about 10 charged chemical molecules, at most about 5 charged chemical molecules, at most about one charged chemical molecule, or less than one charged chemical molecule. In some cases, the adaptor can comprise about one charged chemical molecule, about five charged chemical molecules, about 10 charged chemical molecules, about 15 charged chemical molecules, about 20 charged chemical molecules, about 25 charged chemical molecules, about 30 charged chemical molecules, about 35 charged chemical molecules, about 40 charged chemical molecules, about 45 charged chemical molecules, about 50 charged chemical molecules, about 55 charged chemical molecules, about 60 charged chemical molecules, about 65 charged chemical molecules, about 70 charged chemical molecules, about 75 charged chemical molecules, about 80 charged chemical molecules, about 85 charged chemical molecules, about 90 charged chemical molecules, about 95 charged chemical molecules, or about 100 charged chemical molecules.

In some cases, the adaptor can increase the ion selectivity for anions by the adaptor comprising surface exposed positively charged chemical molecules. In some cases, the adaptor can increase the ion selectivity for cations by the adaptor comprising surface exposed negatively charged chemical molecules. The ion selectivity can be increased, for example, by increasing a net charge of the nanopore. The increase in charge can be negative or positive depending on the desired direction of the electro-osmotic flow.

An adaptor can extend a channel of a nanopore. In some embodiments, the adaptor can extend the circumference of the channel of the nanopore. In some embodiments, the adaptor can extend the channel of a nanopore by between about 0.1% to about 500%. In some cases, the adaptor can extend the channel of a nanopore by between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500%.

In some embodiments, the adaptor can extend the channel of a nanopore by at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more.

In some embodiments, the adaptor can extend the channel of a nanopore by at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less. In some embodiments, the adaptor can extend the channel of a nanopore by about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500%.

In some embodiments, the adaptor can extend at least a portion of a channel of a nanopore. In some embodiments, the adaptor can extend at least about one subunit of the nanopore. In some embodiments, the adaptor can extend at least about one subunit of the nanopore, at least about two subunits of the nanopore, at least about three subunits of the nanopore, at least about four subunits of the nanopore, at least about five subunits of the nanopore, at least about six subunits of the nanopore, at least about seven subunits of the nanopore, at least about eight subunits of the nanopore, or at least about nine subunits of the nanopore. In some cases, the adaptor can extend at most about nine subunits of the nanopore, at most about eight subunits of the nanopore, at most about seven subunits of the nanopore, at most about six subunits of the nanopore, at most about five subunits of the nanopore, at most about four subunits of the nanopore, at most about three subunits of the nanopore, at most about two subunits of the nanopore, at most about one subunits of the nanopore, or less. In some cases, the adaptor can extend about one subunit of the nanopore, about two subunits of the nanopore, about three subunits of the nanopore, about four subunits of the nanopore, about five subunits of the nanopore, about six subunits of the nanopore, about seven subunits of the nanopore, about eight subunits of the nanopore, or about nine subunits of the nanopore.

An adaptor can constrict at least a portion of a channel of a nanopore. In some embodiments, the adaptor can decrease the circumference of the channel of the nanopore. In some embodiments, the adaptor can constrict at least about one subunit of the nanopore. In some embodiments, the adaptor can constrict at least about one subunit of the nanopore, at least about two subunits of the nanopore, at least about three subunits of the nanopore, at least about four subunits of the nanopore, at least about five subunits of the nanopore, at least about six subunits of the nanopore, at least about seven subunits of the nanopore, at least about eight subunits of the nanopore, or at least about nine subunits of the nanopore. In some cases, the adaptor can constrict at most about nine subunits of the nanopore, at most about eight subunits of the nanopore, at most about seven subunits of the nanopore, at most about six subunits of the nanopore, at most about five subunits of the nanopore, at most about four subunits of the nanopore, at most about three subunits of the nanopore, at most about two subunits of the nanopore, at most about one subunits of the nanopore, or less. In some cases, the adaptor can constrict about one subunit of the nanopore, about two subunits of the nanopore, about three subunits of the nanopore, about four subunits of the nanopore, about five subunits of the nanopore, about six subunits of the nanopore, about seven subunits of the nanopore, about eight subunits of the nanopore, or about nine subunits of the nanopore.

In some embodiments, the adaptor can block a portion of the nanopore channel. In some cases, blocking a portion of the nanopore channel can reduce the ability of an analyte to move through the nanopore channel. In some cases, blocking a portion of the nanopore channel can reduce the ability of one or more salts to move through the nanopore channel. In some cases, blocking a portion of the nanopore channel can reduce the ability of one or more ions to move through the nanopore channel. In some cases, blocking a portion of the nanopore channel can reduce the ability of an analyte, one or more salts, and one or more ions to move through the nanopore channel.

In some embodiments, the adaptor can block at least about 0.01%, at least about 0.05%, at least about 0.1%, at least about 0.5%, at least about 1%, at least about 2.5%, at least about 5%, at least 7.5%, at least about 10%, at least about 12%, at least about 15%, at least about 18%, at least about 20%, at least about 25%, at least about 30%, at least about 35%, at least about 40%, at least about 45%, at least about 50%, at least about 60%, at least about 70%, at least about 80%, at least about 90%, at least about 100%, or greater than about 100% of the nanopore channel. In some embodiments, the adaptor can block at most about 100%, at most about 90%, at most about 80%, at most about 70%, at most about 60%, at most about 50%, at most about 45%, at most about 40%, at most about 35%, at most about 30%, at most about 25%, at most about 20%, at most about 18%, at most about 15%, at most about 12%, at most about 10%, at most about 7.5%, at most about 5%, at most about 2.5%, at most about 1%, at most about 0.5%, at most about 0.1%, at most about 0.05%, at most about 0.01%, or less than about 0.01% of the nanopore channel.

In some embodiments, the adaptor can block from about 0.01% to about 20% of the nanopore channel. In some embodiments, the adaptor can block from about 0.01% to about 0.05%, about 0.01% to about 0.1%, about 0.01% to about 0.5%, about 0.01% to about 1%, about 0.01% to about 2%, about 0.01% to about 3%, about 0.01% to about 4%, about 0.01% to about 5%, about 0.01% to about 10%, about 0.01% to about 15%, about 0.01% to about 20%, about 0.05% to about 0.1%, about 0.05% to about 0.5%, about 0.05% to about 1%, about 0.05% to about 2%, about 0.05% to about 3%, about 0.05% to about 4%, about 0.05% to about 5%, about 0.05% to about 10%, about 0.05% to about 15%, about 0.05% to about 20%, about 0.1% to about 0.5%, about 0.1% to about 1%, about 0.1% to about 2%, about 0.1% to about 3%, about 0.1% to about 4%, about 0.1% to about 5%, about 0.1% to about 10%, about 0.1% to about 15%, about 0.1% to about 20%, about 0.5% to about 1%, about 0.5% to about 2%, about 0.5% to about 3%, about 0.5% to about 4%, about 0.5% to about 5%, about 0.5% to about 10%, about 0.5% to about 15%, about 0.5% to about 20%, about 1% to about 2%, about 1% to about 3%, about 1% to about 4%, about 1% to about 5%, about 1% to about 10%, about 1% to about 15%, about 1% to about 20%, about 2% to about 3%, about 2% to about 4%, about 2% to about 5%, about 2% to about 10%, about 2% to about 15%, about 2% to about 20%, about 3% to about 4%, about 3% to about 5%, about 3% to about 10%, about 3% to about 15%, about 3% to about 20%, about 4% to about 5%, about 4% to about 10%, about 4% to about 15%, about 4% to about 20%, about 5% to about 10%, about 5% to about 15%, about 5% to about 20%, about 10% to about 15%, about 10% to about 20%, or about 15% to about 20% of the nanopore channel.

In some embodiments, the adaptor can block from about 20% to about 100% of the nanopore channel. In some embodiments, the adaptor can block from about 20% to about 25%, about 20% to about 30%, about 20% to about 35%, about 20% to about 40%, about 20% to about 45%, about 20% to about 50%, about 20% to about 60%, about 20% to about 70%, about 20% to about 80%, about 20% to about 90%, about 20% to about 100%, about 25% to about 30%, about 25% to about 35%, about 25% to about 40%, about 25% to about 45%, about 25% to about 50%, about 25% to about 60%, about 25% to about 70%, about 25% to about 80%, about 25% to about 90%, about 25% to about 100%, about 30% to about 35%, about 30% to about 40%, about 30% to about 45%, about 30% to about 50%, about 30% to about 60%, about 30% to about 70%, about 30% to about 80%, about 30% to about 90%, about 30% to about 100%, about 35% to about 40%, about 35% to about 45%, about 35% to about 50%, about 35% to about 60%, about 35% to about 70%, about 35% to about 80%, about 35% to about 90%, about 35% to about 100%, about 40% to about 45%, about 40% to about 50%, about 40% to about 60%, about 40% to about 70%, about 40% to about 80%, about 40% to about 90%, about 40% to about 100%, about 45% to about 50%, about 45% to about 60%, about 45% to about 70%, about 45% to about 80%, about 45% to about 90%, about 45% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100% of the nanopore channel.

In some embodiments, the adaptor can block about 0.01%, about 0.05%, about 0.1%, about 0.5%, about 1%, about 2.5%, about 5%, at least 7.5%, about 10%, about 12%, about 15%, about 18%, about 20%, about 25%, about 30%, about 35%, about 40%, about 45%, about 50%, about 60%, about 70%, about 80%, about 90%, or about 100% of the nanopore channel.

In some embodiments, the adaptor can constrict the channel of a nanopore. In some cases, the adaptor can constrict the channel of a nanopore by between about 0.1% to about 100%. In some cases, the adaptor can constrict the channel of a nanopore by between about 0.1% to about 1%, between about 1% to about 10%, between about 10% to about 20%, between about 20% to about 30%, between about 30% to about 40%, between about 40% to about 50%, between about 50% to about 60%, between about 60% to about 70%, between about 70% to about 80%, between about 80% to about 90%, or between about 90% to about 100%. In some cases, the adaptor can constrict the channel of a nanopore by at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, or more. In some cases, the adaptor can constrict the channel of a nanopore by at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less. In some cases, the adaptor can constrict the channel of the nanopore by about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the adaptor can be at least about 0.2 kDa in size. In some cases, the adaptor can be between about 0.2 kDa to about 100 kDa in size. In some cases, the adaptor can be between about 0.2 kDa to about 1 kDa, between about 1 kDa to about 5 kDa, between about 5 kDa to about 10 kDa, between about 10 kDa to about 15 kDa, between about 15 kDa to about 20 kDa, between about 20 kDa to about 25 kDa, between about 25 kDa to about 30 kDa, between about 30 kDa to about 35 kDa, between about 35 kDa to about 40 kDa, between about 40 kDa to about 45 kDa, between about 45 kDa to about 50 kDa, between about 50 kDa to about 55 kDa, between about 55 kDa to about 60 kDa, between about 60 kDa to about 65 kDa, between about 65 kDa to about 70 kDa, between about 70 kDa to about 75 kDa, between about 75 kDa to about 80 kDa, between about 80 kDa to about 85 kDa, between about 85 kDa to about 90 kDa, between about 90 kDa to about 95 kDa, or between about 95 kDa to about 100 kDa in size.

In some embodiments, the adaptor can be at least about 0.2 kDa, at least about 0.3 kDa, at least about 0.4 kDa, at least about 0.5 kDa, at least about 0.6 kDa, at least about 0.7 kDa, at least about 0.8 kDa, at least about 0.9 kDa, at least about 1 kDa, at least about 5 kDa, at least about 10 kDa, at least about 15 kDa, at least about 20 kDa, at least about 25 kDa, at least about 30 kDa, at least about 35 kDa, at least about 40 kDa, at least about 45 kDa, at least about 50 kDa, at least about 55 kDa, at least about 60 kDa, at least about 65 kDa, at least about 70 kDa, at least about 75 kDa, at least about 80 kDa, at least about 85 kDa, at least about 90 kDa, at least about 95 kDa, at least about 100 kDa, or more in size. In some embodiments, the adaptor can be at most about 100 kDa, at most about 95 kDa, at most about 90 kDa, at most about 85 kDa, at most about 80 kDa, at most about 75 kDa, at most about 70 kDa, at most about 65 kDa, at most about 60 kDa, at most about 55 kDa, at most about 50 kDa, at most about 45 kDa, at most about 40 kDa, at most about 35 kDa, at most about 30 kDa, at most about 25 kDa, at most about 20 kDa, at most about 15 kDa, at most about 10 kDa, at most about 5 kDa, at most about 1 kDa, at most about 0.9 kDa, at most about 0.8 kDa, at most about 0.7 kDa, at most about 0.6 kDa, at most about 0.5 kDa, at most about 0.4 kDa, at most about 0.3 kDa, at most about 0.2 kDa, or less in size. In some embodiments, the adaptor can be about 0.2 kDa, about 0.3 kDa, about 0.4 kDa, about 0.5 kDa, about 0.6 kDa, about 0.7 kDa, about 0.8 kDa, about 0.9 kDa, about 1 kDa, about 5 kDa, about 10 kDa, about 15 kDa, about 20 kDa, about 25 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, or about 100 kDa in size.

An adaptor can comprise one or more modules. An adaptor can modularly modify a nanopore.

In some embodiments, the adaptor can be a proteinaceous adaptor. In some cases, the proteinaceous adaptor can be a protein. In some cases, the proteinaceous adaptor can be a monomer. In some cases, the proteinaceous adaptor can comprise more than one protein subunits. In some cases, the proteinaceous adaptor can comprise at least about 1 protein subunit, at least about 2 protein subunits, at least about 3 protein subunits, at least about 4 protein subunits, at least about 5 protein subunits, at least about 6 protein subunits, at least about 7 protein subunits, at least about 8 protein subunits, at least about 9 protein subunits, at least about 10 protein subunits, at least about 12 protein subunits, at least about 15 protein subunits, at least about 18 protein subunits, at least about 20 protein subunits, at least about 25 protein subunits, at least about 30 protein subunits, at least about 35 protein subunits, at least about 40 protein subunits, at least about 45 protein subunits, at least about 50 protein subunits, or greater than about 50 protein subunits. In some cases, the proteinaceous adaptor can comprise at most about 50 protein subunits, at most about 45 protein subunits, at most about 40 protein subunits, at most about 35 protein subunits, at most about 30 protein subunits, at most about 25 protein subunits, at most about 20 protein subunits, at most about 18 protein subunits, at most about 15 protein subunits, at most about 12 protein subunits, at most about 10 protein subunits, at most about 9 protein subunits, at most about 8 protein subunits, at most about 7 protein subunits, at most about 6 protein subunits, at most about 5 protein subunits, at most about 4 protein subunits, at most about 3 protein subunits, at most about 2 protein subunits, at most about 1 protein subunit, or less than about 1 protein subunit.

In some cases, the proteinaceous adaptor can comprise from about 1 protein subunit to about 50 protein subunits. In some cases, the proteinaceous adaptor can comprise from about 1 protein subunit to about 2 protein subunits, about 1 protein subunit to about 3 protein subunits, about 1 protein subunit to about 4 protein subunits, about 1 protein subunit to about 5 protein subunits, about 1 protein subunit to about 10 protein subunits, about 1 protein subunit to about 15 protein subunits, about 1 protein subunit to about 20 protein subunits, about 1 protein subunit to about 25 protein subunits, about 1 protein subunit to about 30 protein subunits, about 1 protein subunit to about 40 protein subunits, about 1 protein subunit to about 50 protein subunits, about 2 protein subunits to about 3 protein subunits, about 2 protein subunits to about 4 protein subunits, about 2 protein subunits to about 5 protein subunits, about 2 protein subunits to about 10 protein subunits, about 2 protein subunits to about 15 protein subunits, about 2 protein subunits to about 20 protein subunits, about 2 protein subunits to about 25 protein subunits, about 2 protein subunits to about 30 protein subunits, about 2 protein subunits to about 40 protein subunits, about 2 protein subunits to about 50 protein subunits, about 3 protein subunits to about 4 protein subunits, about 3 protein subunits to about 5 protein subunits, about 3 protein subunits to about 10 protein subunits, about 3 protein subunits to about 15 protein subunits, about 3 protein subunits to about 20 protein subunits, about 3 protein subunits to about 25 protein subunits, about 3 protein subunits to about 30 protein subunits, about 3 protein subunits to about 40 protein subunits, about 3 protein subunits to about 50 protein subunits, about 4 protein subunits to about 5 protein subunits, about 4 protein subunits to about 10 protein subunits, about 4 protein subunits to about 15 protein subunits, about 4 protein subunits to about 20 protein subunits, about 4 protein subunits to about 25 protein subunits, about 4 protein subunits to about 30 protein subunits, about 4 protein subunits to about 40 protein subunits, about 4 protein subunits to about 50 protein subunits, about 5 protein subunits to about 10 protein subunits, about 5 protein subunits to about 15 protein subunits, about 5 protein subunits to about 20 protein subunits, about 5 protein subunits to about 25 protein subunits, about 5 protein subunits to about 30 protein subunits, about 5 protein subunits to about 40 protein subunits, about 5 protein subunits to about 50 protein subunits, about 10 protein subunits to about 15 protein subunits, about 10 protein subunits to about 20 protein subunits, about 10 protein subunits to about 25 protein subunits, about 10 protein subunits to about 30 protein subunits, about 10 protein subunits to about 40 protein subunits, about 10 protein subunits to about 50 protein subunits, about 15 protein subunits to about 20 protein subunits, about 15 protein subunits to about 25 protein subunits, about 15 protein subunits to about 30 protein subunits, about 15 protein subunits to about 40 protein subunits, about 15 protein subunits to about 50 protein subunits, about 20 protein subunits to about 25 protein subunits, about 20 protein subunits to about 30 protein subunits, about 20 protein subunits to about 40 protein subunits, about 20 protein subunits to about 50 protein subunits, about 25 protein subunits to about 30 protein subunits, about 25 protein subunits to about 40 protein subunits, about 25 protein subunits to about 50 protein subunits, about 30 protein subunits to about 40 protein subunits, about 30 protein subunits to about 50 protein subunits, or about 40 protein subunits to about 50 protein subunits.

In some cases, the proteinaceous adaptor can comprise about 1 protein subunit, about 2 protein subunits, about 3 protein subunits, about 4 protein subunits, about 5 protein subunits, about 6 protein subunits, about 7 protein subunits, about 8 protein subunits, about 9 protein subunits, about 10 protein subunits, about 12 protein subunits, about 15 protein subunits, about 18 protein subunits, about 20 protein subunits, about 25 protein subunits, about 30 protein subunits, about 35 protein subunits, about 40 protein subunits, about 45 protein subunits, or about 50 protein subunits.

In some embodiments, the proteinaceous adaptor can comprise one or more protein subunits. In some cases, the one or more protein subunits can be the same. In some cases, the one or more protein subunits can be different. In some cases, the one or more different subunits can be from different proteins.

A proteinaceous adaptor can comprise a CsgF subunit, a CsgF subunit truncation, CsgF subunit homologs, or any combination thereof. In some cases, the proteinaceous adaptor can be a monomeric adaptor. In some cases, the proteinaceous adaptor can be an oligomeric adaptor. In some cases, the proteinaceous oligomeric adaptor can comprise one or more protein subunits. In some cases, the one or more protein subunits can be identical. In some cases, the one or more protein subunits can be different. In some cases, the one or more different protein subunits can be derived from different proteins.

In some embodiments, the proteinaceous adaptor can comprise a donut shaped structure. In some cases, the donut shaped structure can comprise an inner channel. In some cases, the inner channel can comprise a length of from about 0.2 nm to about 3 nm. In some cases, the inner channel can comprise a length of at least about 0.2 nm, at least about 0.3 nm, at least about 0.4 nm, at least about 0.5 nm, at least about 0.6 nm, at least about 0.7 nm, at least about 0.8 nm, at least about 0.9 nm, at least about 1.0 nm, at least about 1.1 nm, at least about 1.2 nm, at least about 1.3 nm, at least about 1.4 nm, at least about 1.5 nm, at least about 1.6 nm, at least about 1.7 nm, at least about 1.8 nm, at least about 1.9 nm, at least about 2.0 nm, at least about 2.1 nm, at least about 2.2 nm, at least about 2.3 nm, at least about 2.4 nm, at least about 2.5 nm, at least about 2.6 nm, at least about 2.7 nm, at least about 2.8 nm, at least about 2.9 nm, at least about 3.0 nm, or more than 3.0 nm. In some cases, the inner channel can comprise a length of at most about 3.0 nm, at most about 2.9 nm, at most about 2.8 nm, at most about 2.7 nm, at most about 2.6 nm, at most about 2.5 nm, at most about 2.4 nm, at most about 2.3 nm, at most about 2.2 nm, at most about 2.1 nm, at most about 2.0 nm, at most about 1.9 nm, at most about 1.8 nm, at most about 1.7 nm, at most about 1.6 nm, at most about 1.5 nm, at most about 1.4 nm, at most about 1.3 nm, at most about 1.2 nm, at most about 1.1 nm, at most about 1.0 nm, at most about 0.9 nm, at most about 0.8 nm, at most about 0.7 nm, at most about 0.6 nm, at most about 0.5 nm, at most about 0.4 nm, at most about 0.3 nm, at most about 0.2 nm, or less than 0.2 nm. In some cases, the inner channel can comprise a length of about 0.2 nm, about 0.3 nm, about 0.4 nm, about 0.5 nm, about 0.6 nm, about 0.7 nm, about 0.8 nm, about 0.9 nm, about 1.0 nm, about 1.1 nm, about 1.2 nm, about 1.3 nm, about 1.4 nm, about 1.5 nm, about 1.6 nm, about 1.7 nm, about 1.8 nm, about 1.9 nm, about 2.0 nm, about 2.1 nm, about 2.2 nm, about 2.3 nm, about 2.4 nm, about 2.5 nm, about 2.6 nm, about 2.7 nm, about 2.8 nm, about 2.9 nm, or about 3.0 nm.

In some cases, the donut shaped structure can comprise an inner diameter (e.g., horizontal width). In some cases, the inner channel can comprise an inner diameter of from about 0.2 nm to about 3 nm. In some cases, the inner diameter can comprise a horizontal width of at least about 0.2 nm, at least about 0.3 nm, at least about 0.4 nm, at least about 0.5 nm, at least about 0.6 nm, at least about 0.7 nm, at least about 0.8 nm, at least about 0.9 nm, at least about 1.0 nm, at least about 1.1 nm, at least about 1.2 nm, at least about 1.3 nm, at least about 1.4 nm, at least about 1.5 nm, at least about 1.6 nm, at least about 1.7 nm, at least about 1.8 nm, at least about 1.9 nm, at least about 2.0 nm, at least about 2.1 nm, at least about 2.2 nm, at least about 2.3 nm, at least about 2.4 nm, at least about 2.5 nm, at least about 2.6 nm, at least about 2.7 nm, at least about 2.8 nm, at least about 2.9 nm, at least about 3.0 nm, or more than 3.0 nm. In some cases, the inner diameter can comprise a horizontal width of at most about 3.0 nm, at most about 2.9 nm, at most about 2.8 nm, at most about 2.7 nm, at most about 2.6 nm, at most about 2.5 nm, at most about 2.4 nm, at most about 2.3 nm, at most about 2.2 nm, at most about 2.1 nm, at most about 2.0 nm, at most about 1.9 nm, at most about 1.8 nm, at most about 1.7 nm, at most about 1.6 nm, at most about 1.5 nm, at most about 1.4 nm, at most about 1.3 nm, at most about 1.2 nm, at most about 1.1 nm, at most about 1.0 nm, at most about 0.9 nm, at most about 0.8 nm, at most about 0.7 nm, at most about 0.6 nm, at most about 0.5 nm, at most about 0.4 nm, at most about 0.3 nm, at most about 0.2 nm, or less than 0.2 nm. In some cases, the inner diameter can comprise a horizontal width of about 0.2 nm, about 0.3 nm, about 0.4 nm, about 0.5 nm, about 0.6 nm, about 0.7 nm, about 0.8 nm, about 0.9 nm, about 1.0 nm, about 1.1 nm, about 1.2 nm, about 1.3 nm, about 1.4 nm, about 1.5 nm, about 1.6 nm, about 1.7 nm, about 1.8 nm, about 1.9 nm, about 2.0 nm, about 2.1 nm, about 2.2 nm, about 2.3 nm, about 2.4 nm, about 2.5 nm, about 2.6 nm, about 2.7 nm, about 2.8 nm, about 2.9 nm, or about 3.0 nm.

In some embodiments, the proteinaceous adaptor can comprise at most about 10 nm in vertical height. In some embodiments, proteinaceous adaptor can comprise at most about 2 nm in vertical height, at most about 3 nm in vertical height, at most about 4 nm in vertical height, at most about 5 nm in vertical height, at most about 6 nm in vertical height, at most about 7 nm in vertical height, at most about 8 nm in vertical height, at most about 9 nm in vertical height, or at most about 10 nm in vertical height. In some cases, the proteinaceous adaptor can comprise about 2 nm in vertical height, about 3 nm in vertical height, about 4 nm in vertical height, about 5 nm in vertical height, about 6 nm in vertical height, about 7 nm in vertical height, about 8 nm in vertical height, about 9 nm in vertical height, or about 10 nm in vertical height.

In some embodiments, the proteinaceous adaptor can comprise at most about 20 nm in horizontal width. In some embodiments, proteinaceous adaptor can comprise at most about 2 nm in horizontal width, at most about 3 nm in horizontal width, at most about 4 nm in horizontal width, at most about 5 nm in horizontal width, at most about 6 nm in horizontal width, at most about 7 nm in horizontal width, at most about 8 nm in horizontal width, at most about 9 nm in horizontal width, at most about 10 nm in horizontal width, at most about 11 nm in horizontal width, at most about 12 nm in horizontal width, at most about 13 nm in horizontal width, at most about 14 nm in horizontal width, at most about 15 nm in horizontal width, at most about 16 nm in horizontal width, at most about 17 nm in horizontal width, at most about 18 nm in horizontal width, at most about 19 nm in horizontal width, or at most about 20 nm in horizontal width. In some cases, the proteinaceous adaptor can comprise about 2 nm in horizontal width, about 3 nm in horizontal width, about 4 nm in horizontal width, about 5 nm in horizontal width, about 6 nm in horizontal width, about 7 nm in horizontal width, about 8 nm in horizontal width, about 9 nm in horizontal width, about 10 nm in horizontal width, about 11 nm in horizontal width, about 12 nm in horizontal width, about 13 nm in horizontal width, about 14 nm in horizontal width, about 15 nm in horizontal width, about 16 nm in horizontal width, about 17 nm in horizontal width, about 18 nm in horizontal width, about 19 nm in horizontal width, or about 20 nm in horizontal width.

In some embodiments, the adaptor can be a chemical adaptor. In some cases, the chemical adaptor can comprise a non-protein based molecule. In some cases, the chemical adaptor can comprise a non-peptide based molecule. In some cases, a non-peptide based molecule can comprise cyclodextrin, cucurbituril, a cyclic peptide, or any combination thereof. In some embodiments, the chemical adaptor can comprise a macrocyclic molecule. In some cases, the macrocyclic molecule can comprise crown ethers, calixarenes, porphyrins, cyclosporines, cyclems, cyclams, or any combination thereof. A chemical adaptor can comprise a cyclodextrin, a cyclic peptide, a cucurbituril, crown ethers, calixarenes, porphyrins, cyclosporines, cyclems, cyclams, or any combination thereof.

Leader Construct

According to the present disclosure, an analyte may be coupled to a leader construct, for example to create analyte-leader construct complexes that can preload and/or stall translocases.

In some embodiments, it is not a pre-requisite to add leaders to make the system work. It is also possible to use unstalled translocase motors and then when target substrate is captured, there is a good chance of capturing the translocase at some point along the analyte. On the other hand, an advantage of having it stalled is that all the analytes start at the start.

Various leader construct designs are possible.

The leader may comprise some or all of the following elements:

1. A recognition motif
2. A capture motif
3. A stall motif
4. A block motif
5. A coupling motif The individual elements may be arranged in any different order. The elements might be combined in one motif, so that one sequence performs multiple functions.

In some embodiments, the coupling motif is positioned at the end, preceded by a block motif. Variations may include:

Recognition-capture-stall-block-coupling

Capture-stall-block-coupling

Recognition-stall-block-coupling

In some embodiments, translocases are capable of moving through a wide variety of chemical composition polymers, structures and cross-links, (Glynn et al. (2012) Nature Structural & Molecular Biology volume 19, pg. 616-622) so the various motifs may fully or partially consist of amino acids. They might contain no amino acids. The amino acids can be natural, non-natural, or a combination thereof. Since translocases are capable of moving along analytes either in the C-terminal to N-terminal direction or the N-terminal to C-terminal direction. The leader construct can be coupled to the C-terminal of the analyte. The leader construct can be coupled to the N-terminal of the analyte. the components of the leader may be arranged with either C>N or N>C orientation, or different combinations thereof in a single construct. The leader construct may contain stretches of other polymeric molecules, such as polyethylene glycol, PHEMA, polyacrylamide, polynucleotide, peptide nucleic acids or others such as those described in Schmidt et al., 2019, Polymers (Basel), 11, 4, pg. 693. The overall composition of the construct may be optimised for good water solubility. The composition may be optimised for low structural propensity in regions of capture to enable more efficient pore capture.

Leaders may be added to the N- or C-terminus of an analyte, or to both ends. Since translocases can run either N>C or C>N, adding a leader (e.g. of the same design) to both ends of an analyte can enable capture and threading in both the C>N and N>C directions, which can provide different information that can be combined informatically to improve accuracy of the analysis for example. Alternatively, both termini of the analyte are coupled to different leader construct designs, creating separate "leader" and "tail" ends. Leader-tail constructs can be used to control which behaviours occur at which end, for example to control the orientation of the capture of the analyte, the loading and relative direction of the translocase, etc. For example, in combination with a leader that directs binding of translocase and capture in the nanopore (e.g. leader contains translocase recognition motif/capture motif/stall motif/block motif), a simple tail sequence (e.g. simple unstructured amino acid sequence) can be added to the opposite end to add additional sequence for translocase to travel along during nanopore translocation so that the entirety of the analyte sequence passes through the nanopore before the translocase encounters the end of the molecule and unbinds.

Recognition Motif

In some embodiments, the recognition motif can configure the binding of the leader-conjugated analyte to the translocase/unfoldase. In some cases, a recognition motif can comprise the peptide tag ssrA (AANDENYALAA (SEQ ID NO: 19)), or portion thereof, to enhance binding of the analyte to the translocase. In some cases, the translocase can comprise ClpX, ClpA, ClpC, ClpE, PAN, FtsH, VAT, or any combination thereof. In some cases, the recognition motif can comprise a pup tag (Prokaryotic Ubiquitin-like Protein, MAQEQTKRGGGGGGDDDDIAGSTAAGQERREKL-TEETDDLLDEIDDVLEENAEDFVRAYVQK GGQ (SEQ ID NO: 20)). In some cases, the translocases can comprise Mpa. In some cases, the recognition motif can comprise C-terminal residues from SulA (SASSHATRQLSGLKIHSNLYH (SEQ ID NO: 21)). In some cases, the translocase can comprise HslU or Lon. In some cases, the recognition motif can comprise: (i) Pex15$^{254-309}$ AKSKGKQRGVKQKIHHFHEPMLHNSSE-EQVKVEDAFNQRTSTDSRLQSTGTAPRKK (SEQ ID NO: 22), (ii) Pex15$^{43-309}$ SEVFQECVNLFIKRDIKD-CLEKMSEVGFIDITVFKSNPMILD-LFVSACDIMPSFTKLGLTLQSEIL NIFTLDTPQCI-ETRKIILGDLSKLLVINKFFRCCIKVIQFNL TDHTEQEEKTLELESIMSDFIFVYIT KMRTTI-DVVGLQELIEIFIFQVKVKLHHKKPSPNMYWALCK-TLPKLSPTLKGLYLSKDVSIED AILN-SIDNKIQKDKAKSKGKQRGVKQK IHHFHEPMLHNSSEEQVKVEDAFNQRTSTDSRLQST GTAPRKK (SEQ ID NO: 23), (iii) Pex15$^{1-309}$ MAASE-IMNNLPMHSLDSSLRDLLNDDLFIES-DESTKSVNDQRSEVFQEXVNLFIKRDIKDCLE KMSEVGFIDITVFKSNPMILD-LFVSACDIMPSFTKLGLTLQSEILNIFTLDTPQCI-ETRKIILGDLS KLLVINKFFRCCIDVIQFNLTDHTE-QEEKTLELESIMSDFIFVYITKMRTTI DVVGLQELIEIFIFQ VKVKLHHKKPSPNMYWALCK-TLPKLSPTLKGLYLSKDVSEIDAILN-SIDNKIQKDKAKSKGK QRGVKQKIHHFHEPMLHNS-SEEQVKVEDAFNQRTSDRRLQSTGTAPRKK (SEQ ID NO: 24)), or any combination thereof.

Also encompassed are genetically engineered (mutated) variants of (known) recognition elements, e.g. those resulting from a screening to discover what binds (such as described in Flynn et al., 2001, Proc Natl Acad Sci USA, 98, 19, pg. 10584-9), or where translocase is evolved to recognise a chosen sequence.

Capture Motif

In some embodiments, the capture motif is optimised for capture of the analyte in the nanopore. The recognition motif and pore-capture motif may be combined in one, bifunctional motif. The capture motif comprises amino acids with a net charge to facilitate capture in a nanopore under the appropriate applied voltage by mechanisms of electrophoretic attraction. For example, the motif may be comprised of some or all positively charged amino acids, where capture is improved in conditions where a negative applied voltage is applied to the opposite side of the membrane in which the substrate is contained so that it is attracted into the pore (or vice versa for a negatively charged capture motif).

In some embodiments, the capture motif can be unstructured to enable efficient capture in the nanopore. In some cases, the capture motif can be linear. The capture motif is ideally designed to be long enough to aid efficient capture in the pore and in combination with other motifs is designed so that when captured in the nanopore from the cis side it reaches to the trans exit of the nanopore or vice versa when the bound translocase contacts the top of the nanopore and prevents further uncontrolled translocation.

In some cases, a polyanion tag might be wholly or partially created from n repeats of (SGD)n, (SD)n, (D) n or various combinations thereof. Alternatively, a polycation tag might be wholly or partially created from n repeats of (SGR)n, (SR)n, (R) n or various combinations thereof. These are not intended to be limiting, and a person of skill in the art may understand that many more combinations of charged residues are possible and there are straightforward mechanisms of assessing that they enable capture by the nanopore under the chosen conditions (salt type, salt concentration, pH, orientation of applied voltage, polarity of net charge inside nanopore, etc) using the experimental systems described herein. For example, a polyanion capture tag can be used in combination with a nanopore with net positive internal charges in a system with a positive voltage applied to the trans compartment with a net EOF is cis-to-trans, wherein the tagged analyte is added to the cis side. The capture tag is a polycation tag, used in a system with a nanopore with net negative internal charge where a negative voltage is applied to the trans compartment to create a strong net EOF cis-to-trans, wherein the tagged analyte is added to the cis side.

Stall Motif

The stall motif can be a region of low traction for the translocase protein. In some cases, the paddles of the translocase protein may not be able to grip the analyte to move the analyte. That is a region upon which the translocase cannot easily gain traction, e.g. due to a lack of side chains or small side chains, or side chains that do not interact favourably with the "paddles" through which the translocase exerts its NTP driven powerstroke. When encountering the stall region the translocase will struggle to proceed and will undergo futile NTP turnover, most likely undergoing progressive periods of moving, slipping, back sliding, rebinding, moving etc. Without wishing to be limited, the stall motif comprises a suitably long stretch amino acid residues such as glycines, alanines etc. and other sequences based on those described in Hiu-Mei Too et al., 2013, J Biol Chem, 288, 19, pg. 13243-57, for example 3 glycines, or 6 glycines (SEQ ID NO: 4), or 9 glycines (SEQ ID NO: 58) or more. Optionally, the glycines are interspersed with other residues, such as serine, to improve polypeptide properties such as structure and solubility.

In some embodiments, the stall motif can comprise non-amino acid polymeric linker chemistry, such as for example, polyethylene glycol, polyacrylamide, polynucleotide etc, where the length of the polymer is longer than the footprint of the translocase. Many suitable linker chemistries may be used.

Block Motif

The block motif can be a region positioned after the stall region through which the translocase cannot easily progress. A block region after a stall region is to prevent the translocase diffusing past the stall region and regaining traction on the substrate beyond the stall. Alternatively, the block motif can replace the stall region if it is sufficiently robust and which the translocase is unable to overcome on its own.

In some embodiments, the block motif can be designed to provide some type of steric blockade. For example, the block may be formed by a folded analyte structure that is part of the analyte backbone of the translocated substrate that the analyte cannot easily unfold. The block motif can be a protein such as Maltose Binding Protein (MBP), Titin etc. Specific exemplary block motifs include proteins (enzymes) that are resistant to unfolding by ClpX, for example dihydrofolate reductase or barnase in presence of stabilizing ligands.

In some embodiments, the block motif is a large bulky side chain. The large bulky side-chain might for example be a covalently bound large molecule, such as a carbohydrate, a multi-ring molecule, or a branched dextran. Alternatively, the side chain might have a relatively small binder to which a larger species is bound non-covalently (and which is displaced when the motor proceeds through the block), such as for example a biotin to which a streptavidin protein is bound, or a small antigen element to which a nanobody or antibody is bound.

The leader construct may have stall and/or block motif(s) depending on the relative combined ability to limit progression of the translocase through the analyte.

Coupling Motif

The coupling motif can allow for conjugation of the leader construct to the analyte. For example, it provides the chemistry for chemically attaching the leader to the analyte. Chemical coupling systems and coupling motifs are known in the art. They include coupling chemistries for attaching to target analytes with cysteines or lysines. The motif comprises a tag for specifically coupling to either the N- or C-termini of any analyte. For example, N-terminal targeting chemistries are known (Rosen et al. 2017, Nature Chemical Biology Vol. 13, pg. 697-705).

In some embodiments, the coupling motif may be a comprised of sequence that enables an enzymatic mechanism of coupling the leader to the analyte. For example, it comprises a motif for binding/loading of an enzyme having peptide ligase activity, such as a broad spectrum peptiligase (e.g. Toplak et al., 2016, Water. Adv Synth Catal, 358, pg. 2140-7) e.g. omniligase (Nuijens T et al. (2016). Adv Synth Catal 358:4041-4048) or a similar enzyme. The coupling motif may employ recognition sequences that enable enzymes such as Sortases to couple either to the N- or C-terminus (Guimaraes et al. 2013, Nature Prot. Vol. 8, pg. 1787-1799).

In one embodiment, the analyte is conjugated at its N-terminus, or its C-terminus or both its N- and C-terminus to a leader construct of similar composition, so that when added to the nanopore system capture and translocation is enabled both N-to-C and C-to-N depending on what end the captured leader was attached. This enables analytes to be characterized both in an N-to-C direction and a C-to-N direction. This can be advantageous to improve the accuracy of characterization, for example to capture information that is different in the each orientation.

According to the present disclosure, an analyte may be conjugated to the leader construct using chemical or enzymatic mechanism. The method may comprise the operation of conjugating analyte to a leader construct. In one embodiment, analyte conjugation to a leader construct is performed prior to contacting an analyte with protein translocase. See FIG. 7A.

In another embodiment, the leader construct is pre-loaded with protein translocase prior to conjugation to the analyte. See FIG. 7B.

Barcode Motif

The leader construct may also contain a barcode motif/sequence that produces a unique signal when passing through the nanopore so as to uniquely identify the Leader from a mixture of other barcoded leader constructs. Barcodes can be used to label multiple separate samples that are then combined and run as a single pool in nanopore system, enabling the separate barcoded samples to be separated again informatically based on their unique signals. Barcode motifs can be created from different amino-acid sequences, non-natural amino acids, modified amino acids, or other polymer moieties or combinations thereof to create unique signals when passed through a nanopore.

Membrane Binding Motif

The leader construct may also contain a membrane- or nanopore-binding motif to direct the binding of the Leader construct and attached analyte either to a membrane or a nanopore, respectively. Membrane binding molecules are known in the art, and include for example hydrophobic or amphipathic molecules such as cholesterol that can be attached to the Leader via a side chain. Alternatively, the Leader construct may comprise a sequence that forms an amphipathic structure, e.g. an amphipathic alpha helix (Manuel Giménez-Andrés et al., Biomolecules. 2018 September; 8 (3): 45 to enable membrane association.

Binding and Preloading

In another aspect of the present disclosure, provided herein is a method comprising: providing a nanopore system. The nanopore system may comprise a membrane comprising a nanopore. In some cases, the membrane may separate the fluidic chamber into a cis side and a trans side. A non-nucleic acid based polymer analyte may also be provided. In some cases, the method can further comprise adding a combined solution to the cis side of the fluidic chamber. The combined solution can comprise the non-nucleic acid based polymer analyte, a preloading solution, or the non-nucleic acid based polymer analyte and a preloading solution. In some cases, the method can further comprise translocating the non-nucleic acid based polymer analyte. The non-nucleic acid based polymer analyte can be translocated from the cis side of the fluidic chamber to the trans side of the fluidic chamber.

In another aspect of the present disclosure, provided herein is a system comprising: a nanopore system. The nanopore system may comprise a membrane comprising a nanopore. In some cases, the membrane may separate the fluidic chamber into a cis side and a trans side. A non-nucleic acid based polymer analyte may also be provided. In some cases, the cis side of the fluidic chamber can comprise a first solution. In some cases, the trans side of the fluidic chamber can comprise a second solution. The first solution and the second solution may be configured to translocase the non-nucleic acid based polymer analyte across the nanopore. In some cases, the system can further comprise a preloading solution. The preloading solution may be configured to interact with the non-nucleic acid based polymer analyte.

In one embodiment one or more translocases are bound and/or loaded onto the analyte prior to addition to the nanopore system of the present disclosure, which we term "preloading" herein. The preloading is performed under conditions that favour high efficiency of binding and/or loading, and/or optimal translocase movement along the analyte (whether modified or unmodified). For example, in one embodiment the translocase and one or more analytes are incubated at relatively higher concentration, and then diluted when added to the nanopore system of the present disclosure. In some embodiments, the preloading solution can be dilution prior to adding to one or more analytes. In some cases, the preloading solution can be diluted in solvent. In some cases, the preloading solution:solvent dilution can comprise from about 1:1 to about 1:100. In some cases, the preloading solution:solvent dilution can be at least about 1:1, at least about 1:2, at least about 1:5, at least about 1:10, at least about 1:20, at least about 1:25, at least about 1:30, at least about 1:40, at least about 1:50, at least about 1:60, at least about 1:70, at least about 1:75, at least about 1:80, at least about 1:90, at least about 1:100, or more than 1:100. In some cases, the preloading solution:solvent dilution can be at most about 1:100, at most about 1:90, at most about 1:80, at most about 1:75, at most about 1:70, at most about 1:60, at most about 1:50, at most about 1:40, at most about 1:30, at most about 1:25, at most about 1:20, at most about 1:10, at most about 1:5, at most about 1:2, at most about 1:1, or less than 1:1. In some cases, the preloading solution:solvent dilution can comprise about 1:1, about 1:2, about 1:5, about 1:10, about 1:20, about 1:25, about 1:30, about 1:40, about 1:50, about 1:60, about 1:70, about 1:75, about 1:80, about 1:90, or about 1:100.

The preloading is performed in conditions closer to the optimal binding conditions than employed in the nanopore system of the present disclosure. For example, preloading is performed in solutions that are closer to the optimal salt concentration and salt types, the optimal pH, the optimal temperature, and in the presence of optimal co-factors (e.g. NTP, $M^{2+}$ ions, etc). Preloading may also be performed in combination with accessory cofactors that aid in binding. These include but are not limited to proteins derived from naturally occurring substrate adaptors such as those described in Bouchnak et al., 2021, J Biol Chem., 296, pg. 100338 (e.g., NblA/B, ClpS, ClpF), or engineered binding cofactors such as ones derived from antibodies, nanobodies, affimers etc.

In some embodiments, the analyte can be contacted with the preloading solution. In some cases, the preloading solution can comprise one or more translocases or one or more leader constructs. In some cases, the preloading solution can comprise one or more translocases and one or more leader constructs. In some instances, the one or more leader construct can be coupled to the one or more translocases in the preloading solution. In some cases, contacting the analyte with the preloading solution can result in coupling of the analyte with a leader construct of the one or more leader constructs. In some cases, the analyte is coupled to the leader construct via the coupling motif to form an analyte-leader construct complex. In some cases, subsequent to the contacting the analyte with the preloading solution, the analyte-leader construct complex can couple to a translocase of the one or more translocases in the preloading solution. In some cases, the analyte-leader construct complex can couple to the translocase via the capture motif of the leader construct to form an analyte-translocase complex. In some embodiments, the analyte-translocase complex can be added to the nanopore system. In some cases, the analyte-translocase complex can be added to the cis side of the nanopore system. In some cases, the analyte-translocase complex can be added to the trans side of the nanopore system. In some cases, the analyte-translocase complex can contact the nanopore of the nanopore system.

In some embodiments, the analyte can be contacted with one or more leader constructs to form an analyte-leader construct complex. In some cases, the analyte-leader construct complex can be contacted with one or more translocases. In some cases, the analyte-leader construct complex and the one or more translocases mixture can be added to the nanopore system. In some cases, the analyte-leader construct complex and the one or more translocases mixture can be added to the cis side of the nanopore system. In some cases, the analyte-leader construct complex and the one or more translocases mixture can be added to the trans side of the nanopore system.

In some embodiments, the preloading solution can comprise one or more translocases and one or more leader constructs. In some cases, an analyte can be contacted with the preloading solution. In some cases, the analyte-preloading solution mixture can be added to the nanopore system. In some cases, the analyte-preloading solution mixture can be added to the cis side of the nanopore system. In some cases, the analyte-preloading solution mixture can be added to the trans side of the nanopore mixture.

In some embodiments, the preloading solution can comprise one or more translocases. In some cases, an analyte can be contacted with the preloading solution to form an analyte-translocase complex. In some cases, the analyte-translocase complex can be added to the nanopore system. In some cases, the analyte-translocase complex can be added to the cis side of the nanopore system. In some cases, the analyte-translocase complex can be added to the trans side of the nanopore system.

In some aspects, the present disclosure provides a preloading solution. In some embodiments, the preloading solution can have one or more translocases. In some cases, the preloading solution can have between one translocase to about 10,000 translocases. In some cases, the preloading solution can have between about one translocase to about ten translocases, between about ten translocases to about 20 translocases, between about 20 translocases to about 30 translocases, between about 30 translocases to about 40 translocases, between about 40 translocases to about 50 translocases, between about 50 translocases to about 60 translocases, between about 60 translocases to about 70 translocases, between about 70 translocases to about 80 translocases, between about 80 translocases to about 90 translocases, between about 90 translocases to about 100 translocases, between about 100 translocases to about 200 translocases, between about 200 translocases to about 300 translocases, between about 300 translocases to about 400 translocases, between about 400 translocases to about 500 translocases, between about 500 translocases to about 600 translocases, between about 600 translocases to about 700 translocases, between about 700 translocases to about 800 translocases, between about 800 translocases to about 900 translocases, between about 900 translocases to about 1,000 translocases, between about 1,000 translocases to about 2,000 translocases, between about 2,000 to about 3,000 translocases, between about 3,000 translocases to about 4,000 translocases, between about 4,000 translocases to about 5,000 translocases, between about 5,000 translocases to about 6,000 translocases, between about 6,000 translocases to about 7,000 translocases, between about 7,000 translocases to about 8,000 translocases, between about 8,000 translocases to about 9,000 translocases, or between about 9,000 translocases to about 10,000 translocases.

In some embodiments, the preloading solution can have at least about one translocase, at least about five translocases, at least about 10 translocases, at least about 15 translocases, at least about 20 translocases, at least about 25 translocases, at least about 30 translocases, at least about 35 translocases, at least about 40 translocases, at least about 45 translocases, at least about 50 translocases, at least about 55 translocases, at least about 60 translocases, at least about 65 translocases, at least about 70 translocases, at least about 75 translocases, at least about 80 translocases, at least about 85 translocases, at least about 90 translocases, at least about 95 translocases, at least about 100 translocases, at least about 150 translocases, at least about 200 translocases, at least about 250 translocases, at least about 300 translocases, at least about 350 translocases, at least about 400 translocases, at least about 450 translocases, at least about 500 translocases, at least about 550 translocases, at least about 600 translocases, at least about 650 translocases, at least about 700 translocases, at least about 750 translocases, at least about 800 translocases, at least about 850 translocases, at least about 900 translocases, at least about 950 translocases, at least about 1,000 translocases, at least about 1,500 translocases, at least about 2,000 translocases, at least about 2,500 translocases, at least about 3,000 translocases, at least about 3,500 translocases, at least about 4,000 translocases, at least about 4,500 translocases, at least about 5,000 translocases, at least about 5,500 translocases, at least about 6,000 translocases, at least about 6,500 translocases, at least about 7,000 translocases, at least about 7,500 translocases, at least about 8,000 translocases, at least about 8,500 translocases, at least about 9,000 translocases, at least about 9,500 translocases, at least about 10,000 translocases, or more.

In some cases, the preloading solution can have at most about 10,000 translocases, at most about 9,500 translocases, at most about 9,000 translocases, at most about 8,500 translocases, at most about 8,000 translocases, at most about 7,500 translocases, at most about 7,000 translocases, at most about 6,500 translocases, at most about 6,000 translocases, at most about 5,500 translocases, at most about 5,000 translocases, at most about 4,500 translocases, at most about 4,000 translocases, at most about 3,500 translocases, at most about 3,000 translocases, at most about 2,500 translocases, at most about 2,000 translocases, at most about 1,500 translocases, at most about 1,000 translocases, at most about 950 translocases, at most about 900 translocases, at most about 850 translocases, at most about 800 translocases, at most about 750 translocases, at most about 700 translocases, at most about 650 translocases, at most about 600 translocases, at most about 550 translocases, at most about 500 translocases, at most about 450 translocases, at most about 400 translocases, at most about 350 translocases, at most about 300 translocases, at most about 250 translocases, at most about 200 translocases, at most about 150 translocases, at most about 100 translocases, at most about 95 translocases, at most about 90 translocases, at most about 85 translocases, at most about 80 translocases, at most about 75 translocases, at most about 70 translocases, at most about 65 translocases, at most about 60 translocases, at most about 55 translocases, at most about 50 translocases, at most about 45 translocases, at most about 40 translocases, at most about 35 translocases, at most about 30 translocases, at most about 25 translocases, at most about 20 translocases, at most about 15 translocases, at most about 10 translocases, at most about 5 translocases, at most about translocase, or less.

In some cases, the preloading solution can have about one translocase, about five translocases, about ten translocases, about 15 translocases, about 20 translocases, about 25 translocases, about 30 translocases, about 35 translocases, about 40 translocases, about 45 translocases, about 50 translocases, about 55 translocases, about 60 translocases, about 65 translocases, about 70 translocases, about 75 translocases, about 80 translocases, about 85 translocases, about 90 translocases, about 95 translocases, about 100 translocases, about 150 translocases, about 200 translocases, about 250 translocases, about 300 translocases, about 350 translocases, about 400 translocases, about 450 translocases, about 500 translocases, about 550 translocases, about 600 translocases, about 650 translocases, about 700 translocases, about 750 translocases, about 800 translocases, about 850 translocases, about 900 translocases, about 950 translocases, about 1,000 translocases, about 1,500 translocases, about 2,000 translocases, about 2,500 translocases, about 3,000 translocases, about 3,500 translocases, about 4,000 translocases, about 4,500 translocases, about 5,000 translocases, about 5,500 translocases, about 6,000 translocases, about 6,500 translocases, about 7,000 translocases, about 7,500 translocases, about 8,000 translocases, about 8,500 translocases, about 9,000 translocases, about 9,500 translocases, or 10,000 translocases.

In some embodiments, the preloading solution can have a leader construct of the present disclosure. Alternatively, in some embodiments, the preloading solution may not have a leader construct of the present disclosure.

In some embodiments, the preloading solution can further comprise one or more chemical groups. In some cases, the one or more chemical groups can enhance coupling of the analyte to a component of the preloading solution. In some cases, the component can be the one or more translocases. In some instances, the component may not be the one or more translocases. In some cases, the component can be one or more constructs. In some cases, the component can be one or more leader constructs.

In some embodiments, the one or more chemical groups can enhance binding of the analyte to a component of the preloading solution. In some cases, the component of the preloading solution can be one or more translocases. In some embodiments, the binding of the analyte to the one or more translocases is higher in the preloading solution compared to binding of the analyte and one or more translocases in the nanopore system. In some embodiments, the binding of the analyte to the one or more translocases in the preloading solution can be between about 0.1% to about 500% higher compared to binding of the analyte to one or more translocases in the fluidic chamber. In some embodiments, the binding of the analyte to the one or more translocases in the preloading solution can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% higher compared to binding of the analyte to one or more translocases in the fluidic chamber.

In some embodiments, the binding of the analyte to the one or more translocases in the preloading solution can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more higher compared to binding of the analyte to one or more translocases in the fluidic chamber.

In some embodiments, the binding of the analyte to the one or more translocases in the preloading solution can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less higher compared to binding of the analyte to one or more translocases in the fluidic chamber.

In some embodiments, the binding of the analyte to the one or more translocases in the preloading solution can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% higher compared to binding of the analyte to one or more translocases in the fluidic chamber.

In some embodiments, the one or more chemical groups can enhance binding of the analyte to a component of the preloading solution. In some cases, the component of the preloading solution can be one or more constructs. Non-limiting examples of one or more constructs include unfoldases or translocases. In some embodiments, the binding of the analyte to the one or more constructs is higher in the preloading solution compared to binding of the analyte and one or more constructs in the fluidic chamber.

In some embodiments, the binding of the analyte to the one or more constructs in the preloading solution can be between about 0.1% to about 500% higher compared to binding of the analyte to one or more constructs in the fluidic chamber. In some embodiments, the binding of the analyte to the one or more constructs in the preloading solution can be between about 0.1% to about 0.5%, between about 0.5% to about 1%, between about 1% to about 5%, between about 5% to about 10%, between about 10% to about 20%, between about 20% to about 30%, between about 30% to about 40%, between about 40% to about 45%, between about 45% to about 50%, between about 50% to about 55%, between about 55% to about 60%, between about 60% to about 65%, between about 65% to about 70%, between about 70% to about 75%, between about 75% to about 80%, between about 80% to about 85%, between about 85% to about 90%, between about 90% to about 95%, between about 95% to about 100%, between about 100% to about 110%, between about 110% to about 120%, between about 120% to about 130%, between about 130% to about 140%, between about 140% to about 150%, between about 150% to about 160%, between about 160% to about 170%, between about 170% to about 180%, between about 180% to about 190%, between about 190% to about 200%, between about 200% to about 210%, between about 210% to about 220%, between about 220% to about 230%, between about 230% to about 240%, between about 240% to about 250%, between about 250% to about 260%, between about 260% to about 270%, between about 270% to about 280%, between about 280% to about 290%, between about 290% to about 300%, between about 300% to about 310%, between about 310% to about 320%, between about 320% to about 330%, between about 330% to about 340%, between about 340% to about 350%, between about 350% to about 360%, between about 360% to about 370%, between about 370% to about 380%, between about 380% to about 390%, between about 390% to about 400%, between about 400% to about 410%, between about 410% to about 420%, between about 420% to about 430%, between about 430% to about 440%, between about 440% to about 450%, between about 450% to about 460%, between about 460% to about 470%, between about 470% to about 480%, between about 480% to about 490%, or between about 490% to about 500% higher compared to binding of the analyte to one or more constructs in the fluidic chamber.

In some embodiments, the binding of the analyte to the one or more constructs in the preloading solution can be at least about 0.1%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, or more higher compared to binding of the analyte to one or more constructs in the fluidic chamber.

In some embodiments, the binding of the analyte to the one or more constructs in the preloading solution can be at most about 500%, at most about 490%, at most about 480%, at most about 470%, at most about 460%, at most about 450%, at most about 440%, at most about 430%, at most about 420%, at most about 410%, at most about 400%, at most about 390%, at most about 380%, at most about 370%, at most about 360%, at most about 350%, at most about 340%, at most about 330%, at most about 320%, at most about 310%, at most about 300%, at most about 290%, at most about 280%, at most about 270%, at most about 260%, at most about 250%, at most about 240%, at most about 230%, at most about 220%, at most about 210%, at most about 200%, at most about 190%, at most about 180%, at most about 170%, at most about 160%, at most about 150%, at most about 140%, at most about 130%, at most about 120%, at most about 110%, at most about 100%, at most about 95%, at most about 90%, at most about 85%, at most about 80%, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, at most about 5%, at most about 1%, at most about 0.5%, at most about 0.1%, or less higher compared to binding of the analyte to one or more constructs in the fluidic chamber.

In some embodiments, the binding of the analyte to the one or more constructs in the preloading solution can be about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% higher compared to binding of the analyte to one or more constructs in the fluidic chamber.

In some embodiments, the preloading solution can have between one to about 100 chemical groups. In some cases, the preloading solution can have at least about 1 chemical group, at least about 10 chemical groups, at least about 20 chemical groups, at least about 30 chemical groups, at least about 40 chemical groups, at least about 50 chemical groups, at least about 60 chemical groups, at least about 70 chemical groups, at least about 80 chemical groups, at least about 90 chemical groups, at least about 100 chemical groups, or more. In some cases, the preloading solution can have at most about 100 chemical groups, at most about 90 chemical groups, at most about 80 chemical groups, at most about 70 chemical groups, at most about 60 chemical groups, at most about 50 chemical groups, at most about 40 chemical groups, at most about 30 chemical groups, at most about 20 chemical groups, at most about 10 chemical groups, at most about one chemical group, or less. In some cases, the preloading solution can have about one chemical group, about 10 chemical groups, about 20 chemical groups, about 30 chemical groups, about 40 chemical groups, about 50 chemical groups, about 60 chemical groups, about 70 chemical groups, about 80 chemical groups, about 90 chemical groups, or about 100 chemical groups.

In some embodiments, the preloading solution can further comprise one or more factors. Non-limiting examples of cofactors include NTP, $M^{2+}$, NblA/B, ClpS, ClpF, Hsp10, Hsp60, calnexin, Erp29, Erp57, polyethylene glycol, dextran, Ficoll, iron manganese, cobalt, copper, penicillamine, trientine, sodium calcium edetate, or ethylenediaminetetraacetic acid, and any combinations thereof. In some embodiments, the preloading solution can have between one to about 100 cofactors. In some cases, the preloading solution can have at least about 1 cofactor, at least about 10 cofactors, at least about 20 cofactors, at least about 30 cofactors, at least about 40 cofactors, at least about 50 cofactors, at least about 60 cofactors, at least about 70 cofactors, at least about 80 cofactors, at least about 90 cofactors, at least about 100 cofactors, or more. In some cases, the preloading solution can have at most about 100 cofactors, at most about 90 cofactors, at most about 80 cofactors, at most about 70 cofactors, at most about 60 cofactors, at most about 50 cofactors, at most about 40 cofactors, at most about 30 cofactors, at most about 20 cofactors, at most about 10 cofactors, at most about one cofactor, or less. In some cases, the preloading solution can have about one cofactor, about 10 cofactors, about 20 cofactors, about 30 cofactors, about 40 cofactors, about 50 cofactors, about 60 cofactors, about 70 cofactors, about 80 cofactors, about 90 cofactors, or about 100 cofactors.

In some embodiments, the one or more cofactors or the one or more chemicals enhance binding of the analyte to the one or more translocases. In some cases, the one or more chemicals can comprise chaperone molecules. In some cases, the chaperone molecules can comprise heat shock proteins. In some cases, the heat shock proteins can comprise Hsp10, Hsp 60, Hsp70, Hsp40, Hsp90, Hsp100, or any combination thereof. In some cases, the chaperone molecules can comprise phage growth defect, overcome by mutation in page gene E, large subunit protein (GroEL). In some cases, the chaperone molecules can comprise Hsp10, Hsp60, Hsp70, Hsp40, Hsp90, Hsp100, GroEL, GRP78/BiP, GRP94, GRP170, calnexin, calreticulin, HSP47, Erp29, protein disulfide isomerase, peptidyl prolyl cis-trans isomerase, prolyl isomerase, Erp57, or any combination thereof. In some cases. The chaperone molecule can be configured to keep the analyte in a folded structure. In some cases, the one or more chemicals can comprise crowding agents. In some cases, the crowding agents can be configured to reduce the volume of solvent available for other components of the preloading solution. In some cases, the crowding agents can be configured to stabilize analytes in the preloading solution. In some cases, the crowding agents can comprise polyethylene glycol, dextran, Ficoll, or any combination thereof. In some cases, the one or more chemicals can comprise one or more metal cofactors. In some cases, the one or more metal cofactors can comprise iron, magnesium, manganese, cobalt, copper, zinc, molybdenum, or any combination thereof. In some cases, the one or more chemicals can comprise one or more chelating agents. In some cases, the one or more chelating agents can comprise deferoxamine, deferiprone, deferasirox, dimercapto succinic acid (DMSA), penicillamine, trientine, sodium calcium edetate, ethylenediaminetetraacetic acid, or any combination thereof. In some embodiments, the one or more chemicals can comprise Hsp10, Hsp60, Hsp70, Hsp40, Hsp90, Hsp100, GroEL, GRP78/BiP, GRP94, GRP170, calnexin, calreticulin, HSP47, Erp29, protein disulfide isomerase, peptidyl prolyl cis-trans isomerase, prolyl isomerase, Erp57, nucleotide triphosphates, glycine betaine, glycerol, dithiothreitol (DTT), iron, magnesium, manganese, cobalt, copper, zinc, molybdenum, Tris(2-carboxyethyl) phosphine (TCEP), glutathione, polyethylene glycol, dextran, Ficoll, deferoxamine, deferiprone, deferasirox, dimercapto succinic acid (DMSA), penicillamine, trientine, sodium calcium edetate, ethylenediaminetetraacetic acid, or any combination thereof.

In some embodiments, the one or more cofactors or the one or more chemicals increases binding of the analyte to the one or more translocases by between about 0.1% to about 500% compared to the binding of the analyte to the one or more translocases without the one or more cofactors or the one or more chemicals. In some embodiments, the one or more cofactors or the one or more chemicals increases binding of the analyte to the one or more translocases by between about 0.1% to about 1%, between about 10% to about 100%, or between about 100% to about 500%. In some embodiments, the one or more cofactors or the one or more chemicals increases binding of the analyte to the one or more translocases by at least about 0.1%, at least about 1%, at least about 10%, at least about 20%, at least about 30%, at least about 40%, at least about 50%, at least about 60%, at least about 70%, at least about 80%, at least about 90%, at least about 100%, at least about 200%, at least about 300%, at least about 400%, at least about 500%, or more compared to the binding of the analyte to the one or more translocases without the one or more cofactors or the one or more chemicals. In some embodiments, the one or more chemicals increases binding of the analyte to the one or more translocases by at most about 500%, at most about 400%, at most about 300%, at most about 200%, at most about 100%, at most about 90%, at most about 80%, at most about 70%, at most about 60%, at most about 50%, at most about 40%, at most about 30%, at most about 20%, at most about 10%, at most about 1%, at most about 0.1%, or less compared to the binding of the analyte to the one or more translocases without the one or more cofactors or the one or more chemicals.

In some embodiments, the preloading solution further comprises a solvent. Non-limiting examples of solvent include water, phosphate buffer solution (PBS), Tris buffer, Tris-HCL, Tricine buffer, Bicarbonate buffer, MOPS buffer, Bis-tris methan buffer, Bicine buffer, HEPES buffer, MES buffer, CAPS, or any combination thereof.

In some embodiments, the preloading solution is introduced to the analyte prior to introduction of the analyte to the nanopore system. In some cases, the preloading solution and the analyte are combined together in a container separate from the nanopore system. In some cases, the container can be a microcentrifuge tube, a centrifuge tube, a test tube, a beaker, a flask, a pipette, a culture tube, or any combination thereof.

In some embodiments, the preloading solution and the analyte can be combined together to form a translocase-analyte complex. In some cases, the translocase-analyte complex can be formed in a container separate from the nanopore system. In some cases, once the translocase-analyte complex is formed, the translocase-analyte complex can be added to the nanopore system.

In some embodiments, the translocase-analyte complex can be added to the cis side of the nanopore system. In some embodiments, the translocase-analyte complex can be added to the trans side of the nanopore system. In some embodiments, the translocase-analyte complex can be added to the cis side and the trans side of the nanopore system. In some cases, the translocase-analyte complex may not be added to the cis side of the nanopore system. In some cases, the translocase-analyte complex may not be added to the trans side of the nanopore system. In some cases, the translocase-analyte complex can be added to the cis side of the nanopore system and may not be added to the trans side of the nanopore system. In some instances, the translocase-analyte complex can be added to the trans side of the nanopore system and may not be added to the cis side of the nanopore system.

In some embodiments, the preloading solution can comprise one or more translocases. In some embodiments, the preloading solution can comprise one or more leader constructs. In some embodiments, the preloading solution can comprise one or more analytes. In some cases, the preloading solution can comprise one or more translocases and one or more leader constructs. In some cases, the preloading solution can comprise one or more translocases and one or more analytes. In some cases, the preloading solution can comprise one or more leader constructs and one or more analytes. In some cases, the preloading solution can comprise one or more translocases, one or more leader constructs, and one or more analytes.

In other embodiments, multiple translocases can bind to a single analyte. This can be advantageous to provide better controlled movement of the polynucleotide through the nanopore in the methods of the present disclosure, and/or to improve the ability of the translocase to progress through more problematic regions of analytes (e.g. regions of very stable structure, regions with bulky modifications of the side chains, or regions of low traction such those composed of a high percentage of glycines). In one aspect, preloading to load multiple translocases is performed under relatively high ratio of translocase to analyte.

In some embodiments, the ratio of analytes:translocases in the preloading solution can be from about 1:1 to about 1:10,000. In some cases, the ratio of analytes:translocases in the preloading solution can be from about 1:1 to about 1:10, from about 1:10 to about 1:100, from about 1:100 to about 1:1,000, or from about 1:1,000, or from about 1:1,000 to about 1:10,000. In some cases, the ratio of analytes:translocases in the preloading solution can be at least about 1:1, at least about 1:2, at least about 1:5, at least about 1:10, at least about 1:20, at least about 1:30, at least about 1:40, at least about 1:50, at least about 1:60, at least about 1:70, at least about 1:80, at least about 1:90, at least about 1:100, at least about 1:200, at least about 1:300, at least about 1:400, at least about 1:500, at least about 1:600, at least about 1:700, at least about 1:800, at least about 1:900, at least about 1:1,000, at least about 1:2,000, at least about 1:3,000, at least about 1:4,000, at least about 1:5,000, at least about 1:6,000, at least about 1:7,000, at least about 1:8,000, at least about 1:9,000, at least about 1:10,000, or more. In some cases, the ratio of analytes:translocases in the preloading solution can be at most about 1:10,000, at most about 1:9,000, at most about 1:8,000, at most about 1:7,000, at most about 1:6,000, at most about 1:5,000, at most about 1:4,000, at most about 1:3,000, at most about 1:2,000, at most about 1:1,000, at most about 1:1,000, at most about 1:900, at most about 1:800, at most about 1:700, at most about 1:600, at most about 1:500, at most about 1:400, at most about 1:300, at most about 1:200, at most about 1:100, at most about 1:90, at most about 1:80, at most about 1:70, at most about 1:60, at most about 1:50, at most about 1:40, at most about 1:30, at most about 1:20, at most about 1:10, at most about 1:5, at most about 1:2, at most about 1:1, or less than 1:1. In some cases, the ratio of analyte:translocases in the preloading solution can be about 1:1, about 1:2, about 1:5, about 1:10, about 1:20, about 1:30, about 1:40, about 1:50, about 1:60, about 1:70, about 1:80, about 1:90, about 1:100, about 1:200, about 1:300, about 1:400, about 1:500, about 1:600, about 1:700, about 1:800, about 1:900, about 1:1,000, about 1:2,000, about 1:3,000, about 1:4,000, about 1:5,000, about 1:6,000, about 1:7,000, about 1:8,000, about 1:9,000, or about 1:10,000.

In some embodiments, the ratio of translocases:analytes in the preloading solution can be from about 1:1 to about 1:10,000. In some cases, the ratio of translocases:analytes in the preloading solution can be from about 1:1 to about 1:10, from about 1:10 to about 1:100, from about 1:100 to about 1:1,000, or from about 1:1,000, or from about 1:1,000 to about 1:10,000. In some cases, the ratio of translocases:analytes in the preloading solution can be at least about 1:1, at least about 1:2, at least about 1:5, at least about 1:10, at least about 1:20, at least about 1:30, at least about 1:40, at least about 1:50, at least about 1:60, at least about 1:70, at least about 1:80, at least about 1:90, at least about 1:100, at least about 1:200, at least about 1:300, at least about 1:400, at least about 1:500, at least about 1:600, at least about 1:700, at least about 1:800, at least about 1:900, at least about 1:1,000, at least about 1:2,000, at least about 1:3,000, at least about 1:4,000, at least about 1:5,000, at least about 1:6,000, at least about 1:7,000, at least about 1:8,000, at least about 1:9,000, at least about 1:10,000, or more. In some cases, the ratio of translocases:analytes in the preloading solution can be at most about 1:10,000, at most about 1:9,000, at most about 1:8,000, at most about 1:7,000, at most about 1:6,000, at most about 1:5,000, at most about 1:4,000, at most about 1:3,000, at most about 1:2,000, at most about 1:1,000, at most about 1:1,000, at most about 1:900, at most about 1:800, at most about 1:700, at most about 1:600, at most about 1:500, at most about 1:400, at most about 1:300, at most about 1:200, at most about 1:100, at most about 1:90, at most about 1:80, at most about 1:70, at most about 1:60, at most about 1:50, at most about 1:40, at most about 1:30, at most about 1:20, at most about 1:10, at most about 1:5, at most about 1:2, at most about 1:1, or less than 1:1. In some cases, the ratio of translocases:analytes in the preloading solution can be about 1:1, about 1:2, about 1:5, about 1:10, about 1:20, about 1:30, about 1:40, about 1:50, about 1:60, about 1:70, about 1:80, about 1:90, about 1:100, about 1:200, about 1:300, about 1:400, about 1:500, about 1:600, about 1:700, about 1:800, about 1:900, about 1:1,000, about 1:2,000, about 1:3,000, about 1:4,000, about 1:5,000, about 1:6,000, about 1:7,000, about 1:8,000, about 1:9,000, or about 1:10,000.

This is performed in combination with analytes that are modified to optimally bind multiple translocases, for example through attachment of sufficiently long leaders to the terminus (i) of the analytes. For example, leaders are designed to have sufficiently long binding and stall motifs to accommodate the footprint of the multiple translocases and stall the multiple translocases respectively, such as illustrated schematically in FIG. 6.

In another embodiment the translocases are topologically closed around the leader and/or analyte to reduce or prevent unbinding, for example especially when the translocase:analyte is added to nanopore systems that employ conditions relatively unfavourable to binding (e.g. high salt concentration). In some cases, multiple units of oligomeric AAA+ translocases can be fused together by genetic fusion. Alternatively, oligomers can be connected by covalent coupling, e.g. by cross reaction between suitably placed cysteines between subunits. Genetic fusion and chemical coupling can be used in combination.

Translocase Controlled Movement

According to the present disclosure, the EOF arising from the strong net electro-osmotic flow can be created either cis-to-trans or trans-to-cis relative to the polarity of the applied voltage and the orientation of the nanopore. The direction of the EOF determines the direction that the analyte may translocate across the nanopore absent the bound translocase. Without translocase bound and controlling the movement the analyte may either become stuck in the nanopore (in the case that the EOF is insufficient to overcome structure) or translocate through the pore in an uncontrolled manner (e.g. in a slip-stick process, that might be too slow for practical use or too fast to observe current changes from the amino acid sequence). Thus the bound translocase is critical for moving the analyte through the nanopore in a controlled manner that is optimal for making measurements. The controlled movement is tightly coupled to NTP powered translocase function of the translocase. Alternatively, the bound translocase can be used in a bound but inactive state (e.g. under gamma-S-ATP conditions) to slow the movement of analyte that is pulled through the nanopore and translocase through the force of the EOF alone.

In some embodiments, depending on how the translocase bound to the analyte is orientated relative the nanopore, it can act either to control the movement of the analyte into the nanopore, or pull the analyte out of the nanopore.

Figure 3:
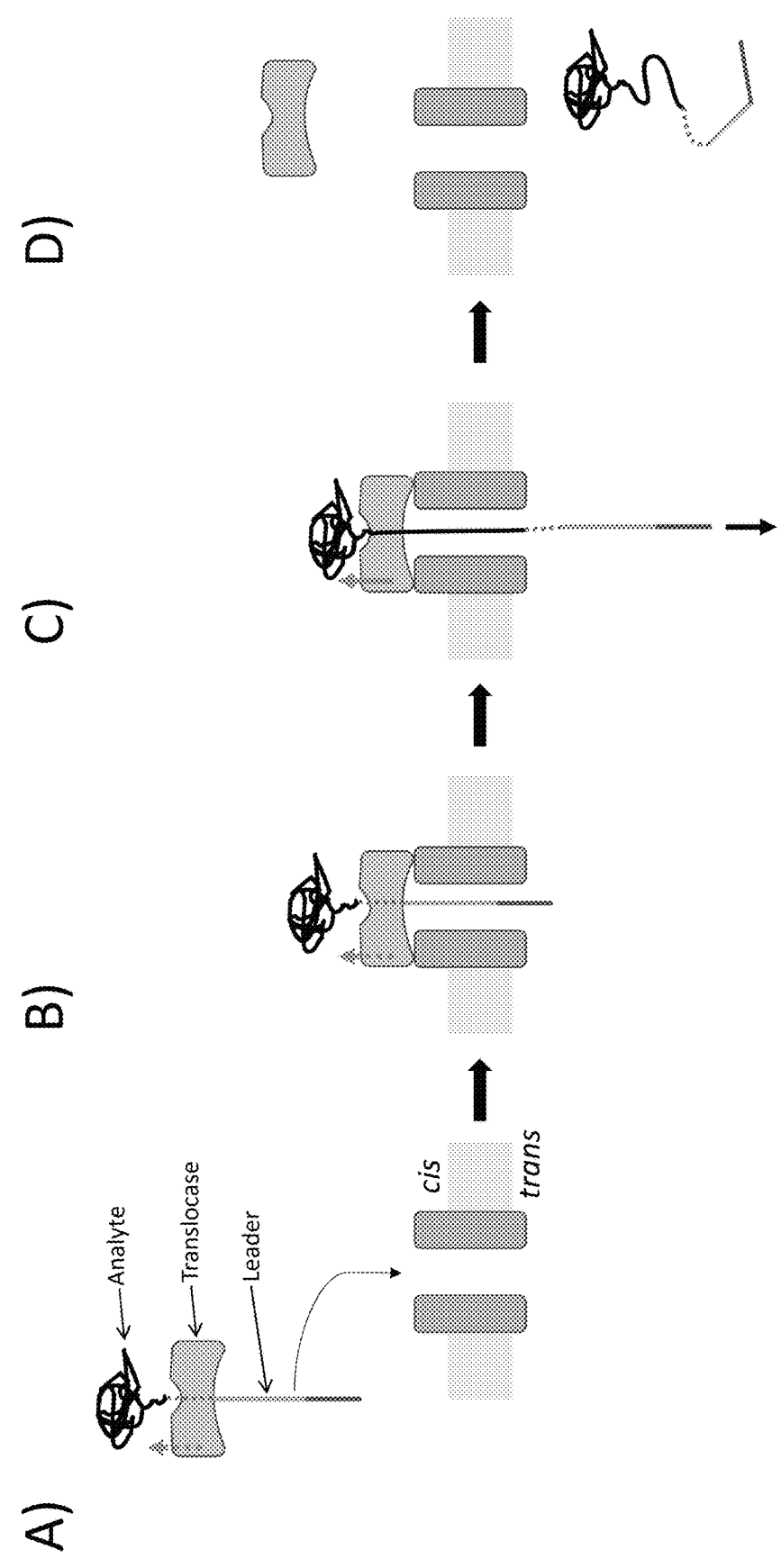
Figure 19:
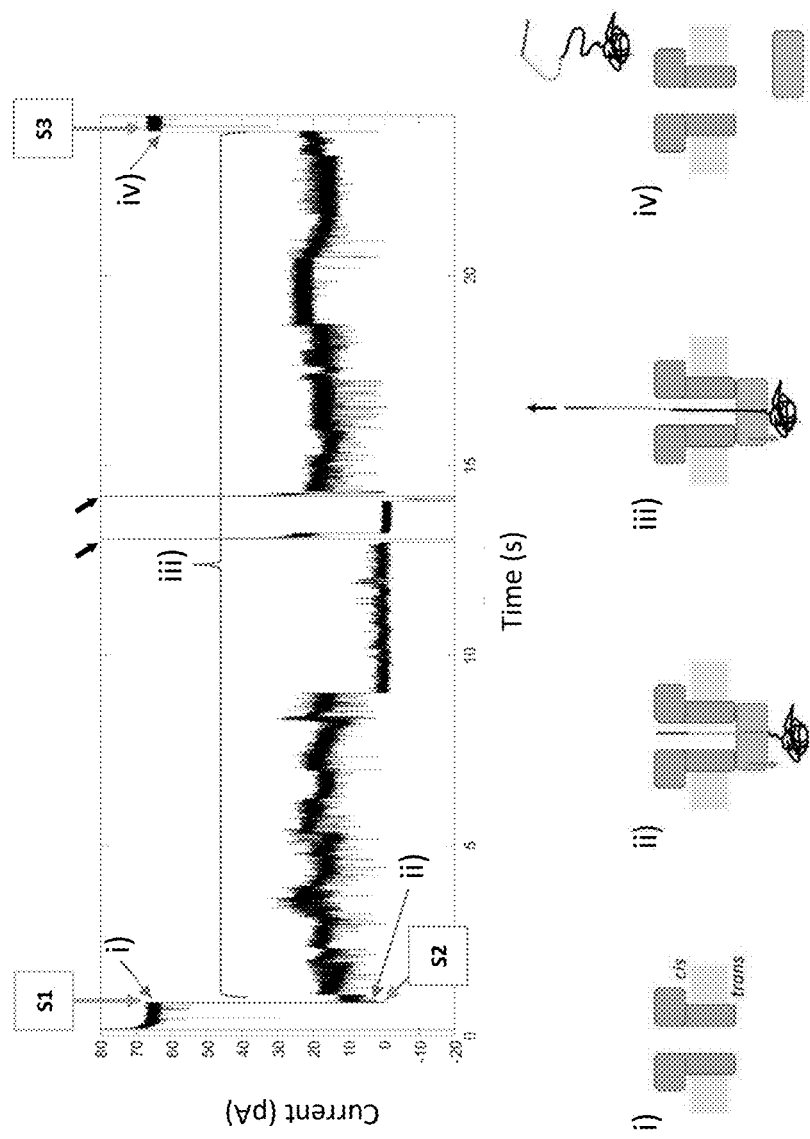

In one embodiment the translocase-analyte complex is captured from the cis compartment in a system with a net cis-to-trans EOF, such as that schematically described in FIG. 3. In this embodiment the translocase is moving away from the end of the analyte that is first captured in the nanopore, and thus acts to feed the analyte into the nanopore on the cis side of the membrane and the analyte comes out of the nanopore on the trans side of the membrane. Similarly, if the system has a net trans-to-cis EOF, then addition of the translocase-analyte complex to the trans compartment with capture of the analyte via the same end will result in translocase controlled feeding of the analyte from the trans side of the membrane to the cis side of the membrane (FIG. 19).

Figure 22:
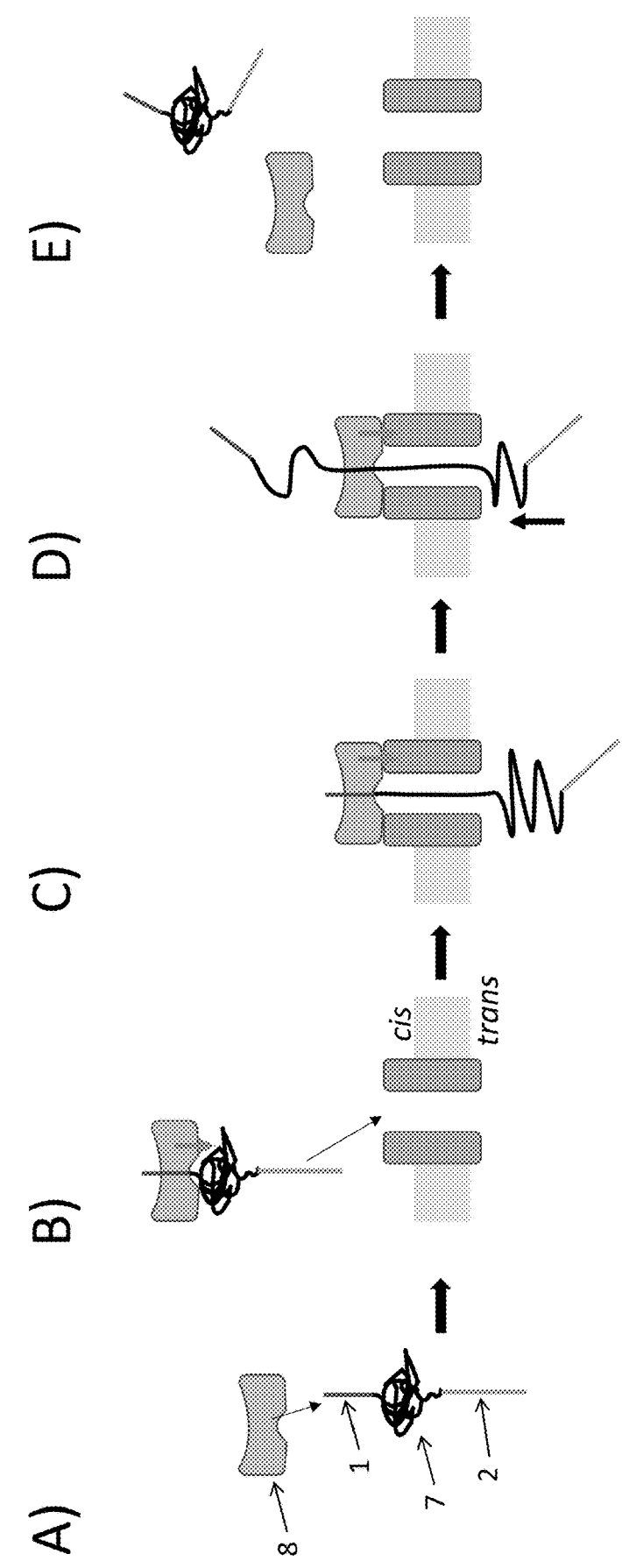

In another embodiment, the present disclosure provides a method or nanopore system wherein analyte(s) is captured from the cis side into a nanopore system with high net cis-to-trans EOF, in conjunction with a protein translocase motor that then pulls the analyte back through the same nanopore to the cis side (FIG. 22). In this embodiment, the protein translocase is orientated in the opposite orientation to previous embodiments so that its entrance is facing the nanopore, such that its ATPase functions acts to pull the analyte strand out of the nanopore.

This method can be of this present disclosure can be the result of strong EOF forces that 1) enables the initial capture and threading (and unfolding) of a portion of the analyte, and 2) thereafter keeps the translocated portion of the analyte held in the nanopore against weak or opposing EPF, thus retaining the bound translocase atop the pore so that it can control the movement of the analyte through the pore.

The present disclosure therefore also can relate to a method for capture and threading of at least part of an analyte through a nanopore, the nanopore being comprised in a membrane separating a fluidic chamber of a nanopore system into a cis side and a trans side, comprising:

(a) allowing a protein translocase in solution in the presence of NTP to capture and form a complex with the analyte to be translocated;

(b) contacting the translocase-analyte complex with the cis side of the nanopore and allowing for translocation of a portion of the analyte to the trans side;

wherein the nanopore system has a cis to trans electro-osmotic force (EOF) resulting from a net cis-to-trans ion current bias of I(cis-to-trans)/I(trans-to-cis) of greater than 3.0 or less than 0.3, greater than 3.5 or less than 0.2, under an applied voltage across the membrane, so that the translocated portion of the analyte is held in the nanopore against a weak or opposing EPF, thus retaining the bound translocase atop the pore so that it can control the movement of the analyte through the pore.

This "out mode" embodiment can suitably achieved by loading translocase proteins onto analytes, and then capturing the termini of the analyte so that the translocase protein is moving towards in the nanopore. In some embodiments, for a ClpX translocase loaded at the C-termini of the analyte translocating along the analyte C-terminal to N-terminal, it may capture the N termini of the analyte in the nanopore. After capture, the strong EOF translocates the analyte through the nanopore from the cis side to trans side, until the bound translocase encounters the top of the nanopore (FIG. 22C). The force of the net cis-to-trans EOF acting on the analyte passing through the nanopore pulls on the translocase:analyte complex and retains the translocase against the top of the pore. The translocase continues to move along the analyte under NTP powered hydrolysis, and in doing so pulls the analyte e back out of the nanopore in the trans-to-cis direction (FIG. 22D). Upon reaching the end of the analyte, the translocase unbinds from the analyte and both the translocase and the analyte are released back into the cis side (FIG. 22E).

In some embodiments, the loading of the translocase and orientated capture of the analyte in the nanopore is directed by modifying analytes with "nanopore-capture tags" and/or "translocase-binding tags" on opposite termini. For example, a translocase-binding tag can be adapted to the C-termini of an analyte, and a nanopore-capture tag can be adapted to the N-termini of an analyte, or vice versa. For example, a translocase-binding tag such as ssrA can be adapted to either the N- or C-terminal end of the analyte to direct binding of the translocase protein to a specific end. However, it is understood that the binding tags are not essential in all cases to achieve translocase loading, for example use of a promiscuous binding translocases can enable it to bind without a sequence specific translocase-binding tag. An analyte of interest is modified at either the N- or C-terminal end with a "Capture tag" (labelled 1 in FIG. 22) to facilitate capture and threading through the nanopore. Ideally, the capture tag (e.g. attached by chemical or enzymatic methods) is a long polymer (>10,>20, most >30 amino-acid) containing a large number of charged residues.

Nanopore System

In some embodiments, a nanopore comprises a biological nanopore or a solid state nanopore. A biological nanopore can comprise a mutation to a portion of the biological nanopore. The mutation can comprise an insert, a substitution, a deletion, or combinations thereof. A nanopore can comprise a geometry. The geometry can comprise a toroidal shape, comprising a ring and a channel. The toroidal shape may comprise a toroidal polyhedral shape comprising a ring and a channel. The ring may comprise the protein or proteins that form the nanopore. The ring may comprise a cross sectional geometry similar to the protein or proteins that form the nanopore. The ring may be wider at the cis side than the trans side, or wider at the trans side than the cis side. The ring can comprise a portion comprising a conical geometry, a cylindrical geometry, an amorphous geometry, or combinations thereof. The channel can comprise the central portion of the nanopore geometry that does not comprise the proteins or peptides of the nanopore. The channel may allow molecules to pass through the nanopore (i.e. through the channel). A channel may restrict molecules from passing through the nanopore. The restriction may be based on a width of the channel or a charge of the channel. The channel can comprise a channel length. The channel length can be the length of the channel as measured along a longitudinal axis of the channel, perpendicular to the ring of the toroidal shape of the geometry of the nanopore. The channel length can be measured as the distance along the longitudinal axis of the channel between the most distant points of the nanopore along the longitudinal axis of the channel. In some embodiment, a channel may have a start point on a cis side of a nanopore, and an end point on a trans side of a nanopore, or a start point on a trans side of a nanopore, and an end point on a cis side of a nanopore. In some embodiments a channel length is less than a linear length or a contour length of an analyte. In some embodiments a channel length is greater than a linear length or a contour length of an analyte.

In some embodiments, a channel comprises a channel length from about 2 nm to about 40 nm. In some cases, the channel can comprise a channel length of at least about 2 nm, at least about 5 nm, at least about 10, at least about 15 nm, at least about 20 nm, at least about 25 nm, at least about 30 nm, at least about 35 nm, at least about 40 nm, or more than 40 nm. In some cases, the channel can comprise a channel length of at most about 40 nm, at most about 35 nm, at most about 30 nm, at most about 25 nm, at most about 20 nm, at most about 15 nm, at most about 10 nm, at most about 5 nm, at most about 2 nm, or less than 2 nm. In some cases, the channel can comprise a channel length of about 2 nm, about 5 nm, about 10 nm, about 15 nm, about 20 nm, about 25 nm, about 30 nm, about 35 nm, or about 40 nm.

In some embodiments the nanopore comprises a lumen. The lumen can be the surface of the nanopore that faces the channel. The lumen can comprise the surfaces of the nanopore's components that face the channel, including proteins, peptides, or amino acid residues that face the channel. These components can comprise a charge. The charge of these components can provide a net charge of the lumen. These components can have a shape. The shape of these components can provide a geometry of the lumen. The net charge of the lumen, the geometry of the lumen, or combinations thereof, can influence a flow of molecules through the lumen (i.e. through the nanopore). The flowing molecules can be analytes, ions, water, or other molecules on a cis or a trans side of a nanopore. The flowing molecules can generate an ionic current from a flow of ions. As an analyte passes through a pore, other molecules, such as ions, can be obstructed from passing through the pore. This can change the ionic current by changing the rate of flow of ions. This change can be measured, for example, by a pair of electrodes configured to measure a current from cis to trans across the nanopore, or the membrane the nanopore may be disposed. A narrow geometry of the lumen can slow a progression of an analyte through a pore. A change to a net charge or a geometry of a lumen can change the flow of molecules through a pore. For example, changing a lumen to have a more positive net charge can reduce a flow of a positively charged molecule (e.g., a sodium ion). For example, changing a lumen to have a wider geometry can increase a flow of a larger molecule (e.g., a glucose molecule or a peptide analyte). For example, changing a lumen to have a more negative net charge and a narrower geometry can reduce a flow of a large, negatively charged molecule (e.g., a glutamate ion). The net charge of the lumen can influence the flow of charged molecules through the nanopore. The net charge can make some charged molecules pass through more easily, or more difficultly.

A channel can comprise a constriction zone. A constriction zone can be a portion of the channel that is narrower than the surrounding section. A channel can comprise multiple constriction zones. The net charge of the lumen, the geometry of the lumen, or combinations thereof, can result in constriction zones. Modifications to the net charge of the lumen, the geometry of the lumen, or combinations thereof, can modify a characteristic of a constriction zone. A characteristic of a constriction zone may be a placement, a location, a width, a charge, or combinations thereof. For example, a change to a geometry of the lumen can change the width of a constriction zone, or a change to a net charge of the lumen can change the charge of a constriction zone.

A nanopore can comprise a permeability to an ion. A permeability to an ion can be the ability or likelihood of an ion to flow or diffuse through the channel of the nanopore. A permeability to an ion (P) may be different for different ions. By comparing different permeabilities, a relative ion selectivity can be generated. A relative ion selectivity can be the permeability of a given cation ($P_{(+)}$) (e.g., a potassium ion) divided by the permeability of a given anion ($P_{(-)}$) (e.g., a chlorine ion), to provide the relative ion selectivity ($P_{(+)}/P_{(-)}$). The net charge and the geometry of the lumen can each influence a permeability of an ion. For example, a positive net charge can reduce a permeability of a cation, or a negative net charge can reduce a permeability of an anion. A geometry of the lumen can influence a permeability of an ion based on the size of an ion. For example a smaller geometry can decrease the permeability of a larger ion (e.g. a potassium ion) relative to a smaller ion (e.g. a lithium ion).

The net charge and the geometry of the lumen can influence a relative ion flux. A relative ion flux can be the net flow of ions through the nanopore. In some embodiments, a nanopore can comprise a relative ion selectivity $P_{(+)}/P_{(-)}$ of greater than about 0.1, 0.2, 0.3, 0.4, 0.5, 0.6, 0.7, 0.8, 0.9, 1.0, 1.2, 1.4, 1.6, 1.8, 2.0, 2.5, 3, 3.2, 3.4, 3.6, 3.8, 4.0, 4.1, 4.2, 4.3, 4.4, 4.5, 4.6, 4.7, 4.8, 4.9, or greater than about 5.0. In some embodiments, a pore can comprise a relative ion selectivity $P_{(+)}/P_{(-)}$ of less than about 0.1, 0.2, 0.3, 0.4, 0.5, 0.6, 0.7, 0.8, 0.9, 1.0, 1.2, 1.4, 1.6, 1.8, 2.0, 2.5, 3, 3.2, 3.4, 3.6, 3.8, 4.0, 4.1, 4.2, 4.3, 4.4, 4.5, 4.6, 4.7, 4.8, 4.9, or less than about 5.0.

A nanopore can comprise at least one inner pore constriction. In some embodiments, the inner pore constriction is at least about 0.2, 0.3 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or at least about 4.0 nm. In some embodiments, the inner pore constriction is at most about 0.2, 0.3 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or at most about 4.0 nm.

In some embodiments, a nanopore channel comprises a lumen. In some embodiments, a nanopore lumen comprises a net charge greater than about 2, 3, 4, 5, 10, 15, 20, 25, 30, 35, 40, 45, 50, 55, 60, 70, 80, 90, 100, 150, or about 200. In some embodiments, a nanopore lumen comprises a net charge less than about 2, 3, 4, 5, 10, 15, 20, 25, 30, 35, 40, 45, 50, 55, 60, 70, 80, 90, 100, 150, or about 200. In some embodiments, a nanopore lumen comprises a net positive charge. In some embodiments, a nanopore lumen comprises a net negative charge.

At least about 1, 2, 3, 4, 5, 6, 7, 8, 10, 11, 12, 13, 14, 15, 16, 17, 18, 19, or at least about 20 charged amino acids may be distributed evenly within the lumen. At most about 1, 2, 3, 4, 5, 6, 7, 8, 10, 11, 12, 13, 14, 15, 16, 17, 18, 19, or at most about 20 charged amino acids may be distributed evenly within the lumen. The amino acids can be positively or negatively charged A nanopore lumen can comprise separate sets of charges oriented along the ring of the toroidal geometry of the nanopore. These sets of charges may be arranged along the longitudinal length of the channel. For example, a nanopore may comprise at least about 2, 3, 4, 5, 6, 7, 8, 9, 10, 11, 12, 13, 14, 15, 16, 17, 18, 19, or at least about 20 separate sets of charges. In some embodiments the sets of charges may each be spaced at least about 0.1, 0.2, 0.3, 0.4, 0.5, 0.6, 0.7, 0.8, 0.9, 1, 2, 3, 4, or at least about 5 nanometers apart from each other along the longitudinal length of the channel. In some embodiments the sets of charges may each be spaced at most about 0.1, 0.2, 0.3, 0.4, 0.5, 0.6, 0.7, 0.8, 0.9, 1, 2, 3, 4, or at most about 5 nanometers apart from each other along the longitudinal length of the channel.

A further embodiment relates to a nanopore system for translocating an analyte through a nanopore, the system comprising (a) a membrane having nanopore therein, said membrane separating a chamber into a cis side and a trans side, wherein the analyte is to be added to the cis side and translocated through the nanopore to the trans side; (b) on the cis side of said chamber an analyte captured by a protein translocase, which can bind and translocate the analyte through the nanopore in a sequential order; and (c) mechanisms for providing a voltage difference between the cis side and the trans side of the membrane, wherein the nanopore system has a cis to trans electro-osmotic force (EOF) resulting from a net ionic current flow cis to trans, so that the analyte is captured in the nanopore with on top of the nanopore the translocase controlling the translocation, wherein the nanopore system has a cis to trans EOF resulting from a net ionic current flow cis-to-trans over total ionic current flow of greater than 0.2 or less than −0.2, greater than 0.3 or less than −0.3, most greater than 0.35 or less than −0.35.

In one aspect, the nanopore system has an ion selectivity $P_{(+)}/P_{(−)}$ of greater 2.0 or less than 0.5, greater than 2.5 or less than 0.4, greater than 3.0 or less than 0.33.

In some embodiments, the large and dominant EOF by inducing a strong ion-selectivity current bias through the nanopore can be achieved in various ways. These include modification engineering of the nanopore, applying specific system conditions, and any combination thereof.

In one embodiment, the system contains cation salts of K+, Na+, NH4+ or other suitably small and highly mobile cation salts on the cis side of the system to provide the majority of the ionic flux through the nanopore from cis to trans under negative applied voltage to trans side of the membrane. In a further aspect, the system contains anionic salts of glutamate, acetate or other suitably large and less mobile anion salts on the trans side of the system to further limit to anionic flux through the nanopore from trans to cis under negative applied voltage to trans side of the membrane.

In certain aspects, a negative voltage is applied to the trans side of the device when analyte-translocase complexes are added to the cis side of the nanopore. In this embodiment, the negative voltage drives a large excess of cations from cis to trans, creating a large cation biased cis-to-trans EOF acting on the system.

The system may further comprise methods for measuring a signal based on ionic current flowing through the nanopore during a period of time of translocation. For example, the measuring devices are set up to detect changes in the signal that reflect characteristics of the analyte as it is translocated. Other measuring methods include those involving tunneling (e.g. such as those described in Zhao et al., 2014, Nat Nanotechnol., 9, 6, pg. 466-473), and surface enhanced raman and other spectroscopic or plasmonic based methods (e.g. such as systems similar to those described in Zhao et al., 2022, ACS Photonics., 9, 3, pg. 730-742).

The system may comprise a circuit that can both apply the voltage and measure the current. Alternatively, it comprises one circuit to apply the voltage difference and another to measure the current. It is also possible to create the voltage difference with an asymmetric salt across the membrane.

Methods and systems for detecting the current between the cis and trans chambers were described in WO 00/79257 U.S. Pat. Nos. 6,46,594, 6,673, 6,673,615, 6,627,067, 6,464, 842, 6,362,002, 6,267,872, 6,015,714, 6,428,959, 6,617,113 and 5,795,782 and US Publications Nos. 2004/0121525, 2003/0104428 and 2003/0104428. They may include electrodes directly associated with the channel or pore at or near the porous opening, electrodes placed within the cis and trans chambers, and insulated glass microelectrodes. Electrodes may be capable of, detecting differences in ionic current around two chambers or tunneling electrical current around the porous opening. In another configuration, the transport property is the flow of electrons around the diameter of the aperture which can be monitored by electrodes placed adjacent to or touching the circumference of the nanopore. Said electrodes can be attached to an amplifier (e.g., Axopatch 200B) amplifier to amplify a signal.

It is understood that acquisition systems described herein is not limited and that other systems for acquiring or measuring nanopore signals can be employed. Alternative electrical schemes can also be employed, on arrayed chip platforms for example, to achieve an equivalent voltage drop across the nanopore and/or membrane.

A further aspect of the present disclosure relates to an analytical device comprising one or more nanopore systems according to the present disclosure.

Also provided herein is the use of a system or analytical device according to the present disclosure for single analyte analysis, for identification and/or sequencing of one or more analyte(s). A person skilled in the art will recognize and appreciate that the present disclosure provides a unique addition to the landscape of emerging proteomics technologies. For example, it finds its application in a broad area of analyte analysis, including next-generation single-molecule protein sequencing and identification technologies and single-cell profiling of proteomes. The method of protein identification may fingerprint certain classes of amino acids (AA fingerprint) or reveal each amino acid down to its physiochemical class.

Kit

In one aspect, the present disclosure provides a kit for characterizing a non-nucleic acid based polymer analyte. In some embodiments, the kit can comprise: (a) a fluidic chamber comprising: (i) a membrane comprising a nanopore, (ii) a first solution, and (iii) a second solution, and (b) a preloading solution. In some cases, the membrane can separate the fluidic chamber into a cis side and a trans side. In some cases, the first solution is present in the cis side. In some cases, the second solution is present in the trans side. In some embodiments, the preloading solution can comprise one or more translocases. In some embodiments, the preloading solution can comprise one or more leader constructs.

In one aspect, the present disclosure provides a method for using the kit of the present disclosure. In some embodiments, the method can comprise (a) combining a sample comprising a non-nucleic acid based polymer analyte with the preloading solution, (b) adding a combination of the non-nucleic acid based polymer analyte and the preloading solution to the cis side of the fluidic chamber; and (c) detecting a characteristic of the non-nucleic acid based polymer analyte.

In one aspect, the disclosure provides kits of analysis of one or more characteristics of one or more analytes. Kits can comprise one or more elements disclosed herein in relation to any of the various aspects, in any combination. In some embodiments, the kit can comprise a nanopore system. In some cases, the nanopore system can comprise a fluidic chamber with a membrane. In some cases, the membrane can split the fluidic chamber into a cis side and a trans side. In some cases, the fluidic chamber can further comprise a nanopore. In some cases, the nanopore is embedded into the membrane. In some embodiments, the kit can further comprise a first solution. In some cases, the first solution can be added to the cis side of the fluidic chamber. In some embodiments, the kit can comprise a second solution. In some cases, the second solution can be added to the trans side of the fluidic chamber. In some cases, the first solution and the second solution can be the same solution. In some cases, the first solution and the second solution can be different solutions. In some cases, the kit can further comprise one or more translocases. In some cases, the kit can further comprise one or more adaptors. In some cases, the can further comprises one or more leader constructs. In some cases, the kit can further comprise a preloading solution. In some instances, the preloading solution can comprise one or more translocases. In some embodiments, the kit can further comprise a sample analyte for testing. In some cases, the sample analyte can be used to set up the system of the present disclosure.

In one aspect, the present disclosure provides a device comprising an array of the system. In some embodiments, the system can comprise any one of the systems disclosed herein.

In one aspect, the present disclosure provides a method of characterizing at least one structural feature of the non-nucleic acid based polymer analyte. In some embodiments, the method can comprise any one of the methods disclosed herein.

In one aspect, the present disclosure provides a method for analysis of an amino acid sequence or amino acid composition of one or more non-nucleic acid based polymer analytes. In some embodiments, the analysis can be performed at a single molecule level. In some embodiments, the method can comprise any one of the methods disclosed herein.

In one aspect, the present disclosure provides a system for characterizing at least one structural feature of the non-nucleic acid based polymer analyte. In some embodiments, the system can comprise any one of the systems disclosed herein.

In one aspect, the present disclosure provides a system for analysis of an amino acid sequence or amino acid composition of one or more non-nucleic acid based polymer analytes. In some embodiments, the analysis can be performed at a single molecule level. In some embodiments, the system can comprise any one of the systems disclosed herein.

Computer Systems

Figure 30:
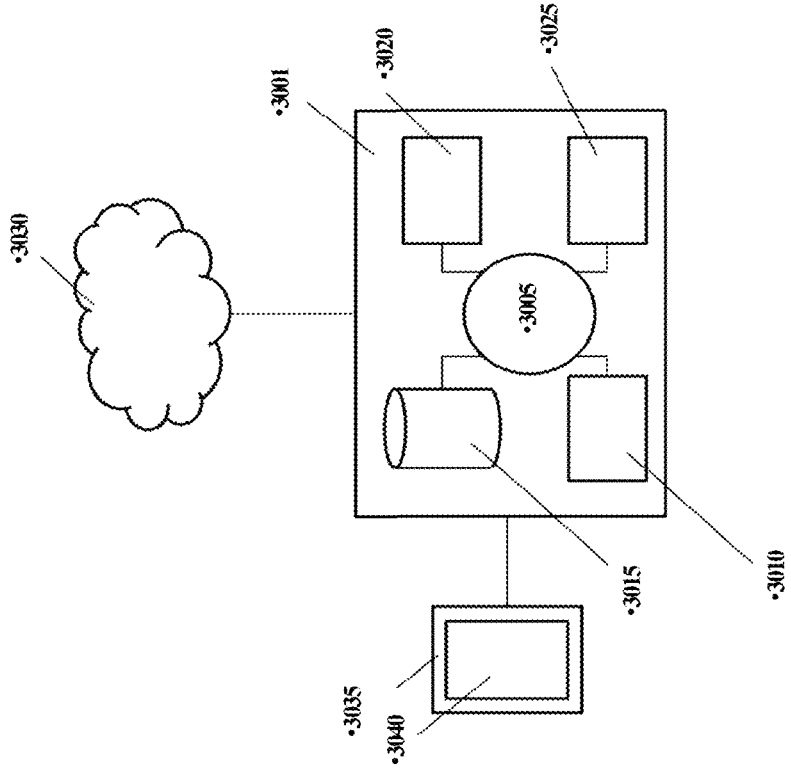

The present disclosure provides computer systems that are programmed to implement methods of determining one or more characteristics of an analyte. FIG. 30 shows a computer system 3001 that is programmed or otherwise configured to determine one or more characteristics of an analyte. The computer system 3001 can regulate various aspects of detecting presence or absence of one or more characteristics of the analyte, such as, for example, determining the sequence of the analyte. The computer system 3001 can be an electronic device of a user or a computer system that is remotely located with respect to the electronic device. The electronic device can be a mobile electronic device.

The computer system 3001 includes a central processing unit (CPU, also "processor" and "computer processor" herein) 3005, which can be a single core or multi core processor, or a plurality of processors for parallel processing. The computer system 3001 also includes memory or memory location 3010 (e.g., random-access memory, read-only memory, flash memory), electronic storage unit 3015 (e.g., hard disk), communication interface 3020 (e.g., network adapter) for communicating with one or more other systems, and peripheral devices 3025, such as cache, other memory, data storage and/or electronic display adapters. The memory 3010, storage unit 3015, interface 3020 and peripheral devices 3025 are in communication with the CPU 3005 through a communication bus (solid lines), such as a motherboard. The storage unit 3015 can be a data storage unit (or data repository) for storing data. The computer system 3001 can be operatively coupled to a computer network ("network") 3030 with the aid of the communication interface 3020. The network 3030 can be the Internet, an internet and/or extranet, or an intranet and/or extranet that is in communication with the Internet. The network 3030 in some cases is a telecommunication and/or data network. The network 3030 can include one or more computer servers, which can enable distributed computing, such as cloud computing. The network 3030, in some cases with the aid of the computer system 3001, can implement a peer-to-peer network, which may enable devices coupled to the computer system 3001 to behave as a client or a server.

The CPU 3005 can execute a sequence of machine-readable instructions, which can be embodied in a program or software. The instructions may be stored in a memory location, such as the memory 3010. The instructions can be directed to the CPU 3005, which can subsequently program or otherwise configure the CPU 3005 to implement methods of the present disclosure. Examples of operations performed by the CPU 3005 can include fetch, decode, execute, and writeback.

The CPU 3005 can be part of a circuit, such as an integrated circuit. One or more other components of the system 3001 can be included in the circuit. In some cases, the circuit is an application specific integrated circuit (ASIC).

The storage unit 3015 can store files, such as drivers, libraries and saved programs. The storage unit 3015 can store user data, e.g., user preferences and user programs. The computer system 3001 in some cases can include one or more additional data storage units that are external to the computer system 3001, such as located on a remote server that is in communication with the computer system 3001 through an intranet or the Internet.

The computer system 3001 can communicate with one or more remote computer systems through the network 3030. For instance, the computer system 3001 can communicate with a remote computer system of a user (e.g., a personal computer). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 3001 via the network 3030.

Methods as described herein can be implemented by way of machine (e.g., computer processor) executable code stored on an electronic storage location of the computer system 3001, such as, for example, on the memory 3010 or electronic storage unit 3015. The machine executable or machine readable code can be provided in the form of software. During use, the code can be executed by the processor 3005. In some cases, the code can be retrieved from the storage unit 3015 and stored on the memory 3010 for ready access by the processor 3005. In some situations, the electronic storage unit 3015 can be precluded, and machine-executable instructions are stored on memory 3010.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 3001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 3001 can include or be in communication with an electronic display 3035 that comprises a user interface (UI) 3040 for providing, for example, the identification of the target nucleic acid sequence. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 3005.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and the computer memory coupled thereto. The computer memory comprises machine executable code that, upon execution by the one or more computer processors, implements any of the methods above or elsewhere herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

LEGEND TO THE FIGURES

FIG. 1: Schematic drawing of strong electro-osmotic nanopore systems for improving the translocation and characterisation of analytes through the nanopores. Figure illustrates nanopores with a strong net Electro-Osmotic Force (EOF) in the direction cis-to-trans across a membrane as indicated by the arrow. The Electrophoretic Forces (EPF) acting on the analyte will depend on the composition of charges on the target analyte in the sections in and near the nanopore channel, and therefore can sometimes act in the net direction from cis-to-trans or the net direction from trans-to-cis. A strong and dominant cis-to-trans EOF enables capture, stretching and efficient translocation of long polymer analytes from the cis compartment to the trans compartment regardless of the net direction of the EPF. A) Schematic of a scenario, illustrating a strong cis-to-trans EOF across the system for enabling capture and translocation of a protein analyte in the cis to trans direction. Arrows through the pore schematically indicate the magnitude of the ion flow in each direction, showing that the EOF is generated by a large net flow of ions from the cis side of the membrane to the trans side of the membrane. The net flow arises from a large cis-to-trans ion flow dominating over any trans-to-cision flows (e.g a lower flow or counter-charged ions under an applied potential). B) A strong cis-to-trans EOF can be established in a system with positive voltage applied to the trans compartment across the membrane using nanopores with net positive internal charge to limit the flow of cations from the trans side of the membrane to the cis side of the membrane. C) A strong cis-to-trans EOF can be established in a system with negative voltage applied to the trans compartment across the membrane using nanopores with net negative internal charge to limit the flow of anions from the trans side of the membrane to the cis side of the membrane.

Figure 2:
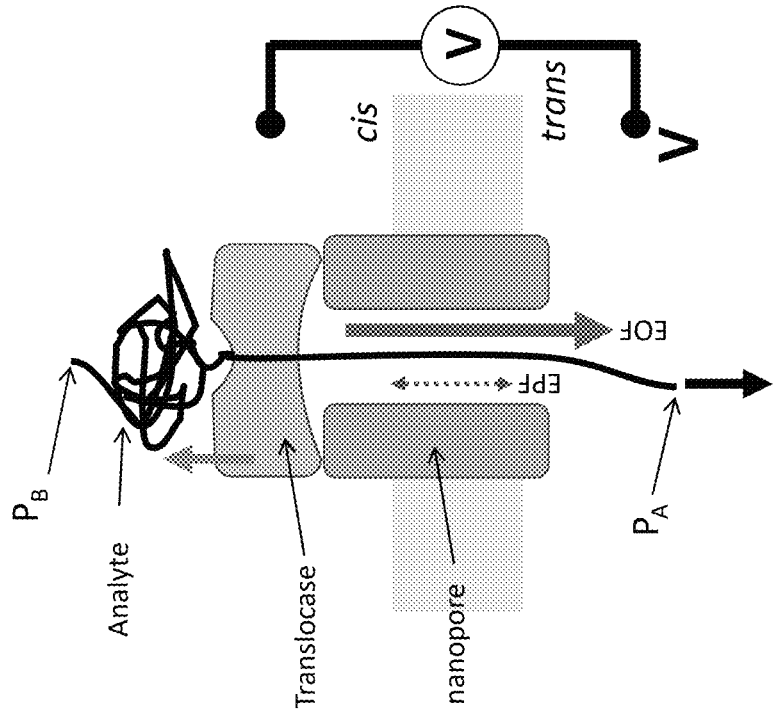

FIG. 2: Exemplary nanopore-based systems for characterising and/or translocating analytes, for example mixed amino-acid composition proteins. System comprising a nanopore in a membrane, where a protein analyte is translocated through the nanopore from the cis compartment to the trans compartment with the aid of a translocase motor that progresses along the protein analyte in the direction of the subset arrow (moving away from termini PA towards termini PB of protein analyte). Depending on the charge composition of the portion of the protein analyte within or near the nanopore central channel at any one time, and on the direction of the applied voltage, the net direction of the EPF acting on the protein may be either cis-to-trans or trans-to-cis or effectively zero as the protein progresses through the nanopore (as indicated by the dotted arrow labelled EPF). To improve characterisation and/or translocation of a protein analyte the system is configured so that the net Electro-Osmotic Force (EOF) acting on the protein is in the direction of cis-to-trans (as indicated by arrow labelled EOF), and is of greater magnitude than the EPF.

FIG. 3: Exemplary system for characterising and translocating polymer analytes, for example mixed amino-acid composition protein analytes, through a nanopore in a membrane. A) A protein analyte comprising a leader, which is loaded with a protein translocase motor (with NTP powered translocase function in the direction away from the leader as indicated by subset arrow) to form a protein: translocase complex, is added to the cis side of a system containing nanopore(s) in a membrane. The protein: translocase complex is captured by the nanopore, for example via the leader construct. B) The entire complex is pulled into the nanopore by the combination of cis-to-trans EPF and/or EOF until the translocase motor encounters the top of the nanopore, whereupon it prevents further uncontrolled translocation. C) The cis-to-trans EPF and/or EOF forces acting on the leading motifs of the polymer region within the nanopore pull the polymer through the translocase so that the translocase can overcome the stall and/or block regions in the leader region, whereupon the translocase will continue to progress along the polymer analyte under chemical energy powered NTP hydrolysis, unfolding protein structures ahead, thus feeding the extruded polypeptide chain into the nanopore cis-to-trans in a controlled manner. D) The protein analyte is fully processed by the translocase, which unbinds upon encountering the end of the molecule, releasing the polypeptide, which is then translocated to the trans compartment of the system, whereupon the nanopore is available to capture and process another protein: translocase complex as per A).

Figure 4:
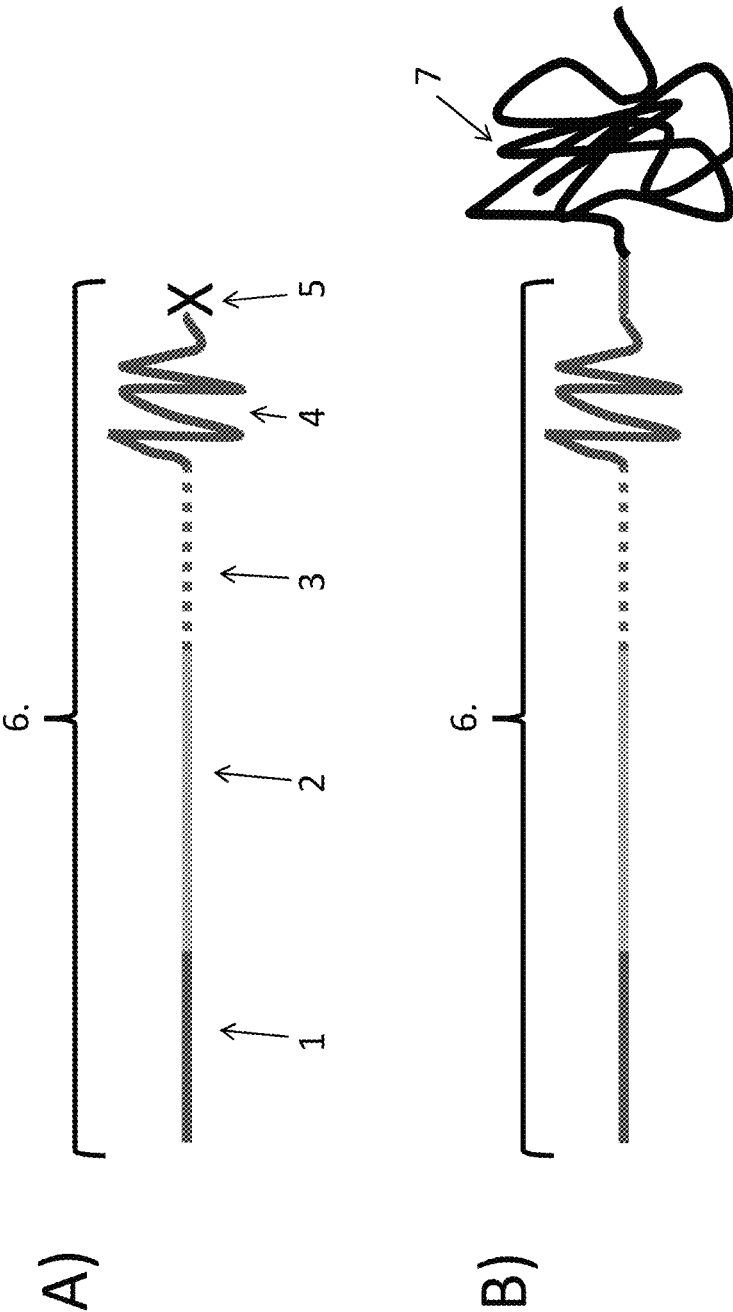

FIG. 4: A) Components of a (peptide based) "leader construct" (6) for attaching to a target protein substrate of interest, which enables loading/binding of protein translocase motor(s) for unfolding and controlling translocation of the target protein substrate through a nanopore. The construct comprises a number of possible elements:

1. Recognition motif
2. Capture motif
3. Stall motif
4. Block motif
5. Coupling motif B) Illustrative schematic of a leader construct (6) that is attached to a target protein substrate(s) of interest (7), e.g. a folded or structured protein.

Figure 5:
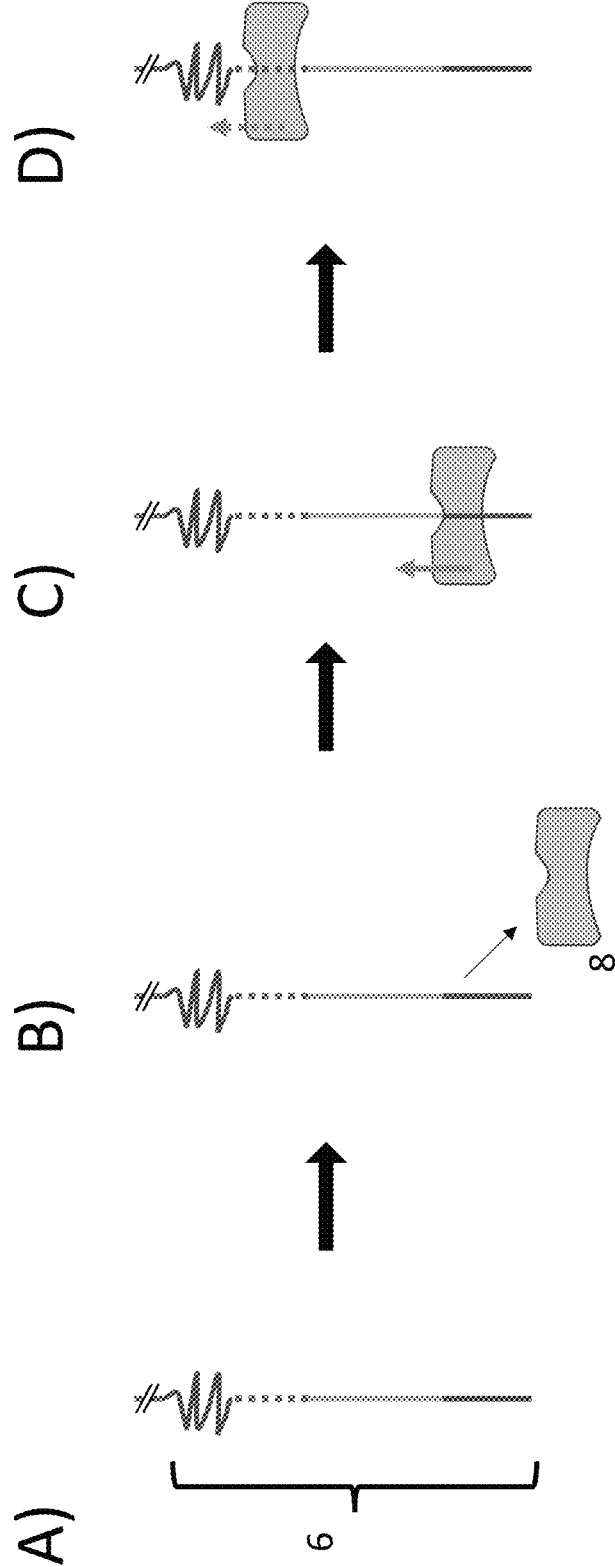

FIG. 5: Exemplary process of a method of loading a protein translocase (8) onto a leader construct (6). A translocase first binds to a leader construct (B) at or near the recognition motif, and then proceeds to translocate along the construct (C) in the direction of the subset arrow via NTP hydrolysis until encountering the stall and/or blocking motifs that stall/pause the progression of the translocase (D).

Figure 6:
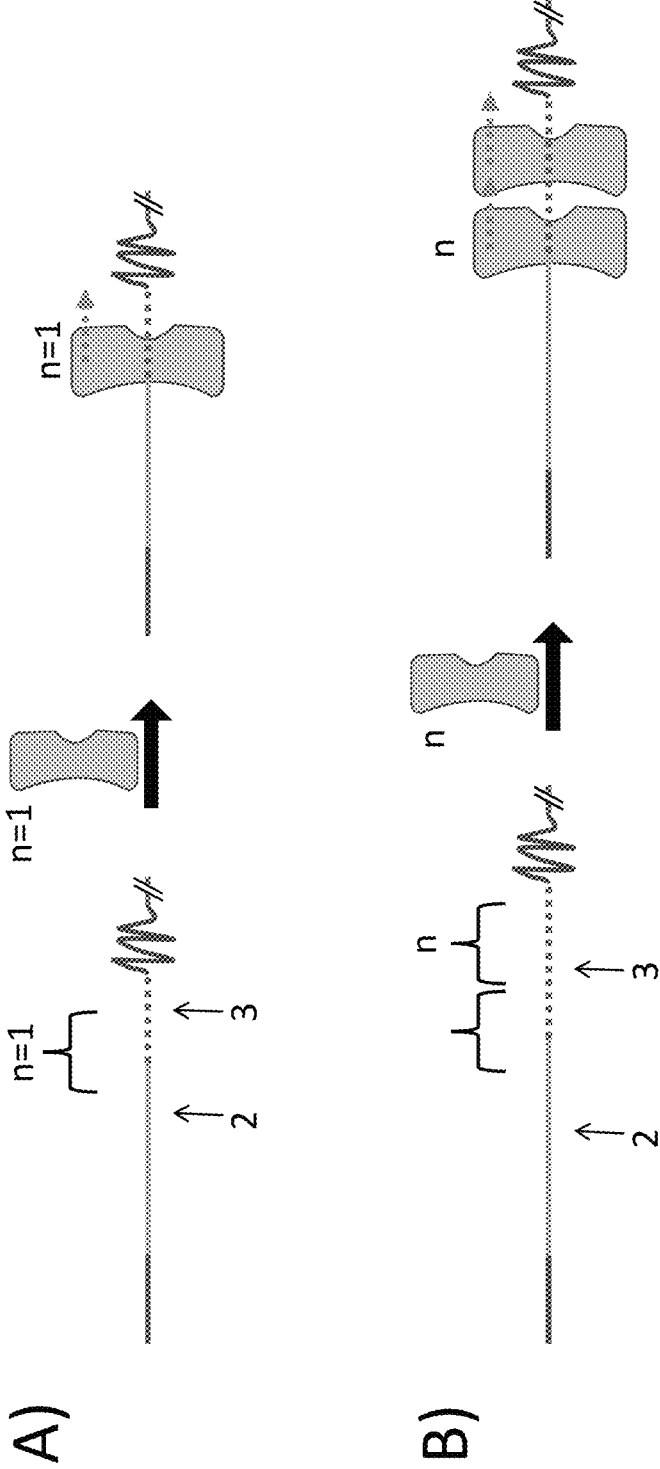

FIG. 6: Exemplary process of loading multiple protein translocases onto a leader construct. A) Schematic of a substrate designed to load and stall one protein translocase. The capture (2) and/or stall (3) motifs in combination have a footprint long enough to accommodate a single translocase. B) Schematic of a substrate designed to load and stall n multiple protein translocase, comprising a longer combination of capture (2) and/or stall (3) motifs that can effectively stall and accommodate the binding footprints of the n multiple translocases, such that the trailing translocase motor(s) cannot push the leading translocase(s) through the stall/block motifs.

Figure 7:
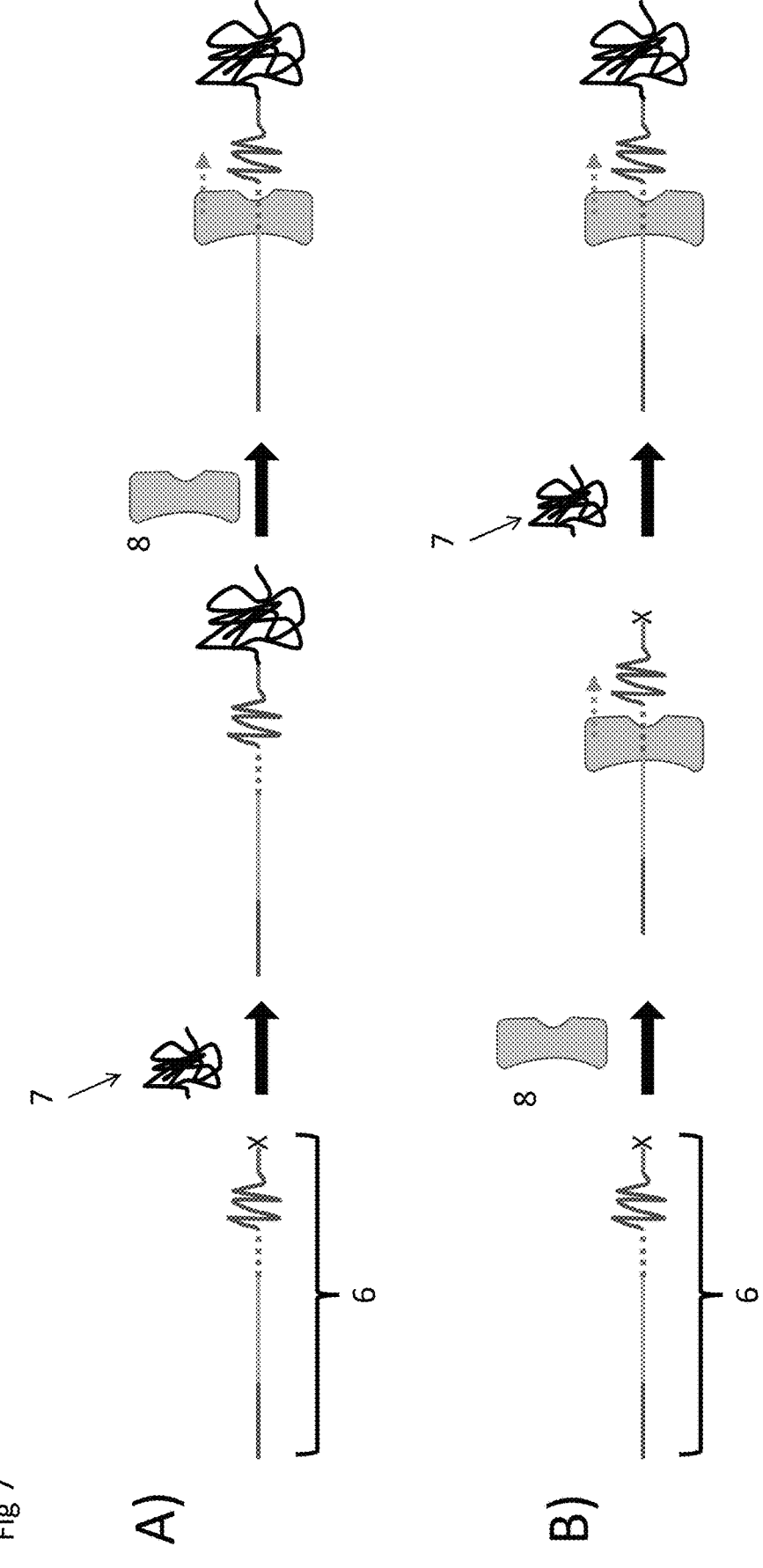

FIG. 7: Exemplary methods of loading a leader construct (6) with protein translocase(s) (8) and attaching the leader construct to a protein of interest (7). A) Leader constructs can first be coupled to target protein analytes, then loaded with translocases. B) Leader substrates can be pre-loaded with translocases, and then coupled to target protein analytes.

Figure 8:
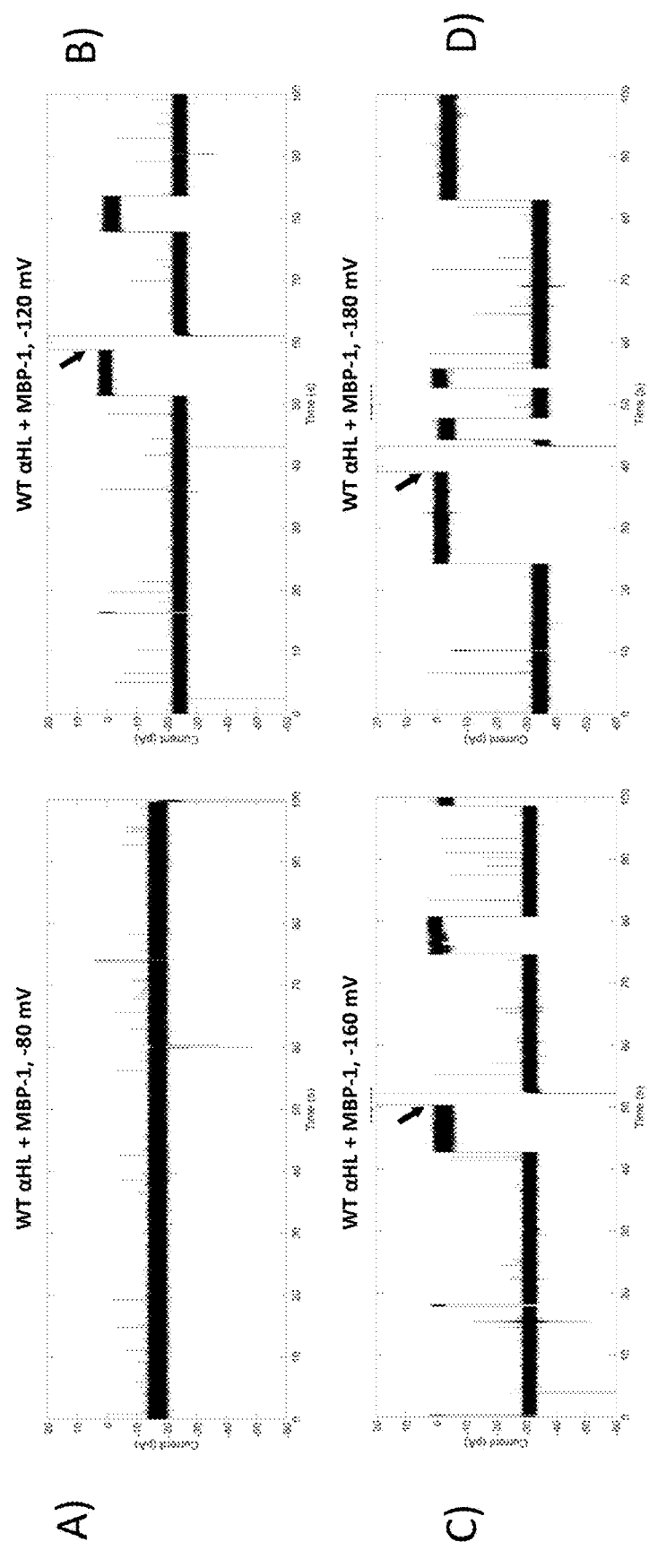

FIG. 8: Electrical recordings of the capture of a Maltose Binding Protein substrate (MBP-1) in wild-type alpha-hemolysin nanopores (WT aHL). Measurements acquired with cis and trans solutions of 1 M potassium glutamate, 50 mM Tris, 25 mM $MgCl_2$, pH 7.5. The cis compartment had a concentration of 0.1 μM MBP-1. Figures show selected representative regions of recording at (A) −80 mV, (B) −120 mV, (C) −160 mV and (D) −180 mV (trans electrode). Very little MBP-1 capture is observed at lower voltages. As the voltage is increased, blockades to almost 0 pA are observed due to capture of MBP-1. Some captures spontaneously clear the pore, but many have to be removed by briefly reversing the applied voltage (marked with arrows).

Figure 9:
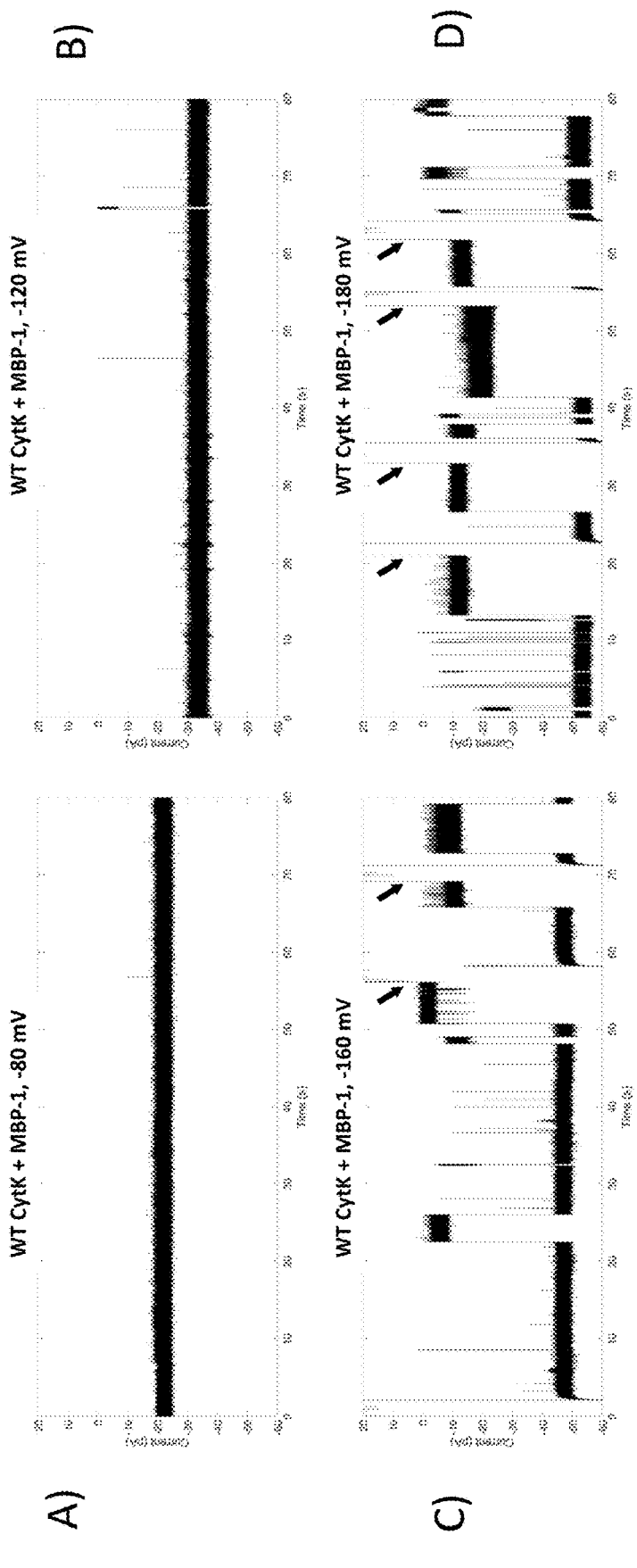

FIG. 9: The same as detailed in FIG. 8, but using wild-type CytK nanopores (WT CytK).

Figure 10:
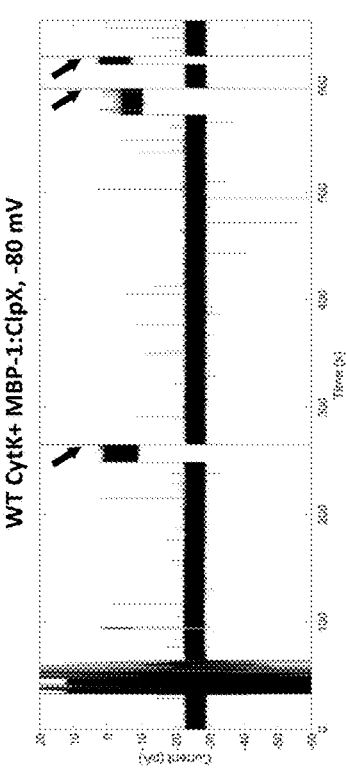
Figure 10:
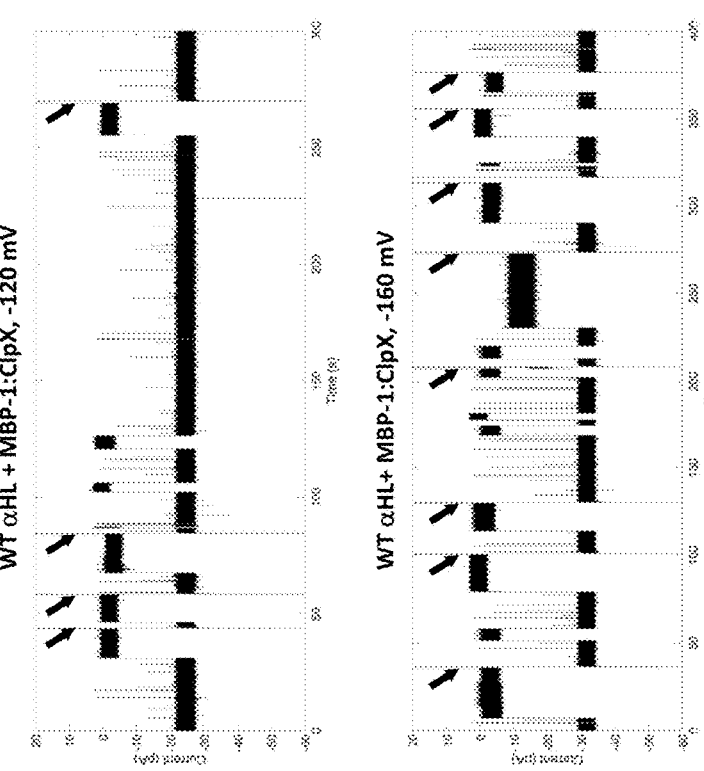

FIG. 10: Representative example of electrical current vs time traces for testing of a Maltose Binding Protein substrate:ClpX translocase complexes (MBP-1:ClpX) in weak EOF wild-type alpha-hemolysin (panels A and B) or wild-type CytK (WT CytK) (C). Measurements were carried out in a system similar to that described in FIG. 3 (except with low or zero EOF nanopores). Pre-loaded MBP-1:ClpX complexes (preloaded according to FIG. 5) were added to the cis side (to a concentration 0.2 μM ClpX, 0.1 μM MBP-1 and 2.5 mM ATP) of the nanopore systems (with cis and trans solutions of 1 M potassium glutamate, 50 mM Tris, 25 mM $MgCl_2$, pH 7.5).

Voltage dependent capture of MBP-1:ClpX complexes are observed in these low EOF nanopores, resulting in ionic current blockades to almost 0 pA. However, no events progress to a translocating peptide stage, and events remain blocked indefinitely unless ejected by a brief reversal of the applied voltage (marked by arrows).

Figure 11:
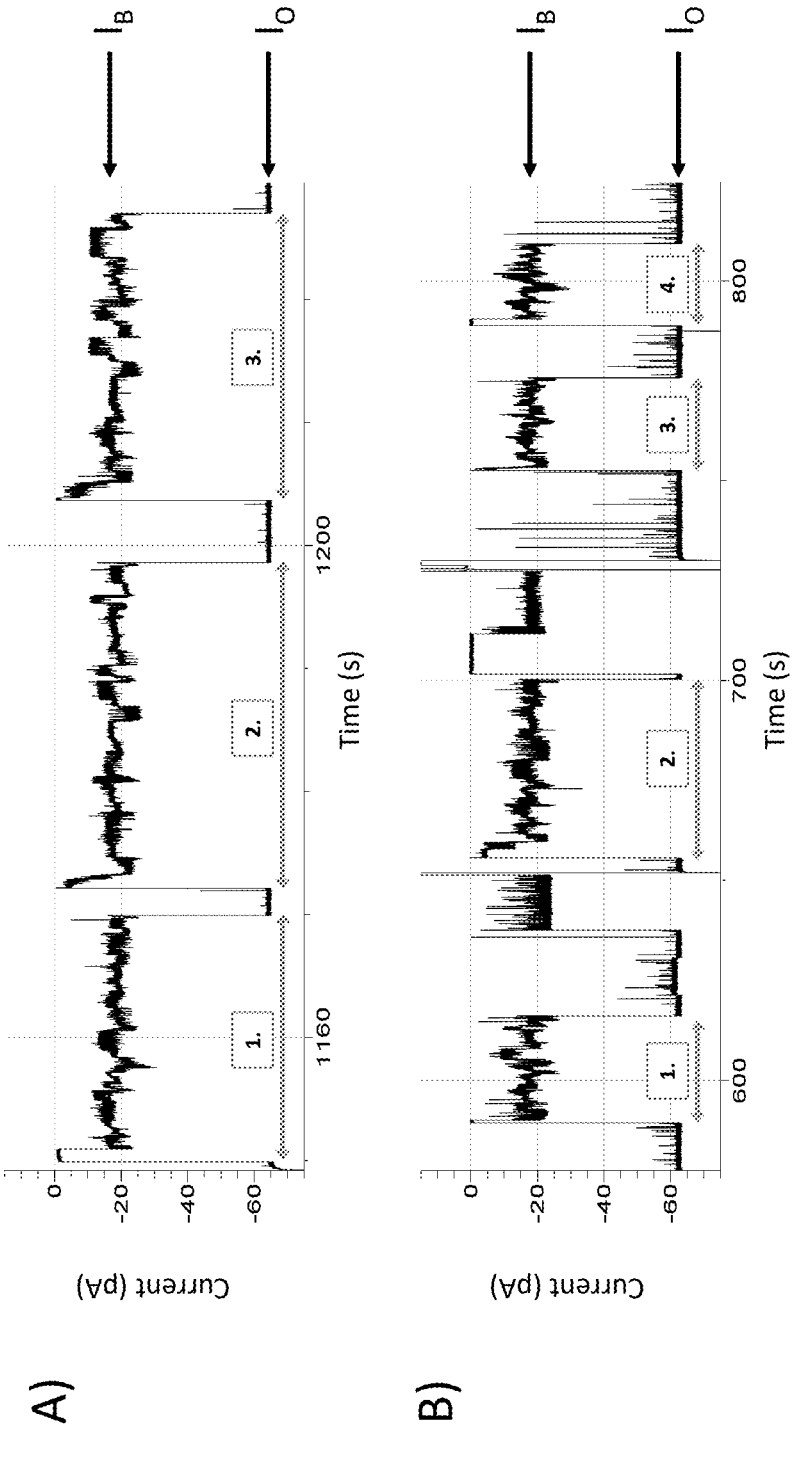

FIG. 11: Representative examples of electrical current vs time traces for testing of a Maltose Binding Protein substrate:ClpX translocase complexes (MBP-1:ClpX) in strong EOF CytK K128D K155D S120D Q122D (CytK 4D2E) nanopores according the system described in FIG. 3. Preloaded MBP-1:ClpX complexes (preloaded according to FIG. 5) were added to the cis side (to a concentration 0.2 μM ClpX, 0.1 μM MBP-1 and 2.5 mM ATP) of the nanopore systems (with cis and trans solutions of 1 M potassium glutamate, 50 mM Tris, 25 mM MgCl$_2$, pH 7.5). A) and B) show representative sections at −80 mV from separate experiments. The characteristic ClpX controlled MBP-1 translocations are marked by numbered arrows. The translocations of the analytes proceed via similar current patterns and share similar characteristic features: All events start with an immediate almost full block of the ionic current from the open pore level (I$_O$) at about −65 pA to a blockade level (I$_B$) of almost 0 pA as a result of the capture of the MBP-1:ClpX complex. After a short period of time, the translocase overcomes the stall and begins to unfold the protein and pass the polypeptide into the nanopore, giving rise to changes in current levels as the polypeptide progresses through the pore as a result of the varying amino acid composition within the nanopore at any one time. Upon reaching the end of the protein, the translocase releases the substrate through the nanopore, resulting in a return to unoccupied open pore current I$_O$.

Figure 12:
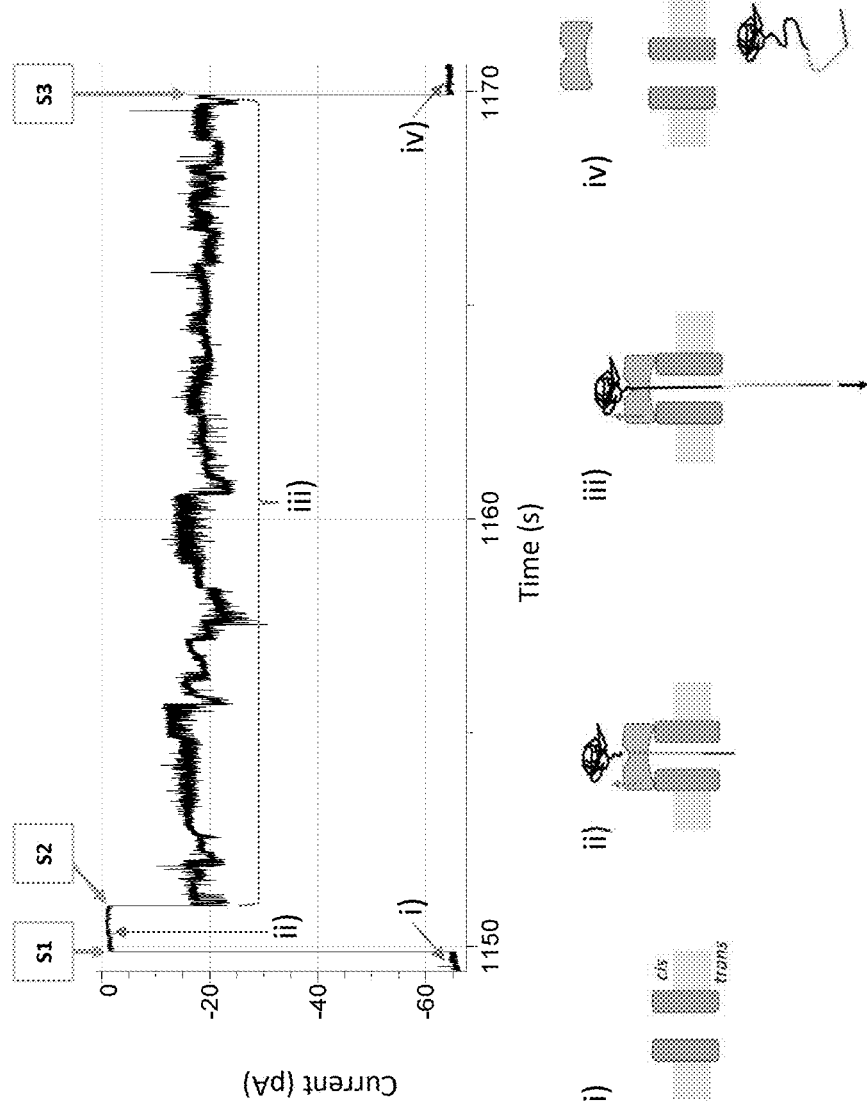

FIG. 12: Representative zoomed single example event of ClpX controlled MBP-1 translocation through CytK K128D K155D S120D Q122D (CytK 4D2E) nanopores. Events start with a blockade (S1) from the open pore level (state i) to an almost 0 pA level (state ii). After a short period the translocase overcomes the stall region (S2) and begins to proceed along the protein, in the process feeding the extruded polypeptide through the nanopore from cis to trans in a controlled manner, which results in changing current levels (section iii) that are dependent on the varying amino-acid composition in the nanopore. Events terminate (S3) with a return to open pore current levels (state iv) when the ClpX reaches the end of the MBP-1.

Figure 13:
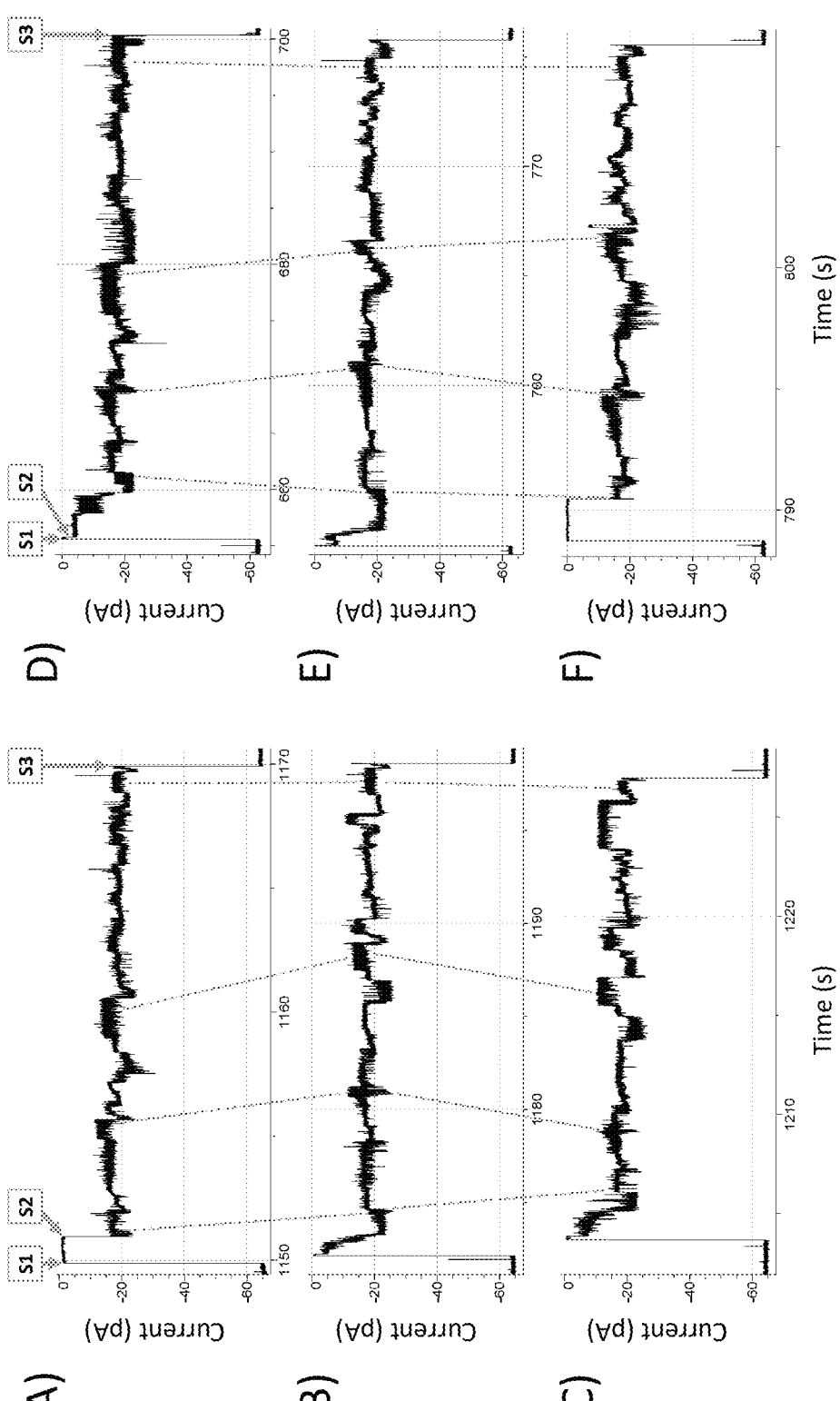

FIG. 13: Further representative zoomed examples of ClpX controlled MBP-1 translocation events through CytK K128D K155D S120D Q122D (CytK 4D2E) nanopores. The figure illustrates the consistent and characteristic current patterns that are observed between S2 and S3 sections of events that are the result the amino acid composition within the nanopore changing in the same sequential manner as the MBP-1 polypeptides are moved through the nanopore under the control of the translocases (dotted lines join similar pattern motifs in the separate events).

Figure 14:
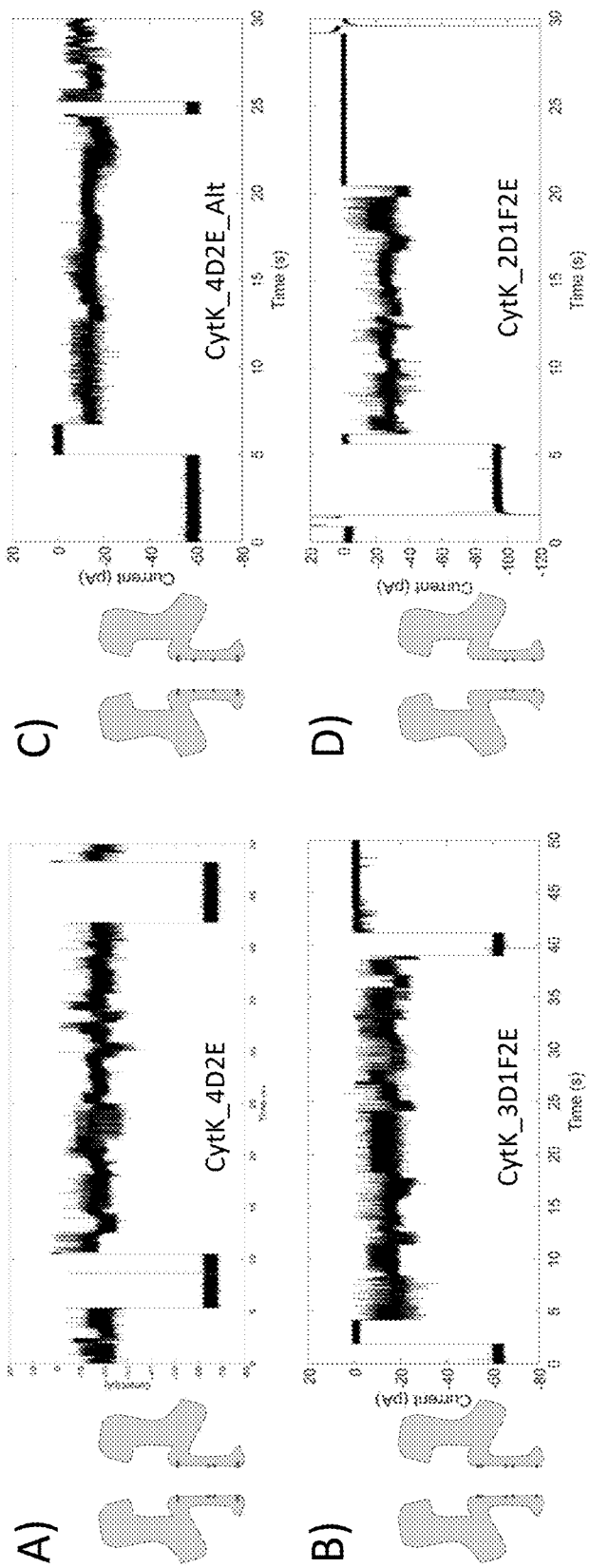

FIG. 14: Example ClpX controlled MBP-1 translocation events for selected high EOF nanopore systems using high ion-selectivity nanopores. Events acquired from A) a CytK_4D2E nanopore (CytK K128D K155D S120D Q122D) system at −80 mV, B) a CytK_3D1F2E nanopore (CytK K128F_S120D_Q122D_K155D) system-80 mV, C) a CytK_4D2E_Alt nanopore (CytK K128D K155D S120D S151D) system at −80 mV, D) a CytK_2DIF2E nanopore (CytK K128F S120D Q122D) system at −120 mV, all in cis and trans solutions of 1 M potassium glutamate, 50 mM Tris, 25 mM MgCl$_2$, pH 7.5, with preloaded MBP-1:ClpX in the cis compartment (to a concentration 0.2 μM ClpX, 0.1 μM MBP-1 and 2.5 mM ATP). Panels include subset schematic showing the location of the net negative charges in the respective nanopores (where a negative residue is balanced by an adjacent positive residue neither are shown).

Figure 15:
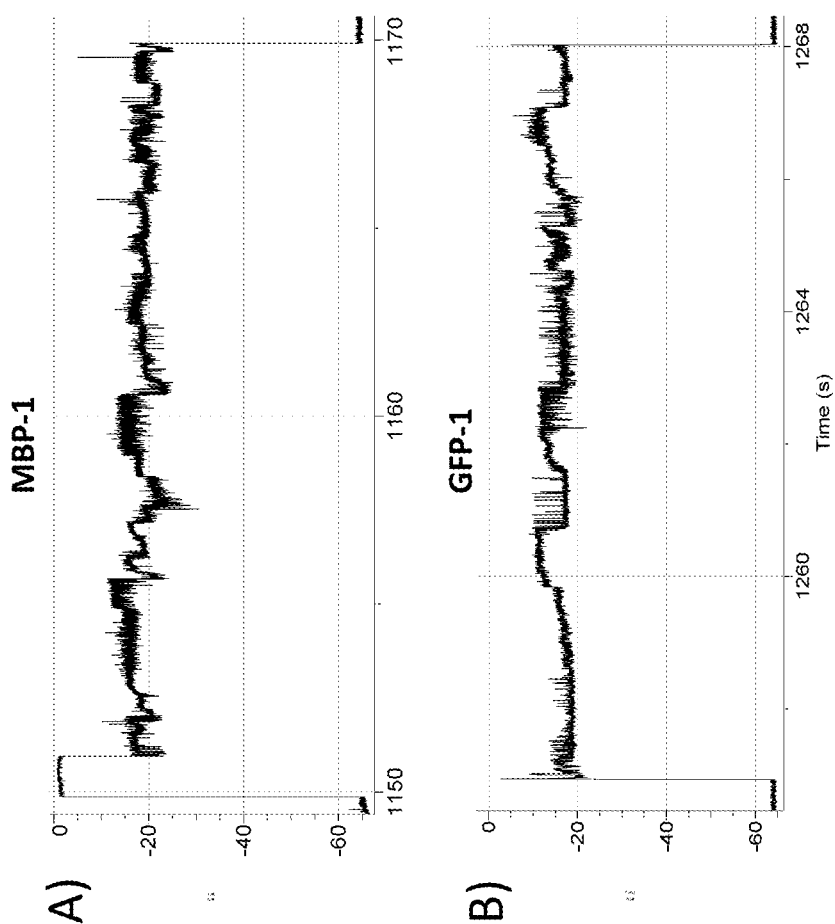

FIG. 15: Representative zoomed exemplary events of ClpX controlled translocation of A) MBP-1 substrates compared to B) GFP-1 substrates through CytK K128D K155D S120D Q122D (CytK 4D2E) nanopores at −80 mV.

Figure 16:
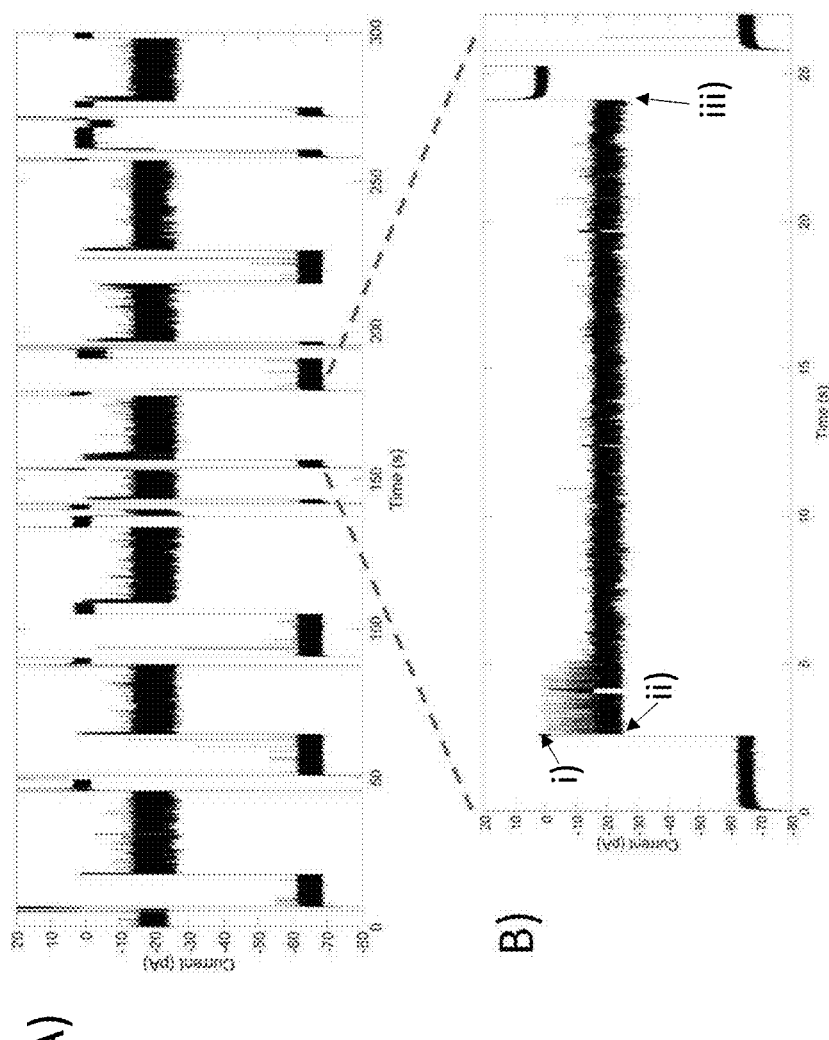

FIG. 16: Exemplary electrical current vs. time traces for testing of a Maltose Binding Protein:ClpX translocase complexes (MBP-1:ClpX) in strong EOF CytK K128D K155D S120D Q122D (CytK 4D2E) nanopores with non-hydrolyzable Gamma-S-ATP. Pre-loaded MBP-1:ClpX complexes (preloaded with standard 10 mM ATP as described herein) were added to the cis side of the nanopore system at −80 mV (cis: 1 M potassium glutamate, 50 mM Tris, 25 mM MgCl$_2$, pH 7.5 containing 0.2 μM ClpX: 0.1 μM MBP-1, 2.5 mM gamma-S-ATP and 0.25 mM ATP; trans: 1 M potassium glutamate, 50 mM Tris, 25 mM MgCl$_2$, pH 7.5). A) Blockade events from the capture of MBP-1:ClpX complexes are observed; a typical zoom example is shown in B). The events display the usual initial block to almost 0 pA (i), which is then followed by an increase to −20 pA (ii). However the events never progress to the translocase controlled movement of polypeptide phase that is observed under regular ATP conditions, resulting in indefinite blockades that have to be cleared by a brief reversal of applied voltage (iii).

Figure 17:
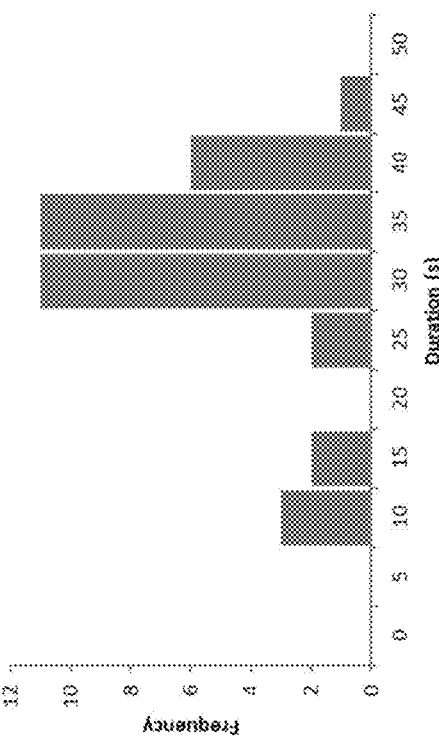

FIG. 17: Histogram of the translocation duration for 35 full-length ClpX controlled MBP-1 translocations through a CytK 4D2E nanopore at −80 mV (cis: 1 M potassium glutamate, 50 mM Tris, 25 mM MgCl$_2$, pH 7.5 containing 0.2 μM ClpX: 0.1 μM MBP-1, 2.5 mM ATP; trans: 1 M potassium glutamate, 50 mM Tris, 25 mM MgCl$_2$, pH 7.5).

Figure 18:
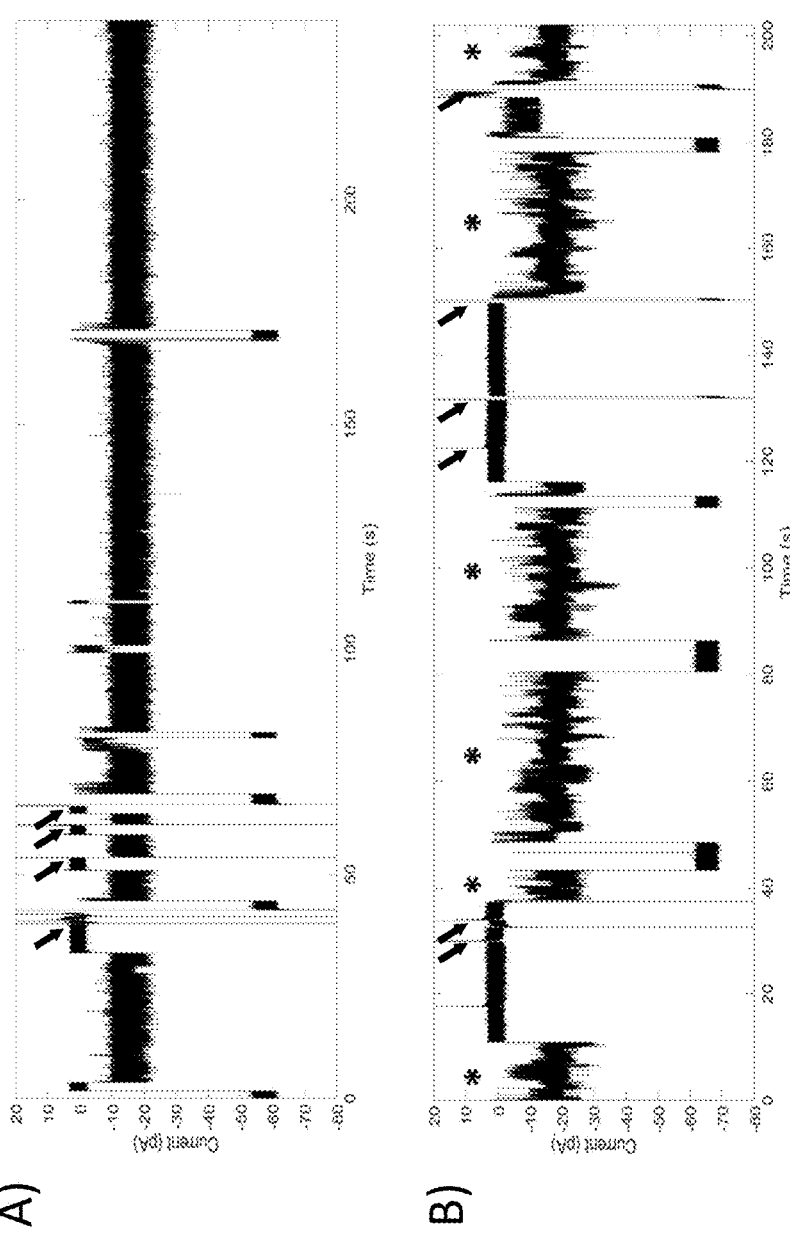

FIG. 18: Comparison of ClpX controlled MBP-1 translocations at −80 mV through CytK 4D2E nanopore systems (cis: 1 M potassium glutamate, 50 mM Tris, 25 mM MgCl$_2$, pH 7.5, 2.5 mM ATP; trans: 1 M potassium glutamate, 50 mM Tris, 25 mM MgCl$_2$, pH 7.5) without (A) and with (B) pre-loading incubation to form the MBP-1:ClpX complexes. A) ClpX (0.2 μM concentration) and MBP-1 (0.1 μM concentration) were added to the cis compartment separately. B) ClpX and MBP-1 pre-incubated (10 μM ClpX, 5 μM ClpX, 10 mM ATP, 25 mM MgCl$_2$) in a 10 μL volume before addition to cis compartment (0.2 μM ClpX, 0.1 μM MBP-1 concentration). Arrows mark voltage reversals, and stars mark ClpX controlled translocations.

FIG. 19: Exemplary capture and ClpX controlled trans-to-cis translocation of MBP-1 through CytK 4D2E nanopores that were inserted from the cis compartment (cis and trans solutions of 1 M potassium glutamate, 50 mM Tris, 25 mM MgCl$_2$). Preloaded MBP-1:ClpX complexes were added to the trans compartment (to a concentration 0.2 μM ClpX, 0.1 μM MBP-1 and 2.5 mM ATP) and captured into the trans entrance of the nanopores at +80 mV, and translocated under ClpX control as a result of the strong trans-to-cis EOF created at positive applied voltage.

Figure 20:
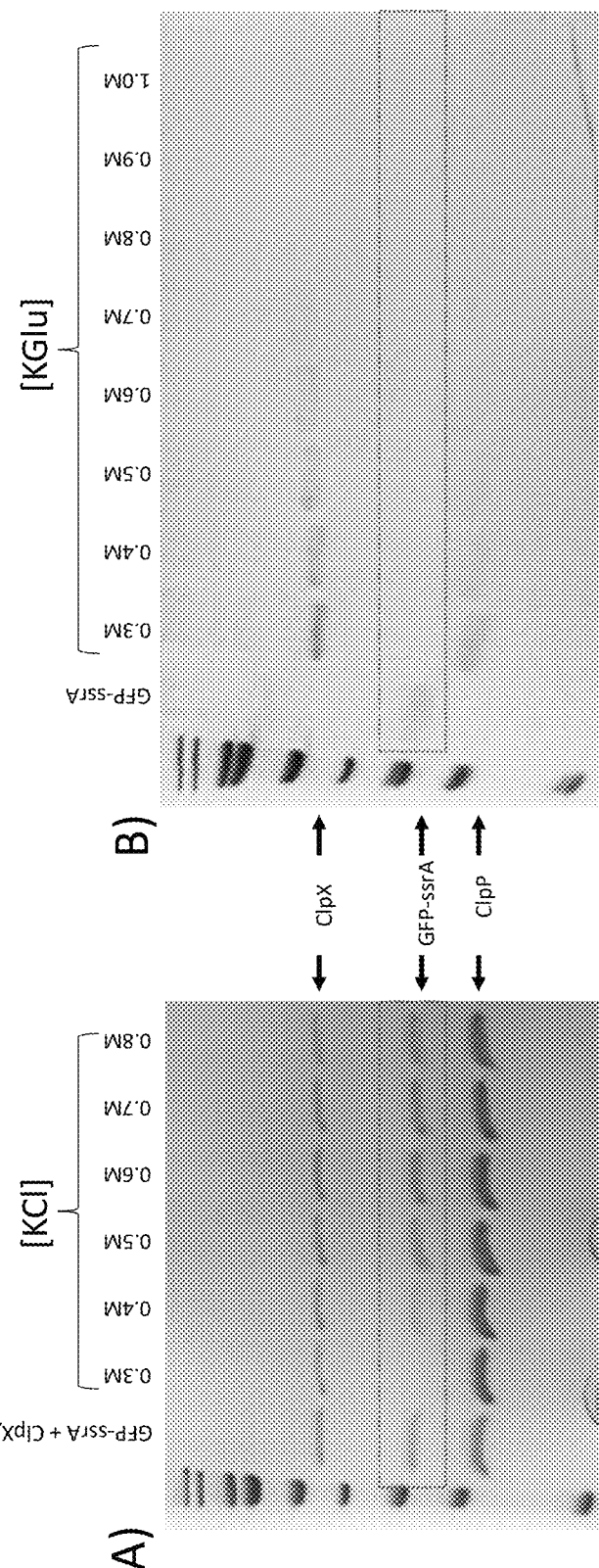

FIG. 20: A) gel showing the results of a ClpX/ClpP degradation assay of a GFP-ssrA substrate (GFP-0) under varying concentrations of KCl. B) gel showing the results of a degradation assay of GFP-O under varying concentration of potassium glutamate (KGlu). (65 nM ClpX, 65 nM ClpP, 2800 nM GFP).

Figure 21:
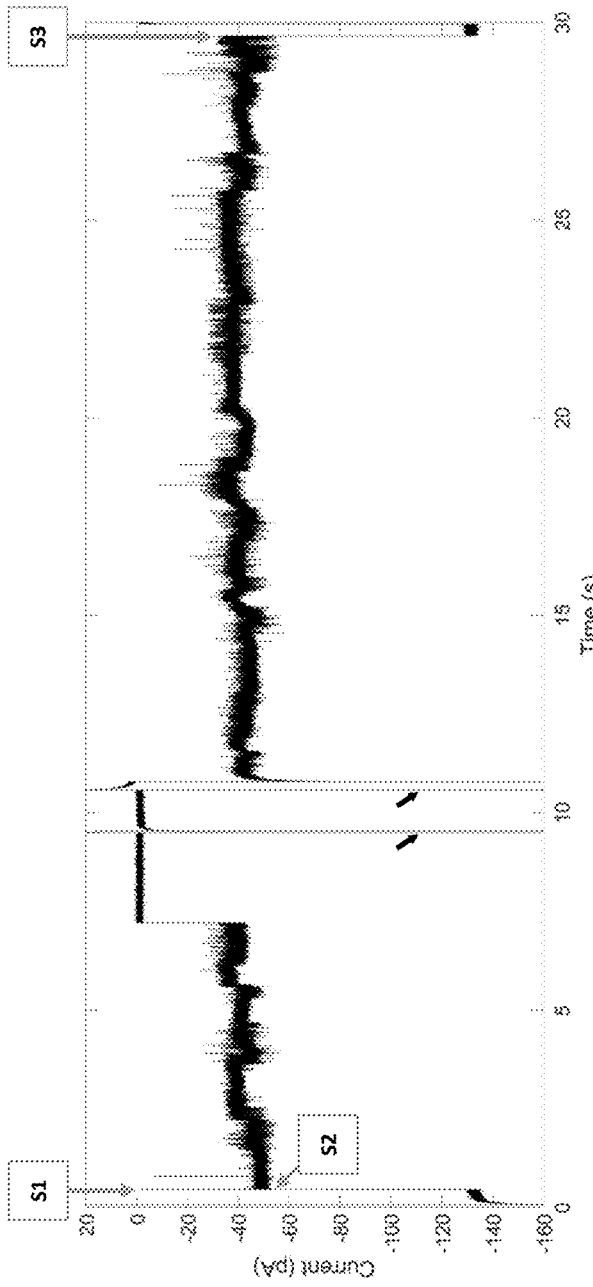

FIG. 21: Representative ClpX controlled translocation of MBP-1 through a CytK 4D2E nanopore at −120 mV in a system containing 1 m KGlu in the cis compartment and 1M KCl in the trans compartment (cis: 1 M potassium glutamate, 50 mM Tris, 25 mM MgCl$_2$, pH 7.5 containing 0.2 μM ClpX:0.1 μM MBP-1, 2.5 mM ATP; trans: 1 M potassium chloride, 50 mM Tris, 25 mM MgCl$_2$, pH 7.5).

FIG. 22: Schematic showing an exemplary "Out mode" method for characterising a target protein by capturing it from the cis side into the nanopore of a system setup with high net cis-to-trans EOF, in conjunction with a protein translocase orientated on the target protein such that it then pulls the polypeptide back out through the same nanopore to the cis side. A) A protein translocase (8) binds to a target protein (7), which is modified with terminal tags to enable directed binding to the translocase (1) and capture in the nanopore (2), to create a translocase:target protein complex. B) The translocase:target protein complex is captured in a nanopore via the terminal capture tag via a combination of EPF and/or EOF forces so that the target protein portion of the complex translocates partially through the nanopore from the cis side to trans side, until the bound translocase encounters the top of the nanopore (C). The force of the net cis-to-trans EOF acting on the polypeptide passing through the nanopore pulls on the translocase:target protein complex and retains the translocase against the top of the pore. D) The translocase continues to move along the target protein under NTP powered hydrolysis in the direction of the sub-arrow (in the cis-to-trans direction), and in doing so pulls the polypeptide back out of the nanopore in the trans-to-cis direction. E) Upon reaching the end of the target protein molecule the translocase unbinds from the target protein and both the translocase and the target protein are released back into the cis side.

Figure 23:
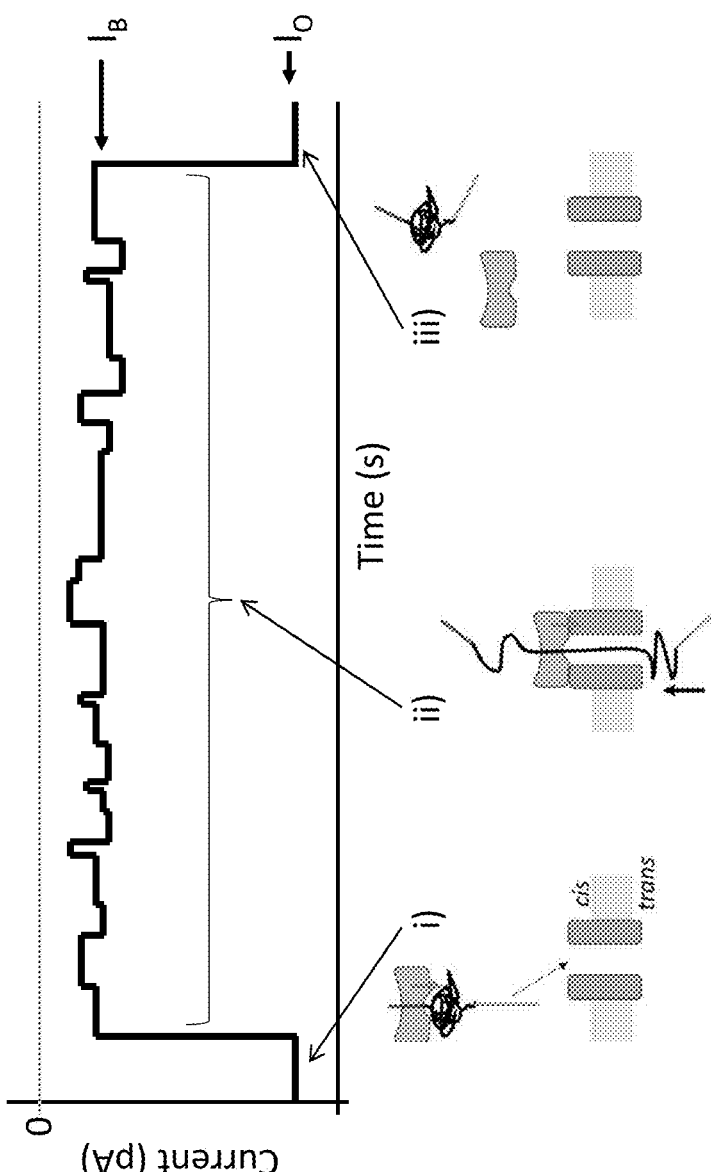

FIG. 23: Schematic current vs time translocation event resulting from translocase controlled polypeptide translocation through a nanopore as described by the scheme in FIG. 22.

Figure 24:
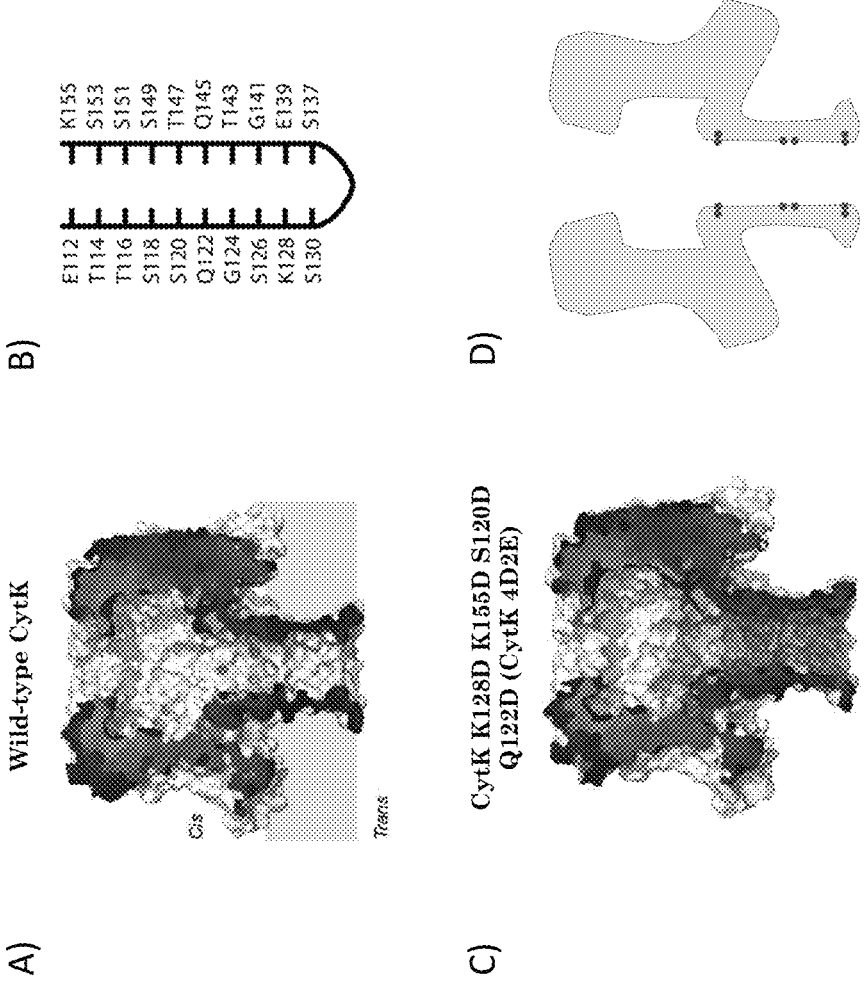

FIG. 24: A) Structural model of the wild-type CytK nanopore from homology mapping onto the structure of the alpha-hemolysin nanopore. The model shows the low net charge inside the nanopore from the water facing residues. B) A schematic of the residues in each beta strand of the transmembrane beta-barrel region of wild-type CytK, marking water-facing residues of the down- and up-strands most suitable for mutagenesis. C) Model of the CytK 4D2E nanopore (CytK K128D K155D S120D Q122D), showing very high net negative internal charge due to mutations. D) Schematic location of mutations to negative residues in the barrel region of the Cytk 4D2E nanopore.

Figure 25:
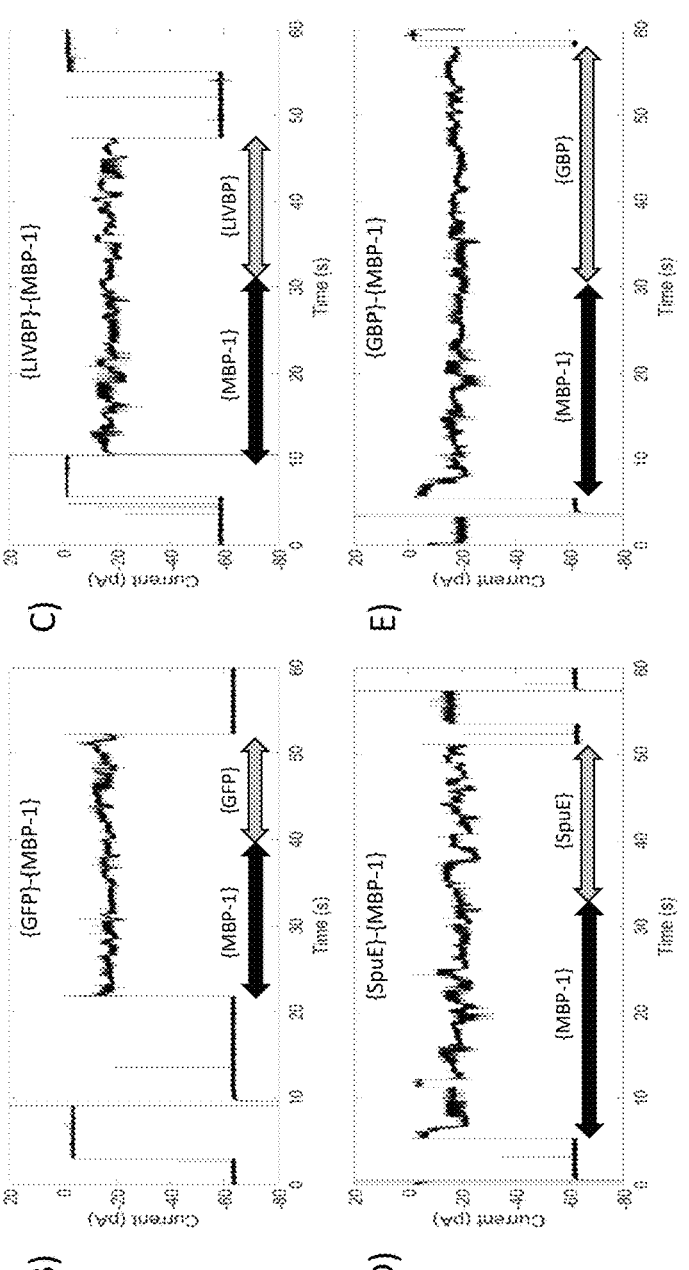
Figure 25:
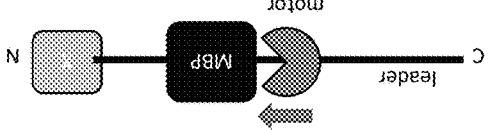

FIG. 25: Recordings of different substrates in CytK nanopores. A) Schematic of the substrate design. B-D) Exemplary electrophysiology reads acquired from {GFP}-{MBP-1}, {LIVBP}-{MBP-1}, {SpuE}-{MBP-1}, and {GBP}-{MBP-1} substrates. Each substrate shows a similar ionic current pattern in the region corresponding to MBP as marked by the underlying arrows, and a unique ionic current signature specific to the attached protein in the second sections as marked by the indicated arrows below. Measurements obtained with CytK_4D2E nanopore in 1 M potassium glutamate, 50 mM Tris, 25 MgCl$_2$, 10 mM DTT and 1 mM EDTA, buffered to pH 7.5 at −80 mV. The cis compartment had a concentration of 0.2 μM ClpX, 0.1 μM of the respective indicated substrate, and 2.5 mM ATP.

Figure 26:
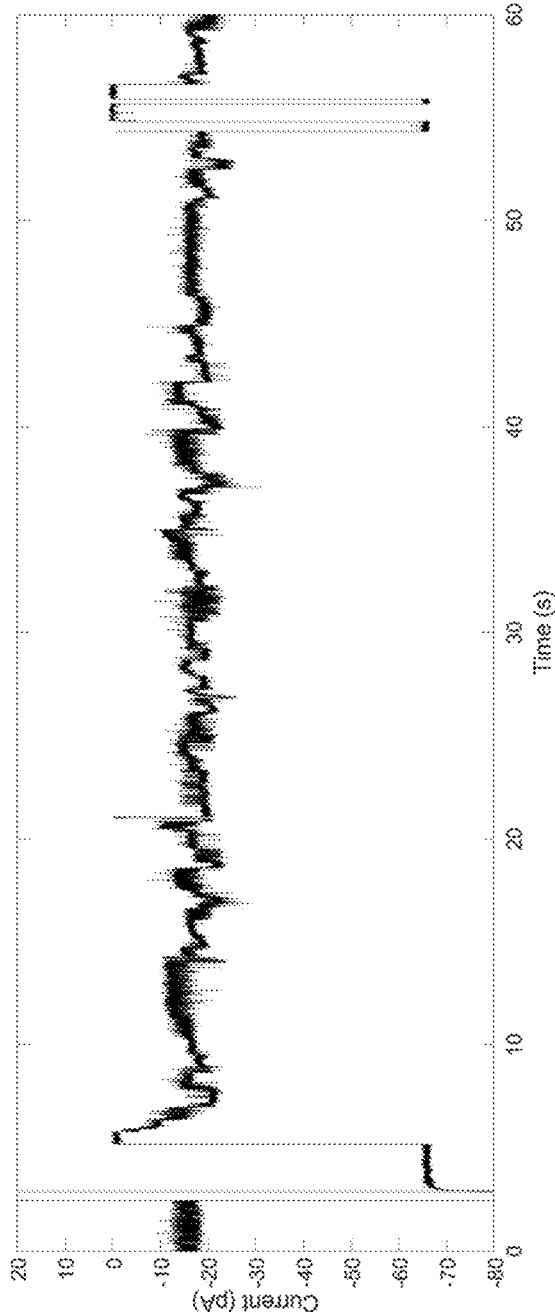

FIG. 26: Exemplary single-molecule read of a 88 kDa MBP-MBP fusion protein. Measurements obtained with a CytK_4D2E nanopore in 1 M potassium glutamate, 50 mM Tris, 25 MgCl$_2$, 10 mM DTT and 1 mM EDTA, buffered to pH 7.5 at −80 mV. The cis compartment had a concentration of 0.2 μM ClpX, 0.1 μM MBP-MBP and 2.5 mM ATP.

Figure 27:
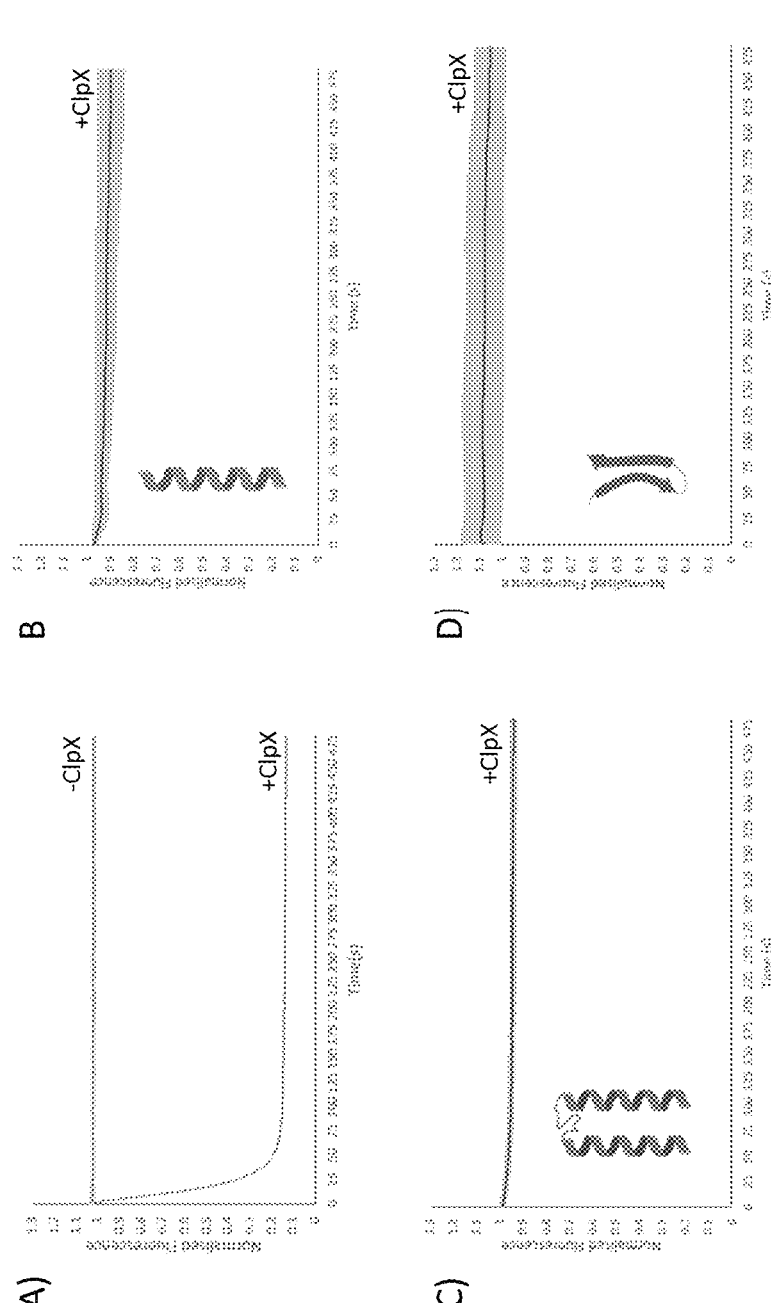

FIG. 27: Stalling of ClpX at 37° C. using blocking domains. A) Unfolding of GFP-1 with (+ClpX) and without ClpX (−ClpX), B) mNG with an alpha-helical blocking domain, C) mNG with a helix-turn-helix blocking domain, and D) mNG with a hairpin blocking domain. Measurements were performed with a 1:4 substrate:unfoldase molar ratio (0.065 μM substrate and 0.26 μM ClpX) in the presence of 10 mM ATP in a solution containing 1 M potassium glutamate, 50 mM Tris, 25 mM MgCl$_2$, 10 mM DTT and 1 mM EDTA, buffered to pH 7.5.

Figure 28:
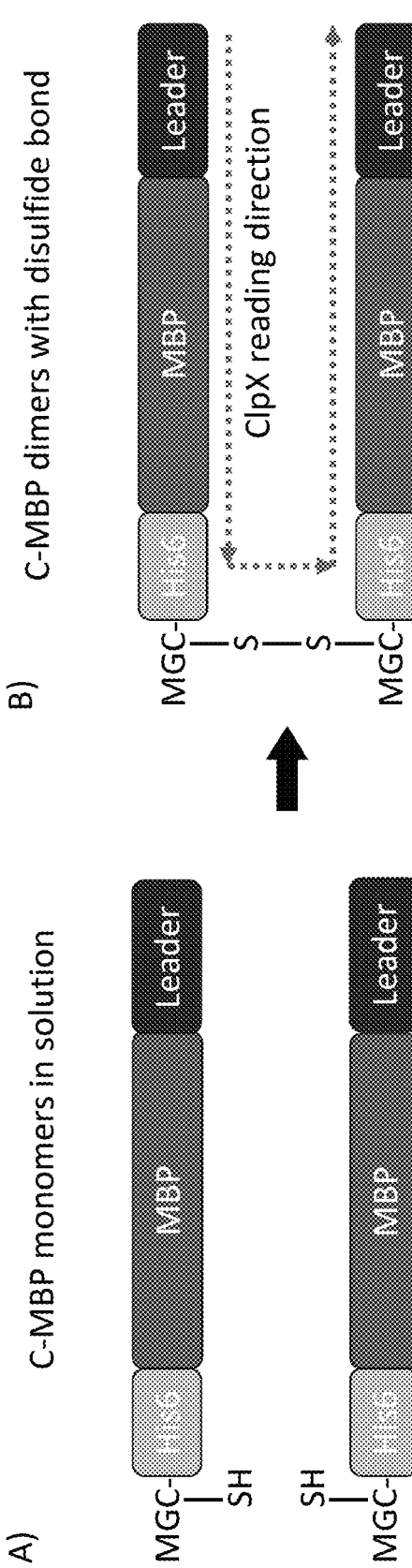

FIG. 28: Depictions of maltose-binding protein (MBP) monomers and maltose-binding protein dimers for analysis in the present disclosure.

Figure 29:
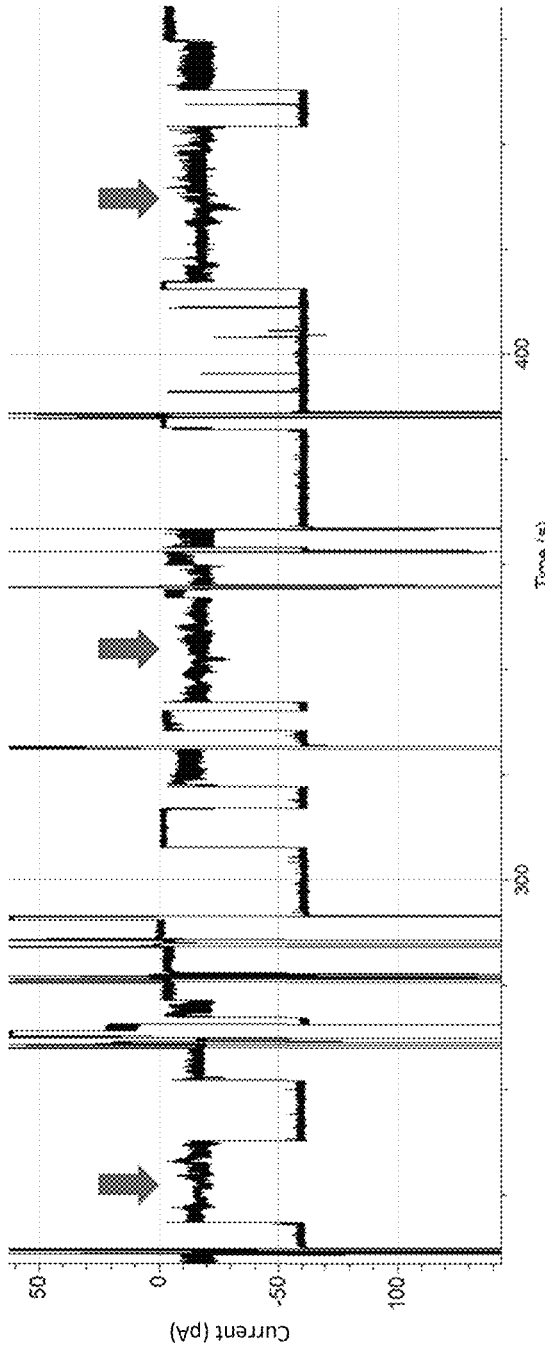

FIG. 29: Exemplary electrophysiology recording of a MBP protein lacking the ssrA recognition motif, that was tagged on the C-terminus to allow binding of ClpX. ClpX controlled MBP translocations (marked by arrows) are evident from the characteristic pattern of changing ionic current signals. Measurements obtained with a CytK_4D2E nanopore in 1 M potassium glutamate, 50 mM Tris, 25 MgCl$_2$, 10 mM DTT and 1 mM EDTA, buffered to pH 7.5 at −80 mV. The cis compartment contained has a concentration of 0.2 μM ClpX, 0.1 μM tagged-MBP and 2.5 mM ATP.

FIG. 30: Depiction of a computer system that is programmed or otherwise configured to implement methods provided herein.

EXPERIMENTAL SECTION

Example 1: CytK Pores with ClpX Translocase

Example 1 examined whether it was possible to create a sufficiently strong electro-osmotic flow (FIG. 1) to capture and translocate complex polypeptides against opposing electrophoretic forces (EPF), and to control the movement of the translocated polypeptide through the nanopore (FIG. 2). To create a large electro-osmotic force (EOF) a wide range of engineered (mutated) CytK nanopores were generated with varying extents of ion-selectivity to create strong ion-selective current flow under high salt conditions. These were examined versus wild-type or moderately mutated nanopores with low ion-selectively. These nanopores were all tested against their ability to translocate net negative model substrate proteins, based on Maltose Binding Protein (MBP) and Green Fluorescent Protein (GFP). The Maltose Binding protein had a net charge of about −7.5 at pH 7.5, and was tested in a system with an applied voltage where the net EPF may be acting to repel/eject the net negative protein from the nanopore (e.g., the net EPF is acting trans-to-cis on the negatively charged protein when a negative voltage was applied to the trans electrode as described herein), so it was an substrate to test if the EOF enabled translocation against the direction of EPF. GFP was also tested, which likewise had a net negative charge of about −5.1 at pH 7.5, for the ability to translocate a structurally quite different and more stable protein against the net EPF.

Preparation of ClpX Translocase

*E. coli* ClpX was employed as exemplary translocase to control the movement of the polypeptide through the nanopore (FIGS. 2 and 3). ClpX was selected as a AAA+ translocase systems, and can unfold and translocate along a wide variety of proteins, generating a high force through NTP hydrolysis [(Olivares et al. 2016, Nature Reviews Microbiology Vol. 14, pg. 33-44). The monomer and covalently linked trimer of N-terminal truncated ClpX variants (residues 61-423) were purified as previously described (Singh, et al. J. Biol. Chem. 276.31 (2001): 29420-29429;

Martin et al., Nature 437.7062 (2005): 1115-1120) with minor modifications and used for ClpX nanopore experiments. Specifically, the gene encoding for monomer and trimer of ClpX-ΔN were separately transformed into *E. coli* BL21 (DE3) electrocompetent cells. Transformants were selected after overnight growth at 37° C. on lysogeny broth (LB) agar plates supplemented with ampicillin (100 mg/L). The resulting colonies were inoculated into 200 mL LB medium containing 100 mg/L of ampicillin. The ClpX protein expression was induced at an A600 of ~0.6 by addition of 0.5 mM isopropyl β-D-1-thiogalactopyranoside (IPTG) and incubated at 25° C. overnight. The cells were harvested by centrifugation for 20 min (4000×g) at 4° C. and the pellets were stored at −80° C. About 100 mL of cell culture pellet was thawed and solubilized with ~20 mL lysis buffer (50 mM HEPES, pH 7.5, 300 mM KCl, 20 mM imidazole, 1 mM dithiothreitol (DTT), 0.1 units/mL DNase I, 10 μg/mL lysozyme) and stirred with a vortex shaker for 1 hour at 4° C. The bacteria were then lysed by sonication (duty cycle 10%, output control 3, Branson Sonifier 450). The lysate was subsequently centrifuged at 6000×g at 4° C. for 20 min and the cellular debris discarded. The supernatant was mixed with 100 μL of Ni-NTA resin (Qiagen) to a 50 mL falcon tube, which was pre-equilibrated with wash buffer (50 mM HEPES, pH 7.5, 300 mM KCl, 20 mM imidazole, 1 mM dithiothreitol (DTT)). Proteins were purified from the supernatant via Ni-NTA resin (Qiagen) using standard procedures and eluted with approximately 600 μL elution buffer (600 mM imidazole, 1 mM dithiothreitol (DTT), 100 μM EDTA, 200 mM KCl, 25 mM MgCl₂, 50 mM Tris, pH 7.5). The proteins were further purified using a Superose 6 column Increase 10/600 GL and eluted in 200 ul fractions in elution buffer 2 (1 mM dithiothreitol (DTT), 100 μM EDTA, 200 mM KCl, 25 mM MgCl₂, 50 mM Tris, pH 7.5). The fractions with pure protein were concentrated using Amicon Ultra Centrifugal Filters. Purified proteins were then flash frozen in small aliquots supplemented with 30% glycerol and stored at −80° C. Protein concentrations were determined by Bradford assay with bovine serum albumin as a standard Preparation of Protein Analytes The well-known model proteins, Maltose Binding Protein (MBP) and Green Fluorescent protein (GFP), were used to test protein translocation through the nanopores. The model proteins were provided with a His-affinity tag and further modified via genetic fusions to express full length substrates with C-terminal "leader construct" extensions (of design similar to that shown in FIG. 4B). The leader constructs had elements that enabled binding to ClpX (ssrA recognition motif), stalling of the ClpX (polyglycine stall motif) and EPF capture motifs that enabled nanopore capture (polyanion or polycation stretches).

The gene encoding for target proteins GFP-0, GFP-1, GFP-2, GFP-3, MBP-1, MBP-2, or MBP-4 (see Table 1 below) was separately transformed into *E. coli* BL21 (DE3) electrocompetent cells. Transformants were selected after overnight growth at 37° C. on lysogeny broth (LB) agar plates supplemented with kanamycin (50 mg/L). The resulting colonies were inoculated into 200 mL LB medium with 50 mg/L of kanamycin. The cells were induced at an A600 of ~0.6 by addition of 0.5 mM isopropyl β-D-1-thiogalactopyranoside (IPTG) and incubated at 25° C. overnight. The cells were harvested by centrifugation and the pellets were stored at −80° C. 100 mL cell culture pellets were thawed and solubilized before removing the cellular debris by centrifugation. Proteins were purified from the supernatant via Ni-NTA resin (Qiagen) used standard procedures and eluted with approximately 100 μL elution buffer (600 mM imidazole, 1 mM dithiothreitol (DTT), 150 mM KCl, 50 mM HEPES, pH 7.5). Purified proteins were then flash frozen in small aliquots and stored at −80° C. Protein concentrations were determined by Bradford assay with bovine serum albumin as a standard.

TABLE 1

| | Amino acid sequences of target proteins used. | |
| --- | --- | --- |
| Target | Amino acid sequence (from N- to C-terminus) | Net charge at pH 7.5 (Target protein + purification tag) |
| GFP-0 (SEQ ID NO: 25) | Affinity purification tag: MGHHHHHHSS GFP protein: ASKGEELFTGVVPILVELDGDVNGHKFSVSG EGEGDATYGKLTLKFICTTGKLPVPWPTLVT TFSYGVQCFSRYPDHMKRHDFFKSAMPEGYV QERTIFFKDDGNYKTRAEVKFEGDTLVNRIE LKGIDFKEDGNILGHKLEYNYNSHNVYIMAD KQKNGIKVNFKIRHNIEDGSVQLADHYQQNT PIGDGPVLLPDNHYLSTQSALSKDPNEKRDH MVLLEFVTAAGI Recognition motif: AANDENYALAA | −5.1 |
| GFP-1 (SEQ ID NO: 26) | Affinity purification tag: MGHHHHHHSS GFP protein: ASKGEELFTGVVPILVELDGDVNGHKFSVSG EGEGDATYGKLTLKFICTTGKLPVPWPTLVT TFSYGVQCFSRYPDHMKRHDFFKSAMPEGYV QERTIFFKDDGNYKTRAEVKFEGDTLVNRIE LKGIDFKEDGNILGHKLEYNYNSHNVYIMAD KQKNGIKVNFKIRHNIEDGSVQLADHYQQNT PIGDGPVLLPDNHYLSTQSALSKDPNEKRDH MVLLEFVTAAGI | −5.1 |

TABLE 1-continued

Amino acid sequences of target proteins used.

| Target | Amino acid sequence (from N- to C-terminus) | Net charge at pH 7.5 (Target protein + purification tag) |
|---|---|---|
| | Stall motif:<br>GGGGGGGGGGGGGS<br>Capture motif:<br>RRRRRRRRRRRRRRR<br>Recognition motif<br>AANDENYALAA | |
| GFP-2 (SEQ ID NO: 27) | Affinity purification tag:<br>MGHHHHHHSS<br>GFP protein:<br>ASKGEELFTGVVPILVELDGDVNGHKFSVSG<br>EGEGDATYGKLTLKFICTTGKLPVPWPTLVT<br>TFSYGVQCFSRYPDHMKRHDFFKSAMPEGYV<br>QERTIFFKDDGNYKTRAEVKFEGDTLVNRIE<br>LKGIDFKEDGNILGHKLEYNYNSHNVYIMAD<br>KQKNGIKVNFKIRHNIEDGSVQLADHYQQNT<br>PIGDGPVLLPDNHYLSTQSALSKDPNEKRDH<br>MVLLEFVTAAGI<br>Capture motif:<br>RRRRR<br>Recognition motif:<br>AANDENYALAA | −5.1 |
| GFP-3 (SEQ ID NO: 28) | Affinity purification tag:<br>MGHHHHHHSS<br>GFP protein:<br>ASKGEELFTGVVPILVELDGDVNGHKFSVSG<br>EGEGDATYGKLTLKFICTTGKLPVPWPTLVT<br>TFSYGVQCFSRYPDHMKRHDFFKSAMPEGYV<br>QERTIFFKDDGNYKTRAEVKFEGDTLVNRIE<br>LKGIDFKEDGNILGHKLEYNYNSHNVYIMAD<br>KQKNGIKVNFKIRHNIEDGSVQLADHYQQNT<br>PIGDGPVLLPDNHYLSTQSALSKDPNEKRDH<br>MVLLEFVTAAGI<br>Stall/capture motif:<br>GEGDGEGDGEGD<br>Recognition motif:<br>AANDENYALAA | −5.1 |
| MBP-1 (SEQ ID NO: 29) | Affinity purification tag:<br>MHHHHHHSS<br>MBP protein:<br>PWKIEEGKLVIWINGDKGYNGLAEVGKKFEK<br>DTGIKVTVEHPDKLEEKFPQVAATGDGPDII<br>FWAHDRFGGYAQSGLLAEITPDKAFQDKLYP<br>FTWDAVRYNGKLIAYPIAVEALSLIYNKDLL<br>PNPPKTWEEIPALDKELKAKGKSALMENLQE<br>PYFTWPLIAADGGYAFKYENGKYDIKDVGVD<br>NAGAKAGLTFLVDLIKNKHMNADTDYSIAEA<br>AFNKGETAMTINGPWAWSNIDTSKVNYGVTV<br>LPTFKGQPSKPFVGVLSAGINAASPNKELAK<br>EFLENYLLTDEGLEAVNKDKPLGAVALKSYE<br>EELAKDPRIAATMENAQKGEIMPNIPQMSAF<br>WYAVRTAVINAASGRQTVDEALKDAQTRITK<br>HM<br>Stall/capture motif:<br>GGGGGGGGGGGGGSRRRRRRRRRRRRRRR<br>Recognition motif:<br>AANDENYALAA | −7.5 |
| MBP-2 (SEQ ID NO: 30) | Affinity purification tag:<br>MHHHHHHSS<br>MBP protein:<br>PWGAPKIEEGKLVIWINGDKGYNGLAEVGKK<br>FEKDTGIKVTVEHPDKLEEKFPQVAATGDGP<br>DIIFWAHDRFGGYAQSGLLAEITPDKAFQDK<br>LYPFTWDAVRYNGKLIAYPIAVEALSLIYNK<br>DLLPNPPKTWEEIPALDKELKAKGKSALMFN<br>LQEPYFTWPLIAADGGYAFKYENGKYDIKDV<br>GVDNAGAKAGLTFLVDLIKNKHMNADTDYSI<br>AEAAFNKGETAMTINGPWAWSNIDTSKVNYG<br>VTVLPTFKGQPSKPFVGVLSAGINAASPNKE | −7.5 |

TABLE 1-continued

Amino acid sequences of target proteins used.

| Target | Amino acid sequence (from N- to C-terminus) | Net charge at pH 7.5 (Target protein + purification tag) |
|---|---|---|
| | LAKEFLENYLLTDEGLEAVNKDKPLGAVALK SYEEELAKDPRIAATMENAQKGEIMPNIPQM SAFWYAVRTAVINAASGRQTVDEALKDAQTR ITKHM Stall/capture motif: GGGGGGSRRRRRRRRRRRRRRRR Recognition motif: AANDENYALAA | |
| MBP-4 (SEQ ID NO: 31) | Affinity purification tag: MHHHHHHSS MBP protein: PWGAPKIEEGKLVIWINGDKGYNGLAEVGKK FEKDTGIKVTVEHPDKLEEKFPQVAATGDGP DIIFWAHDRFGGYAQSGLLAEITPDKAFQDK LYPFTWDAVRYNGKLIAYPIAVEALSLIYNK DLLPNPPKTWEEIPALDKELKAKGKSALMFN LQEPYFTWPLIAADGGYAFKYENGKYDIKDV GVDNAGAKAGLTFLVDLIKNKHMNADTDYSI AEAAFNKGETAMTINGPWAWSNIDTSKVNYG VTVLPTFKGQPSKPFVGVLSAGINAASPNKE LAKEFLENYLLTDEGLEAVNKDKPLGAVALK SYEEELAKDPRIAATMENAQKGEIMPNIPQM SAFWYAVRTAVINAASGRQTVDEALKDAQTR ITKHM Stall/capture motif: GGGGGGGGGGGG GSDDDDDDDDDD Recognition motif: AANDENYALA | -7.5 |

Preloading of the Translocase onto Target Protein

To improve the percentage of ClpX:target-protein complexes formed, the complexes were formed prior to addition to the nanopore system as illustrated schematically in FIG. 5. Pre-loading the ClpX translocase onto target protein was performed by mixing and incubating translocase with the given target protein in the presence of ATP and MgCl₂ in a suitable binding buffer (e.g. 50 mM Tris-HCl, 200 mM KCl, 25 mM MgCl₂, 1 mM DTT, 1 mM EDTA, PH 7.5). A range of pre-loading conditions and incubation times was found to result in a high percentage of ClpX loaded complex. Pre-loading was typically performed at ratios of 1:1 up to 5:1 ClpX:target-protein. For the examples used herein, the ClpX:Target-protein complexes were preloaded by mixing the components at a concentration of about 10 µM ClpX, 5 µM target protein in a 2:1 ratio, in a solution with 10 mM ATP and 25 mM MgCl₂ in a volume of 10 ul (50 mM Tris-HCl, 200 mM KCl, 10 mM ATP, 25 mM MgCl₂, 1 mM DTT, 1 mM EDTA, PH 7.5). The mixture was then incubated for at least 10 minutes at room temperature to allow sufficient time for the ClpX to bind to the target proteins and translocate along the Leader construct sequence up to the stall motif.

Preparation of CytK Nanopores

To identify the beta-barrel region of the CytK nanopore, and the putative analyte recognition region of the CytK nanopore, a homology model was built by mapping the CytK sequence to the sequence and structure of the alpha-hemolysin nanopore from Staphylococcus aureus (FIG. 24A). The beta-barrel region was identified as comprising the stretch running from amino acid E112 to amino acid S134, and from amino acid S137 to amino acid K155. The even residues in the range E112-S130 and odd residues in the range S137-K155 were identified as the inward lumen water-facing residues most appropriate for engineering to alter ion-selectivity (FIG. 24A).

Cytk was prepared as follows. A plasmid with a gene encoding for the CytK gene elongated by six histidine residues (SEQ ID NO: 32) at the C-terminus was transformed into BL21 (DE3) cells by electroporation. Transformed cells were grown overnight at 37° C. on LB agar plates (1% glucose, 100 µg/ml ampicillin). Colonies were resuspended and grown in 200 mL 2YT medium at 37° C. until OD600 0.6-0.8, then expression was induced by addition of 0.5 mM IPTG and the culture was incubated overnight at 25° C. Cells were pelleted by centrifugation and stored at −80° C. for at least 30 minutes. Cell pellets were lysed by resuspension in lysis buffer (150 mM NaCl, 20 mM imidazole, 15 mM Tris pH 7.5, 1 mM MgCl₂, 0.2 units/ml DNase1, ~1 mg of lysozyme), incubated for 30 minutes at RT, then sonicated (Branson Sonifier 450, 2 minutes). Cellular debris was pelleted by centrifugation and the supernatant containing CytK was recovered. CytK was extracted from the supernatant and purified using Ni-NTA beads, with elution in 200 µl aliquots (150 mM NaCl, 300 mM imidazole, 15 mM Tris buffered at pH 7.5) before storage at 4° C.

Polypeptide Sequences of His-Tagged Nanopore Monomers

1. WT aHL (SEQ ID NO: 33)
MADSDINIKTGTTDIGSNTTVKTGDLVTYDKENGMHKKVFYSFIDDKNHN

KKLLVIRTKGTIAGQYRVYSEEGANKSGLAWPSAFKVQLQLPDNEVAQIS

DYYPRNSIDTKEYMSTLTYGFNGNVTGDDTGKIGGLIGANVSIGHTLKYV

-continued

QPDFKTILESPTDKKVGWKVIFNNMVNQNWGPYDRDSWNPVYGNQLFMKT

RNGSMKAADNFLDPNKASSLLSSGFSPDFATVITMDRKASKQQTNIDVIY

ERVRDDYQLHWTSTNWKGTNTKDKWTDRSSERYKIDWEKEEMTNRGSGSS

GGSSHHHHHH

2. WT CytK (SEQ ID NO: 34)

MAQTTSQVVTDIGQNAKTHTSYNTFNNEQADNMTMSLKVTFIDDPSADKQ

IAVINTTGSFMKANPTLSDAPVDGYPIPGASVTLRYPSQYDIAMNLQDNT

SRFFHVAPTNAVEETTVTSSVSYQLGGSIKASVTPSGPSGESGATGQVTW

SDSVSYKQTSYKTNLIDQTNKHVKWNVFFNGYNNQNWGIYTRDSYHALYG

NQLFMYSRTYPHETDARGNLVPMNDLPTLTNSGFSPGMIAVVISEKDTEQ

SSIQVAYTKHADDYTLRPGFTFGTGNWVGNNIKDVDQKTFNKSFVLDWKN

KKLVEKKGSAHHHHHH

3. CytK K128D K155D S120D Q122D
(CytK 4D2E)

(SEQ ID NO: 35)

MAQTTSQVVTDIGQNAKTHTSYNTFNNEQADNMTMSLKVTFIDDPSADKQ

IAVINTTGSFMKANPTLSDAPVDGYPIPGASVTLRYPSQYDIAMNLQDNT

SRFFHVAPTNAVEETTVTSSVDYDLGGSIDASVTPSGPSGESGATGQVTW

SDSVSYDQTSYKTNLIDQTNKHVKWNVFFNGYNNQNWGIYTRDSYHALYG

NQLFMYSRTYPHETDARGNLVPMNDLPTLTNSGFSPGMIAVVISEKDTEQ

SSIQVAYTKHADDYTLRPGFTFGTGNWVGNNIKDVDQKTFNKSFVLDWKN

KKLVEKKGSAHHHHHH

4. CytK K128D K155D S120D T147D (SEQ ID NO: 36)

MAQTTSQVVTDIGQNAKTHTSYNTFNNEQADNMTMSLKVTFIDDPSADKQ

IAVINTTGSFMKANPTLSDAPVDGYPIPGASVTLRYPSQYDIAMNLQDNT

SRFFHVAPTNAVEETTVTSSVDYQLGGSIDASVTPSGPSGESGATGQVDW

SDSVSYDQTSYKTNLIDQTNKHVKWNVFFNGYNNQNWGIYTRDSYHALYG

NQLFMYSRTYPHETDARGNLVPMNDLPTLTNSGFSPGMIAVVISEKDTEQ

SSIQVAYTKHADDYTLRPGFTFGTGNWVGNNIKDVDQKTFNKSFVLDWKN

KKLVEKKGSAHHHHHH

5. CytK K128D K155D S120D S151D
(CytK 4D2E_Alt)

(SEQ ID NO: 37)

MAQTTSQVVTDIGQNAKTHTSYNTFNNEQADNMTMSLKVTFIDDPSADKQ

IAVINTTGSFMKANPTLSDAPVDGYPIPGASVTLRYPSQYDIAMNLQDNT

SRFFHVAPTNAVEETTVTSSVDYQLGGSIDASVTPSGPSGESGATGQVTW

SDDVSYDQTSYKTNLIDQTNKHVKWNVFFNGYNNQNWGIYTRDSYHALYG

NQLFMYSRTYPHETDARGNLVPMNDLPTLTNSGFSPGMIAVVISEKDTEQ

SSIQVAYTKHADDYTLRPGFTFGTGNWVGNNIKDVDQKTFNKSFVLDWKN

KKLVEKKGSAHHHHHH

6. CytK K128F S120D Q122D
(CytK_2D1F2E)

(SEQ ID NO: 38)

MAQTTSQVVTDIGQNAKTHTSYNTFNNEQADNMTMSLKVTFIDDPSADKQ

IAVINTTGSFMKANPTLSDAPVDGYPIPGASVTLRYPSQYDIAMNLQDNT

-continued

SRFFHVAPTNAVEETTVTSSVDYDLGGSIFASVTPSGPSGESGATGQVTW

SDSVSYKQTSYKTNLIDQTNKHVKWNVFFNGYNNQNWGIYTRDSYHALYG

NQLFMYSRTYPHETDARGNLVPMNDLPTLTNSGFSPGMIAVVISEKDTEQ

SSIQVAYTKHADDYTLRPGFTFGTGNWVGNNIKDVDQKTFNKSFVLDWKN

KKLVEKKGSAHHHHHH

7. CytK K128F_S120D_Q122D_K155D
(CytK_3D1F2E)

(SEQ ID NO: 39)

MAQTTSQVVTDIGQNAKTHTSYNTFNNEQADNMTMSLKVTFIDDPSADKQ

IAVINTTGSFMKANPTLSDAPVDGYPIPGASVTLRYPSQYDIAMNLQDNT

SRFFHVAPTNAVEETTVTSSVDYDLGGSIFASVTPSGPSGESGATGQVTW

SDSVSYDQTSYKTNLIDQTNKHVKWNVFFNGYNNQNWGIYTRDSYHALYG

NQLFMYSRTYPHETDARGNLVPMNDLPTLTNSGFSPGMIAVVISEKDTEQ

SSIQVAYTKHADDYTLRPGFTFGTGNWVGNNIKDVDQKTFNKSFVLDWKN

KKLVEKKGSAHHHHHH

Planar Lipid Bilayer Electrophysiological Recordings System

For each experiment a single nanopore was inserted in a planar lipid bilayer system as described previously (Maglia et al., 2010, Methods Enzymol, 475, pg. 591-623). Briefly, the electrophysiology chamber had two compartments separated by a 25 μm thick Teflon (Goodfellow Cambridge Ltd) membrane. The Teflon membrane had an aperture with a diameter of approximately 100-200 μm. Lipid membranes were formed by first applying 5 μl of 5% hexadecane (Sigma Aldrich) in pentane (Sigma Aldrich) to the Teflon membrane, near the aperture. The pentane was left to dry and 400 μl of the appropriate buffered solution was added to each compartment. 20 μl of a 6.25 mg/ml solution of DPhPC dissolved in pentane was added on top of the buffer on each side of the chamber. The chamber was left to dry for ~2 minutes to allow evaporation of pentane. Silver/silver chloride electrodes were attached to each compartment. The cis compartment was connected to the ground electrode and the trans was connected to the working electrode. Planar lipid bilayers were created using the Langmuir-Blodgett method. Purified nanopore solutions were added to the cis compartment to obtain insertion of single nanopores. Once a single nanopore had inserted the orientation and properties of the nanopore was confirmed by the asymmetry of the current-voltage relationship and compared to previous characterization metrics from multiple insertion tests to ensure that the nanopore was in the correct state. Analytes were then added to the cis or trans compartment of the chamber for the methods described herein.

Recordings of ionic currents were obtained using Axopatch 200B patch clamp amplifiers (Axon Instruments) combined with Digidata 1550B A/D converters (Axon instruments). Recordings were typically acquired at 10 kHz with a 2 kHz Bessel filter, and recorded using Clampex 10 (Molecular Devices). Unless stated otherwise, all recordings were carried out at 22° C.

All applied voltages stated herein followed the convention of stating the polarity at the active trans electrode, thus positive applied voltages have a positive voltage applied at the trans electrode relative to a ground electrode in the cis compartment.

Determination of Nanopore System EOF from Ion-Selectivity and Electro-Osmotic Flow The ion-selectivity and electro-osmotic flow parameters of various nanopore systems according the methods and GHK derived equations described earlier were determined.

The ion-permeability parameters (e.g. $P_{(K+)}$, $P_{(Cl-)}$, $P_{(Glu-)}$) for the various ions (e.g. K+, Cl–, Glu–) were determined as described earlier by carrying out ion-selectivity measurements using asymmetric salt concentrations of the appropriate ions to reveal the relative cation:anion selectivity of each nanopore system. Briefly, reverse voltage from ion-selectivity measurements were performed in the Planar lipid bilayer electrophysiological recording system described. During reversal potential measurements, the electrodes were not in direct contact with the buffer solution but were connected via agarose bridges containing 2.5% agarose in a 3 M KCl solution. For reverse voltage measurements, both compartments were first filled with 500 μL of "solution-A". The electrodes were balanced to zero offset under these symmetrical salt conditions, and the IV current-voltage curve was measured between −140 and +140 mV in variations of 20 mV. Afterwards, the concentration of the trans compartment was decreased by perfusion to "solution-B" to create the asymmetrical salt condition. The permeability parameters $P_{(K+)}$ and $P_{(Cl-)}$ for K+ and Cl– were determined using a solution-A of 2 M KCl and a solution-B of 0.5 M KCl. The permeability parameters $P_{(K+)}$ and $P_{(Glu-)}$ for K+ and Glu– were determined using a solution-A of 2 M KGlu and a solution-B of 0.5 M KGlu.

The IV curve was measured between −140 and +140 m V in variations of 20 mV in the asymmetric solution-A: solution-B system, and the reversal potential (Vr), which is the voltage offset to achieve zero ionic current flow, was estimated by linear regression of the curve between −20 and +20 mV. The pores were measured in triplicates. The reversal voltage for a given system were then used in the following equation to determine the relative permeability ratio:

$$\frac{P_{(X+)}}{P_{(Y-)}} = \frac{[a_{Y-}]_{trans} - [a_{Y-}]_{cis} * e^{\frac{V_r F}{RT}}}{[a_{X+}]_{trans} * e^{\frac{V_r F}{RT}} - [a_{X+}]_{cis}}$$

wherein $P_{(X+)}$ and $P_{(Y-)}$ denote the permeability of the nanopore system for cation species X and anion species Y respectively. $[\alpha_{Y-}]$ and $[\alpha_{X-}]$ are the activity of ion Y and X respectively in the indicated compartment, calculated by multiplying the concentration with the mean ion activity coefficient. The activity coefficients for KCl in 0.5 M and 2.0 M solutions are 0.649 and 0.573 respectively (Lide, D. R., 2003, CRC handbook of chemistry and physics, 84th edition, Handb. Chem. Phys. 53, 2616). The mean activity coefficients of KGlu in 0.5 M and 2.0 M are 0.68 and 0.719 respectively (Bonner et al., 1981, J. Chem. Eng. Data., 26, 2, pg. 147-148). The empirical ion-selectivity ratios (e.g. $P_{(K+)}/P_{(Cl-)}$ and $P_{(K+)}/P_{(Glu-)}$) were then used in the GHK flux equations and applied to further experimental measurements of ionic current versus applied voltage (I-V curves) as described previously to determine the absolute values of $P_{(K+)}$, $P_{(Cl-)}$, and $P_{(Glu-)}$.

To a first approximation (ignoring the minor component from other ionic species in the systems as very low concentration), the separate ionic current (Is) contributions from the flow of K+, Cl– and Glu– ions in systems with various symmetric and asymmetric combinations of KCl and KGlu were calculated using the specific GHK flux equation for each ion of:

$$I_{(K+)} = P_{(K+)} * \frac{V_m F^2}{RT} \frac{[K^+]_{trans} - [K^+]_{cis} e^{-\frac{V_m F}{RT}}}{1 - e^{-\frac{V_m F}{RT}}}$$

$$I_{(Cl-)} = P_{(Cl-)} * \frac{V_m F^2}{RT} \frac{[Cl^-]_{trans} - [Cl^-]_{cis} e^{+\frac{V_m F}{RT}}}{1 - e^{+\frac{V_m F}{RT}}}$$

$$I_{(Glu-)} = P_{(Glu-)} * \frac{V_m F^2}{RT} \frac{[Glu^-]_{trans} - [Glu^-]_{cis} e^{+\frac{V_m F}{RT}}}{1 - e^{+\frac{V_m F}{RT}}}$$

The predicted current $I=I_{(K+)}+I_{(Cl-)}+I_{(Glu-)}$ closely matched that measured current in electrical recordings. The net ionic current flowing cis-to-trans ($I_{\Delta c \to t}$), the total current flowing the nanopore ($I_{total}$), and the relative proportion of net ionic current flowing cis-to-trans over the total current ($I_{rel}$) was determined as described previously. The values determined for a number of nanopore systems are shown in table 2.

TABLE 2

| Pore | Voltage (mV) | Salt in cis | Salt in trans | $I_{rel}$ | P(+)/P(−) | ClpX:MBP-1 events |
|---|---|---|---|---|---|---|
| aHL_WT | −80 to −180 | 1M KCl | 1M KCl | −0.12 | 0.78 | No |
| | −80 to −180 | 1M KGlu | 1M KGlu | 0.30 | 1.86 | No |
| CytK_WT | −80 to −180 | 1M KGlu | 1M KGlu | 0.20 | 1.51 | No |
| CytK_2D1F2E | −120 | 1M KGlu | 1M KGlu | 0.39 | 2.28 | Yes, C > T |
| CytK_3D1F2E | −80 | 1M KGlu | 1M KGlu | 0.49 | 2.89 | Yes, C > T |
| CytK_4D2E | −80 | 1M KGlu | 1M KGlu | 0.47 | 2.78 | Yes, C > T |
| | +80 | 1M KGlu | 1M KGlu | −0.47 | 2.78 | Yes, T > C |
| | −80 | 1M KGlu | 1M KCl | 0.58 | 3.91 | Yes, C > T |
| CytK_4D2E_alt | −80 | 1M KGlu | 1M KGlu | 0.57 | 3.68 | Yes, C > T |

Recordings of Protein Translocation

Measurements of translocase controlled protein translocation were carried out according to the system schematically described in FIG. 3. Both compartments of the nanopore system were filled with an electrolyte solution (1 M potassium glutamate, 20 mM $MgCl_2$ and 50 mM Tris, buffered to pH 7.5). Unless stated otherwise, the appropriate purified CytK nanopore was added to the cis compartment to achieve a single inserted nanopore. After detecting the insertion of a single nanopore the open pore current was recorded at a range of voltages to assess the nanopore. Separately, translocase (ClpX) and target protein substrate (e.g. MBP-1) were preincubated, typically at a 2:1 translocase:target-protein molar ratio, for >10 minutes at room temperature in 10 mM ATP and 25 mM $MgCl_2$. After pre-incubation, the translocase:target-protein complex was added to the cis-compartment (unless stated otherwise).

No or weak EOF nanopore systems. It was found that nanopore systems with weak or no ion-selectivity were unable to generate a significant net electro-osmotic flow (Table 2), and thus a weak EOF, under symmetric salt conditions. As a result, under low to moderate applied voltages the nanopores were unable to effectively capture either free MBP-1 substrate or the pre-loaded ClpX: MBP-1 complex. Effective capture of the analyte meeded the application of much higher voltages (thus significantly increasing the EPF acting on the leader and protein), despite the protein analyte having a leader construct with a highly charged region of 15 consecutive arginine residues to aid electrophoretic capture. FIGS. 8 and 9 show representative MBP-1 capture data for wild-type alpha-hemolysin and wild-type CytK nanopores acquired at voltages from −80 mV to −180 mV etc. FIG. 10 shows representative sections of recordings from wild-type alpha-hemolysin (panels A and B), and wild-type CytK (CytK-WT) (panel C) respectively in systems with pre-loaded ClpX:MBP-1 (added to a concentration of 0.2 µM ClpX, 0.1 µM MBP-1, 2.5 mM ATP in the cis chamber). In all the above nanopore systems a range of blockade types were observed that can be attributed either to capture of ClpX:MBP-1 complex, capture or free MBP-1 or some pore gating (where the nanopores shutdown spontaneously under the applied voltage). However, the blockade events all displayed a mostly stable blockade current level that was indicative of a static state where the polypeptide was not moving through the nanopore (e.g. under the control of the ClpX). Events corresponding to capture of ClpX: MBP-1 complex blocked the currently indefinitely, and can be cleared from the nanopore by briefly reversing the voltage (marked by arrows in FIGS. Aug. 9, 2010), illustrating that there was no progression of the polypeptide through the nanopore.

Strong EOF nanopore systems. In comparison, when the nanopore systems designed to have a strong EOF by employing mutated CytK nanopores with a strong ion-selectivity of >3.0 P(+)/P(−) were tested, clear and consistent capture and subsequent ClpX-controlled translocation of MBP-1 was observed. For example, FIGS. 11A and 11B show representative sections of electrical recordings acquired at −80 mV from CytK-4D2E nanopores (CytK K128D K155D S120D Q122D) in a system set up according to FIG. 3, where pre-loaded ClpX: MBP-1 complex was added to the cis compartment (preloaded according to FIG. 5 and as described herein, then added to a concentration of 0.2 µM ClpX, 0.1 µM MBP-1, 2.5 mM ATP in the chamber). FIG. 11A shows a representative example with 3 consecutive ClpX controlled MBP-1 translocation events labelled 1-3. FIG. 11B shows a further example from a separate experiment with 4 events labelled 1-4 that are easily identifiable interspersed between some of the other blockades that were observed (e.g. blockades from unproductive enzyme complexes or free MBP-1 without ClpX bound). The capture and translocation events all had the same characteristic and consistent patterns. Events started with an almost instant blockage of the current from the open pore level $(I_O)$ of about −65 pA at −80 mV (state i in FIG. 12) to a blocked level of about 0 to 5 pA (S1 in FIG. 12) that corresponded to the initial capture of the ClpX:MBP-1 complex. This was followed by a brief static level that probably corresponded to the ClpX:MBP-1 complex held on top of the pore where the motor remained stalled by the leader motifs so that the polypeptide within the nanopore was held in place (state ii in FIG. 12). After a brief period the event proceeded (S2 in FIG. 12) to a highly characteristic pattern of changing current levels (state iii in FIG. 12) corresponded to the motor overcoming the stall (due to a combination of the EPF force acting on the charged section of the leader and/or the EOF acting on the leader) and continued to unfold and translocate along the protein, in the process passed the polypeptide through the nanopore from the cis side of the membrane to the trans side of the membrane. All the while the strong EOF pulled on the extruded polypeptide to retain the translocase against the top of the pore. The events ended when the translocase reached the end of the protein (S3 in FIG. 12) and the polypeptide was fully translocated from the cis to the trans compartment (state iv in FIG. 12), whereupon the ClpX was no longer retained on top of the pore, which returned to the open pore level where it was available to capture a fresh ClpX:MBP-1 complex.

FIG. 13 illustrates the highly consistent nature of the MBP-1 protein capture and translocation events. The figure shows selected representative events, and connects easily recognisable features in the current levels with dotted lines to aid the eye. It was expected to see the changes in current level that were observed due to the progression of differing amino acid composition as the polypeptide translocated through the nanopore. Moreover, a highly similar pattern of current levels was observed when comparing between separate MBP-1 events. This clearly demonstrated that the translocation of separate proteins sharing the identical underlying amino acid sequence altered the ionic current in a consistent and characteristic manner. Further, the majority of events started with an almost full blockade to almost 0 pA, which was attributed to the polyarginine motif of the leader being in the nanopore channel, and then progressed through the same start and end current levels. This indicated the events are full length protein translocations, demonstrated the effectiveness of the stall elements of the Leader construct at retaining the ClpX translocase to the start of the protein. If the stall were not effective at preventing the translocation of ClpX in solution it may be not expected to see a large number of events where the current levels start part way through due to capture of a complex with the translocase at a random point along the protein. The effectiveness of the stall was confirmed by Gel assays comparing degradation of GFP-0 (no stall) to GFP-1 when mixed with ClpX and ClpP, which showed that GFP-0 can be digested while GFP-1 is stable.

FIGS. 13 and 17 also illustrate that the duration and step-size of the polypeptide translocation is highly consistent and reproducible. FIG. 17 shows a histogram of the duration of ClpX controlled MBP-1 events from a single experiment. The event durations were normally distributed with a mean duration of about 30 seconds. This distribution was achieved when the movement of the polypeptide through the nanopore was tightly controlled by the ClpX translocase translocating along the polypeptide via NTP hydrolysis at an approximately constant rate (about 12-15 aa/second in these conditions). This was further supported by control experiments which replaced ATP with 2.5 mM Gamma-S-ATP(FIG. 16), which was a minimally hydrolysable analog of ATP. These experiments showed capture of ClpX:MBP-1 complexes that resulted in long blockades that never progressed to the changing current levels phase associated with ClpX translocase controlled movement of polypeptide that was observed under regular ATP conditions, and events can be cleared from the nanopore by briefly reversing the applied voltage.

FIG. 14 shows some example ClpX translocase controlled MBP-1 events from different nanopores with varying degrees of medium to high ion-selectivity, and thus varying levels of EOF in symmetrical salt conditions. Table 2 summarises data for further systems, along with determinations of ion-selectivity and the relative net ionic flow that creates the EOF. While the patterns of current level changes were different for each nanopore, the events all possessed the same characteristic changes in current levels, indicating an aspect of the present disclosure that sufficiently strong EOF were produced (and determined) by a wide range of nanopore mutations to create systems capable of ClpX controlled polypeptide transport.

Alternative substrates. To further prove that the pattern of current level changes is characteristic of the protein's amino-acid composition the ClpX controlled translocation of the model protein GFP under the same conditions described above for MBP-1 was tested. FIG. 15 shows representative events from ClpX controlled translocation of MBP-1 (FIG. 15A) and GFP-1 (FIG. 15B), illustrating the different pattern of current levels that are observed for the proteins. This data illustrates that the current levels were unique to the underlying amino acid sequence, enabling the protein targets to be unambiguously identified by comparing the data to previously acquired signals. In principle it will be possible to train software to learn the underlying sequence-to-signal relationship to characterise target proteins, in principle to determine the amino-acid sequence.

Pre-Loading ClpX:Target Protein Complexes.

If is often optimal to bind proteins under conditions that are quite different from those employed in nanopore systems (which may be optimised for ionic current signal for example). For example, the high salt concentrations often employed in nanopore systems can inhibit protein-substrate binding. Mixing the components at high relative concentration can improve binding efficiency, however, the amount of a target protein may be limited (e.g. in a real-world sample) and/or the nanopore system may not have high concentrations of substrate for efficient capture. In some cases, to the components can be pre-incubated at high relative concentration in a small volume before addition into the nanopore system in a diluted form. In this example preloading of translocases onto target proteins was explored by incubating the components under optimal binding conditions (i.e. optimal temperature, pH, salt content, salt concentration, cofactor concentration, etc.) at high relative translocase and target protein concentration (>1 µM) prior to addition to the nanopore system. In all nanopore systems, preloading significantly improved the proportion of translocase:target-protein complexes captured versus free target-protein captured when compared to systems where the components were added to the system separately (where they bind in the bulk solution). FIG. 18 illustrates the difference between addition of preloaded ClpX:MBP-1 (FIG. 18B) versus separate addition of ClpX and MBP-1 (FIG. 18A). Without pre-loading, the system was dominated by the capture of free MBP-1 substrate (no translocase bound), while preloading yielded a higher percentage of MBP-1:ClpX complex capture that lead to ClpX controlled MBP-1 translocations.

Trans-to-cis translocations. As described herein, EOF from net electro-osmotic flow can be created in either the cis-to-trans direction or the trans-to-cis direction across the nanopore relative to the polarity of the applied voltage and the normal orientation of the nanopore. Compared to examples above (net cis-to-trans flow is created with a negative voltage at the trans electrode), if the voltage polarity was reversed, and the pore was also inserted from the trans compartment, then an equal and directly equivalent net trans-to-cis flow was created (in the case that the cis and trans salts are symmetrical), enabling polypeptides to be translocated trans-to-cis when added to the trans compartment. However, to test the ability to translocate a polypeptide through the a nanopore in the reverse direction with respect the nanopore orientation (FIG. 19), CytK_4D2E nanopores (inserted from cis) at positive applied voltage in trans to create a net trans-to-cis electro-osmotic flow were tested, and preloaded ClpX:MBP-1 complexes were added to the trans compartment. Under the strong trans-to-cis electroosmotic flow characteristic ClpX controlled MBP-1 translocation events occurred trans-to-cis (FIG. 19). Further, a different pattern of current levels from the polypeptide translocation was observed, which was expected since the orientation of the polypeptide relative to the pore was reversed, and different orientations of analyte in a nanopore were known to change discrimination. This example illustrates that the direction of the EOF can be set up to enable polypeptide translocation across a nanopore in either direction relative to the nanopore. Since nanopores are most often asymmetrical, this can be advantageous to exploit other properties of their shape that change aspects such as capture of analyte, unwanted capture, location and orientation of nanopore constriction (typically where the majority of the discrimination occurs), and what surface the translocase interacts with for example.

Alternative salts. Tests Assays of ClpX in KCl demonstrated that ClpX unfoldase function was inhibited in greater than 0.3 M KCl, while function was largely retained in 1M KGlu (FIG. 20). Therefore, for the examples herein, experiments employed KGlu at high 1M concentration in the cis compartment to maximise the net cis-to-trans electro-osmotic flow that was dominated by the flux of K ions from the cis side of the membrane to the trans side of the membrane.

Asymmetric nanopore systems with a different salt on the cis and trans sides can also be employed. For example, ClpX controlled MBP-1 translocations were obtained from CytK 4D2E nanopores systems with 1M KGlu in the cis and 1 M KCl in trans due to the strong cis-to-trans EOF (FIG. 21).

Example 2: Cis-to-Cis Protein Measurements

This example describes a system and method to enable characterisation a target protein by capturing it from the cis side into the nanopore with high net cis-to-trans EOF, in conjunction with a protein translocase motor that then pulls the polypeptide back through the same nanopore to the cis side. This process (also referred to as "Out mode") is illustrated schematically in FIG. 22.

A target protein of interest was provided on the C-terminus with the ssrA capture motif AANDENYALAA (SEQ ID NO: 19) thar facilitated binding with a ClpX translocase.

The target protein was also provided on the N-terminus with a long >30 amino acid tag that was designed to have no secondary structure, a high cation content that enabled efficient capture in a nanopore, and no ability to bind or stall ClpX translocase. A suitable tag was composed of repeating (SR) n residues.

The adapted target protein was premixed with ClpX translocase under preloading conditions (0.4 µM ClpX, 0.2 µM adapted target protein, 10 mM ATP and 25 mM MgCl$_2$ in a volume of 10 µl) and incubated for at least 10 minutes to enable loading of the ClpX onto the target protein. The preloaded ClpX:target protein complex was then added to this cis compartment (concentration of 0.2 µM ClpX, 0.1 µM target protein) of a system with a single CytK-4D2E nanopore in a membrane under a negative applied voltage (−60 mV to −120 mV) at the trans electrode (1M KGlu cis, 1M KGlu trans, 50 mM TRIS, 2.5 mM ATP, 25 mM MgCl$_2$, pH 7.5). Ionic current measurements through the nanopore were performed by the standard methods described herein.

ClpX:target protein complex captures were observed by a sharp blockade of the ionic current passing through the open nanopore as first the capture motif on the N-termini of the target protein and then a portion of the target protein itself was partially translocated through the pore nanopore from cis to trans as a result of the strong cis-to-trans EOF acting on the polypeptide (and initially EPF acting on the polycation capture tag) (FIG. 23). The initial fast translocation of the polypeptide stopped when the bound translocase encountered the top of the nanopore, and then the strong cis-to-trans EOF continued to pull on the polypeptide within the nanopore and thus kept the translocase atop the nanopore. A sequence of amino-acid dependent changes in current levels were then observed as the translocase atop the nanopore continued to move along the polypeptide (i.e. C-terminal to N-terminal according to this protein design, and in the cis-to-trans direction relative to the nanopore system) under the power of ATP hydrolysis, in the process pulled the translocated portion of the polypeptide in the nanopore and trans compartment back out of the nanopore from trans-to-cis against the EOF. A return to the open pore current level (I$_O$) was observed when the translocase motor reached the end of the adapted target protein, and pulled it fully back through the pore trans-to-cis, where it unbinded and both components were released into the cis solution.

Example 3: Protein Identification and Long Proteins

Example 3 describes a system and method to that enabled the identification of proteins based on their unique ionic current signature during translocation. The target proteins were captured into the nanopore by a high EOF, in conjunction with a protein translocase motor that unfolded and transported the polypeptide through the pore.

Target protein analytes of interest were provided with a long >30 amino acid tag that had an AANDENYALAA (SEQ ID NO: 19) capture recognition motif that facilitated binding with a ClpX translocase, a domain with high cation content that enabled efficient capture into the nanopore (RRRRRRRRRRRRRR (SEQ ID NO: 40)) and a domain to that stalled the ClpX translocase (GGGGGGGGGGGGGG (SEQ ID NO: 41)).

The adapted target protein was added to the cis compartment in a concentration of 0.1 µM together with 0.2 µM ClpX and 2.5 mM ATP in a system with a single CytK-4D2E nanopore in a membrane under −80 mV applied potential.

The ionic current measurements were then performed using the standard methods described herein.

Four different substrates ({GFP}-{MBP-1}, {LIVBP}-{MBP-1}, {SpuE}-{MBP-1} and {GBP}-{MBP-1}) were shown to each have similar ionic current signals in the initial section corresponding to MBP-1, and unique ionic current signals in the respective attached proteins during translocation (FIG. 25). Different (but reproducible) ionic current levels were observed for the regions of difference between the substrates, which indicated that the ionic current that was measured reflected the amino acid composition of the proteins. This example demonstrated the ability of such a system to identify proteins based on their ionic current characteristics.

Additionally, MBP-MBP-1 was a genetic fusion protein of two MBP proteins with a total length of 805 amino acids and a molecular weight of 88 kDa. Despite its large size, full length reads of the protein were reliably obtained (FIG. 26), which indicated that this system was able to read long proteins from C-terminus to N-terminus during translocation events.

TABLE 6

| Amino acid sequences of proteins used in Example 3 | |
|---|---|
| Protein | Amino acid sequence |
| {GFP}-{MBP-1} | MHHHHHHSSPWGAPKIEEGKLVIWINGDKGYNGLAEVGK KFEKDTGIKVTVEHPDKLEEKFPQVAATGDGPDIIFWAH DRFGGYAQSGLLAEITPDKAFQDKLYPFTWDAVRYNGKL IAYPIAVEALSLIYNKDLLPNPPKTWEEIPALDKELKAK GKSALMENLQEPYFTWPLIAADGGYAFKYENGKYDIKDV GVDNAGAKAGLTFLVDLIKNKHMNADTDYSIAEAAFNKG ETAMTINGPWAWSNIDTSKVNYGVTVLPTFKGQPSKPFV GVLSAGINAASPNKELAKEFLENYLLTDEGLEAVNKDKP LGAVALKSYEEELAKDPRIAATMENAQKGEIMPNIPQMS AFWYAVRTAVINAASGRQTVDEALKDAQTRITKHMGGGG GGGGGGGGGSRRRRRRRRRRRRRRRAANDENYALAA (SEQ ID NO: 42) |
| {LIVBP}-{MBP-1} | MHHHHHHSSGEDIKVAVVGAMSGPVAQYGDQEFTGAEQA VADINAKGGIKGNKLQIVKYDDACDPKQAVAVANKVVND GIKYVIGHLCSSSTQPASDIYEDEGILMITPAATAPELT ARGYQLILRTTGLDSDQGPTAAKYILEKVKPQRIAIVHD KQQYGEGLARAVQDGLKKGNANVVFFDGITAGEKDFSTL VARLKKENIDFVYYGGYHPEMGQILRQARAAGLKTQFMG PEGVANVSLSNIAGESAEGLLVTKPKNYDQVPANKPIVD AIKAKKQDPSGAFVWTTYAALQSLQAGLNQSDDPAEIAK YLKANSVDTVMGPLTWDEKGDLKGFEFGVFDWHANGTAT DAKVKIEEGKLVIWINGDKGYNGLAEVGKKFEKDTGIKV TVEHPDKLEEKFPQVAATGDGPDIIFWAHDRFGGYAQSG LLAEITPDKAFQDKLYPFTWDAVRYNGKLIAYPIAVEAL SLIYNKDLLPNPPKTWEEIPALDKELKAKGKSALMFNLQ EPYFTWPLIAADGGYAFKYENGKYDIKDVGVDNAGAKAG LTFLVDLIKNKHMNADTDYSIAEAAFNKGETAMTINGPW AWSNIDTSKVNYGVTVLPTFKGQPSKPFVGVLSAGINAA SPNKELAKEFLENYLLTDEGLEAVNKDKPLGAVALKSYE EELAKDPRIAATMENAQKGEIMPNIPQMSAFWYAVRTAV INAASGRQTVDEALKDAQTRITKHMGGGGGGGGGGGGGSR RRRRRRRRRRRRRRAANDENYALAA (SEQ ID NO: 43) |
| {SpuE}-{MBP-1} | MHHHHHHSSGEKKSLHIYNWTDYIAPTTLKDFTKESGID VSYDVFDSNETLEGKLVSGHSGYDIVVPSNNFLGKQIQA GAFQKLDKSKLPNWKNLDPALLKQLEVSDPGNQYAVPYL WGTNGIGYNVAKVKEVLGDQPIDSWAILFEPENMKKLAK CGVAFMDSGDEMLPAALNYLGLDPNTHDPKDYKKAEEVL TKVRPYVSYFHSSKYISDLANGNICVAFGYSGDVFQAAA RAEEAGKGIDIQYVIPKEGANLWFDLMAIPADAKAADNA YAFIDYLLRPEVIAKVSDYVGYANAIPGARPLMDKSVSD SEEVYPPQAVLDKLYVSAVLPAKVLRLQTRTWTRIKTGK LEKIEEGKLVIWINGDKGYNGLAEVGKKFEKDTGIKVTV EHPDKLEEKFPQVAATGDGPDIIFWAHDRFGGYAQSGLL AEITPDKAFQDKLYPFTWDAVRYNGKLIAYPIAVEALSL |

TABLE 6-continued

Amino acid sequences of proteins used
in Example 3

| Protein | Amino acid sequence |
|---------|---------------------|
| | IYNKDLLPNPPKTWEEIPALDKELKAKGKSALMFNLQEP |
| | YFTWPLIAADGGYAFKYENGKYDIKDVGVDNAGAKAGLT |
| | FLVDLIKNKHMNADTDYSIAEAAFNKGETAMTINGPWAW |
| | SNIDTSKVNYGVTVLPTFKGQPSKPFVGVLSAGINAASP |
| | NKELAKEFLENYLLTDEGLEAVNKDKPLGAVALKSYEEE |
| | LAKDPRIAATMENAQKGEIMPNIPQMSAFWYAVRTAVIN |
| | AASGRQTVDEALKDAQTRITKHMGGGGGGGGGGGGSRRR |
| | RRRRRRRRRRRRAANDENYALAA (SEQ ID NO: 44) |
| {GBP}- | MHHHHHHSSGADTRIGVTIYKYDDNFMSVVRKAIEQDAK |
| {MBP-1} | AAPDVQLLMNDSQNDQSKQNDQIDVLLAKGVKALAINLV |
| | DPAAAGTVIEKARGQNVPVVFFNKEPSRKALDSYDKAYY |
| | VGTDSKESGIIQGDLIAKHWAANQGWDLNKDGQIQFVLL |
| | KGEPGHPDAEARTTYVIKELNDKGIKTEQLQLDTAMWDT |
| | AQAKDKMDAWLSGPNANKIEVVIANNDAMAMGAVEALKA |
| | HNKSSIPVFGVDALPEALALVKSGALAGTVLNDANNQAK |
| | ATFDLAKNLADGKGAADGTNWKIDNKVVRVPYVGVDKDN |
| | LAEFSKKGKIEEGKLVIWINGDKGYNGLAEVGKKFEKDT |
| | GIKVTVEHPDKLEEKFPQVAATGDGPDIIFWAHDRFGGY |
| | AQSGLLAEITPDKAFQDKLYPFTWDAVRYNGKLIAYPIA |
| | VEALSLIYNKDLLPNPPKTWEEIPALDKELKAKGKSALM |
| | FNLQEPYFTWPLIAADGGYAFKYENGKYDIKDVGVDNAG |
| | AKAGLTFLVDLIKNKHMNADTDYSIAEAAFNKGETAMTI |
| | NGPWAWSNIDTSKVNYGVTVLPTFKGQPSKPFVGVLSAG |
| | INAASPNKELAKEFLENYLLTDEGLEAVNKDKPLGAVAL |
| | KSYEEELAKDPRIAATMENAQKGEIMPNIPQMSAFWYAV |
| | RTAVINAASGRQTVDEALKDAQTRITKHMGGGGGGGGGG |
| | GGSRRRRRRRRRRRRRRRRAANDENYALAA (SEQ ID |
| | NO: 45) |
| {MBP}- | MGSSHHHHHHSSGLVPRGSHNKIEEGKLVIWINGDKGYN |
| {MBP-1} | GLAEVGKKFEEDTGIKVTVEHPDKLEEKFPQVAATGDGP |
| | DIIFWAHDRFGGYAQSGLLAEITPDKAFQDKLYPFTWDA |
| | VRYNGKLIAYPIAVEALSLIYNKDLLPNPPKTWEEIPAL |
| | DKELKAKGKSALMFNLQEPYFTWPLIAADGGYAFKYENG |
| | KYDIKDVGVDNAGAKAGLTFLVDLIKNKHMNADTDYSIA |
| | EAAFNKGETAMTINGPWAWSNIDTSKVNYGVTVLPTFKG |
| | QPSKPFVGVLSAGINAASPNKELAKEFLENYLLTDEGLE |
| | AVNKDKPLGAVALKSYEEELAKDPRIAATMENAQKGEIM |
| | PNIPQMSAFWYAVRTAVINAASGRQTVDEALKDAQTRIT |
| | KGAPKIEEGKLVIWINGDKGYNGLAEVGKKFEKDTGIKV |
| | TVEHPDKLEEKFPQVAATGDGPDIIFWAHDRFGGYAQSG |
| | LLAEITPDKAFQDKLYPFTWDAVRYNGKLIAYPIAVEAL |
| | SLIYNKDLLPNPPKTWEEIPALDKELKAKGKSALMFNLQ |
| | EPYFTWPLIAADGGYAFKYENGKYDIKDVGVDNAGAKAG |
| | LTFLVDLIKNKHMNADTDYSIAEAAFNKGETAMTINGPW |
| | AWSNIDTSKVNYGVTVLPTFKGQPSKPFVGVLSAGINAA |
| | SPNKELAKEFLENYLLTDEGLEAVNKDKPLGAVALKSYE |
| | EELAKDPRIAATMENAQKGEIMPNIPQMSAFWYAVRTAV |
| | INAASGRQTVDEALKDAQTRITKHMGGGGGGGGGGGGSR |
| | RRRRRRRRRRRRRRAANDENYALA (SEQ ID NO: |
| | 46) |

Example 4: Stalling of Unfoldase at Higher
Temperatures Using Blocking Domains

This example demonstrates improved stalling of unfoldases, such as at higher temperatures, using a block motif.

Fluorescence Assay for the Stalling Efficiency of Block Motif

141 μL of a solution containing 1M KGlu, 50 mM Tris, 25 mM MgCl$_2$, 10 mM DTT and 1 mM EDTA was added in two different wells of a 96-well black plate for fluorescent assays. Then, 1 μL of a solution with 10 μM of a Green Fluorescent Protein carrying the ssrA tag at the C-terminus was added to each well. Subsequently, 8 μL of a solution with 5 μM of ClpX was added to one well, to achieve the desired volume of 150 μL and the desired molar ratio of 1:4, substrate:ClpX. The well where ClpX was not added was used as positive control. The plate was then inserted in a plate reader set at an incubation temperature of 37° C.

The measurement of fluorescence over time was carried out one well at a time. To measure fluorescence, the well was excited with a light pulse of optimal excitation wavelength for the analyzed fluorescent protein, and the emitted light was collected at the optimal emission wavelength using an appropriate bandwidth filter. After an initial shaking of 30 seconds to ensure proper mixing of the solution, fluorescence was tracked for 1 minute to ensure no spontaneous loss of fluorescence. Subsequently, 16 μL of a solution with 100 mM ATP and 200 mM KOH was automatically injected into the well, to achieve a concentration of 10 mM ATP. The fluorescence was then measured for 8 minutes at intervals of 30 seconds.

TABLE 8

Amino acid sequence of the proteins used.

| Protein | Amino acid sequence |
|---------|---------------------|
| GFP-1 | MGHHHHHHSSASKGEELFTGVVPILVELDGDVNGH |
| | KFSVSGEGEGDATYGKLTLKFICTTGKLPVPWPTL |
| | VTTFSYGVQCFSRYPDHMKRHDFFKSAMPEGYVQE |
| | RTIFFKDDGNYKTRAEVKFEGDTLVNRIELKGIDF |
| | KEDGNILGHKLEYNYNSHNVYIMADKQKNGIKVNF |
| | KIRHNIEDGSVQLADHYQQNTPIGDGPVLLPDNHY |
| | LSTQSALSKDPNEKRDHMVLLEFVTAAGIGGGGGG |
| | GGGGGGSRRRRRRRRRRRAANDENYALAA (SEQ |
| | ID NO: 47) |
| mNG- | MKHHHHHHGVSKGEEDNMASLPATHELHIFGSING |
| alpha_helix | VDFDMVGQGTGNPNDGYEELNLKSTKGDLQFSPWI |
| | LVPHIGYGFHQYLPYPDGMSPFQAAMVDGSGYQVH |
| | RTMQFEDGASLTVNYRYTYEGSHIKGEAQVKGTGF |
| | PADGPVMTNSLTAADWCRSKKTYPNDKTIISTFKW |
| | SYTTGNGKRYRSTARTTYTFAKPMAANYLKNQPMY |
| | VFRKTELKHSKTELNFKEWQKAFTDVMGMDELYKG |
| | GSGSGDYMERWYRYYNEFSGGVAANDENYALAA |
| | (SEQ ID NO: 48) |
| mNG-HTH | MKHHHHHHGVSKGEEDNMASLPATHELHIFGSING |
| | VDFDMVGQGTGNPNDGYEELNLKSTKGDLQFSPWI |
| | LVPHIGYGFHQYLPYPDGMSPFQAAMVDGSGYQVH |
| | RTMQFEDGASLTVNYRYTYEGSHIKGEAQVKGTGF |
| | PADGPVMTNSLTAADWCRSKKTYPNDKTIISTFKW |
| | SYTTGNGKRYRSTARTTYTFAKPMAANYLKNQPMY |
| | VFRKTELKHSKTELNFKEWQKAFTDVMGMDELYKG |
| | GSGSGDELAQLERELMKLKAQGVDSDELEALARKL |
| | AMLARSGGVAANDENYALAA (SEQ ID NO: |
| | 49) |
| mNG- | MKHHHHHHGVSKGEEDNMASLPATHELHIFGSING |
| beta_hairpin | VDFDMVGQGTGNPNDGYEELNLKSTKGDLQFSPWI |
| | LVPHIGYGFHQYLPYPDGMSPFQAAMVDGSGYQVH |
| | RTMQFEDGASLTVNYRYTYEGSHIKGEAQVKGTGF |
| | PADGPVMTNSLTAADWCRSKKTYPNDKTIISTFKW |
| | SYTTGNGKRYRSTARTTYTFAKPMAANYLKNQPMY |
| | VFRKTELKHSKTELNFKEWQKAFTDVMGMDELYKG |
| | GSGSGRGKITVNGKTYEGRSGGVAANDENYALAA |
| | (SEQ ID NO: 50) |

Fluorescence experiments adding ClpX to the fluorescent protein GFP (also comprising a ssrA recognition sequence) at 37° C. resulted in a loss of fluorescence, indicative of the unfoldase's ability to proceed through the substrate and unfold the protein (FIG. 27A).

However, the insertion of block motifs comprising high stability protein structures, such as alpha-helices, helix-turn-helix structures and/or beta-hairpins, were able to stall ClpX to prevent it proceeding through the attached fluorescent protein, thus resulting in no decrease in fluorescence (FIG. 27B-D).

This example demonstrated that such stable structures can effectively stall ClpX when placed between the recognition tag and the protein of interest Such stable blocking motifs can help to ensure that the unfoldase was placed at the start of the target polypeptide before the unfoldase-substrate complex was captured by the pore, which increased the probability of obtaining full-length reads of the protein of interest.

Example 5: Protein Unfolding and Translocation Using VAT-ΔN Protein Translocase This example describes a system in which the translocase was based on the VAT unfoldase from *Thermoplasma aci-dophilum*. VAT unfoldase used herein (VAT-ΔN) had a N-terminal truncation to remove a regulatory domain, which increased the unfoldase activity. This VAT-ΔN, where 183 amino acids of the N-terminus were truncated, was used to test its ability to unfold and translocate proteins across the nanopore.

Preparation of VAT-ΔN Unfoldase

A plasmid with a gene encoding the VAT-ΔN gene elongated by six histidine residues (SEQ ID NO: 32) was transformed into *E. coli* BL21 (DE3) cells by electroporation. Expressed VAT-ΔN protein was extracted from the supernatant and purified using Ni-NTA beads, with elution in 200 µl aliquots (150 mM NaCl, 300 mM imidazole, 15 mM Tris buffered at pH 7.5) before storage at 4° C.

TABLE 9

Amino acid sequence of the translocase used in this example.

| Protein | Amino acid sequence |
|---------|---------------------|
| VAT-ΔN | MGSSHHHHHHGSGLVPRGSAGEVSRISYEDIGGLSEQLGK |
| | IREMIELPLKHPELFERLGITPPKGVILYGPPGTGKTLIA |
| | RAVANESGANFLSINGPEIMSKYYGQSEQKLREIFSKAEE |
| | TAPSIIFIDEIDSIAPKREEVQGEVERRVVAQLLTLMDGM |
| | KERGHVIVIGATNRIDAIDPALRRPGRFDREIEIGVPDRN |
| | GRKEILMIHTRNMPLGMSEEEKNKFLEEMADYTYGFVGAD |
| | LAALVRESAMNALRRYLPEIDLDKPIPTEILEKMVVTEDD |
| | FKNALKSIEPSSLREVMVEVPNVHWDDIGGLEDVKREIKE |
| | TVELPLLKPDVFKRLGIRPSKGFLLYGPPGVGKTLLAKAV |
| | ATESNANFISIKGPEVLSKWVGESEKAIREIFKKAKQVAP |
| | AIVFLDEIDSIAPRRGTTSDSGVTERIVNQLLTSLDGIEV |
| | MNGVVVIGATNRPDIMDPALLRAGRFDKLIYIPPPDKEAR |
| | LSILKVHTKNMPLAPDVDLNDIAQRTEGYVGADLENLCRE |
| | AGMNAYRENPDATSVSQKNFLDALKTIRPSVDEEVIKFYR |
| | TLSETMSKSVSERRKQLQDQGLYL (SEQ ID NO: 51) |

MBP-1 target proteins of interest (as described previously) were provided with a long >30 amino acid tag that had an AANDENYALAA (SEQ ID NO: 19) capture motif that facilitated binding with a VAT translocase, a domain with high cation content that enabled efficient capture into the nanopore.

The adapted MBP-1 target protein was added to the cis compartment in a concentration of 0.1 µM together with 0.2 µM VAT-AN and 2.5 mM ATP in a system containing a nanopore in a membrane under-80 mV applied potential. The ionic current measurements were performed using the standard methods described in this patent.

VAT-ΔN, originating from a thermophilic organism, was active at increasing temperatures. Therefore, the temperature of the system was increased to 37° C. This further showed that various types of protein translocases, in particular AAA+protein unfoldases, can be used in a method or system provided herein.

Example 6: N-Terminus to N-Terminus Linked Proteins

To test the ability of the system to process proteins with different linkages, such as a N-terminus to N-terminus linkage, we measured a C-MBP construct, a MBP-variant with a cysteine on the third residue from the N-terminus of the protein. The C-MBP construct protein naturally formed homodimers in non-reducing conditions (confirmed by appearance of a dimer band with SDS-PAGE). These dimers were covalently linked and had proteins that were coupled N-terminus to N-terminus (FIG. 28).

The C-MBP target protein dimer solution was added to the cis compartment of the nanopore system in a concentration of 0.1 µM together with 0.2 µM ClpX and 2.5 mM ATP in a nanopore system with a single CytK-4D2E nanopore in a membrane under −80 mV applied potential. The ionic current measurements were then performed using the standard methods described herein.

After reading the first monomer of C-MBP, the unfoldase was able to pass through the disulfide bond, after which it reads the second C-MBP monomer in the N- to C-terminus direction. This demonstrates the translocase reading in both the C-to-N and N-to-C direction through the protein analytes. This also demonstrates that the EOF of the system enables the translocase to process through unnatural chemical linkages.

TABLE 10

Amino acid sequence of the proteins used in this study

| Protein | Amino acid sequence |
|---------|---------------------|
| C-MBP | MGCHHHHHHSSGLVPRGSHNKIEEGKLVIWINGDKGYNGL |
| | AEVGKKFEEDTGIKVTVEHPDKLEEKFPQVAATGDGPDII |
| | FWAHDRFGGYAQSGLLAEITPDKAFQDKLYPFTWDAVRYN |
| | GKLIAYPIAVEALSLIYNKDLLPNPPKTWEEIPALDKELK |
| | AKGKSALMFNLQEPYFTWPLIAADGGYAFKYENGKYDIKD |
| | VGVDNAGAKAGLTFLVDLIKNKHMNADTDYSIAEAAFNKG |
| | ETAMTINGPWAWSNIDTSKVNYGVTVLPTFKGQPSKPFVG |
| | VLSAGINAASPNKELAKEFLENYLLTDEGLEAVNKDKPLG |
| | AVALKSYEEELAKDPRIAATMENAQKGEIMPNIPQMSAFW |
| | YAVRTAVINAASGRQTVDEALKDAQTRITKSS (SEQ ID |
| | NO: 52) |

Example 7: Tagging of the C-Terminus of a Maleimide-Peptide Tag

This example demonstrated the ability to tag a target protein substrate to improve translocase loading and subsequent capture in a nanopore.

A MBP target protein comprising a C-terminal cysteine was chemically tagged on the C-terminus by chemical coupling to a maleimide modified leader as described below to create a cysteine-maleimide linkage between the tag and target protein. The leader tag had an AANDENYALAA (SEQ ID NO: 19) recognition motif to facilitate binding with a ClpX translocase, a domain with high cation content to enable efficient capture into the nanopore (RRRRRRRRRRRRRRR (SEQ ID NO: 40)), and a domain to stall the ClpX translocase (GGGGGGGGGGGGG (SEQ ID NO: 41)).

The tagged target protein was added to the cis compartment of the nanopore system in a concentration of 0.1 µM together with 0.2 µM ClpX and 2.5 mM ATP in a nanopore system with a single CytK-4D2E nanopore in a membrane under-80 mV applied potential. The ionic current measurements were then performed using the standard methods described in this patent. See FIG. 29 for an exemplary electrophysiology reads. This example showed that tagged target proteins were captured into the nanopore by a high EOF, in conjunction with a protein translocase motor that unfolded and transported the polypeptide through the pore (translocase controlled translocations are marked with arrows).

Tagging of MBP-C:

MBP-C was an N-terminally His-tagged MBP protein with a C-terminal extension of SSC. The Cysteine was engineered there to serve as a handle to modify MBP with a maleimide-peptide. MBP-C was expressed in *E. coli* BL21 (DE3) (pET28a_MBP-C). Cells were grown in LB with 50 µg/ml kanamycin. Expression was induced by adding 1 mM IPTG concentration when the culture reached OD600 of 0.8. The cells were harvested after overnight growth at 25° C. Pellet was resuspended in MBP binding buffer (200 mM Tris-HCl pH 7.4, 200 mM NaCl, 1 mM EDTA, 1 mM DTT) with protease inhibitors and the cells were sonicated. The cell extract was centrifuged for 30 min at 8000×g and the supernatant was filtered over a 0.45 µm filter. The filtered extract was loaded on a 1 ml MBPtrap column, that was preequilibrated with MBP binding buffer. The column was washed with 5 ml MBP binding buffer. 0.5 ml of 1 mg/ml solution of Peptide-2 (Maleimide-G12SR15-ssrA) in MBP binding buffer was applied to the column. The column was left overnight at room temperature to let the reaction proceed. Next day, the column was washed with MBP binding buffer to remove excess Peptide-2 tag. MBP protein was eluted from the column with MBP elution buffer (MBP binding buffer+10 mM maltose). The tagged protein was further purified using the 1 ml HiTrap SP column. The Peptide-2 tag which had a polyarginine sequence has high affinity for cation exchange column. 0.5 ml of MBP column elution was mixed with 1 ml salt buffer (1.5 M NaCl, 1 mM EDTA, 10 mM Tris-HCl pH 8.0). The HiTrap SP column (preequilibrated with 1 M NaCl buffer) was loaded with the protein sample and washed with 3 ml 1 M NaCl buffer (1 M NaCl, 1 mM EDTA, 10 mM Tris-HCl pH 8.0) to wash away untagged protein. The tagged protein was eluted with 1.5 M NaCl (1.5 M NaCl, 1 mM EDTA, 10 mM Tris-HCl pH 8.0). Subsequent analysis of the fractions with SDS-PAGE showed that a small percentage of protein was tagged.

TABLE 11

| Amino acid sequence of the proteins used in this study | |
| --- | --- |
| Protein/ peptide | Amino acid sequence |
| MBP-C | MGSSHHHHHHSSGLVPRGSHNKIEEGKLVIWINGDKGYN GLAEVGKKFEEDTGIKVTVEHPDKLEEKFPQVAATGDGP DIIFWAHDRFGGYAQSGLLAEITPDKAFQDKLYPFTWDA VRYNGKLIAYPIAVEALSLIYNKDLLPNPPKTWEEIPAL DKELKAKGKSALMFNLQEPYFTWPLIAADGGYAFKYENG KYDIKDVGVDNAGAKAGLTFLVDLIKNKHMNADTDYSIA EAAFNKGETAMTINGPWAWSNIDTSKVNYGVTVLPTFKG QPSKPFVGVLSAGINAASPNKELAKEFLENYLLTDEGLE AVNKDKPLGAVALKSYEEELAKDPRIAATMENAQKGEIM PNIPQMSAFWYAVRTAVINAASGRQTVDEALKDAQTRIT KSSC (SEQ ID NO: 53) |
| Peptide- 2 Tag | Maleimide-GGGGGGGGGGGGGRRRRRRRRRRRRRRSG GVAANDENYALAA (SEQ ID NO: 54) |

Example 8: Nanopore with a Molecular Adaptor

The methods and systems disclosed herein can be used to determine (e.g., sequence) a non-nucleic acid based polymer analyte (e.g., polypeptide).

Preparation of Nanopores with Adaptor

The alpha-haemolysin (aHL) nanopore of the present example are prepared to have a chemical adaptor coupled to the channel of the nanopore. Wildtype aHL nanopores are designed with glutamate mutations to the inwards facing residues (positions 119/121/123/125) of the beta-strands of the beta barrel to increase the net negative charge inside the barrel of the nanopore. To introduce an attachment site within aHL nanopores one of the subunits also comprises a L135C mutation. amino acid sequence of aHL used:

```
(SEQ ID NO: 55)
ADSDINIKTGTTDIGSNTTVKTGDLVTYDKENGMHKKVFYSFIDDKNHNK

KLLVIRTKGTIAGQYRVYSEEGANKSGLAWPSAFKVQLQLPDNEVAQISD

YYPRNSIDTKEYMSTLTYDFDGDVDGDDTGKIGGCIGANVSIGHTLKYVQ

PDFKTILESPTDKKVGWKVIFNNMVNQNWGPYDRDSWNPVYGNQLFMKTR

NGSMKAADNFLDPNKASSLLSSGFSPDFATVITMDRKASKQQTNIDVIYE

RVRDDYQLHWTSTNWKGTNTKDKWTDRSSERYKIDWEKEEMTN
```

Alpha-haemolysin (aHL) nanopores are expressed, assembled, and purified for use in the nanopore system. To prepare the heteroheptamers, a sequence encoding a C-terminal tail of eight aspartate residues is added to the genes of the cysteine mutant nanopores. The aspartate tail allows the resolution of heptamers with different combinations of subunits by protein electrophoresis (e.g., SDS-PAGE), enabling heteroheptamers containing a single cysteine modified subunit to be excised from the final protein (e.g., SDS-PAGE) gel.

A modified beta-cyclodextrin (heptakis(6-deoxy-6-amino)-6-N-mono(2-pyridyl)dithiopropanoyl-b-cyclodextrin, bCD) with a reactive side-arm linker is additionally prepared. The modified beta-cyclodextrin then attaches to the channel of the generated aHL nanopore.

Recordings of Protein Translocation

Measurements of translocase controlled protein translocation are carried out according to the system schematically described in FIG. 3. Experiments are run on a nanopore system (e.g., axopatch planar bilayer system) as described herein at room temperature. Both compartments of the nanopore system are filled with 0.4 mL of an electrolyte solution (1 M potassium glutamate, 20 mM MgCl$_2$ and 50 mM Tris, buffered to pH 7.5). 1 uL of a preparation of purified aHL nanopore solution is added to the cis compartment with mixing to achieve a single inserted nanopore. The insertion of a single nanopores is detected by the characteristic step-wise change in open pore current. The nanopore is characterised at a range of voltages to assess the quality of the nanopore to ensure suitability for the experiment. bCD is added to the trans compartment. bCD binding to the nanopore is evident by ionic current blockades under an applied voltage (variable from −180 mV to +180 mV), and permanent covalent reaction of the bCD to the nanopore is evident by the permanence of the reduced ionic current bCD blockade level. Reacted bCD-aHL nanopores with an open-pore current of >20 pA at 100 mV are selected for protein translocation experiments. Separately, ClpX translocase (prepared as described herein) and target MBP-1 protein analyte (prepared as described herein) are preincubated as described at a 2:1 translocase:target-protein molar ratio, for >10 minutes at room temperature in a preloading solution (e.g., 10 mM ATP and 25 mM MgCl$_2$). After pre-incubation, the translocase:target-protein complex is added to the cis-compartment.

Electrical recordings are acquired over a range of voltages from −60 mV to −180 mV. ClpX:MBP-1 complex translocation events through bCD-aHL nanopores are evident by their characteristic blockade reduction in ionic current flowing through the nanopore, followed by a characteristic pattern of amino-acid dependent changes in current levels lasting for about 10-30 seconds before the events end and the ionic current returns to the open-pore level.

Example 9—Nanopore with a Protein Adapter

Preparation of ClpX Translocase

E. coli ClpX was employed as exemplary translocase to control the movement of the polypeptide through the nanopore (FIGS. 2 and 3). ClpX was selected as a AAA+ translocase systems, and can unfold and translocate along a wide variety of proteins, generating a high force through NTP hydrolysis. The monomer and covalently linked trimer of N-terminal truncated ClpX variants (residues 61-423) were purified as with minor modifications and used for ClpX nanopore experiments. Specifically, the gene encoding for monomer and trimer of ClpX-AN were separately transformed into electrocompetent cells (e.g., E. coli BL21 (DE3) electrocompetent cells). Transformants were selected after overnight growth at 37° C. on agar plates (e.g., lysogeny broth (LB) agar plates) supplemented with ampicillin (100 mg/L). The resulting colonies were inoculated into 200 mL culture media (e.g., LB medium) containing 100 mg/L of ampicillin. The ClpX protein expression was induced at an A600 of ~0.6 by addition of 0.5 mM isopropyl β-D-1-thiogalactopyranoside (IPTG) and incubated at 25° C. overnight. The cells were harvested by centrifugation for 20 min (4000×g) at 4° C. and the pellets were stored at −80° C. About 100 mL of cell culture pellet was thawed and solubilized with ~20 mL lysis buffer (e.g., 50 mM HEPES, pH 7.5, 300 mM KCl, 20 mM imidazole, 1 mM dithiothreitol (DTT), 0.1 units/mL DNase I, 10 μg/mL lysozyme) and stirred with a vortex shaker for 1 hour at 4° C. The bacteria were then lysed by sonication (duty cycle 10%, output control 3, Branson Sonifier 450). The lysate was subsequently centrifuged at 6000×g at 4° C. for 20 min and the cellular debris discarded. The supernatant was mixed with 100 μL of Ni-NTA resin (Qiagen) to a 50 mL falcon tube, which was pre-equilibrated with wash buffer (e.g., 50 mM HEPES, pH 7.5, 300 mM KCl, 20 mM imidazole, 1 mM dithiothreitol (DTT)). Proteins were purified from the supernatant via Ni-NTA resin (Qiagen) using standard procedures and eluted with approximately 600 uL elution buffer (e.g., 600 mM imidazole, 1 mM dithiothreitol (DTT), 100 μM EDTA, 200 mM KCl, 25 mM MgCl₂, 50 mM Tris, pH 7.5). The proteins were further purified using a Superose 6 column Increase 10/600 GL and eluted in 200 ul fractions in elution buffer 2 (e.g., 1 mM dithiothreitol (DTT), 100 μM EDTA, 200 mM KCl, 25 mM MgCl₂, 50 mM Tris, pH 7.5). The fractions with pure protein were concentrated using Amicon Ultra Centrifugal Filters. Purified proteins were then flash frozen in small aliquots supplemented with 30% glycerol and stored at −80° C. Protein concentrations were determined by Bradford assay with bovine serum albumin as a standard.

Preparation of Protein Analytes

The analyte MBP-1 based on the well-known model protein Maltose Binding Protein (MBP) was used to test protein translocation through the nanopores with adapters. The protein was prepared as described herein in Example 1. MBP-1 comprised a long >30 amino acid leader with a AANDENYALAA (SEQ ID NO: 19) capture recognition motif that facilitated binding with ClpX translocase, a domain with high cation content that enabled efficient capture into the nanopore (RRRRRRRRRRRRRRRR (SEQ ID NO: 40)) and a domain to that stalled the ClpX translocase (GGGGGGGGGGGGGG (SEQ ID NO: 41)).

Briefly, MBP-1 was prepared transforming the gene encoding MBP-1 into electrocompetent cells (e.g., E. coli BL21 (DE3) electrocompetent cells). Transformants were selected after overnight growth at 37° C. on agar plates (e.g., lysogeny broth (LB) agar plates) supplemented with kanamycin (50 mg/L). The resulting colonies were inoculated into 200 mL culture media (e.g., LB medium) with 50 mg/L of kanamycin. The cells were induced at an A600 of ~0.6 by addition of 0.5 mM isopropyl β-D-1-thiogalactopyranoside (IPTG) and incubated at 25° C. overnight. The cells were harvested by centrifugation and the pellets were stored at −80° C. 100 mL cell culture pellets were thawed and solubilized before removing the cellular debris by centrifugation. Proteins were purified from the supernatant via Ni-NTA resin (Qiagen) used standard procedures and eluted with approximately 100 μL elution buffer (e.g., 600 mM imidazole, 1 mM dithiothreitol (DTT), 150 mM KCl, 50 mM HEPES, pH 7.5). Purified protein as then flash frozen in small aliquots and stored at −80° C. Protein concentrations were determined by Bradford assay with bovine serum albumin as a standard.

```
MBP-1 (SEQ    Affinity purification tag:
ID NO: 29)    MHHHHHHSS

MBP protein:
              PWKIEEGKLVIWINGDKGYNGLAEVGKKFEKDTGIKV
              TVEHPDKLEEKFPQVAATGDGPDIIFWAHDRFGGYAQ
              SGLLAEITPDKAFQDKLYPFTWDAVRYNGKLIAYPIA
              VEALSLIYNKDLLPNPPKTWEEIPALDKELKAKGKSA
              LMENLQEPYFTWPLIAADGGYAFKYENGKYDIKDVGV
              DNAGAKAGLTFLVDLIKNKHMNADTDYSIAEAAFNKG
              ETAMTINGPWAWSNIDTSKVNYGVTVLPTFKGQPSKP
              FVGVLSAGINAASPNKELAKEFLENYLLTDEGLEAVN
              KDKPLGAVALKSYEEELAKDPRIAATMENAQKGEIMP
              NIPQMSAFWYAVRTAVINAASGRQTVDEALKDAQTRI
              TKHM Stall/capture motif:
              GGGGGGGGGGGGGGSRRRRRRRRRRRRRRRR Recognition motif:
              AANDENYALAA
```

Preloading of the Translocase onto Target Protein

To improve the percentage of ClpX:target-protein complexes formed, the complexes are formed prior to addition to the nanopore system. ClpX:Target-protein complexes are preloaded by mixing the components at a concentration of about 10 μM ClpX, 5 μM target protein in a 2:1 ratio, in a solution with 10 mM ATP and 25 mM MgCl₂ in a volume of 10 ul (50 mM Tris-HCl, 200 mM KCl, 10 mM ATP, 25 mM MgCl₂, 1 mM DTT, 1 mM EDTA, PH 7.5). The mixture is incubated for at least 10 minutes at room temperature to allow sufficient time for the ClpX to bind to the target proteins.

Preparation of CsgG/F Nanopores

CsgG-F56D/CsgF nanopores are prepared. Briefly, E. coli cells is transformed with genes coding for CsgG-F56D and CsgF subunits are resuspended in 50 mM Tris-HCl pH 8.0, 200 mM NaCl, 1 mM EDTA, 5 mM MgCl₂, 0.4 mM AEBSF, 1 μg ml-1 leupeptin, 0.5 mg ml-1 DNase I and 0.1 mg ml-1 lysozyme. The cells are lysed and then incubated for 30 min with 1% n-dodecyl-β-D-maltopyranoside (DDM)

to extract the outer membrane components. Cell debris is removed by ultracentrifugation at 100,000 g for 40 min and supernatant is loaded onto a 5-ml HisTrap column (GE Healthcare) equilibrated in buffer A (e.g., 25 mM Tris pH 8, 200 mM NaCl, 10 mM imidazole, 10% sucrose and 0.06% DDM). The column is washed with >10 column volumes of 5% buffer B (e.g., 25 mM Tris pH 8, 200 mM NaCl, 500 mM imidazole, 10% sucrose and 0.06% DDM) in buffer A, and elutes with a gradient of 5-100% buffer B over 60 ml. The eluate is diluted twofold before loading overnight on a 5-ml Strep-Tactin column (IBA GmbH) equilibrated with buffer C (e.g., 25 mM Tris pH 8, 200 mM NaCl, 10% sucrose and 0.06% DDM). The column is washed with >10 column volumes of buffer C and the bound protein is eluted in buffer C complemented with 2.5 mM desthiobiotin. The co-expressed complex is injected on a Superose 6 10/30 column (GE Healthcare) equilibrated with buffer F (e.g., 25 mM Tris pH 8, 200 mM NaCl and 0.03% DDM) and run at 0.5 ml min-1. The CsgG-CsgF complexes are digested at room temperature overnight with TEV protease in buffer F. The mixture is then run back through a 5-ml HisTrap (GE Healthcare) column and the flow-through is collected, heated at 60° C. for 15 min and centrifuged at 21,000 g for 10 min before use in electrophysiology. Protein concentrations are determined on the basis of calculated absorbance at 280 nm and assuming 1/1 stoichiometry.

CsgG protein sequence
(SEQ ID NO: 56)
CLTAPPKEAARPTLMPRAQSYKDLTHLPAPTGKIFVSVYNIQDETGQFKP

YPASNDSTAVPQSATAMLVTALKDSRWFIPLERQGLQNLLNERKIIRAAQ

ENGTVAINNRIPLQSLTAANIMVEGSIIGYESNVKSGGVGARYFGIGADT

QYQLDQIAVNLRVVNVSTGEILSSVNTSKTILSYEVQAGVFRFIDYQRLL

EGEVGYTSNEPVMLCLMSAIETGVIFLINDGIDRGLWDLQNKAERQNDIL

VKYRHMSVPPES

CsgF protein sequence
(SEQ ID NO: 57)
GTMTFQFRNPNFGGNPNNGAFLLNSAQAQNSYKDPSYNDDFGIETPSALD

NFTQAIQSQILGGLLSNINTGKPGRMVTNDYIVDIANRDGQLQLNVTDRK

TGQTSTIQVSGLQNNSTDF

Planar Lipid Bilayer Electrophysiological Recordings System

For each experiment a single nanopore is inserted in a planar lipid bilayer system. Briefly, an electrophysiology chamber with two compartments separated by a 25 μm thick membrane (e.g., Teflon (Goodfellow Cambridge Ltd) membrane) is used. The Teflon membrane has an aperture with a diameter of approximately 100 μm. Lipid membranes are formed by first applying 5 μl of 5% hexadecane (Sigma Aldrich) in pentane (Sigma Aldrich) to the Teflon membrane, near the aperture. The pentane is left to dry and 400 μl of buffered solution (1 M potassium glutamate, 20 mM $MgCl_2$ and 50 mM Tris, buffered to pH 7.5) is added to each compartment. 20 μl of a 6.25 mg/ml solution of DPhPC dissolved in pentane is added on top of the buffer on each side of the chamber. The chamber is left to dry for ~2 minutes to allow evaporation of pentane. Silver/silver chloride electrodes are attached to each compartment. The cis compartment is connected to the ground electrode and the trans is connected to the working electrode. Planar lipid bilayers are created using the Langmuir-Blodgett method. Purified nanopore solutions are added to the cis compartment to obtain insertion of single nanopores. Once a single nanopore is inserted the orientation and properties of the nanopore are confirmed by the asymmetry of the current-voltage relationship.

Recordings of ionic currents are obtained using an amplifier (Axopatch 200B patch clamp amplifiers (Axon Instruments)) combined with a A/D converter (Digidata 1550B A/D converters (Axon instruments)). Recordings are acquired at 10 kHz with a 2 kHz Bessel filter, and recorded using Clampex 10 (Molecular Devices) at 22° C.

Recordings of Protein Translocation

Measurements of translocase controlled protein translocation are carried out according to the system schematically described in FIG. 3. Both compartments of the nanopore system are filled with 0.4 mL of an electrolyte solution (e.g., 1 M potassium glutamate, 20 mM $MgCl_2$ and 50 mM Tris, buffered to pH 7.5). 1 uL of a preparation of purified CgsG/F nanopore solution is added to the cis compartment with mixing to achieve a single inserted nanopore. After detecting the insertion of a single nanopore by the characteristic step-wise change in open pore current, the nanopore is characterised at a range of voltages to assess the quality of the nanopore to ensure suitability for the experiment. Nanopores with an open-pore current of >40 pA at 180 mV are selected for protein translocation experiments. Separately, ClpX translocase (prepared as described above) and MBP-1 target protein substrate (prepared as described) are preincubated as described at a 2:1 translocase:target-protein molar ratio, for >10 minutes at room temperature in 10 mM ATP and 25 mM $MgCl_2$. After pre-incubation, the ClpX:MBP-1 complex is added to the cis-compartment.

Electrical recordings are acquired over a range of voltages from −60 mV to −200 mV. ClpX:MBP-1 complex translocation events are evident by their characteristic blockade reduction in ionic current flowing through the nanopore, followed by a characteristic pattern of amino-acid dependent changes in current levels which lasts for about 10-30 seconds before the events end and the ionic current returns to the open-pore level.

The invention claimed is:

1. A method comprising:
   (a) providing:
      (i) a nanopore system, wherein the nanopore system comprises (1) a fluidic chamber, (2) a membrane that separates the fluidic chamber into a first side and a second side, and (3) at least a portion of a nanopore disposed in the membrane;
      (ii) an analyte comprising a polypeptide or fragment thereof; and
      (ii) a translocase;
   (b) translocating at least a first portion of the analyte from the first side toward the second side using an electro-osmotic force or an electrophoretic force; and
   (c) translocating at least a second portion of the analyte toward the first side using the translocase.

2. The method of claim 1, wherein the at least the first portion of the analyte and the at least the second portion of the analyte are a same portion of the analyte.

3. The method of claim 1, wherein the analyte is coupled to at least one construct.

4. The method of claim 3, wherein the at least one construct comprises a stall motif, a block motif, a coupling motif, a barcode motif, a membrane-binding motif, a capture motif, or a recognition motif, or any combination thereof.

5. The method of claim 3, wherein the analyte comprises a first construct at a first end of the analyte and a second construct at a second end of the analyte.

6. The method of claim 5, wherein the first construct is a recognition motif and the second construct is a capture motif.

7. The method of claim 1, further comprising contacting the analyte with the translocase.

8. The method of claim 7, wherein the contacting occurs outside of the nanopore system.

9. The method of claim 1, wherein the translocase disrupts a quaternary, tertiary, or secondary structure of the analyte.

10. The method of claim 1, wherein the translocase is an adenosine triphosphate (ATP)-driven unfoldase or a nucleotide triphosphate (NTP)-driven unfoldase.

11. The method of claim 1, wherein the translocase is a protein translocase.

12. The method of claim 11, wherein the protein translocase comprises an NTP-dependent or ATP-dependent AAA+ protease or translocase.

13. The method of claim 11, wherein the protein translocase comprises an ATP-dependent Clp protease ATP-binding subunit ClpX (ClpX) and ClpX-like proteases, an ATP-dependent Clp protease ATP-binding subunit ClpA (ClpA), a proteasome-activating nucleotidase (PAN), a LON protease, VCP-like ATPase (VAT), AMA, 854, ATP-dependent Clp protease ATP-binding subunit ClpC (ClpC), ATP-dependent Clp protease ATP-binding subunit ClpE (ClpE), ATP-dependent protease ATPase subunit HslU (HsIU), caseinolytic mitochondrial matrix peptidase chaperone subunit Y (ClpY), LonA, LonB, ATP-dependent zinc metalloprotease FtsH (FtsH), proteasome-associated ATPase (Mpa), cell division cycle protein 48 (Cdc48, also called p97 and VCP) and Cdc48-like protein of actinobacteria (Cpa), outer mitochondrial transmembrane helix translocase (Msp1), or a protein translocase subunit SecA (SecA), or functional homologs thereof, or orthologs thereof, or paralogs thereof.

14. The method of claim 1, wherein the translocating of (b) is performed using the electrophoretic force.

15. The method of claim 1, wherein the translocating of (b) is performed using the electro-osmotic force.

16. The method of claim 1, wherein the translocase moves in a direction toward the second side as the at least the second portion of the analyte translocates toward the first side.

17. The method of claim 1, further comprising measuring a signal generated by the translocating of (b), the translocating of (c), or a combination thereof.

18. The method of claim 17, wherein the measuring comprises measuring the signal for states of (i) an open channel of the nanopore; (ii) capture of the at least the first portion of the analyte or the at least the second portion of the analyte by the nanopore; or (iii) passage of the at least the first portion of the analyte or the at least the second portion of the analyte in the nanopore.

19. The method of claim 1, wherein the at least the first portion of the analyte is translocated from the first side toward the second side or the at least the second portion of the analyte is translocated toward the first side.

20. The method of claim 1, wherein the nanopore comprises an alpha-helical pore forming protein or fragment thereof, or a beta-barrel oligomeric pore forming protein or fragment thereof.

21. The method of claim 1, wherein a portion of the analyte comprises a nucleic acid molecule.

22. The method of claim 1, wherein at least 60% of the analyte is protein.

23. The method of claim 1, wherein the analyte is at least 5 amino acids in length.

24. The method of claim 1, wherein the nanopore is a biological nanopore.

25. The method of claim 1, wherein the nanopore is a solid state nanopore or a de novo nanopore.

26. The method of claim 1, wherein the nanopore comprises one or more monomers of an Aerolysin (Aer) pore, a Cytolysin K (CytK) pore, a *Mycobacterium smegmatis* (Msp) pore, an alpha-hemolysin (aHL) pore, a Curli production assembly/transport component CsgG pore, a Fragaceatoxin C (FraC) pore, a Lysenin pore, an outer membrane porin F (OmpF) pore, an outer membrane porin G (OmpG) pore, or a ferric hydroxamate uptake component A (FhuA) pore, or homolog thereof, paralog thereof, ortholog thereof, or phage derived portal proteins, or modified variants thereof, or ion-selective mutants thereof.

27. The method of claim 1, wherein the nanopore comprises a proteinaceous adaptor comprising a Curli production assembly/transport component CsgF subunit, a CsgF subunit truncation, a CsgF subunit homolog, a CsgF subunit paralog, or a CsgF subunit ortholog.

28. The method of claim 1, wherein the nanopore system further comprises a pair of electrodes that provides an applied voltage to generate the electrophoretic force.

\* \* \* \* \*